US010500249B2

(12) United States Patent
Lander et al.

(10) Patent No.: US 10,500,249 B2
(45) Date of Patent: Dec. 10, 2019

(54) COMPOSITIONS AND METHODS FOR PREVENTING OR TREATING DISEASES, CONDITIONS, OR PROCESSES CHARACTERIZED BY ABERRANT FIBROBLAST PROLIFERATION AND EXTRACELLULAR MATRIX DEPOSITION

(71) Applicant: MOERAE MATRIX, INC., Morristown, NJ (US)

(72) Inventors: Cynthia Lander, Mendham, NJ (US); Colleen Brophy, Nashville, TN (US)

(73) Assignee: MOERAE MATRIX INC., Morristown, NJ (US)

( * ) Notice: Subject to any disclaimer, the term of this patent is extended or adjusted under 35 U.S.C. 154(b) by 0 days.

(21) Appl. No.: 14/943,752

(22) Filed: Nov. 17, 2015

(65) Prior Publication Data
US 2016/0136234 A1    May 19, 2016

Related U.S. Application Data

(60) Provisional application No. 62/080,784, filed on Nov. 17, 2014.

(51) Int. Cl.
| *A61K 38/16* | (2006.01) |
| *A61K 38/17* | (2006.01) |
| *A61K 45/06* | (2006.01) |
| *A61K 31/7072* | (2006.01) |
| *A61K 31/4025* | (2006.01) |
| *A61K 31/427* | (2006.01) |
| *A61K 31/506* | (2006.01) |
| *A61K 31/513* | (2006.01) |
| *A61P 29/00* | (2006.01) |
| *A61P 35/00* | (2006.01) |

(52) U.S. Cl.
CPC .......... *A61K 38/17* (2013.01); *A61K 31/4025* (2013.01); *A61K 31/427* (2013.01); *A61K 31/506* (2013.01); *A61K 31/513* (2013.01); *A61K 31/7072* (2013.01); *A61K 38/16* (2013.01); *A61K 45/06* (2013.01); *A61P 29/00* (2018.01); *A61P 35/00* (2018.01)

(58) Field of Classification Search
None
See application file for complete search history.

(56) References Cited

U.S. PATENT DOCUMENTS

| 4,105,027 A | 8/1978 | Lundquist |
| 4,192,309 A | 3/1980 | Poulsen |
| 4,227,522 A | 10/1980 | Carris |
| 4,627,432 A | 12/1986 | Newell et al. |
| 4,778,054 A | 10/1988 | Newell et al. |
| 4,811,731 A | 3/1989 | Newell et al. |
| 5,035,237 A | 7/1991 | Newell et al. |
| 5,352,461 A | 10/1994 | Feldstein et al. |
| 5,503,852 A | 4/1996 | Steiner et al. |
| 6,071,497 A | 6/2000 | Steiner et al. |
| 6,331,318 B1 | 12/2001 | Milstein |
| 6,428,771 B1 | 8/2002 | Steiner et al. |
| 6,440,463 B1 | 8/2002 | Feldstein et al. |
| 6,444,226 B1 | 9/2002 | Steiner et al. |
| 6,652,885 B2 | 11/2003 | Steiner et al. |
| 6,921,527 B2 | 7/2005 | Platz et al. |
| 7,799,344 B2 | 9/2010 | Oberg |
| 7,803,404 B2 | 9/2010 | Hokenson et al. |
| 8,536,303 B2 | 9/2013 | Panitch et al. |
| 8,741,849 B2 | 6/2014 | Panitch et al. |
| 2006/0040953 A1 | 2/2006 | Leone-Bay et al. |
| 2006/0041133 A1 | 2/2006 | Stevenson et al. |
| 2006/0099269 A1 | 5/2006 | Cheatham et al. |
| 2007/0196503 A1 | 8/2007 | Wilson et al. |
| 2009/0196927 A1* | 8/2009 | Panitch .................... C07K 7/06 424/484 |
| 2012/0263680 A1 | 10/2012 | Lander et al. |

FOREIGN PATENT DOCUMENTS

| WO | 1991/016038 A1 | 10/1991 |
| WO | 2008/085191 A1 | 7/2008 |
| WO | WO 2010/068692 A1 | 6/2010 |
| WO | WO 2011/149964 A2 | 12/2011 |
| WO | 2013/134636 A1 | 9/2013 |

(Continued)

OTHER PUBLICATIONS

Borthwick et al., "Cytokine mediated tissue fibrosis", Biochimica et Biophysica Acta, 2013, 1049-1060.*
López-Novoa, "Inflammation and EMT: an alliance towards organ fibrosis and cancer progression", EMBO Molecular Medicine, 2009; 303-314.*
Borensztajn et al., FXa-inducedintracellular signaling links coagulation to neoangiogenesis: Potential implications for fibrosis, Biochimica et Biophysica Acta, 2009, 798-805 (Year: 2009).*
Connolly et al., "In liver fibrosis, dendritic cells govern hepatic inflammation in mice via TNF-a", The Journal of Clinical Investigation, 2009, 3213-3225 (Year: 2009).*
Xu et al., "MMI-0100 inhibits cardiac fibrosis in myocardial infarction by direct actions on cardiomyocyts and fibroblasts via MK inhibition", Journal of Molecular and Cellular Cardiology, available online Oct. 1, 2014; pp. 86-101 (Year: 2014).*

(Continued)

*Primary Examiner* — Lianko G Garyu
(74) *Attorney, Agent, or Firm* — Cooley LLP

(57) ABSTRACT

The described invention provides compositions and methods for reducing progression of a fibrosis in a tissue of a subject selected from liver, kidney or vascular fibrosis, the progression of the fibrosis being characterized by aberrant fibroblast proliferation and extracellular matrix deposition in the tissue. The method includes administering a therapeutic amount of a pharmaceutical composition containing a polypeptide having the amino acid sequence YARAAAR-QARAKALARQLGVAA (SEQ ID NO: 1) or functional equivalent thereof, and a pharmaceutically acceptable carrier, wherein the therapeutic amount of the polypeptide is effective to reduce progression of the fibrosis, to treat remodeling of the tissue, or a combination thereof.

16 Claims, 26 Drawing Sheets

Specification includes a Sequence Listing.

(56) References Cited

FOREIGN PATENT DOCUMENTS

| WO | WO 2014093711 A1 * | 6/2014 | ......... A61K 31/4025 |
|---|---|---|---|
| WO | WO-2014093711 A1 * | 6/2014 | ......... A61K 31/4025 |

OTHER PUBLICATIONS

Ward et al., "Peptide inhibitors of MK2 show promise for inhibition of abdominal adhesions"; Journal of Surgical Research, 2011, vol. 169, No. 1, pp. e27-e36 (2011) See abstract.

Vittal et al., "Peptide-mediated inhibition of MK2 ameliorates bleomycin-induced pulmonary fibrosis"; American Journal of Respiratory Cell and Molecular Biology, vol. 49, Issue 1, pp. 47-57 (2013) See abstract.

Coker and Laurent, "Pulmonary fibrosis: cytokines in the balance"; Eur Respir J, 1998,: 11:1218-1221.

Richards et al,"Peripheral Blood Proteins Predict Mortality in Idiopathic Pulmonary Fibrosis"; Am J Respir Crit Care Med, 2012, 185:67-76.

Liu, T., et al; "Lack of MK2 Inhibits Myofibroblast Formation and Exacerbates Pulmonary Fibrosis"; Am J Respir Cell Mol Biol, 2007, 37:507-517.

Raghu, G., :An Official ATS/ERS/JRS/ALAT Statement: Idiopathic Pulmonary Fibrosis: Evidence-based Guidelines for Diagnosis and Management; Am J Respir Crit Care Med, 183(6):788-824; 2011.

Thannickal, V., et al; "Evolving Concepts of Apoptosis in Idiopathic Pulmonary Fibrosis"; Proc Am Thorac Soc., 3(4):350-356, 2006.

Neininger, A., et al; "MK2 Targets AU-rich Elements and Regulates Biosynthesis of Tumor Necrosis Factor and Interleukin-6 Independently at Different Post-transcriptional Levels*"; J Biol Chem., 277(5):3065-8, 2002.

Thomas, T., et al; "MAPKAP kinase 2-deficiency prevents neurons from cell death by reducing neuroinflammation—relevance in a mouse model of Parkinson's disease"; J Neurochem, 105(5):2039-52, 2008.

Zhang, Y, et al; Enhanced il-lp and Tumor Necrosis Factor—a Release and Messenger RNA Expression in Macrophages from Idiopathic Pulmonary Fibrosis or after Asbestos Exposure; J. Immunol; 150(9):4188-4196; 1993.

Kolb, M., et al_J.; "Transient expression of IL-1β induces acute lung injury and chronic repair leading to pulmonary fibrosis"; J Clin Invest. Jun. 15, 2001; 107(12): 1529-153.

Selman, M., et al; "Idiopathic Pulmonary Fibrosis: Prevailing and Evolving Hypotheses about Its Pathogenesis and Implications for Therapy"; Ann Intern Med. 2001;134:136-151.

Noble, P. and Homer R.; "Idiopathic pulmonary fibrosis: new insights into pathogenesis"; Clin Chest Med, 25(4):749-58, 2004.

Strieter, R.; "Pathogenesis and Natural History of Usual Interstitial Pneumonia"; Chest 128 (5 Suppl 1):526S-532S, 2005.

Vittal, R., et al; "Effects of the Protein Kinase Inhibitor, Imatinib Mesylate, on Epithelial/Mesenchymal Phenotypes: Implications for Treatment of Fibrotic Diseases"; J Pharmacol Exp Ther., 321(1):35-44, 2007.

Vittal, R., et al; "Modulation of Prosurvival Signaling in Fibroblasts by a Protein Kinase Inhibitor Protects against Fibrotic Tissue Injury"; American Journal of Pathology, vol. 166, No. 2, 367-75; Feb. 2005.

Hecker L., et al; "NADPH Oxidase-4 Mediates Myofibroblast Activation and Fibrogenic Responses to Lung Injury"; Nat Med Sep. 2009; 15(9): 1077-1081.

Umezawa, H., et al; "Studies on bleomycin"; Cancer 20:891-895, 1967.

Umezawa, H.; "Chemistry and mechanism of action of bleomycin. "; Fed Proc, 33:2296-2302, 1974.

Muggia, F., et al; "Pulmonary toxicity of antitumor agents"; Cancer Treat Rev, 10:221-243, 1983.

Phan, S., et al; "Bleomycin-induced Pulmonary Fibrosis in Rats: Biochemical Demonstration of Increased Rate of Collagen Synthesis"; Am Rev Respir Dis 121:501-506, 1980.

Snider, G., et al; "Chronic Interstitial Pulmonary Fibrosis Produced in Hamsters by Endotracheal Bleomycin Lung Volumes, Volume-Pressure Relations, Carbon Monoxide Uptake, and Arterial Blood Gas Studies1,2"; Am Rev Respir Dis. 177:289-297, 1978.

Thrall, R., et al; "Bleomycin-Induced Pulmonary Fibrosis in the Rat" Am J Pathol, 95:117-130, 1979.

Janick-Buckner, D., et al; "Alteration of bronchoalveolar lavage cell populations following bleomycin treatment in mice"; Toxicol Appl Pharmacol., 100(3):465-73; 1989.

Schrier, D., et al., "The Role of Strain Variation in Murine Bleomycin-Induced Pulmonary Fibrosis"; Am Rev Respir Dis., 127(1):63-6, 1983.

Izbicki, G., et al., "Time course of bleomycin-induced lung fibrosis"; int J Exp Pathol., 83(3):111-9, 2002.

Phan S., et al; "A Comparative Study of Pulmonary Fibrosis Induced by Bleomycin and an 0 2 Metabolite Producing Enzyme System*"; Chest vol. 83, Issue 5, Supplement, pp. 44S-45S, 1983.

Goldstein, R., et al; "Failure of Mechanical Properties to Parallel Changes in Lung Connective Tissue Composition in Bleomycin-Induced Pulmonary Fibrosis in Hamsters"; Am Rev Respir Dis., 120(1)67-73, 1979.

Starcher, B., et al"Increased Elastin and Collagen Content in the Lungs of Hamsters Receiving an Intratracheal Injection of Bleomycin"; Am Rev Respir Dis., 117(2):299-305, 1978.

Lawson, W., et al; "IIncreased and Prolonged Pulmonary Fibrosis in Surfactant Protein C-Deficient Mice Following Intratracheal Bleomycin"; Am J Pathol, 2005; 167(5):1267-1277.

Ware, L. and Matthay, M.; "The Acute Respiratory Distress Syndrome"; N Engl J Med, 342:1334-1349, 2000.

Nuckton, T., et al; "Pulmonary Dead-Space Fraction as a Risk Factor for Death in the Acute Respiratory Distress Syndrome"; N Engl J Med, vol. 346, No. 17, 1301-1308; Apr. 25, 2002.

Fan, E., et al; "Ventilatory Management of Acute Lung Injury and Acute Respiratory Distress Syndrome"; JAMA, 294:2889-2896, 2005.

MacIntyre, N.; "Current Issues in Mechanical Ventilation for Respiratory Failure"; Chest, 128:561S-567, 2005.

Members of the ARDS Ventilation with Lower Tidal Volumes as Compared with Traditional Tidal Volumes for Acute Lung Injury and the Acute Respiratory Distress Syndrome; N Engl J Med; 342:1301-1308, 2000.

Damarla, M., et al; "Mitogen Activated Protein Kinase Activated Protein Kinase 2 Regulates Actin Polymerization and Vascular Leak in Ventilator Associated Lung Injury"; PLoS ONE, 4(2):E4600, 2009.

Tager et al; "The lysophosphatidic acid receptor LPA1 links pulmonary fibrosis to lung injury by mediating fibroblast recruitment and vascular leak"; Nat. Med. 14:45-54, 2008.

Ley, K. and Zarbock, A.; "From lung injury to fibrosis"; Nat. Med. 14:20-21; 2008.

Bentzen, S., et al; "Latent-time estimation for late cutaneous and subcutaneous radiation reactions in a single-follow-up clinical study"; Radiother. Oncol. 15:267-274, 1989.

Brocheriou, C., et al; "Radiation Damage to Skin"; Br. J. Radiol. Suppl. 19:101-108, 1986.

Wilson and Wynn; "Pulmonary fibrosis: pathogenesis, etiology and regulation"; Mucosal Immunol., 2009, 3 (2):103-121.

Lopes-Cardoza, B., et al; "Lung damage following bone marrow transplantation: I. The contribution of irradiation"; Int.J. Radiat. Oncol.Biol. Phys., 11:907-914, 1985.

Fajardo, L. and Stewart, J.; "Pathogenesis of radiation-induced myocardial fibrosis"; Lab Invest., 29:244-257, 1973.

Ingold, J., et al; "Radiation Hepatitis"; Am. J. Roentgenol, 93:200-208, 1965.

Gross, N., et al.; "Replicative Activity of Lung Type 2 Cells following Lung X Irradiation1"; Radiation Research., III:143-50, 1981.

Guerry-Force, M., et al.; "Early Structural Changes in Sheep Lung Following Thoracic Irradiation"; Radiation Research, Apr. 1988, vol. 114, No. 1, pp. 138-153.

Hendry, J., "Biological response modifiers and normal tissue injury after irradiation*" Radiat. Oncol., vol. 4,2:123-132, 1994.

(56) References Cited

OTHER PUBLICATIONS

Rosiello R., et al; "Radiation Pneumonitis: Bronchoalveolar Lavage Assessment and Modulation by a Recombinant Cytokine"; Am Rev Respir Dis., Dec. 1993; 148:1671-1676.
Travis, E. and Terry, N.; "Cell Depletion and Initial and Chronic Responses in Normal Tissues"; Front. Radiat. Ther. Oncol., 23:41-59, 1989.
Vergara, J., et al; "Changes in lung morphology and cell number in radiation pneumonitis and fibrosis: A quantitative ultrastructural study"; Int. J. Radiat. Oncol. Biol. Phys. 2:723-732, 1987.
Maasilta, P. et al., "Procollagen-III in serum, plasminogen activation and fibronectin in bronchoalveolar lavage fluid during and following irradiation of human lung"; Int. J. Radiat. Oncol. Biol. Phys. 20:973-980, 1991.
Remy, J. et al.; Long-Term Overproduction of Collagen in Radiation-Induced Fibrosis; Radiat. Res. 125:14-19, 1991.
Rodemann, H. and Bamberg, M.; "Cellular basis of radiation-induced fibrosis"; Radiotherapy and Oncology vol. 35, Issue 2, May 1995, pp. 83-90.
Schlesinger, C., et al; "Constrictive (obliterative) bronchiolitis"; Curr Opin Pulm Med., 4(5): 288-93, 1998.
Clarkson, Michael R..and Sayegh, Mohamed H.; "T-Cell Costimulatory Pathways in Allograft Rejection and Tolerance"; Transplantation: Sep. 15, 2005—vol. 80—Issue 5—pp. 555-563.
Wilkes, D.; "Chronic lung allograft rejection and airway microvasculature: Is HIF-1 the missing link?"; J Clin Invest. Jun. 1, 2011; 121(6): 2155-2157.
Chmiel, et al; "The Role of Inflammation in the Pathophysiology of CF Lung Disease"; Clin Rev Allergy Immunol., 3(1):5-27 (2002).
Bondfield, T., et al; "Inflammatory Cytokines in Cystic Fibrosis Lungs"; Am J Respir Crit Care Med vol. 1S2. pp. 2111-2118, 1995.
Liaw, L., et al; "Altered Wound Healing in Mice Lacking a Functional Osteopontin Gene (spp1)"; J, Clin. Invest. vol. 101, No. 7, Apr. 1998, 1468-1478.
Naldini, A., et al; "Cutting Edge: IL-1 Mediates the Proangiogenic Activity of Osteopontin-Activated Human Monocytes1"; J Immunol 2006; 177:4267-4270.
Weber, G. F. and Cantor, H.; "Cytokine & Growth Factor Reviews"; Cytokine Growth Factor Reviews; vol. 7, Issue 3, Oct. 1996, pp. 241-248.
Satoh, M., et al; "Expression of cytokine genes and presence of enteroviral genomic RNA in endomyocardial biopsy tissues of myocarditis and dilated cardiomyopathy"; Virchows Arch (1996) 427:503-509.
Ebrahimi, B., et al; "Murine Gammaherpesvirus-68 Infection Causes Multi-Organ Fibrosis and Alters Leukocyte Trafficking in Interferon-γ Receptor Knockout Mice"; American Journal of Pathology, vol. 158, No. 6, 2117-2125, Jun. 2001.
Bousse-Kerdiles, M., et al; "Dual implication of fibrogenic cytokines in the pathogenesis of fibrosis and myeloproliferation in myeloid metaplasia with myelofibrosis"; Ann Hematol (1999) 78:437-444.
Demko, T., et al; "Obstructive nephropathy as a result of retroperitoneal fibrosis: a review of its pathogenesis and associations"; Journal of the American Society of Nephrology, 1996, 684-688.
Saxena, S., et al.; "Nephrogenic systemic fibrosis: an emerging entity"; Int. Urol. Nephrol. 40:715-724, 2008.
Steger-Hartmann, T., et al; "The involvement of pro-inflammatory cytokines in nephrogenic systemic fibrosis—A mechanistic hypothesis based on preclinical results from a rat model treated with gadodiamide"; Exper. Tox. Pathol. vol. 61, Issue 6, Nov. 2009, pp. 537-552.
Moshage, H.; "Cytokines and the hepatic acute phase response"; J. Pathol., 1997; 181:257-266.
Giannelli, G., et al; "Tissue remodelling in liver diseases"; Histol Histopathol (2003) 18: 1267-1274.
Strongin, A. Y., et al; "Plasma Membrane-dependent Activation of the 72-kDa Type IV Collagenase Is Prevented by Complex Formation with TIMP-2*"; Biol Chem. vol. 268, No. 19., 14033-14039,1993.

Fridman, R., et al; "Expression of human recombinant 72 kDa gelatinase and tissue inhibitor of metalloproteinase-2 (TIMP-2): characterization of complex and free enzyme"; Biochem. J. (1993) 289, 411-416.
Mormone, E., et al; "Molecular pathogenesis of hepatic fibrosis and current therapeutic approaches"; Chem. Biol. Interact.,vol. 193, Issue 3, Sep. 30, 2011, pp. 225-231.
Pellicoro et al.; "Reversibility of liver fibrosis"; Fibrogenesis & Tissue Repair 2012, 5(Suppl 1):S26.
Benyon, R. C. and Iredale, J. P.; "Is liver fibrosis reversible?"; Gut 2000; 46:443-446 (April).
Miller, A. M., et al; "Molecular Mechanisms of Alcoholic Liver Disease: Innate Immunity and Cytokines"; Alcoholism—Clinical and Experimental Research vol. 35, Issue 5, May 2011, pp. 787-793.
Anania, F. A., et al; "Activation by Acetaldehyde of the Promoter of the Mouse α2(I) Collagen Gene When Transfected into Rat Activated Stellate Cells"; Archives of Biochemistry and Biophysics, vol. 331, Issue 2, Jul. 15, 1996, pp. 187-193.
Weng, H.L., et al; "The Etiology of Liver Damage Imparts CytokinesTransforming Growth Factor 1 or Interleukin-13 as Driving Forces in Fibrogenesis"; Hepatology, vol. 50, No. 1, 230-243, 2009.
Greenwel, P. et al; "Hydrogen Peroxide: A Link Between Acetaldehyde-Elicited a1(I)Collagen Gene Up-regulation and Oxidative Stress in Mouse Hepatic Stellate Cells"; Hepatology Jan. 2000, 31(1):109-116.
Chen, A.; "Acetaldehyde stimulates the activation of latent transforming growth factor-b1 and induces expression of the type II receptor of the cytokine in rat cultured hepatic stellate cells"; Biochem. J. (2002) 368, 683-693.
Parola, M. and Robino, G.; Journal of Hepatology 35 (2001) 297-306.
Haorah, J., et al; "Mechanism of alcohol-induced oxidative stress and neuronal injury"; Free Radical Biology and Medicine, vol. 45, Issue 11, Dec. 1, 2008, pp. 1542-1550.
Cederbaum, A. I.; "Hepatoprotective effects of S-adenosyl-L-methionine against alcohol- and cytochrome P450 2E1-induced liver injury"; World J Gastroenterol Mar. 21, 2010; 16(11): 1366-1376.
Hui, L., et al; "p38α A Suppressor of Cell Proliferation and Tumorigenesis"; Cell Cycle, 2007; 6(20): 2429-2433.
Nakagawa, H. and Maeda, S.; "MolecularMechanisms of Liver Injury and Hepatocarcinogenesis: Focusing on the Role of Stress-ActivatedMAPK"; Pathology Research International, 2012; doi: 10.1155/2012/172894.
Hui, L., et al; "p38α suppresses normal and cancer cell proliferation by antagonizing the JNK—c-Jun pathway"; Nature Genetics 39(6), 741-749 (2007).
Hui, L., et al; "Proliferation of human HCC cells and chemically induced mouse liver cancers requires JNK1-dependent p21 downregulation"; J Clin Invest. 2008;118(12):3943-3953.
Sakurai T., et al; "Hepatocyte necrosis induced by oxidative stress and IL-1α release mediate carcinogen-induced compensatory proliferation and liver tumorigenesis"; Cancer Cell. Aug. 12, 2008; 14(2): 156-165.
Maeda, S.; "NF-κB, JNK, and TLR Signaling Pathways in Hepatocarcinogenesis"; Gastroenterology Research and Practice, vol. 2010 (2010); doi:10.1155/2010/367694.
Wagner, E. F. and Nebreda, A.R.; "Signal integration by JNK and p38 MAPK pathways in cancer development"; Nature Reviews Cancer, 2009; 9(8): 537-549.
Min, L., et al; "Mitogen-activated protein kinases in hepatocellular carcinoma development"; Seminars in Cancer Biology, vol. 21, Issue 1, Feb. 2011, pp. 10-20.
Goto, T., et al; "Mechanical stretch induces matrix metalloproteinase 1 production in human hepatic stellate cells"; Pathophysiology, vol. 11, Issue 3, Dec. 2004, pp. 153-158.
Iredale, J. P., et al; "Tissue inhibitor of metalloproteinase-I and interstitial collagenase expression in autoimmune chronic active hepatitis and activated human hepatic lipocytes"; Clinical Science (1995) 89, 75-81.

(56) References Cited

OTHER PUBLICATIONS

Benyon, R.C. and Arthur, M. J.; "Extracellular Matrix Degradation and the Role of Hepatic Stellate Cells"; Semin Liver Dis 2001; 21(3): 373-384.
Iredale, J. P., et als; "Tissue Inhibitor of Metalloproteinase-1 Messenger RNA Expression is Enhanced Relative to Interstitial Collagenase Messenger RNA in Experimental Liver Injury and Fibrosis"; Hepatology, 1996; 24(1): 176-184.
Murphy, F. R., et al; "Inhibition of Apoptosis of Activated Hepatic Stellate Cells by Tissue Inhibitor of Metalloproteinase-1 Is Mediated via Effects on Matrix Metalloproteinase Inhibition"; Journal of Biological Chemistry vol. 277, No. 13, Issue of Mar. 29, pp. 11069-11076, 2002.
Liu, Y.; "Renal fibrosis: New insights into the pathogenesis and therapeutics"; Kidney International (2006) 69, 213-217.
Schieppati, A., et al; "Chronic renal diseases as a public health problem: Epidemiology, social, and economic implications"; Kidney International, vol. 68, Supplement 98 (2005), pp. S7-S10.
Eddy, AA; "Molecular basis of renal fibrosis"; Pediatr Nephrol (2000) 15:290-301.
Iwano, M. and Neilson, EG; "Mechanisms of tubulointerstitial fibrosis"; Curr. Opin. Nephrol. Hypertens. 2004; 13:279-284.
Liu, Y.; "Epithelial to Mesenchymal Transition in Renal Fibrogenesis: Pathologic Significance, Molecular Mechanism, and Therapeutic Intervention"; J. Am. Soc. Nephrol. 2004; 15: 1-12.
Bottinger, EP and Bitzer, M.; "TGF-β Signaling in Renal Disease"; J Am Soc Nephrol 13: 2600-2610, 2002.
Schnaper_HW, et al; "TGF-signal transduction and mesangial cell fibrogenesis"; Am J Physiol Renal Physiol 284: F243-F252, 2003.
Yang, J., et al; "Downregulation of Smad Transcriptional Corepressors SnoN and Ski in the Fibrotic Kidney: An Amplification Mechanism for TGF-1 Signaling"; J Am Soc Nephrol 14: 3167-3177, 2003.
Yang, J.; "Disruption of tissue-type plasminogen activator gene in mice reduces renal interstitial fibrosis in obstructive nephropathy"; J. Clin. Invest. 110:1525-1538 (2002).
Edgtton, KL, et al; "Plasmin is not protective in experimental renal interstitial fibrosis1"; Kidney International, vol. 66 (2004), pp. 68-76.
Cheng, S. and Lovett, DH; "Gelatinase A (MMP-2) Is Necessary and Sufficient for Renal Tubular Cell Epithelial-Mesenchymal Transformation"; American Journal of Pathology, vol. 162, No. 6, 1937-1949, Jun. 2003.
Radisky, DC, et al; "Rac1b and reactive oxygen species mediate MMP-3-induced EMT and genomic instability"; Nature. Jul. 7, 2005; 436(7047): 123-127.
Naughton, C.A., "Drug-Induced Nephrotoxicity"; American Family Physician, vol. 78, No. 6, pp. 743-750, 2008.
Cassidy, H., et al; "The Role of MAPK in Drug-Induced Kidney Injury"; Journal of Signal Transduction, vol. 2012, Article ID 463617, 15 pages.
Volpini, R.A.; "Increased expression of p38 mitogenactivated protein kinase is related to the acute renal lesions induced by gentamicin"; Brazilian Journal of Medical and Biological Research (2006) 39: 817-823.
Ozbek, E., et al; "Atorvastatin Prevents Gentamicin-Induced Renal Damage in Rats through the Inhibition of p38-MAPK and NF-kB Pathways"; Renal Failure, 31:382-392, 2009.
Sutherland, B.W., et al; "Akt phosphorylates the Y-box binding protein 1 at Ser102 located in the cold shock domain and affects the anchorage-independent growth of breast cancer cells"; Oncogene (2005) 24, 4281-4292.
Shihab, F.S., et al; "Sodium depletion enhances fibrosis and the expression of TGF-β1 and matrix proteins in experimental chronic cyclosporine nephropathy"; American Journal of Kidney Diseases vol. 30, Issue 1, Jul. 1997, pp. 71-81.
Ignotz, R.A. and Massague, J.; "Transforming growth factor-beta stimulates the expression of fibronectin and collagen and their incorporation into the extracellular matrix"; Journal of Biological Chemistry, vol. 261, No. 9, pp. 4337-4345, 1986.

Lu, Z.H., et al; "YB-1 Is Important for Late-Stage Embryonic Development, Optimal Cellular Stress Responses, and the Prevention of Premature Senescence"; Molecular and Cellular Biology, vol. 25, No. 11, pp. 4625-4637, 2005.
Fraser, D.J., et al; "Y-box protein-1 controls transforming growth factor-β1 translation in proximal tubular cells"; Kidney International, vol. 73, No. 6, pp. 724-732, 2008.
Hanssen, L., et al; "Y-Box Binding Protein-1 Mediates Profibrotic Effects of Calcineurin Inhibitors in the Kidney"; Journal of Immunology, vol. 187, No. 1, pp. 298-308, 2011.
Vogelzang, N.J., "Nephrotoxicity from chemotherapy: prevention and management"; Oncology, vol. 5, No. 10, pp. 97-105, 1991.
Arany, I., et al; "Cisplatin-induced cell death is EGFR/src/ERK signaling dependent in mouse proximal tubule cells"; Am J Physiol Renal Physiol 287: F543-F549, 2004.
Ramesh, G. and Reeves, W. B.; "p38 MAP kinase inhibition ameliorates cisplatin nephrotoxicity in mice"; Am J Physiol Renal Physiol 289: F166-F174, 2005.
Francescato, H.D.C., et al; "Treatment with a p38 MAPK inhibitor attenuates cisplatin nephrotoxicity starting after the beginning of renal damage"; Life Sciences, vol. 84, Issues 17-18, Apr. 24, 2009, pp. 590-597.
Francescato, H.D.C., et al; "Effect of JNK inhibition on cisplatin-induced renal damage"; Nephrol Dial Transplant (2007) 22: 2138-2148.
Sakurai, T., et al; "Loss of hepatic NF-B activity enhances chemical hepatocarcinogenesis through sustained c-Jun N-terminal kinase 1 activation"; PNAS, 2006; 103(28):10544-10551.
Hirschberg, R.J.; "Wound Healing in the Kidney: Complex Interactions in Renal Interstitial Fibrogenesis"; J. Am. Soc. Nephrol. 2005; 16: 9-11.
Pabla, N., et al; "Inhibition of PKCσ reduces cisplatin-induced nephrotoxicity without blocking chemotherapeutic efficacy in mouse models of cancer"; Journal of Clinical Investigation, vol. 121, No. 7, pp. 2709-2722, 2011.
Perazella, M. A. and Tray, K.,; "Selective Cyclooxygenase-2 Inhibitors: A Pattern of Nephrotoxicity Similar to Traditional Nonsteroidal Anti-inflammatory Drugs"; American Journal of Medicine, vol. 111, No. 1, pp. 64-67, 2001.
Ejaz, P., et al; "NSAIDs and Kidney"; Journal of Association of Physicians of India, vol. 52, pp. 632-640, 2004.
Schrier, R.W. and Henrich, W.L.; "Nonsteroidal Anti-inflammatory Drugs Caution Still Indicated"; Journal of the American Medical Association, vol. 251, No. 10, pp. 1301-1302, 1984.
Hou, C.C., et al; "Celecoxib Induces Heme-Oxygenase Expression in Glomerular Mesangial Cells"; Annals of the New York Academy of Sciences, vol. 1042, pp. 235-245, 2005.
Lan, T-H et al; "Vascular fibrosis in atherosclerosis"; Cardiovascular Pathology 22 (2013) 401-407.
Sun Y., "The Renin-Angiotensin-Aldosterone System and Vascular Remodeling"; Congest. Heart Fail. 2002;8:11-6.
Ruiz-Ortega, M. et al; "Role of the Renin-Angiotensin System in Vascular Diseases Expanding the Field"; Hypertension 2001;38:1382-7.
Hunyady; L. and Catt, KJ; "Pleiotropic AT1 Receptor Signaling Pathways Mediating Physiological and Pathogenic Actions of Angiotensin II"; Mol Endocrinol 2006;20: 953-70.
Suzuki, H., et al: "Recent Progress in Signal Transduction Research of the Angiotensin II Type-1 Receptor: Protein Kinases, Vascular Dysfunction and Structural Requirement"; Curr Med Chem Cardiovasc Hematol Agents 2005;3:305-22.
Eguchi, S. et al; "Calcium-dependent Epidermal Growth Factor Receptor Transactivation Mediates the Angiotensin II-induced Mitogen-activated Protein Kinase Activation in Vascular Smooth Muscle Cells"; J Biol Chem 1998;273:8890-6.
Ushio-Fukai, M., et al "Epidermal Growth Factor Receptor Transactivation by Angiotensin II Requires Reactive Oxygen Species in Vascular Smooth Muscle Cells"; Arterioscler Thromb Vasc Biol 2001;21:489-95.
Heeneman, S., et al; "Angiotensin II Induces Transactivation of Two Different Populations of the Platelet-derived Growth Factor b Receptor"; J Biol Chem 2000;275: 15926-32.

(56) References Cited

OTHER PUBLICATIONS

Folli, F., et al: "Angiotensin II Inhibits Insulin Signaling in Aortic Smooth Muscle Cells at Multiple Levels"; J Clin Invest 1997;100: 2158-69.
Natarajan, R., et al; "Angiotensin II Signaling in Vascular Smooth Muscle Cells Under High Glucose Conditions"; Hypertension 1999;33:378-84.
Border, WA and Noble, NA; "Interactions of Transforming Growth Factor-β and Angiotensin II in Renal Fibrosis"; Hypertension 1998;31:181-8.
Wolf, G.; "Renal injury due to renin-angiotensin-aldosterone system activation of the transforming growth factor-b pathway"; Kidney Int 2006;70:1914-9.
Rodriguez-Vita, J., et al; "Angiotensin II Activates the Smad Pathway in Vascular Smooth Muscle Cells by a Transforming Growth Factor-Independent Mechanism"; Circulation 2005;111:2509-17.
Yang, F., et al; "Angiotensin II Induces Connective Tissue Growth Factor and Collagen I Expression via Transforming Growth Factor-Dependent and -Independent Smad Pathways The Role of Smad3"; Hypertension 2009; 54:877-84.
Brilla, CG, et al; "Collagen Metabolism in Cultured Adult Rat Cardiac Fibroblasts: Response to Angiotensin II and Aldosterone"; J Mol Cell Cardiol 1994;26:809-20.
Epstein, M.; "Aldosterone receptor blockade and the role of eplerenone: evolving perspectives"; Nephrol Dial Transplant 2003;18:1984-92.
Brown, NJ, et al; "Aldosterone modulates plasminogen activator inhibitor-1 and glomerulosclerosis in vivo"; Kidney International, vol. 58 (2000), pp. 1219-1227.
Lee, YS., etr al; "Aldosterone Upregulates Connective Tissue Growth Factor Gene Expression via p38 MAPK Pathway and Mineralocorticoid Receptor in Ventricular Myocytes"; J Korean Med Sci 2004; 19: 805-11.
Rude, MK, et al; "Aldosterone Stimulates Matrix Metalloproteinases and Reactive Oxygen Species in Adult Rat Ventricular Cardiomyocytes"; Hypertension 2005;46:555-61.
Massague, J., et al; "TGFβ Signaling in Growth Control, Cancer, and Heritable Disorders"; Cell, vol. 103, 295-309, Oct. 13, 2000.
Derynck, R., et al; "TGF-β signaling in tumor suppression and cancer progression"; Nat Genet 2001;29:117-2.
Derynck, R. and Feng, XH; TGF-b receptor signaling; Biochim Biophys Acta 1997;1333:F105-50.
Massague, J., et al; "Smad transcription factors"; Genes and Development, 19:2783-2810, 2005.
Singh, NN abd Ramji, DP; "The role of transforming growth factor-β in atherosclerosis"; Cytokine Growth Factor Rev 2006;17:487-99.
Nakao, A., et al; "Smad7: a new key player in TGF-β-associated"; Trends Mol Med 2002;8: 361-3.
Wang, M., et al; "Matrix Metalloproteinase 2 Activation of Transforming Growth Factor-1 (TGF-1) and TGF-1—Type II Receptor Signaling Within the Aged Arterial Wall"; Arterioscler Thromb Vasc Biol 2006;26:1503-9.
Ikedo, H., et al; "Smad protein and TGF-β signaling in vascular smooth muscle cells"; Int J Mol Med 2003;11: 645-50.
Ruiz-Ortega, M., et al; "TGF-β signaling in vascular fibrosis"; Cardiovascular Research 74 (2007) 196-206.
Bobik, A.; "Transforming Growth Factor-s and Vascular Disorders"; Arterioscler Thromb Vasc Biol 2006;26: 1712-20.
Zhang, F., et al; "Transforming Growth Factor—Promotes Recruitment of Bone Marrow Cells and Bone Marrow-derived Mesenchymal Stem Cells through Stimulation of MCP-1 Production in Vascular Smooth Muscle Cells*"; J Biol Chem 2009;284:17564-74.
Perbal, B.; "CCN proteins: multifunctional signalling regulators"; Lancet 2004; 363: 62-64.
Hayashida, T., et al; "Cross-talk between ERK MAP kinase and Smad signaling pathways enhances TGF-β-dependent responses in human mesangial cells"; FASEB J 2003;17:1576-8.

Samarakoon, R., et al; "Plasminogen activator inhibitor type-1 gene expression and induced migration in TGF-β1-stimulated smooth muscle cells is pp60c-src/MEK-dependent"; J Cell Physiol 2005;204:236-46.
Seay, U. et al; "Transforming Growth Factor-Dependent Growth Inhibition in Primary Vascular Smooth Muscle Cells Is p38-Dependent"; J Pharmacol Exp Ther 2005;315:1005-12.
Ruiz-Ortega, M., et al; "Molecular mechanisms of angiotensin II-induced vascular injury"; Curr Hypertens Rep 2003;5:73-79.
Bataller, R., et al; "Liver fibrosis"; Journal of Clinical Investigation, vol. 115 No. 2, 209-218, Feb. 2005.
Custer, B., et al, "Global Epidemiology of Hepatitis B Virus"; J. Clinical Gastroenterol. vol. 38—Issue 10—pp. S158-S168 2004.
Das, K., et al.; "Nonobese Population in a Developing Country Has a High Prevalence of Nonalcoholic Fatty Liver and Significant Liver Disease"; Hepatology, 2010; 51(5):1593-1602.
Lim, Y.S., et al; "Susceptibility to type 1 autoimmune hepatitis is associated with shared amino acid sequences at positions 70-74 of the HLA-DRB1 molecule"; J. Hepatology, 2008; 48(1):133-139.
Andersson, K.L. and Chung, R.T.; "Hepatic schistosomiasis"; Curr. Treat. Options Gastroenterol., 2007; 10(6):504-512.
Lefkowitch, J. H.; "Hepatobiliary pathology"; Current Opinion in Gastroenterology: May 2006—vol. 22—Issue 3, p. 198-208.
Sikorska, K., et al; "Pathogenesis and clinical consequences of iron overload in chronic hepatitis C—impact of host and viral factors related to iron metabolism"; J. Biotech., Computational Bio. and Bionanotech., 2011; 92(1): 54-65.
Zhang, S., et al; "Rescue of ATP7B function in hepatocyte-like cells from Wilson's disease induced pluripotent stem cells using gene therapy or the chaperone drug curcumin"; Human Molecular Genetics, 2011, vol. 20, No. 16 3176-3187.
Fanni, D., et al; "Effects of Iron and Copper Overload on the Human Liver: An Ultrastructural Study"; Curr. Med. Chem., 2014; DOI: 10.2174/0929867321666140601163244.
George J, et al.; "siRNA-mediated knockdown of connective tissue growth factor prevents N nitrosodimethylamineinduced hepatic fibrosis in rats"; Gene Therapy, 2007; 14(10): 790-803.
Domoenicali, M., et al; "A novel model of CCl4-induced cirrhosis with ascites in the mouse"; Journal of Hepatology vol. 51, Issue 6, Dec. 2009, pp. 991-999.
Salguero, P R, et al.,"Activation of hepatic stellate cells is associated with cytokine expression in thioacetamide-induced hepatic fibrosis in mice"; Lab. Invest. 2008; 88(11): 1192-1203.
Friedman, S.L.; "Mechanisms of Hepatic Fibrogenesis"; Gastroenterology, 2008; 134(6): 1655-1669.
Gressner, A M,; "Transdifferentiation of hepatic stellate cells (Ito cells) to myofibroblasts: A key event in hepatic fibrogenesis"; Kidney International, 1996; 49: S39-S45.
Nieto, N., et al; "Cytochrome P450 2E1-derived Reactive Oxygen Species Mediate Paracrine Stimulation of Collagen I Protein Synthesis by Hepatic Stellate Cells*"; J. Biol. Chem. 2002; 277(12): 9853-986.
Nieto, N.; "Oxidative-Stress and IL-6 Mediate the Fibrogenic Effects of Rodent Kupffer Cells on Stellate Cells"; Hepatology, 2006; 44(6): 1487-1501.
Tsukamoto, H.; "Cytokine Regulation of Hepatic Stellate Cells in Liver Fibrosis"; Alcoholism—Clinical and Experimental Research, 1992; 23(5): 911-916.
Cubero, F. J. and Nieto, N.; "Ethanol and arachidonic acid synergize to activate Kupffer cells and modulate the fibrogenic response via tumor necrosis factor α, reduced glutathione, and transforming growth factor β-dependent mechanisms"; Hepatology, 2008; 48(6): 2027-2039.
Tuchweber, B., et al; "Proliferation and phenotypic modulation of portal fibroblasts in the early stages of cholestatic fibrosis in the rat"; Laboratory Investigation, 1996; 74(1): 265-278.
Li, Z., et al; "Transforming growth factor-β and substrate stiffness regulate portal fibroblast activation in culture"; Hepatology, 2007; 46(4): 1246-1256.
Desmouliere A , et al; "Extracellular matrix deposition, lysyl oxidase expression, and myofibroblastic differentiation during the initial stages of cholestatic fibrosis in the rat"; Lab Invest, 1997; 76(6): 765-778).

(56) References Cited

OTHER PUBLICATIONS

Chang, Y J., et al; "Mesenchymal stem cells facilitate recovery from chemically induced liver damage and decrease liver fibrosis"; Life Sci. vol. 85, Issues 13-14, Sep. 23, 2009, pp. 517-525.
Higashiyama, R. et al; "Bone Marrow-Derived Cells Express Matrix Metalloproteinases and Contribute to Regression of Liver Fibrosis in Mice"; Hepatology, 2007; 45(1): 213-222.
Bird, T.G.; et al; "Activation of stem cells in hepatic diseases"; Cell Tissue Res., 2008; 331(1): 283-300.
Forbes, S. J. et al; "A significant proportion of myofibroblasts are of bone marrow origin in human liver fibrosis"; , Gastroenterology, 2004; 126(4): 955-963.
Dooley, S., et al ; "Hepatocyte-Specific Smad7 Expression Attenuates TGF-β-Mediated Fibrogenesis and Protects Against Liver Damage"; Gastroenterology; vol. 135, Issue 2, Aug. 2008, pp. 642-659.
Zeisberg, M., et al; "Fibroblasts Derive from Hepatocytes in Liver Fibrosis via Epithelial to Mesenchymal Transition*"; J. Biol. Chem., 2007; 282(32): 23337-23347.
Kaimori, A., et al; "Transforming Growth Factor-1 Induces an Epithelial-to-Mesenchymal Transition State in Mouse Hepatocytes in Vitro*"; J. Biol. Chem., 2007; 282(30): 22089-22101.
Robertson, H., et al; "Biliary epithelial-mesenchymal transition in posttransplantation recurrence of primary biliary cirrhosi"; Hepatology, 2007; 45(4): 977-981.
Rygiel, K.A.; "Epithelial-mesenchymal transition contributes to portal tract fibrogenesis during human chronic liver disease"; Lab. Invest., 2008; 88(2): 112-123.
Bucala, R., et al; "Circulating Fibrocytes Define a New Leukocyte Subpopulation That Mediates Tissue Repair"; Mol. Med. 1994; 1(1): 71-81.
Moore, B.B., et al; "CCR2-Mediated Recruitment of Fibrocytes to the Alveolar Space after Fibrotic Injury"; Am . J. Pathol., 2005:166(3): 675-684.
Roderfeld, M., et al.; "Bone Marrow Transplantation Demonstrates Medullar Origin of CD34 Fibrocytes and Ameliorates Hepatic Fibrosis in Abcb4/ Mice"; Hepatology, 2010; 51(1): 267-276.
Zeisberg, M., et al; "De-differentiation of primary human hepatocytes depends on the composition of specialized liver basement membrane"; Mol. Cell Biochem., 2006; 283(1-2): 181-189.
George, J., et al; "Expression of hyaluronic acid in N-nitrosodimethylamine induced hepatic fibrosis in rats"; The International Journal of Biochemistry & Cell Biology, vol. 36, Issue 2, Feb. 2004, pp. 307-319.
Hernandez-Gea, V. and Friedman, S. L.; "Pathogenesis of Liver Fibrosis"; Annual Review of Pathology: Mechanisms of Disease 2011 6:1, 425-456.
Tilg, H. and Hotamisligil, G. S.; "Nonalcoholic Fatty Liver Disease: Cytokine-Adipokine Interplay and Regulation of Insulin Resistance"; Gastroenterology, 2006; 131(3): 934-945.
De Minicis, S., et al; "NADPH Oxidase in the Liver: Defensive, Offensive, or Fibrogenic?"; Gastroenterology 2006;131:272-275.
George, J.; "Ascorbic acid concentrations in dimethylnitrosamine-induced hepatic fibrosis in rats"; Clinica Chimica Acta, vol. 335, Issues 1-2, Sep. 2003, pp. 39-47.
Tormos, A. M., et al; "Liver-Specific p38a Deficiency Causes Reduced Cell Growth and Cytokinesis Failure During Chronic Biliary Cirrhosis in Mice"; Hepatology, 2013; 57(5): 1950-1961.
Feder, J N, et al: "The discovery of the new haemochromatosis gene"; Hepatol_38_2003.
Nitta, T, et al; "Murine Cirrhosis Induces Hepatocyte EpithelialMesenchymal Transition and Alterations in SurvivalSignaling Pathways"; Hepatology, 48(3):909-919; 2008.
Higgins and Sharp; "CLUSTAL: A package for performing multiple sequence alignment on a microcompute"; Gene 73:237-244 (1988).
Higgins and Sharp; "Fast and sensitive multiple sequence alignments on a microcomputer."; CABIOS 5:151-153 (1989).
Corpet, et al; Multiple Sequence Alignment with Hierarchical Cluster; Nucleic Acids Research 16:10881-90 (1988).
Huang, X., et al; "Parallelization of a Local Similarity Algorithm," Computer Applications in The Biosciences, 8, 155-165, 1992.
Pearson W.R. (1994) Using the FASTA Program to Search Protein and DNA Sequence Databases. In: Griffin A.M., Griffin H.G. (eds) Computer Analysis of Sequence Data. Methods in Molecular Biology, vol. 24. Humana Press.
Altschul, P., et al; "Gapped BLAST and PSI-BLAST: a new generation of protein database search programs"; Nucleic Acids Res. 25:3389-3402 (1997).
Henikoff & Henikoff; "Amino acid substitution matrices from protein blocks"; Proc. Natl. Acad. Sci. USA vol. 89, pp. 10915-10919, Nov. 1992.
Karlin & Altschul; "Applications and statistics for multiple high-scoring segments in molecular sequences"; Proc. Natl. Acad. Sci. USA, vol. 90, pp. 5873-5877, Jun. 1993.
Wootton, J. and Federhen, S.; "Statistics of Local Complexity in Amino Acid Sequences and Sequence Databases"; Comput. Chem., 17:149-163 (1993).
Claverie and States; "Information Enhancement Methods for Large Scale Sequence Analysis"; Comput. Chem., 17:191-201 (1993).
Meyers and Miller; "Optimal alignments in linear space"; Computer Applic. Biol. Sci., 4:11-17 (1988).
Merrifield, R. B.; "Solid Phase Peptide Synthesis. I. The Synthesis of a Tetrapeptide"; 1963, J. Am. Chem. Soc. 85:2149-2154.
Carpino, L. and Han, G.; "The 9-Fluorenylmethoxycarbonyl Amino-Protecting Group"; J . Org. Chem., vol. 37, No. 62, 3404-3409; 1976.
Fields and Noble; "Solid phase peptide synthesis utilizing 9-fluorenylmethoxycarbonyl amino acids"; Int. J. Pept. Protein Res. 35:161-214, 1990.
Neuman, R. and Logan, M.; "The determination of collagen and elastin in tissues"; J Biol Chem. Oct. 1950;186(2):549-56.
Liu, et al; "Lack of MK2 Inhibits Myofibroblast Formation and Exacerbates Pulmonary Fibrosis"; Am J Respir Cell Mol Biol, 37: 507-517, 2007.
Wilson M. et al; "Bleomycin and IL-1+-mediated pulmonary fibrosis is IL-17A dependent"; The Journal of Experimental Medicine, 207(3): 535-552, 2010.
Wilkes, D., et al; "Instillation of allogeneic lung macrophages and dendritic cells cause differential effects on local IFN-g production, lymphocytic bronchitis, and vasculitis in recipient murine lungs"; Journal of Leukocyte Biology, 64(5):578-586, 1998.
Pottier, N., et al; "Relationships between Early Inflammatory Response to Bleomycin and Sensitivity to Lung Fibrosis"; American Journal of Respiratory and Critical Care Medicine, 176(11): 1098-1107, 2007.
Horowitz, J. and Thannickal, V.; "Idiopathic pulmonary fibrosis : new concepts in pathogenesis and implications for drug therapy"; Treatments in Respiratory Medicine, 5(5):325-42, 2006.
Tomasek, J., et al; "Myofibroblasts and mechano-regulation of connective tissue remodelling"; Nature Reviews Molecular Cell Biology, 3(5): 349-63, 2002.
Yamashita, C, et al; "Matrix Metalloproteinase 3 is a Mediator of Pulmonary Fibrosis"; The American Journal of Pathology, 179(4): 1733-45, 2011.
Liedtke, C., et al; "Experimental liver fibrosis research: update on animal models, legal issues and translational aspects"; Fibrogenesis & Tissue Repair, 2013; 6:19.
Heindryckx, F., et al; "Experimental mouse models for hepatocellular carcinoma research"; Int. J. Exp. Pathol., 2009; 90: 367-386.
Iredale, J P, et al; "Mechanisms of spontaneous resolution of rat liver fibrosis. Hepatic stellate cell apoptosis and reduced hepatic expression of metalloproteinase inhibitors"; J. Clin. Invest., 1998; 102: 538-549.
Kisseleva, T, et al; "Myofibroblasts revert to an inactive phenotype during regression of liver fibrosis"; PNAS, 2012; 109: 9448-9453.
Salazar-Montes, et al; "Potent antioxidant role of Pirfenidone in experimental cirrhosis"; European Journal of Pharmacology, 2008; 595(1-3): 69-77.
Salgado, et al; "Liver Cirrhosis is Reverted by Urokinase-Type Plasminogen Activator Gene Therapy"; Molecular Therapy, 2000; 2: 545-551.

(56) References Cited

OTHER PUBLICATIONS

Bascands, J-L and Schanstra, J P.; "Obstructive nephropathy: Insights from genetically engineered animals"; Kidney Int. 2005; 68(3): 925-937.
Yamashita, et al; "Activin A is a Potent Activator of Renal Interstitial Fibroblasts"; Journal of the American Society of Nephrology 2004; 15(1): 91-101.
Derynck, R. and Zhang, YE; "Smad-dependent and Smad-independent pathways in TGF-β family signalling"; Nature 2003;425:577-84.
Ruperez, M., et al "Connective Tissue Growth Factor is a Mediator of Angiotensin II-Induced Fibrosis"; Circulation 2003;108:1499-505.
Leask, A., et al; "Connective tissue growth factor: A new and important player in the pathogenesis of fibrosis"; Curr Rheumatol Rep 2002;4: 136-42.
Lau, LF and Lam, SC; "The CCN Family of Angiogenic Regulators: The Integrin Connection" SC, Exp Cell Res 1999;248: 44-57.
Leask, A. et al; "Connective Tissue Growth Factor Gene Regulation"; J Biol Chem 2003;278: 13008-15.
Leask, A. and Abraham, DJ; "The role of connective tissue growth factor, a multifunctional matricellular protein, in fibroblast biology"; Biochem Cell Biol 2003;81: 355-63.
Fan, WH. and Karnovsky, MJ; "Increased MMP-2 Expression in Connective Tissue Growth Factor Over-expression Vascular Smooth Muscle Cells*"; J Biol Chem 2002;277: 9800-5.
Crean, JK, et al: "The Role of p42/44 MAPK and Protein Kinase B in Connective Tissue Growth Factor Induced Extracellular Matrix Protein Production, Cell Migration, and Actin Cytoskeletal Rearrangementin Human Mesangial Cells*"; J Biol Chem 2002;277:44187-94.
Chung, K.; "Cytokines in chronic obstructive pulmonary disease"; Eur Respir J., 2001, 18:Supp. 34:50-59.
Amalinei, C., et al; "Matrix metalloproteinases involvement in pathologic conditions"; Rom J Morphol Embryol 2010;51: 215-28.
Galis, ZS and Khatri, JJ; "Matrix Metalloproteinases in Vascular Remodeling and Atherogenesis The Good, the Bad, and the Ugly"; Circ Res 2002;90: 251-62.
Mauviel, A.; "Cytokine regulation of metalloproteinase gene expression"; J Cell Biochem 1993;53: 288-95.
Nagase, H., et al; "Structure and function of matrix metalloproteinases and TIMPs"; Cardiovasc Res 2006;69: 562-73.
Wei, J., et al; "Peroxisome proliferator-activated receptor γ: innate protection from excessive fibrogenesis and potential therapeutic target in systemic sclerosis"; Curr Opin Rheumatol 2010;22: 671-6.
Ghosh, AK, et al; "Disruption of Transforming Growth Factor Signaling and Profibrotic Responses in Normal Skin Fibroblasts by Peroxisome Proliferator-Activated Receptor"; Arthritis Rheum 2004;50: 1305-18.
Burgess, HA, et al; "PPAR agonists inhibit TGF-induced pulmonary myofibroblast differentiation and collagen production: implications for therapy of lung fibrosis"; Am J Physiol Lung Cell Mol Physiol 2005;288: L1146-53.
Ghosh, AH, et al; "Peroxisome proliferator-activated receptor-abrogates Smad-dependent collagen stimulation by targeting the p300 transcriptional coactivator"; FASEB J 2009;23: 2968-77.
Datta, et al; "Novel therapeutic approaches for pulmonary fibrosis"; British Journal of Pharmacology, 163: 141-172, 2011.
Shiratori, Y., et al; "Histologic Improvement of Fibrosis in Patients with Hepatitis C Who Have Sustained Response to Interferon Therapy"; Ann. Intern. Med. 2000; 132(7): 517-524.

Brenner, D.A., and Alcorn, J.M.; "Therapy for Hepatic Fibrosis"; Semin. Liver Dis. 1990; 10(1): 75-83.
Takase, S., et al; "Effects of malotilate treatment on the serum markers of hepatic fibrogenesis in liver cirrhosis"; Gastroenterol. Jpn., 1988; 23(6): 639-645.
Fu, Y. M., e tal; "Curcumin Protects the Rat Liver from CCl4-Caused Injury and Fibrogenesis by Attenuating Oxidative Stress and Suppressing Inflammation"; Mol. Pharm., 2008; 3(2): 399-409.
George, J., et al; "Efficacy of Silymarin and Curcumin on Dimethyl Nitrosamine Induced Liver Fibrosis in Rats"; Biomedicine, 2006; 26(3-4): 18-26.
Keatings, V., et al; "Differences in interleukin-8 and tumor necrosis factor-alpha in induced sputum from patients with chronic obstructive pulmonary disease or asthma"; Am J Resp Crit Care Med, 1996, 153:530-534.
Lim, S. et al; Balance of Matrix Metalloprotease-9 and Tissue Inhibitor of Metalloprotease-1 from Alveolar Macrophages in Cigarette Smokers; Am J Respir Crit Care Med, vol. 162, pp. 1355-1360, 2000.
Richards, T., et al; "Peripheral Blood Biomarkers Predict Disease Progression and Mortality in IPF"; Am J Respir Crit Care Med, 181: A1120, 2010.
Moodley, Y, et al; "Inverse Effects of Interleukin-6 on Apoptosis of Fibroblasts from Pulmonary Fibrosis and Normal Lungs"; Am J Respir Cell Mol Biol., 29(4): 490-498, 2003.
El-Sayed, A., et al; "Delivery of Macromolecules Using Arginine-Rich Cell-Penetrating Peptides: Ways to Overcome Endosomal Entrapment"; AAPS J. 11, 13-22, 2009.
Wender, P., et al; "The design of guanidinium-rich transporters and their internalization mechanisms"; Adv. Drug Deliv. Rev. 60, 452-472, 2008.
Lopes, L., et al; Inhibition of HSP27 Phosphorylation by a Cell-permeant MAPKAP Kinase 2 Inhibitor; Biochem Biophys Res Commun., 382(3):535-9, 2009.
Horowitz, J., et al; "Epithelial—Mesenchymal Interactions in Pulmonary Fibrosis"; Semin Respir Crit Care Med., 27(6):600-612, 2006.
Johansen, C., et al; "Protein Expression of TNF—in Psoriatic Skin Is Regulated at a Posttranscriptional Level by MAPK-Activated Protein Kinase 21"; J Immunol., 176(3):1431-8, 2006.
Rousseau, S., et al; "Inhibition of SAPK2a/p38 prevents hnRNP A0 phosphorylation by MAPKAP-K2 and its interaction with cytokine mRNAs";The EMBO Journal (2002) 21, 6505-6514.
Ward, B., et al; "Peptide Inhibitors of MK2 Show Promise for Inhibition of Abdominal Adhesions"; J Surg Res. Jul. 2011 ; 169(1): e27-e36.
Veevers-Lowe, J., et al; "Mesenchymal stem cell migration is regulated by fibronectin through a5b1-integrin mediated activation of PDGFR-b and potentiation of growth factor signals"; J Cell Sci, 124: 1288-1300, 2011.
Cho, M.H.; "Renal fibrosis"; Korean J. Pediatr. 2010; 53(7): 735-740.
Smith, TF and Waterman, MS; "Comparison of biosequences"; Adv. Appl. Math. 2:482 (1981).
Needleman, S. and Wunsch, C; "A General Method Applicable to the Search for Similarities in the Amino Acid Sequence of Two Proteins"; J. Mol. Biol. 48:443.
Pearson, W. and Lipman, D.; "Improved tools for biological sequence comparison"; Proc. Natl. Acad. Sci. 85:2444.
Osinusi A. et al. "Efficacy of Sofosbuvir and Ribavirin for treatment of Hepatitis C Genotype-1 in an Inner City Population: Virus and Host Factors that Predict Relapse: A Randomized Controlled Trial", JAMA, vol. 310, No. 8, p. 804-11 (2013).

* cited by examiner

NEAT SPRAY DRIED INSULIN

FIG. 4

FLOW-RATE INDEPENDENCE

FINE PARTICLE DOSE

☐ FPD < 4.7 μm

▨ FPD < 3.3 μm

*SPRAY-DRIED NEAT PEPTIDE 250 mcg*

FIGURE 5

Activated MK2 Differentially Expressed in Human IPF vs. Normal Lung

MMI-0100 Dose-Response Data in Idiopathic Pulmonary Fibrosis
Prevention Model

Reduced Activated MK2 with MMI-0100 in IPF Treatment Model

50 µg/kg      50 µg/kg

SEQUENCE LISTING

```
<160> NUMBER OF SEQ ID NOS: 29

<210> SEQ ID NO 1
<211> LENGTH: 22
<212> TYPE: PRT
<213> ORGANISM: Unknown
<220> FEATURE:
<223> OTHER INFORMATION: Mammalian

<400> SEQUENCE: 1

Tyr Ala Arg Ala Ala Ala Arg Gln Ala Arg Ala Lys Ala Leu Ala Arg
1               5                   10                  15

Gln Leu Gly Val Ala Ala
            20

<210> SEQ ID NO 2
<211> LENGTH: 11
<212> TYPE: PRT
<213> ORGANISM: Unknown
<220> FEATURE:
<223> OTHER INFORMATION: Mammalian

<400> SEQUENCE: 2
```

```
Lys Ala Leu Ala Arg Gln Leu Gly Val Ala Ala
1               5                   10

<210> SEQ ID NO 3
<211> LENGTH: 21
<212> TYPE: PRT
<213> ORGANISM: Unknown
<220> FEATURE:
<223> OTHER INFORMATION: Mammalian

<400> SEQUENCE: 3

Phe Ala Lys Leu Ala Ala Arg Leu Tyr Arg Lys Ala Leu Ala Arg Gln
1               5                   10                  15

Leu Gly Val Ala Ala
            20

<210> SEQ ID NO 4
<211> LENGTH: 23
<212> TYPE: PRT
<213> ORGANISM: Unknown
<220> FEATURE:
<223> OTHER INFORMATION: Mammalian

<400> SEQUENCE: 4

Lys Ala Phe Ala Lys Leu Ala Ala Arg Leu Tyr Arg Lys Ala Leu Ala
1               5                   10                  15

Arg Gln Leu Gly Val Ala Ala
            20

<210> SEQ ID NO 5
<211> LENGTH: 21
<212> TYPE: PRT
<213> ORGANISM: Unknown
<220> FEATURE:
<223> OTHER INFORMATION: Mammalian

<400> SEQUENCE: 5

Tyr Ala Arg Ala Ala Ala Arg Gln Ala Arg Ala Lys Ala Leu Ala Arg
1               5                   10                  15

Gln Leu Ala Val Ala
            20

<210> SEQ ID NO 6
<211> LENGTH: 21
<212> TYPE: PRT
<213> ORGANISM: Unknown
<220> FEATURE:
<223> OTHER INFORMATION: Mammalian

<400> SEQUENCE: 6

Tyr Ala Arg Ala Ala Ala Arg Gln Ala Arg Ala Lys Ala Leu Ala Arg
1               5                   10                  15

Gln Leu Gly Val Ala
            20

<210> SEQ ID NO 7
<211> LENGTH: 22
<212> TYPE: PRT
<213> ORGANISM: Unknown
<220> FEATURE:
<223> OTHER INFORMATION: Mammalian

<400> SEQUENCE: 7

His Arg Arg Ile Lys Ala Trp Leu Lys Lys Ile Lys Ala Leu Ala Arg
```

```
1               5                  10                 15

Gln Leu Gly Val Ala Ala
            20

<210> SEQ ID NO 8
<211> LENGTH: 10
<212> TYPE: PRT
<213> ORGANISM: Unknown
<220> FEATURE:
<223> OTHER INFORMATION: Mammalian

<400> SEQUENCE: 8

Lys Ala Leu Ala Arg Gln Leu Ala Val Ala
1               5                  10

<210> SEQ ID NO 9
<211> LENGTH: 10
<212> TYPE: PRT
<213> ORGANISM: Unknown
<220> FEATURE:
<223> OTHER INFORMATION: Mammalian

<400> SEQUENCE: 9

Lys Ala Leu Ala Arg Gln Leu Gly Val Ala
1               5                  10

<210> SEQ ID NO 10
<211> LENGTH: 11
<212> TYPE: PRT
<213> ORGANISM: Unknown
<220> FEATURE:
<223> OTHER INFORMATION: Mammalian

<400> SEQUENCE: 10

Lys Ala Leu Ala Arg Gln Leu Gly Val Ala Ala
1               5                  10

<210> SEQ ID NO 11
<211> LENGTH: 11
<212> TYPE: PRT
<213> ORGANISM: Unknown
<220> FEATURE:
<223> OTHER INFORMATION: Mammalian

<400> SEQUENCE: 11

Tyr Ala Arg Ala Ala Ala Arg Gln Ala Arg Ala
1               5                  10

<210> SEQ ID NO 12
<211> LENGTH: 14
<212> TYPE: PRT
<213> ORGANISM: Unknown
<220> FEATURE:
<223> OTHER INFORMATION: Mammalian

<400> SEQUENCE: 12

Trp Leu Arg Arg Ile Lys Ala Trp Leu Arg Arg Ile Lys Ala
1               5                  10

<210> SEQ ID NO 13
<211> LENGTH: 7
<212> TYPE: PRT
<213> ORGANISM: Unknown
<220> FEATURE:
<223> OTHER INFORMATION: Mammalian

<400> SEQUENCE: 13
```

```
Trp Leu Arg Arg Ile Lys Ala
1               5
```

<210> SEQ ID NO 14
<211> LENGTH: 11
<212> TYPE: PRT
<213> ORGANISM: Unknown
<220> FEATURE:
<223> OTHER INFORMATION: Mammalian

<400> SEQUENCE: 14

```
Tyr Gly Arg Lys Lys Arg Arg Gln Arg Arg
1               5                   10
```

<210> SEQ ID NO 15
<211> LENGTH: 12
<212> TYPE: PRT
<213> ORGANISM: Unknown
<220> FEATURE:
<223> OTHER INFORMATION: Mammalian

<400> SEQUENCE: 15

```
Trp Leu Arg Arg Ile Lys Ala Trp Leu Arg Ile
1               5                   10
```

<210> SEQ ID NO 16
<211> LENGTH: 10
<212> TYPE: PRT
<213> ORGANISM: Unknown
<220> FEATURE:
<223> OTHER INFORMATION: Mammalian

<400> SEQUENCE: 16

```
Phe Ala Lys Leu Ala Ala Arg Leu Tyr Arg
1               5                   10
```

<210> SEQ ID NO 17
<211> LENGTH: 12
<212> TYPE: PRT
<213> ORGANISM: Unknown
<220> FEATURE:
<223> OTHER INFORMATION: Mammalian

<400> SEQUENCE: 17

```
Lys Ala Phe Ala Lys Leu Ala Ala Arg Leu Tyr Arg
1               5                   10
```

<210> SEQ ID NO 18
<211> LENGTH: 11
<212> TYPE: PRT
<213> ORGANISM: Unknown
<220> FEATURE:
<223> OTHER INFORMATION: Mammalian

<400> SEQUENCE: 18

```
His Arg Arg Ile Lys Ala Trp Leu Lys Lys Ile
1               5                   10
```

<210> SEQ ID NO 19
<211> LENGTH: 21
<212> TYPE: PRT
<213> ORGANISM: Unknown
<220> FEATURE:
<223> OTHER INFORMATION: Mammalian

<400> SEQUENCE: 19

Tyr Ala Arg Ala Ala Ala Arg Gln Ala Arg Ala Lys Ala Leu Asn Arg
1               5                   10                  15

Gln Leu Gly Val Ala
            20

<210> SEQ ID NO 20
<211> LENGTH: 9
<212> TYPE: PRT
<213> ORGANISM: Unknown
<220> FEATURE:
<223> OTHER INFORMATION: Mammalian

<400> SEQUENCE: 20

Arg Lys Lys Arg Arg Gln Arg Arg Arg
1               5

<210> SEQ ID NO 21
<211> LENGTH: 10
<212> TYPE: PRT
<213> ORGANISM: Unknown
<220> FEATURE:
<223> OTHER INFORMATION: Mammalian

<400> SEQUENCE: 21

Lys Lys Leu Asn Arg Thr Leu Ser Val Ala
1               5                   10

<210> SEQ ID NO 22
<211> LENGTH: 13
<212> TYPE: PRT
<213> ORGANISM: Unknown
<220> FEATURE:
<223> OTHER INFORMATION: Mammalian

<400> SEQUENCE: 22

Lys Lys Lys Ala Leu Asn Arg Gln Leu Gly Val Ala Ala
1               5                   10

<210> SEQ ID NO 23
<211> LENGTH: 17
<212> TYPE: PRT
<213> ORGANISM: Unknown
<220> FEATURE:
<223> OTHER INFORMATION: Mammalian
<220> FEATURE:
<221> NAME/KEY: MISC_FEATURE
<222> LOCATION: (3)..(12)
<223> OTHER INFORMATION: Wherein the "Xaa's" represent any amino acid
      and a sequence of amino acids with a length of 10 residues.

<400> SEQUENCE: 23

Lys Lys Xaa Xaa Xaa Xaa Xaa Xaa Xaa Xaa Xaa Xaa Lys Arg Arg Lys
1               5                   10                  15

Lys

<210> SEQ ID NO 24
<211> LENGTH: 7
<212> TYPE: PRT
<213> ORGANISM: Unknown
<220> FEATURE:
<223> OTHER INFORMATION: Mammalian

<400> SEQUENCE: 24

Leu Leu Lys Arg Arg Lys Lys
1               5

-continued

```
<210> SEQ ID NO 25
<211> LENGTH: 6
<212> TYPE: PRT
<213> ORGANISM: Unknown
<220> FEATURE:
<223> OTHER INFORMATION: Mammalian
<220> FEATURE:
<221> NAME/KEY: MISC_FEATURE
<222> LOCATION: (1)..(1)
<223> OTHER INFORMATION: Wherein the "Xaa" represents a bulky
      hydrophobic residue selected from the group consisting of Val,
      Ile, Leu, Met, and Phe.
<220> FEATURE:
<221> NAME/KEY: MISC_FEATURE
<222> LOCATION: (2)..(2)
<223> OTHER INFORMATION: Wherein the "Xaa" represents any amino acid
<220> FEATURE:
<221> NAME/KEY: MISC_FEATURE
<222> LOCATION: (4)..(5)
<223> OTHER INFORMATION: Wherein the "Xaa's" represent any amino acid
      and a sequence of amino acids with a length of 2 residues.
<220> FEATURE:
<221> NAME/KEY: MISC_FEATURE
<222> LOCATION: (6)..(6)
<223> OTHER INFORMATION: Wherein the "Xaa" represents phosphorylated Ser
      or phosphorylated Thr.

<400> SEQUENCE: 25

Xaa Xaa Arg Xaa Xaa Xaa
1               5

<210> SEQ ID NO 26
<211> LENGTH: 22
<212> TYPE: PRT
<213> ORGANISM: Unknown
<220> FEATURE:
<223> OTHER INFORMATION: Mammalian

<400> SEQUENCE: 26

Tyr Ala Arg Ala Ala Ala Arg Gln Ala Arg Ala Lys Ala Leu Asn Arg
1               5                   10                  15

Gln Leu Ala Val Ala Ala
            20

<210> SEQ ID NO 27
<211> LENGTH: 20
<212> TYPE: PRT
<213> ORGANISM: Unknown
<220> FEATURE:
<223> OTHER INFORMATION: Mammalian

<400> SEQUENCE: 27

Tyr Ala Arg Ala Ala Arg Gln Ala Arg Ala Lys Ala Leu Asn Arg Gln
1               5                   10                  15

Leu Ala Val Ala
            20

<210> SEQ ID NO 28
<211> LENGTH: 11
<212> TYPE: PRT
<213> ORGANISM: Unknown
<220> FEATURE:
<223> OTHER INFORMATION: Mammalian

<400> SEQUENCE: 28

Lys Ala Leu Asn Arg Gln Leu Ala Val Ala Ala
1               5                   10

<210> SEQ ID NO 29
```

```
<211> LENGTH: 10
<212> TYPE: PRT
<213> ORGANISM: Unknown
<220> FEATURE:
<223> OTHER INFORMATION: Mammalian

<400> SEQUENCE: 29

Lys Ala Leu Asn Arg Gln Leu Ala Val Ala
1               5                   10
```

COMPOSITIONS AND METHODS FOR PREVENTING OR TREATING DISEASES, CONDITIONS, OR PROCESSES CHARACTERIZED BY ABERRANT FIBROBLAST PROLIFERATION AND EXTRACELLULAR MATRIX DEPOSITION

CROSS REFERENCE TO RELATED APPLICATIONS

This Application claims the benefit of priority to U.S. Provisional Application No. 62/080,784 filed Nov. 17, 2014, entitled "COMPOSITIONS AND METHODS FOR PREVENTING OR TREATING DISEASES, CONDITIONS, OR PROCESSES CHARACTERIZED BY ABERRANT FIBROBLAST PROLIFERATION AND EXTRACELLULAR MATRIX DEPOSITION," the content of which is incorporated by reference herein in its entirety.

FIELD OF THE INVENTION

The invention is in the fields of cell and molecular biology, polypeptides, and therapeutic methods of use.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: SEQLISTING.txt, date recorded Nov. 17, 2015, file size 7354 bytes).

BACKGROUND

1. Mechanisms of Wound Healing and Fibrosis

The term "wound healing" refers to the process by which the body repairs trauma to any of its tissues, especially those caused by physical means and with interruption of continuity.

A wound-healing response often is described as having three distinct phases-injury, inflammation and repair. Generally speaking, the body responds to injury with an inflammatory response, which is crucial to maintaining the health and integrity of an organism. If however it goes awry, it can result in tissue destruction.

Phase I: Injury

Injury caused by factors including, but not limited to, autoimmune or allergic reactions, environmental particulates, infection or mechanical damage often results in the disruption of normal tissue architecture, initiating a healing response. Damaged epithelial and endothelial cells must be replaced to maintain barrier function and integrity and prevent blood loss, respectively. Acute damage to endothelial cells leads to the release of inflammatory mediators and initiation of an anti-fibrinolytic coagulation cascade, temporarily plugging the damaged vessel with a platelet and fibrin-rich clot. For example, lung homogenates, epithelial cells or bronchoalveolar lavage fluid from idiopathic pulmonary fibrosis (IPF) patients contain greater levels of the platelet-differentiating factor, X-box-binding protein-1, compared with chronic obstructive pulmonary disease (COPD) and control patients, suggesting that clot-forming responses are continuously activated. In addition, thrombin (a serine protease required to convert fibrinogen into fibrin) is also readily detected within the lung and intra-alveolar spaces of several pulmonary fibrotic conditions, further confirming the activation of the clotting pathway. Thrombin also can directly activate fibroblasts, increasing proliferation and promoting fibroblast differentiation into collagen-producing myofibroblasts. Damage to the airway epithelium, specifically alveolar pneumocytes, can evoke a similar anti-fibrinolytic cascade and lead to interstitial edema, areas of acute inflammation and separation of the epithelium from the basement membrane.

Platelet recruitment, degranulation and clot formation rapidly progress into a phase of vasoconstriction with increased permeability, allowing the extravasation (movement of white blood cells from the capillaries to the tissues surrounding them) and direct recruitment of leukocytes to the injured site. The basement membrane, which forms the extracellular matrix underlying the epithelium and endothelium of parenchymal tissue, precludes direct access to the damaged tissue. To disrupt this physical barrier, zinc-dependent endopeptidases, also called matrix metalloproteinases (MMPs), cleave one or more extracelluar matrix constituents allowing extravasation of cells into, and out of, damaged sites. Specifically, MMP-2 (gelatinase A, Type N collagenase) and MMP-9 (gelatinase B, Type IV collagenase) cleave type N collagens and gelatin, two important constituents of the basement membrane. Recent studies have found that MMP-2 and MMP-9 are upregulated, highlighting that tissue-destructive and regenerative processes are common in fibrotic conditions. The activities of MMPs are controlled by several mechanisms including transcriptional regulation, proenzyme regulation, and specific tissue inhibitors of MMPs. The balance between MMPs and the various inhibitory mechanisms can regulate inflammation and determine the net amount of collagen deposited during the healing response.

Previous studies using a model of allergic airway inflammation and remodeling with MMP-2$^{-/-}$, MMP-9$^{-/-}$ and MMP-2$^{-/-}$ MMP-9$^{-/-}$ double knockout mice showed that MMP-2 and MMP-9 were required for successful egression and clearance of inflammatory cells out of the inflamed tissue and into the airspaces. In the absence of these MMPs, cells were trapped within the parenchyma of the lung and were not able to move into the airspaces, which resulted in fatal asphyxiation.

Phase II: Inflammation

Once access to the site of tissue damage has been achieved, chemokine gradients recruit inflammatory cells. Neutrophils, eosinophils, lymphocytes, and macrophages are observed at sites of acute injury with cell debris and areas of necrosis cleared by phagocytes.

The early recruitment of eosinophils, neutrophils, lymphocytes, and macrophages providing inflammatory cytokines and chemokines can contribute to local TGF-β and IL-13 accumulation. Following the initial insult and wave of inflammatory cells, a late-stage recruitment of inflammatory cells may assist in phagocytosis, in clearing cell debris, and in controlling excessive cellular proliferation, which together may contribute to normal healing. Late-stage inflammation may serve an anti-fibrotic role and may be required for successful resolution of wound-healing responses. For example, a late-phase inflammatory profile rich in phagocytic macrophages, assisting in fibroblast clearance, in addition to IL-10-secreting regulatory T cells, suppressing local chemokine production and TGF-β, may prevent excessive fibroblast activation.

The nature of the insult or causative agent often dictates the character of the ensuing inflammatory response. For example, exogenous stimuli like pathogen-associated molecular patterns (PAMPs) are recognized by pathogen recognition receptors, such as toll-like receptors and NOD-like receptors (cytoplasmic proteins that have a variety of functions in regulation of inflammatory and apoptotic responses), and influence the response of innate cells to invading pathogens. Endogenous danger signals also can influence local innate cells and orchestrate the inflammatory cascade.

The nature of the inflammatory response dramatically influences resident tissue cells and the ensuing inflammatory cells. Inflammatory cells themselves also propagate further inflammation through the secretion of chemokines, cytokines, and growth factors. Many cytokines are involved throughout a wound-healing and fibrotic response, with specific groups of genes activated in various conditions. For example, chronic allergic airway disease in asthmatics is associated commonly with elevated type-2 helper T cell ($Th_2$) related cytokine profiles (including, but not limited to, interleukin-4 (IL-4), interleukin-5 (IL-5), interleukin-6 (IL-6), interleukin-13 (IL-13), and interleukin-9 (IL-9)), whereas chronic obstructive pulmonary disease and fibrotic lung disease (such as idiopathic pulmonary fibrosis) patients more frequently present pro-inflammatory cytokine profiles (including, but not limited to, interleukin-1 alpha (IL-1α), interleukin-1 beta (IL-1β), interleukin-6 (IL-6), tumor necrosis factor alpha (TNF-α), transforming growth factor beta (TGF-β), and platelet-derived growth factors (PDGFs)). Each of these cytokines has been shown to exhibit significant pro-fibrotic activity, acting through the recruitment, activation and proliferation of fibroblasts, macrophages, and myofibroblasts.

Phase III: Tissue Repair and Contraction

The closing phase of wound healing consists of an orchestrated cellular re-organization guided by a fibrin (a fibrous protein that is polymerized to form a "mesh" that forms a clot over a wound site)-rich scaffold formation, wound contraction, closure and re-epithelialization. The vast majority of studies elucidating the processes involved in this phase of wound repair have come from dermal wound studies and in vitro systems.

Myofibroblast-derived collagens and smooth muscle actin (α-SMA) form the provisional extracellular matrix, with macrophage, platelet, and fibroblast-derived fibronectin forming a fibrin scaffold. Collectively, these structures are commonly referred to as granulation tissues. Primary fibroblasts or alveolar macrophages isolated from idiopathic pulmonary fibrosis patients produce significantly more fibronectin and α-SMA than control fibroblasts, indicative of a state of heightened fibroblast activation. It has been reported that IPF patients undergoing steroid treatment had similar elevated levels of macrophage-derived fibronectin as IPF patients without treatment. Thus, similar to steroid resistant IL-13-mediated myofibroblast differentiation, macrophage-derived fibronectin release also appears to be resistant to steroid treatment, providing another reason why steroid treatment may be ineffective. From animal models, fibronectin appears to be required for the development of pulmonary fibrosis, as mice with a specific deletion of an extra type III domain of fibronectin (EDA) developed significantly less fibrosis following bleomycin administration compared with their wild-type counterparts.

In addition to fibronectin, the provisional extracellular matrix consists of glycoproteins (such as PDGF), glycosaminoglycans (such as hyaluronic acid), proteoglycans and elastin. Growth factor and TGF-β-activated fibroblasts migrate along the extracellular matrix network and repair the wound. Within skin wounds, TGF-β also induces a contractile response, regulating the orientation of collagen fibers. Fibroblast to myofibroblast differentiation, as discussed above, also creates stress fibers and the neo-expression of α-SMA, both of which confer the high contractile activity within myofibroblasts. The attachment of myofibroblasts to the extracellular matrix at specialized sites called the "fibronexus" or "super mature focal adhesions" pull the wound together, reducing the size of the lesion during the contraction phase. The extent of extracellular matrix laid down and the quantity of activated myofibroblasts determines the amount of collagen deposition. To this end, the balance of matrix metalloproteinases (MMPs) to tissue inhibitor of metalloproteinases (TIMPs) and collagens to collagenases vary throughout the response, shifting from pro-synthesis and increased collagen deposition towards a controlled balance, with no net increase in collagen. For successful wound healing, this balance often occurs when fibroblasts undergo apoptosis, inflammation begins to subside, and granulation tissue recedes, leaving a collagen-rich lesion. The removal of inflammatory cells, and especially α-SMA-positive myofibroblasts, is essential to terminate collagen deposition. Interestingly, in idiopathic pulmonary fibrosis patients, the removal of fibroblasts can be delayed, with cells resistant to apoptotic signals, despite the observation of elevated levels of pro-apoptotic and FAS-signaling molecules. This relative resistance to apoptosis may potentially underlie this fibrotic disease. However, several studies also have observed increased rates of collagen-secreting fibroblast and epithelial cell apoptosis in idiopathic pulmonary fibrosis, suggesting that yet another balance requires monitoring of fibroblast apoptosis and fibroblast proliferation. From skin studies, re-epithelialization of the wound site re-establishes the barrier function and allows encapsulated cellular re-organization. Several in vitro and in vivo models, using human or rat epithelial cells grown over a collagen matrix, or tracheal wounds in vivo, have been used to identify significant stages of cell migration, proliferation, and cell spreading. Rapid and dynamic motility and proliferation, with epithelial restitution from the edges of the denuded area occur within hours of the initial wound. In addition, sliding sheets of epithelial cells can migrate over the injured area assisting wound coverage. Several factors have been shown to regulate re-epithelialization, including serum-derived transforming growth factor alpha (TGF-α), and matrix metalloproteinase-7 (MMP-7) (which itself is regulated by TIMP-1).

Collectively, the degree of inflammation, angiogenesis, and amount of extracellular matrix deposition all contribute to ultimate development of a fibrotic lesion. Thus, therapeutic intervention that interferes with fibroblast activation, proliferation, or apoptosis requires a thorough understanding and appreciation of all of the phases of wound repair. Although these three phases are often presented sequentially, during chronic or repeated injury these processes function in parallel, placing significant demands on regulatory mechanisms. (Wilson and Wynn, *Mucosal Immunol.*, 2009, 3(2):103-121).

2. Fibrosis as a Pathology

Fibrosis represents the formation or development of excess fibrous connective tissue in an organ or tissue, which is formed as a consequence of the normal or abnormal/reactive wound healing response leading to a scar. Fibrosis is characterized by, for example, without limitation, an aberrant deposition of an extracellular matrix protein, an aberrant promotion of fibroblast proliferation, an aberrant induction of differentiation of a population of fibroblasts into a population of myofibroblasts, an aberrant promotion of attachment of myofibroblasts to an extracellular matrix, or a combination thereof.

Pro-Inflammatory Mediators

Accumulating evidence has suggested that polypeptide mediators known as cytokines, including various lymphokines, interleukins, and chemokines, are important stimuli to collagen deposition in fibrosis. Released by resident tissue cells and recruited inflammatory cells, cytokines are thought to stimulate fibroblast proliferation and increased synthesis of extracellular matrix proteins, including collagen. For example, an early feature in the pathogenesis of idiopathic pulmonary fibrosis is alveolar epithelial and/or capillary cell injury. This promotes recruitment into the lung of circulating immune cells, such as monocytes, neutrophils, lymphocytes and eosinophils. These effector cells, together with resident lung cells, such as macrophages, alveolar epithelial and endothelial cells, then release cytokines, which stimulate target cells, typically fibroblasts, to replicate and synthesize increased amounts of collagen. Breakdown of extracellular matrix protein also may be inhibited, thereby contributing to the fibrotic process. (Coker and Laurent, *Eur Respir J,* 1998; 11:1218-1221)

Numerous cytokines have been implicated in the pathogenesis of fibrosis, including, without limitation, transforming growth factor-β (TGF-β), tumor necrosis factor-α (TNF-α), platelet-derived growth factor (PDGF), insulin-like growth factor-1 (IGF-1), endothelin-1 (ET-1) and the interleukins, interleukin-1 (IL-1), interleukin-6 (IL-6), interleukin-8 (IL-8), and interleukin-17 (IL-17). Chemokine leukocyte chemoattractants, including the factor Regulated upon Activation in Normal T-cells, Expressed and Secreted (RANTES), are also thought to play an important role. Elevated levels of pro-inflammatory cytokines, such as Interleukin 8 (IL-8), as well as related downstream cell adhesion molecules (CAMs) such as intercellular adhesion molecule-1 (ICAM-1) and vascular cell adhesion molecule-1 (VCAM-1), matrix metalloproteinases such as matrix metalloproteinase-7 (MMP-7), and signaling molecules such as S100 calcium-binding protein A12 (S100A12, also known as calgranulin C), in the peripheral blood have been found to be associated with mortality, lung transplant-free survival, and disease progression in patients with idiopathic pulmonary fibrosis (Richards et al, *Am J Respir Crit Care Med,* 2012, 185: 67-76).

The TGF-β family of proteins has a potent stimulatory effect on extracellular matrix deposition, and in fact has been used in constructing induced animal models of fibrosis through gene transfer. In vitro studies show that TGF-β1, secreted as a latent precursor, promotes fibroblast procollagen gene expression and protein synthesis. The data suggest that the other mammalian isoforms, TGF-β2 and TGF-β3, also stimulate human lung fibroblast collagen synthesis and reduce breakdown in vitro. In animal models of pulmonary fibrosis, enhanced TGF-β1 gene expression is temporally and spatially related to increased collagen gene expression and protein deposition. TGF-β1 antibodies reduce collagen deposition in murine bleomycin-induced lung fibrosis, and human fibrotic lung tissue shows enhanced TGF-β1 gene and protein expression.

TNF-α can stimulate fibroblast replication and collagen synthesis in vitro, and pulmonary TNF-α gene expression rises after administration of bleomycin in mice. Soluble TNF-α receptors reduce lung fibrosis in murine models, and pulmonary overexpression of TNF-α in transgenic mice is characterized by lung fibrosis. In patients with IPF or asbestosis (a chronic inflammatory and fibrotic medical condition affecting the parenchymal tissue of the lungs caused by the inhalation and retention of asbestos fibers), bronchoalveolar lavage fluid-derived macrophages release increased amounts of TNF-α compared with controls.

Endothelin (ET-1) also fulfills the criteria for a profibrotic cytokine. This molecule promotes fibroblast proliferation and chemotaxis and stimulates procollagen production. It is present in the lungs of patients with pulmonary fibrosis, and a recent report suggests that the ET-1 receptor antagonist, bosentan, ameliorates lung fibrosis when administered to experimental animals.

Unchecked Myofibroblast Proliferation/Activation and Fibrotic Foci Formation

Differentiation of fibroblasts into myofibroblasts has long been believed to be an important event in many conditions, including wound repair and fibrosis. For example, it has been reported that myofibroblasts occur in areas of active fibrosis and are responsible for production and deposition of extracellular matrix (ECM) proteins in pulmonary fibrosis. (Liu, T. et al., *Am J Respir Cell Mol Biol,* 2007, 37:507-517).

One hypothesis for the causation of idiopathic pulmonary fibrosis suggests that a still-unidentified stimulus produces repeated episodes of acute lung injury. Wound healing at these sites of injury ultimately leads to fibrosis, with loss of lung function. Fibroblast foci, the hallmark lesions of idiopathic pulmonary fibrosis, feature vigorous replication of mesenchymal cells and exuberant deposition of fresh extracellular matrix. Such foci are typical of alveolar epithelial-cell injury, with endoluminal plasma exudation and collapse of the distal air space. Mediators normally associated with wound healing, such as transforming growth factor-β1 (TGF-β1) and connective-tissue growth factor, are expressed also at these sites. The driving force for this focal acute lung injury and wound repair is unknown. 3. Disease or Conditions in which Fibrosis Plays a Role Fibrosis has been implicated in a number of heterogeneous diseases or conditions, including, but not limited to, interstitial lung disease, such as idiopathic pulmonary fibrosis, acute lung injury (ALI), radiation-induced fibrosis, transplant rejection, liver fibrosis, renal fibrosis and vascular fibrosis.

3.1. Idiopathic Pulmonary Fibrosis (IPF)

Idiopathic Pulmonary fibrosis (IPF, also known as cryptogenic fibrosing alveolitis, CFA, or Idiopathic Fibrosing Interstitial Pneumonia) is defined as a specific form of chronic, progressive fibrosing interstitial pneumonia of uncertain etiology that occurs primarily in older adults, is limited to the lungs, and is associated with the radiologic and histological pattern of usual interstitial pneumonia (UIP) (Raghu G. et al., *Am J Respir Crit Care Med.,* 183(6):788-824, 2011; Thannickal, V. et al., *Proc Am Thorac Soc.,* 3(4):350-356, 2006). It may be characterized by abnormal and excessive deposition of fibrotic tissue in the pulmonary interstitium. On high-resolution computed tomography (HRCT) images, UIP is characterized by the presence of reticular opacities often associated with traction bronchiectasis. As IPF progresses, honeycombing becomes more prominent (Neininger A. et al., *J Biol Chem.,* 277(5):3065-8, 2002). Pulmonary function tests often reveal restrictive impairment and reduced diffusing capacity for carbon monoxide (Thomas, T. et al., *J Neurochem.,* 105(5): 2039-52, 2008). Studies have reported significant increases in TNF-α and IL-6 release in patients with idiopathic pulmonary fibrosis (IPF) (Zhang, Y, et al. *J. Immunol.* 150(9):4188-4196, 1993), which has been attributed to the level of expression of IL-1β (Kolb, M., et al. *J. Clin. Invest,* 107 (12):1529-1536, 2001). The onset of IPF symptoms, shortness of breath and cough, are usually insidious but gradually progress, with death occurring in 70% of patients within five years after diagnosis. This grim prognosis is similar to numbers of annual deaths attributable to breast cancer (Raghu G. et al., *Am J Respir Crit Care Med.*, 183(6):788-824, 2011).

IPF afflicts nearly 130,000 patients in the United States, with approximately 50,000 new patients annually and nearly 40,000 deaths each year worldwide (Raghu G. et al., *Am J Respir Crit Care Med.*, 183(6):788-824, 2011). While these data are notable, a recent study reported that IPF may be 5-10 times more prevalent than previously thought, perhaps due to increasing prevalence or enhanced diagnostic capabilities (Thannickal, V. et al., *Proc Am Thorac Soc.*, 3(4): 350-356, 2006). Lung transplantation is considered a definitive therapy for IPF, but the five year survival post lung transplantation is less than 50%. Accordingly, even lung transplantation cannot be considered a "cure" for IPF. In addition to the physical and emotional toll on the patient, IPF is extremely expensive to treat and care for with national healthcare costs to in the range of $2.8 billion dollars for every 100,000 patients annually.

In addition, previous studies have suggested that superimposed environmental insults may be important in the pathogenesis of idiopathic pulmonary fibrosis. In most reported case series, up to 75 percent of index patients with idiopathic pulmonary fibrosis are current or former smokers. In large epidemiologic studies, cigarette smoking has been strongly associated with idiopathic pulmonary fibrosis. In addition, many of the inflammatory features of idiopathic pulmonary fibrosis are more strongly linked to smoking status than to the underlying lung disease. Thus, cigarette smoking may be an independent risk factor for idiopathic pulmonary fibrosis. Latent viral infections, especially those of the herpes virus family, have also been reported to be associated with idiopathic pulmonary fibrosis.

Since there is no known effective treatment for IPF, including lung transplantation, there remains a critical need for the development of novel therapeutics. There are a variety of therapeutic approaches currently being investigated, including anti-fibrotic therapies that may slow or inhibit the body's ability to produce scar or fibrotic tissue and pulmonary vasodilators to increase the tissue area for gas exchange in the lung. Aside from lung transplantation, potential IPF treatments have included corticosteroids, azathioprine, cyclophosphamide, anticoagulants, and N-acetylcysteine (Raghu G. et al., *Am J Respir Crit Care Med.*, 183(6):788-824, 2011). In addition, supportive therapies such as oxygen therapy and pulmonary rehabilitation are employed routinely. However, none of these have definitely impacted the long term survival of IPF patients, which further highlights the unmet medical need for treatment options in IPF. As an example, despite mixed clinical program results, InterMune's oral small-molecule Esbriet® (pirfenadone) received European and Japanese approvals for patients with IPF. Esbriet® thus became the first medication specifically indicated for the treatment of IPF; due to equivocal trial outcomes and drug side effects, the drug's utility is viewed with skepticism in the United States, and did not receive an FDA approval based on the data submitted at that time. Accordingly, a large phase 3 clinical trial is in progress to determine its efficacy to support a New Drug Application in the United States.

Histopathologically, IPF can be described as accumulation of activated myofibroblasts (or mesenchymal cells) in fibroblastic foci (Thannickal, V. et al., *Proc Am Thorac Soc.*, 3(4):350-356, 2006). Impaired apoptosis of myofibroblasts may result in a persistent and dysregulated repair process that culminates in tissue fibrosis. Arguably, inflammation also plays a critical role in IPF, perhaps through cyclic acute stimulation of fibroblasts. These findings point to potential targets for therapeutic intervention.

3.1.1. Pathogenesis of Idiopathic Pulmonary Fibrosis (IPF)

While pathogenic mechanisms are incompletely understood, the currently accepted paradigm proposes that injury to the alveolar epithelium is followed by a burst of pro-inflammatory and fibroproliferative mediators that invoke responses associated with normal tissue repair. For unclear reasons, these repair processes never resolve and progressive fibrosis ensues. (Selman M, et al., *Ann Intern Med*, 134(2):136-151, 2001; Noble, P. and Homer R., *Clin Chest Med*, 25(4):749-58, 2004; Strieter, R., *Chest*, 128 (5 Suppl 1):526S-532S, 2005).

3.1.2. Bleomycin Mouse Model of Pulmonary Fibrosis

Although a number of animal models exist and can be useful (e.g., the TGF-β adenovirus transduction model or the radiation-induced fibrosis model), the bleomycin model is well-documented and the best characterized murine model in use today to demonstrate efficacy of a particular drug or protein kinase inhibitor in the post-inflammatory/pre-fibrotic/fibro-preventive stages (Vittal, R. et al., *J Pharmacol Exp Ther.*, 321(1):35-44, 2007; Vittal, R. et al., *Am J Pathol.*, 166(2):367-75, 2005; Hecker L. et al., *Nat Med.*, 15(9): 1077-81, 2009).

The antibiotic bleomycin was originally isolated from *Streptomyces verticillatus* (Umezawa, H. et al., *Cancer* 20: 891-895, 1967). This antibiotic was subsequently found to be effective against squamous cell carcinomas and skin tumors (Umezawa, H., *Fed Proc*, 33: 2296-2302, 1974); however, its usefulness as an anti-neoplastic agent was limited by dose-dependent pulmonary toxicity resulting in fibrosis (Muggia, F. et al., *Cancer Treat Rev*, 10: 221-243, 1983). The delivery of bleomycin via the intratracheal route (generally 1.25-4 U/kg, depending on the source) has the advantage that a single injection of the drug produces lung injury and resultant fibrosis in rodents (Phan, S. et al., *Am Rev Respir Dis* 121: 501-506, 1980; Snider, G. et al., *Am Rev Respir Dis.* 117: 289-297, 1978; Thrall, R. et al., *Am J Pathol*, 95: 117-130, 1979). Intratracheal delivery of the drug to rodents results in direct damage initially to alveolar epithelial cells. This event is followed by the development of neutrophilic and lymphocytic pan-alveolitis within the first week (Janick-Buckner, D. et al., *Toxicol Appl Pharmacol.*, 100(3):465-73, 1989). Subsequently, alveolar inflammatory cells are cleared, fibroblast proliferation is noted, and extracellular matrix is synthesized (Schrier D. et al., *Am Rev Respir Dis.*, 127(1):63-6, 1983). The development of fibrosis in this model can be seen biochemically and histologically by day 14 with maximal responses generally noted around days 21-28 (Izbicki G. et al., *Int J Exp Pathol.*, 83(3):111-9, 2002; Phan, S. et al., *Chest.*, 83(5 Suppl):44S-45S, 1983). Beyond 28 days, however, the response to bleomycin is more variable. Original reports suggest that bleomycin delivered intratracheally may induce fibrosis that progresses or persists for 60-90 days (Thrall R. et al., *Am J Pathol.*, 95(1):117-30, 1979; Goldstein R., et al., *Am Rev Respir Dis.*, 120(1):67-73, 1979; Starcher B. et al., *Am Rev Respir Dis.*, 117(2):299-305, 1978); however, other reports demonstrate a self-limiting response that begins to resolve after this period (Thrall R. et al., *Am J Pathol.*, 95(1):117-30, 1979; Phan, S. et al., *Chest*, 83(5 Suppl): 44S-45S, 1983; Lawson W. et al., *Am J Pathol.* 2005; 167(5):1267-1277). While the resolving nature of this model does not mimic human disease, this aspect of the model offers an opportunity for studying fibrotic resolution at these later time points.

3.2. Acute Lung Injury (ALI)

Acute lung injury (ALI) and its more severe form, the acute respiratory distress syndrome (ARDS), are syndromes of acute respiratory failure that result from acute pulmonary edema and inflammation. ALI/ARDS is a cause of acute respiratory failure that develops in patients of all ages from a variety of clinical disorders, including sepsis (pulmonary and nonpulmonary), pneumonia (bacterial, viral, and fungal), aspiration of gastric and oropharyngeal contents, major trauma, and several other clinical disorders, including severe acute pancreatitis, drug over dose, and blood products (Ware, L. and Matthay, M., *N Engl J Med*, 342:1334-1349, 2000). Most patients require assisted ventilation with positive pressure. The primary physiologic abnormalities are severe arterial hypoxemia as well as a marked increase in minute ventilation secondary to a sharp increase in pulmonary dead space fraction. Patients with ALI/ARDS develop protein-rich pulmonary edema resulting from exudation of fluid into the interstitial and airspace compartments of the lung secondary to increased permeability of the barrier. Additional pathologic changes indicate that the mechanisms involved in lung edema are complex and that edema is only one of the pathophysiologic events in ALI/ARDS. One physiologic consequence is a significant decrease in lung compliance that results in an increased work of breathing (Nuckton T. et al., *N Engl J Med*, 346:1281-1286, 2002), one of the reasons why assisted ventilation is required to support most patients.

It was suggested that mechanical ventilation (MV), a mainstay treatment for ALI, potentially contributes to and worsens permeability by exacting mechanical stress on various components of the respiratory system causing ventilator-associated lung injury (VALI) (Fan, E. et al., *JAMA*, 294:2889-2896, 2005; MacIntyre N., *Chest*, 128:561S-567, 2005). A recent trial demonstrated a significant improvement in survival in patients ventilated with low ($LV_T$) compared to high tidal volumes ($HV_T$) (The Acute Respiratory Distress Syndrome N. Ventilation with Lower Tidal Volumes as Compared with Traditional Tidal Volumes for Acute Lung Injury and the Acute Respiratory Distress Syndrome. *N Engl J Med;* 342:1301-1308, 2000). Other than ventilating at lower tidal volumes, which presumably imparts lower mechanical stress, there is little mechanistic understanding of the pathophysiology and no directed therapies for VALI.

It was suggested that the high tidal volumes ($HV_T$) mechanical ventilation (MV) results in phosphorylation of p38 MAP kinase, activation of MK2, and phosphorylation of HSPB1, a process that causes actin to disassociate from HSPB1 and polymerize to form stress fibers, which ultimately leads to paracellular gaps and increased vascular permeability. Furthermore, it was shown that inhibiting p38 MAP kinase or its downstream effector MK2 prevents the phosphorylation of HSPB1 and protects from vascular permeability by abrogating actin stress fiber formation and cytoskeletal rearrangement, suggesting that targeted inhibition of MK2 could be a potential therapeutic strategy for the treatment of acute lung injury (Damarla, M. et al., *PLoS ONE*, 4(2): E4600, 2009).

Moreover, studies have suggested that pulmonary fibrosis can also result from ALI. ALI may completely resolve or proceed to fibrosing alveolitis accompanied by persistent low oxygen in the blood (hypoxemia) and a reduced ability of the lung to expand with every breath (reduced pulmonary compliance). It was suggested that while the etiology of injury-induced lung fibrosis is different from idiopathic pulmonary fibrosis, both diseases share a common pathological mechanism, i.e., infiltration of fibroblasts into the airspaces of lung (Tager et al., *Nat. Med.* 14: 45-54, 2008; Ley, K. and Zarbock, A., *Nat. Med.* 14: 20-21; 2008).

3.3. Radiation-Induced Fibrosis

Fibrosis is a common sequela of both cancer treatment by radiotherapy and accidental irradiation. Fibrotic lesions following radiotherapy have been described in many tissues, including skin (Bentzen, S. et al., *Radiother. Oncol.* 15: 261-214, 1989; Brocheriou, C., et al., *Br. J. Radiol. Suppl.* 19: 101-108, 1986), lung (Lopez Cardozo, B. et al., *Int. J. Radiat. Oncol. Biol. Phys.*, 11: 907-914, 1985), heart (Fajardo, L. and Stewart, J., Lab. *Invest.*, 29: 244-257, 1973), and liver (Ingold, J. et al., *Am. J. Roentgenol.*, 93: 200-208, 1965).

In the lung (late responding tissue), two radiation toxicity syndromes, radiation pneumonitis and pulmonary fibrosis, may occur. Pneumonitis is manifested 2-3 months after radiotherapy is completed. Pathologically, pneumonitis is characterized by interstitial edema, the presence of interstitial and alveolar inflammatory cells, and an increase in the number of type II pneumocytes (Gross, N. et al., *Radiat. Res.*, III: 143-50, 1981; Guerry-Force, M. et al., *Radiat. Res.* 114: 138-53, 1988). In pneumonitis, the primary damage to the tissue is most likely caused by depletion of parenchymal cells (Hendry, J., *Radiat. Oncol*. Vol. 4, 2: 123-132, 1994; Rosiello, R. et al., *Am. Rev. Respir. Dis.*, 148: 1671-1676, 1993; Travis, E. and Terry, N., *Front. Radiat. Ther. Oncol.*, 23: 41-59, 1989).

The fibrotic reaction is typified by increased interstitial collagen deposition, thickening of vascular walls and vascular occlusions (Vergava, J. et al., *Int. J. Radiat. Oncol. Biol. Phys.* 2: 723-732, 1987). Histological examinations of fibrotic lesions have revealed that fibrotic tissue contains infiltrating inflammatory cells, fibroblasts, and larger amounts of various extracellular matrix components. In fibrotic tissues, an enhanced synthesis and deposition of the interstitial collagens, fibronectin, and proteoglycans have been described (Maasiha, P. et al., *Int. J. Radiat. Oncol. Biol. Phys.* 20: 973-980, 1991), and this has been interpreted as the result of the radiation-induced modulation of the fibroblast cell system (Remy, J. et al., *Radiat. Res.* 125: 14-19, 1991).

Radiation-induced fibrosis, especially of the lung, was suggested to be due to an interplay of cellular and molecular events between several cell systems engaged in a fibrotic reaction. Irradiation alone is able to induce a premature terminal differentiation process of the fibroblast/fibrocyte cell system resulting in the enhanced accumulation of post-mitotic fibrocytes, which are characterized by a several-fold increase in the synthesis of interstitial collagens. Concomitantly, irradiation of accompanying parenchymal cell types, such as alveolar macrophages and alveolar type II pneumocytes, induces the immediate synthesis of specific cytokines, like TGF-β1, which then alter the interaction of the parenchymal cells with the fibroblast cell system. TGF-β1, as one of the major cytokines responsible for the fibrotic reaction, induces the fibroblast proliferation via an expansion of the progenitor fibroblast cell types as well as a premature terminal differentiation of progenitor fibroblasts into post-mitotic fibrocytes. This leads to an accumulation of post-mitotic fibrocytes due to a disturbance of the well-balanced cell type ratio of progenitor fibroblasts and post-mitotic fibrocytes. It was proposed that the pathophysiological tissue response following irradiation is caused by an altered cytokine- and growth factor-mediated interaction of multi-cellular cell systems resulting in the disturbance of the well-balanced cell type ratio of the interstitial fibroblast/fibrocyte cell system. (Rodemann, H. and Bamberg, M., *Radiotherapy and Oncology,* 35, 83-90, 1995).

3.4. Transplant Rejection

Transplantation is the act of transferring cells, tissues, or organs from one site to another. The malfunction of an organ system can be corrected with transplantation of an organ (e.g., kidney, liver, heart, lung, or pancreas) from a donor. However, the immune system remains the most formidable barrier to transplantation as a routine medical treatment, and rejection of such organ often corresponds to a fibrotic phenotype in the grafted organ. The immune system has developed elaborate and effective mechanisms to combat foreign agents. These mechanisms are also involved in the rejection of transplanted organs, which are recognized as foreign by the host's immune system.

The degree of immune response to a graft depends partly on the degree of genetic disparity between the grafted organ and the host. Xenografts, which are grafts between members of different species, have the most disparity and elicit the maximal immune response, undergoing rapid rejection. Autografts, which are grafts from one part of the body to another (e.g., skin grafts), are not foreign tissue and, therefore, do not elicit rejection. Isografts, which are grafts between genetically identical individuals (e.g., monozygotic twins), also undergo no rejection.

Allografts are grafts between members of the same species that differ genetically. This is the most common form of transplantation. The degree to which allografts undergo rejection depends partly on the degree of similarity or histocompatibility between the donor and the host.

The degree and type of response also vary with the type of the transplant. Some sites, such as the eye and the brain, are immunologically privileged (i.e., they have minimal or no immune system cells and can tolerate even mismatched grafts). Skin grafts are not initially vascularized and so do not manifest rejection until the blood supply develops. The lungs, heart, kidneys, and liver are highly vascular organs and often lead to a vigorous cell mediated response in the host, requiring immunosuppressive therapies.

Constrictive bronchiolitis (CB), also termed in lung transplant patients obliterative bronchiolitis, is inflammation and fibrosis occurring predominantly in the walls and contiguous tissues of membranous and respiratory bronchioles with resultant narrowing of their lumens. CB is found in a variety of settings, most often as a complication of lung and heart-lung transplantation (affecting 34% to 39% of patients, usually in the first 2 years after transplantation) and bone marrow transplantation, but also in rheumatoid arthritis, after inhalation of toxic agents such as nitrogen dioxide, after ingestion of certain drugs such as penicillamine and ingestion of the East Asian vegetable *Sauropus androgynous*, and as a rare complication of adenovirus, influenza type A, measles, and *Mycoplasma pneumoniae* infections in children. In lung transplants, CB is the single most important factor leading to death thereafter. In one study, the overall mortality rate was 25%. However, at the same time, 87% of patients who were asymptomatic and diagnosed solely by transbronchial biopsy had resolution or stabilization of disease. Decreases in $FEV_1$ from baseline can be used to clinically support CB in transplant patients; the term bronchiolitis obliterans syndrome is used to denote this clinical dysfunction, and a grading system has been established for it that is now widely used in the literature. Significant risk factors for the development of CB in lung transplants include alloantigen-dependent and -independent mechanisms. In the former group are late acute rejection and HLA mismatches at the A loci; in the latter are ischemia/reperfusion injuries to airways that result from the transplantation surgery and cytomegalovirus infection (Schlesinger C. et al, *Curr Opin Pulm. Med.,* 4(5): 288-93, 1998).

Mechanisms of Rejection

The immune response to a transplanted organ consists of both cellular (lymphocyte mediated) and humoral (antibody mediated) mechanisms. Although other cell types are also involved, the T cells are central in the rejection of grafts. The rejection reaction consists of the sensitization stage and the effector stage.

Sensitization Stage

In this stage, the CD4 and CD8 T cells, via their T-cell receptors, recognize the alloantigens expressed on the cells of the foreign graft. Two signals are needed for recognition of an antigen; the first is provided by the interaction of the T cell receptor with the antigen presented by MHC molecules, the second by a co-stimulatory receptor/ligand interaction on the T cell/APC surface. Of the numerous co-stimulatory pathways, the interaction of CD28 on the T cell surface with its APC surface ligands, B7-1 or B7-2 (commonly known as CD80 or CD86, respectively), has been studied the most (Clarkson, M. and Sayegh, M., *Transplantation;* 80(5): 555-563, 2005). In addition, cytotoxic T lymphocyte-associated antigen-4 (CTLA4) also binds to these ligands and provides an inhibitory signal. Other co-stimulatory molecules include CD40 and its ligand CD40L (CD154). Typically, helices of the MHC molecules form the peptide-binding groove and are occupied by peptides derived from normal cellular proteins. Thymic or central tolerance mechanisms (clonal deletion) and peripheral tolerance mechanisms (e.g., anergy) ensure that these self-peptide MHC complexes are not recognized by the T cells, thereby preventing autoimmune responses.

Effector Stage

Alloantigen-dependent and independent factors contribute to the effector mechanisms. Initially, nonimmunologic "injury responses" (ischemia) induce a nonspecific inflammatory response. Because of this, antigen presentation to T cells is increased as the expression of adhesion molecules, class II MHC, chemokines, and cytokines is upregulated. It also promotes the shedding of intact, soluble MHC molecules that may activate the indirect allorecognition pathway. After activation, CD4-positive T cells initiate macrophage-mediated delayed type hypersensitivity (DTH) responses and provide help to B cells for antibody production.

Various T cells and T cell-derived cytokines such as IL-2 and IFN-γ are upregulated early after transplantation. Later, β-chemokines like RANTES (regulated upon activation, normal T cell expressed and secreted), IP-10, and MCP-1 are expressed, and this promotes intense macrophage infiltration of the allograft. IL-6, TNF-α, inducible nitric oxide synthase (iNOS) and growth factors, also play a role in this process. Growth factors, including TGF-β and endothelin, cause smooth muscle proliferation, intimal thickening, interstitial fibrosis, and, in the case of the kidney, glomerulosclerosis.

Endothelial cells activated by T cell-derived cytokines and macrophages express class II MHC, adhesion molecules, and co-stimulatory molecules. These can present antigen and thereby recruit more T cells, amplifying the rejection process. CD8-positive T cells mediate cell-mediated cytotoxicity reactions either by delivering a "lethal hit" or, alternatively, by inducing apoptosis.

In addition, emerging studies have suggested involvement of fibrotic processes in chronic transplant rejection of an organ transplant. For example, it was shown that chronic lung allograft rejection is mediated by a relative deficiency of allograft endothelial cell-derived HIF-1α, leading to fibrotic remodeling of the transplanted organ (Wilkes, D., *J Clin Invest.*, 121(6): 2155-2157, 2011; Jiang, X. et al., *J Clin Invest.*, 121(6): 2336-2349, 2011).

3.5. Chronic Obstructive Pulmonary Disease (COPD)

Chronic obstructive pulmonary disease (COPD) is a collective description for lung diseases represented by chronic and relatively irreversible expiratory airflow dysfunction due to some combination of chronic obstructive bronchitis, emphysema, and/or chronic asthma. COPD is caused by a range of environmental and genetic risk factors, including smoking that contributes to the disease.

The prevalence of COPD is increasing worldwide, and COPD has become the fourth leading cause of death in the United States. In the United States, despite the decrease in cigarette smoking in recent decades, both the prevalence of, and the mortality associated with, COPD have increased and are projected to continue to increase for some years yet. Furthermore, COPD is costly, and acute exacerbations, which occur roughly once a year in patients with COPD of moderate or greater severity, constitute the most expensive component.

In COPD, airflow obstruction can occur on the basis of either of two very different pathophysiological processes in the lung: 1) inflammation of the parenchyma resulting in proteolysis of the lung parenchyma and loss of lung elasticity (emphysema); and 2) inflammation, scarring and narrowing of the small airways ("small airway disease"). In an individual patient, one of these processes, which may be controlled by different genetic factors, may predominate although both usually co-exist. Ultimately, both of these processes produce similar patterns of functional impairment: decreased expiratory flow, hyperinflation and abnormalities of gas exchange.

At an early stage of COPD, the following symptoms are found in the lungs of COPD patients: 1) breach of airway epithelium by damaging aerosols, 2) accumulation of inflammatory mucous exudates, 3) infiltration of the airway wall by inflammatory immune cells, 4) airway remodeling/thickening of the airway wall and encroachment on lumenal space, and 5) increased resistance to airflow. During this early stage, smooth muscle contraction and hyper-responsiveness also increase resistance, but the increased resistance is relieved by bronchodilators.

At an advanced stage, COPD patients characteristically develop deposition of fibrous connective tissue in the subepithelial and aventitial compartments surrounding the airway wall. Such peribronchiolar fibrosis contributes to fixed airway obstruction by restricting the enlargement of airway caliber that occurs with lung inflation.

3.5.1. Chronic Bronchitis

Chronic bronchitis is defined as the presence of chronic cough and sputum production for at least three months of two consecutive years in the absence of other diseases recognized to cause sputum production. In chronic bronchitis, epidemiologically the bronchial epithelium becomes chronically inflamed with hypertrophy of the mucus glands and an increased number of goblet cells. The cilia are also destroyed and the efficiency of the mucociliary escalator is greatly impaired. Mucus viscosity and mucus production are increased, leading to difficulty in expectorating. Pooling of the mucus leads to increased susceptibility to infection.

Microscopically there is infiltration of the airway walls with inflammatory cells. Inflammation is followed by scarring and remodeling that thickens the walls and also results in narrowing of the airways. As chronic bronchitis progresses, there is squamous metaplasia (an abnormal change in the tissue lining the inside of the airway) and fibrosis (further thickening and scarring of the airway wall). The consequence of these changes is a limitation of airflow. Repeated infections and inflammation over time leads to irreversible structural damage to the walls of the airways and to scarring, with narrowing and distortion of the smaller peripheral airways.

3.5.2. Emphysema

Emphysema is defined in terms of its pathological features, characterized by abnormal dilatation of the terminal air spaces distal to the terminal bronchioles, with destruction of their wall and loss of lung elasticity. Bullae (blisters larger than 1 cm wide) may develop as a result of overdistention if areas of emphysema are larger than 1 cm in diameter. The distribution of the abnormal air spaces allows for the classification of the two main patterns of emphysema: panacinar (panlobular) emphysema, which results in distension, and destruction of the whole of the acinus, particularly the lower half of the lungs. Centriacinar (centrilobular) emphysema involves damage around the respiratory bronchioles affecting the upper lobes and upper parts of the lower lobes of the lung. Certain forms of emphysema are furthermore known to be associated with fibrosis.

The destructive process of emphysema is predominantly associated with cigarette smoking. Cigarette smoke is an irritant and results in low-grade inflammation of the airways and alveoli. It is known that cigarettes contain over 4,000 toxic chemicals, which affect the balance between the antiprotease and proteases within the lungs, causing permanent damage. Inflammatory cells (macrophages and neutrophils) produce a proteolytic enzyme known as elastase, which destroys elastin, an important component of lung tissue.

The alveoli or air sacs of the lung contain elastic tissue, which supports and maintains the potency of the intrapulmonary airways. The destruction of the alveolar walls allows narrowing in the small airways by loosening the guy ropes that help keep the airways open. During normal inspiration, the diaphragm moves downwards while the rib cage moves outwards, and air is drawn into the lungs by the negative pressure that is created. On expiration, as the rib cage and diaphragm relax, the elastic recoil of the lung parenchyma pushes air upwards and outwards. With destruction of the lung parenchyma, which results in floppy lungs and loss of the alveolar guy ropes, the small airways collapse and air trapping occurs, leading to hyperinflation of the lungs. Hyperinflation flattens the diaphragm, which results in less effective contraction and reduced alveolar efficiency, which in turn leads to further air trapping. Over time the described mechanism leads to severe airflow obstruction, resulting in insufficient expiration to allow the lungs to deflate fully prior to the next inspiration.

3.5.3 Chronic Asthma

Asthma is defined as a chronic inflammatory condition of the airways, leading to widespread and variable airways obstruction that is reversible spontaneously or with treatment. In some patients with chronic asthma, the disease progresses, leading to irreversible airway obstruction, particularly if the asthma is untreated, either because it has not been diagnosed or mismanaged, or if it is particularly severe. Children with asthma have a one in ten chance of developing irreversible asthma, while the risk for adult-onset asthmatics is one in four. Studies also have found that in both children and adults that asthma might lead to irreversible deterioration in lung function if their asthma was not treated appropriately, particularly with corticosteroid therapy.

The airway inflammation in asthma over time can lead to remodeling of the airways through increased smooth muscle, disruption of the surface epithelium increased collagen deposition and thickening of the basement membrane.

3.6 Other Types of Fibrosis

Other types of fibrosis include, without limitation, cystic fibrosis of the pancreas and lungs, injection fibrosis, endomyocardial fibrosis, mediastinal fibrosis, myelofibrosis, retroperitoneal fibrosis, and nephrogenic systemic fibrosis.

Cystic fibrosis (CF, mucovidosis, mucovisidosis) is an inherited autosomal recessive disorder. It is one of the most common fatal genetic disorders in the United States, affecting about 30,000 individuals, and is most prevalent in the Caucasian population, occurring in one of every 3,300 live births. The gene involved in cystic fibrosis, which was identified in 1989, codes for a protein called the cystic fibrosis transmembrane conductance regulator (CFTR). CFTR normally is expressed by exocrine epithelia throughout the body and regulates the movement of chloride ions, bicarbonate ions and glutathione into and out of cells. In cystic fibrosis patients, mutations in the CFTR gene lead to alterations or total loss of CFTR protein function, resulting in defects in osmolarity, pH and redox properties of exocrine secretions. In the lungs, CF manifests itself by the presence of a thick mucus secretion which clogs the airways. In other exocrine organs, such as the sweat glands, CF may not manifest itself by an obstructive phenotype, but rather by abnormal salt composition of the secretions (hence the clinical sweat osmolarity test to detect CF patients). The predominant cause of illness and death in cystic fibrosis patients is progressive lung disease. The thickness of CF mucus, which blocks the airway passages, is believed to stem from abnormalities in osmolarity of secretions, as well as from the presence of massive amounts of DNA, actin, proteases and prooxidative enzymes originating from a subset of inflammatory cells, called neutrophils. Indeed, CF lung disease is characterized by early, hyperactive neutrophil-mediated inflammatory reactions to both viral and bacterial pathogens. The hyperinflammatory syndrome of CF lungs has several underpinnings, among which an imbalance between pro-inflammatory chemokines, chiefly IL-8, and anti-inflammatory cytokines, chiefly IL-10, has been reported to play a major role. See Chmiel et al., *Clin Rev Allergy Immunol.* 3(1):5-27 (2002). Studies have reported that levels of TNF-α, IL-6 and IL-1β were higher in the bronchoalveolar lavage fluid of cystic fibrosis patients, than in healthy control bronchoalveolar lavage fluid (Bondfield, T. L., et al. *Am. J. Resp. Crit. Care Med.* 152(1):2111-2118, 1995).

Injection fibrosis (IF) is a complication of intramuscular injection often occurring in the quadriceps, triceps and gluteal muscles of infants and children in which subjects are unable to fully flex the affected muscle. It typically is painless, but progressive. Studies have reported that the glycoprotein osteopontin (OPN) plays a role in tissue remodeling (Liaw, L., et al. *J. Clin. Invest,* 101(7):1469-1478, 1998) and that this proinflammatory mediator induces IL-1β up-regulation in human monocytes and an accompanying enhanced production of TNF-α and IL-6 (Naldini, A., et al. *J. Immunol.* 177:4267-4270, 2006; Weber, G. F., and Cantor, H. *Cytokine Growth Factor Reviews.* 7(3):241-248, 1996).

Endomyocardial disease (hyperosinophilic syndrome (HS)) is a disease process characterized by a persistently elevated eosinophil count (1500 eosinophils/mm$^3$) in the blood. HS simultaneously affects many organs. Studies have reported that IL-1β, IL-6 and TNF-α are expressed at high levels in viral-induced myocarditis patients (Satoh, M., et al. *Virchows Archiv.* 427(5):503-509, 1996). Symptoms may include cardiomyopathy, skin lesions, thromboembolic disease, pulmonary disease, neuropathy, hepatosplenomegaly (coincident enlargement of the liver and spleen), and reduced ventricular size. Treatment may include utilizing corticosteroids to reduce eosinophil levels.

Mediastinal fibrosis (MF) is characterized by invasive, calcified fibrosis centered on lymph nodes that blocks major vessels and airways. MF is a late complication of histoplasmosis. Studies in murine models of fibrosis have reported that IL-10 and TNF-α are elevated significantly (Ebrahimi, B, et al. *Am. J. Pathol.* 158:2117-2125, 2001).

Myelofibrosis (myeloid metaplasia, chronic idiopathic myelofibrosis, primary myelofibrosis) is a disorder of the bone marrow in which the marrow undergoes fibrosis. Myelofibrosis leads to progressive bone marrow failure. The mean survival is five years and causes of death include infection, bleeding, organ failure, portal hypertension, and leukemic transformation. It has been reported that TNF-α and IL-6 levels are elevated in animal models of viral-induced myelofibrosis (Bousse-Kerdiles, M., et al. *Ann. Hematol.* 78:434-444, 1999).

Retroperitoneal fibrosis (Ormond's disease) is a disease featuring the proliferation of fibrous tissue in the retroperitoneum. The retroperitoneum is the body compartment containing the kidneys, aorta, renal tract, and other structures. It has been reported that IL-1, IL-6 and TNF-α have key roles in the pathogenesis of retroperitoneal fibrosis (Demko, T., et al, *J. Am. Soc. Nephrol.* 8:684-688, 1997). Symptoms of retroperitoneal fibrosis may include, but are not limited to, lower back pain, renal failure, hypertension, and deep vein thrombosis.

Nephrogenic systemic fibrosis (NSF, nephrogenic fibrosing dermopathy) involves fibrosis of the skin, joints, eyes and internal organs. NSF may be associated with exposure to gadolinium. Patients develop large areas of hardened skin with fibrotic nodules and plaques. Flexion contractures with an accompanying limitation of range of motion also may occur. NSF shows a proliferation of dermal fibroblasts and dendritic cells, thickened collagen bundles, increased elastic fibers, and deposits of mucin. Some reports have suggested that a proinflammatory state provides a predisposing factor for causing nephrogenic systemic fibrosis (Saxena, S., et al. *Int. Urol. Nephrol.* 40:715-724, 2008), and that the level of TNF-α is elevated in animal models of nephrogenic systemic fibrosis (Steger-Hartmann, T., et al. *Exper. Tox. Pathol.* 61(6): 537-552, 2009).

4. Risk Factors 4.1. Primary Risk Factors 4.1.1. Cigarette Smoking

While a number of risk factors for fibrotic airway diseases have been identified (some of which may play a role in their causation), tobacco smoke remains the principal and most important cause of COPD. The greater the number of cigarettes smoked, the greater is the risk of developing fibrotic airway diseases. An overwhelming majority of people who develop fibrotic airway diseases are smokers, and their lung function decreases faster than that of non-smokers.

The most effective intervention is to stop smoking, preferably at an early stage. Smokers who quit will not recover lost lung function, but the rate of decline may revert to that of a non-smoker. Stopping smoking at an early stage improves the prognosis, regardless of how many attempts are needed to quit. Individual susceptibility to developing fibrotic airway diseases. in relation to cigarette smoking varies. Approximately 15% of smokers will develop clinically significant COPD, while approximately 50% will never develop any symptoms. The decrease in lung function is gradual, and the disease is usually diagnosed late because patients may adapt to symptoms of shortness of breath, or may not notice the symptoms. Studies have shown that depending on the number of cigarettes smoked per day, 24-47% of smokers develop airflow obstruction. Exposure to passive smoking increases susceptibility to the disease.

4.1.2. Alpha-1 Antitrypsin Deficiency

This rare inherited condition results in the complete absence of one of the key antiprotease protection systems in the lung. It is a recessive disorder affecting 1:4000 of the population. Patients with alpha-1 antitrypsin deficiency are at risk of developing emphysema at an early age-between the ages of 20 and 40 years- and often have a strong family history of the disease. Patients with the deficiency and emphysema inherit one abnormal gene from each parent; that is to say, the parents are carriers of the gene. Such parents will have half the normal levels of the antitrypsin in the blood, which may be enough to protect from developing emphysema. Likewise, all the children of an alpha-1 antitrypsin deficient patient will carry one abnormal gene, but will not be affected. The two common forms of alpha-1 antitrypsin deficiency result from point mutations in the gene that codes for alpha-1 antitrypsin.

4.2. Associated Risk Factors 4.2.1. Environmental Pollution

There is strong evidence that fibrotic airway diseases may be aggravated by air pollution, but the role of pollution in the etiology of fibrotic airway diseases is small when compared with that of cigarette smoking. Air pollution with heavy particulate matter, carbon, and sulphur dioxide, which are produced by the burning of coal and petroleum fossil fuels, are important causes or cofactors in the development of fibrotic airway diseases. These originate mainly from vehicle exhaust emissions, and photochemical pollutants such as ozone, in particular, are to be blamed. Indoor air pollution from biomass fuel burned for cooking and heating in poorly ventilated homes may be an important risk factor for fibrotic airway diseases, such as COPD, in developing countries, in particular for women.

4.2.2. Occupational Factors

Some occupations in which workers are exposed to coal, silica and cation, such as miners, textile workers and cement workers, are associated with an increased risk of fibrotic airway diseases. Exposure to cadmium, a heavy metal, and welding fumes has been recognized as a cause of emphysema since the 1950s.

Many dusty occupations are more hazardous than exposure to gas or fumes and are associated with the development of chronic bronchitis and various forms of airway obstructive disease. Shipyard welders and caulkers are also known to have an increased risk of developing fibrotic airway diseases, as well as those working in the construction industries that are exposed to cement dust.

4.2.3. Childhood Respiratory Infections

Chest infections in the first year of life, such as pneumonia and bronchiolitis, may predispose to the development of COPD in later life. This may be as a result or incomplete development of the respiratory system at birth until lung growth ends in early adulthood. If developing lungs are damaged, maximum potential lung function will not be achieved, producing symptoms of COPD at an early age.

4.3. Other Risk Factors

Other risk factors, which may play a role in causation and/or serves as early symptoms of fibrotic airway diseases, such as pulmonary fibroses, include hypersensitivity pneumonitis (most often resulting from inhaling dust contaminated with bacterial, fungal, or animal products), some typical connective tissue diseases (such as rheumatoid arthritis, systemic lupus erythematosus (SLE) and scleroderma), other diseases that involve connective tissue (such as sarcoidosis and Wegener's granulomatosis), infections, certain medications (e.g. amiodarone, bleomycin, busulfan, methotrexate, and nitrofurantoin), and radiation therapy to the chest.

5. Liver Tissue Remodeling

Liver tissue remodeling is of clinical interest because chronic damage to the liver induces necrosis or the parenchyma with consequent increased deposition of extracellular matrix (ECM) that underlies the occurrence of liver cirrhosis, hepatocellular carcinoma and liver fibrosis (Moshage H., J. Pathol. 1997; 181: 257-266). During remodeling, the liver undergoes rearrangement of the original architecture, with consequent changes in the spatial organization and redefinition of the histological borders (Giannelli G. et al., Histol. Histopathol. 2003; 18: 1267-1274). The break-down of tissue boundaries and rearrangement of tissue architecture seem to be regulated by matrix metalloproteinases (MMPs), a large family of zinc-endopeptidases with proteolytic activity toward ECM components (Giannelli G. et al., Histol. Histopathol. 2003; 18: 1267-1274).

One member of the MMP family, MMP2, is found throughout the human body and possesses a wide spectrum of action toward the ECM (Giannelli G. et al., Histol. Histopathol. 2003; 18: 1267-1274). It is secreted as a pro-enzyme and activated at the cellular surface by a membrane-type MMP (MT1-MMP) with the aid of an MMP inhibitor, tissue inhibitor of metalloproteinase-2 (TIMP2) (Strongin A. Y., et al., Biol. Chem. 1993; 268: 14033-14039). The proteolytic activity of MMP2 is balanced by the presence of TIMP2, which not only activates MMP2 by facilitating binding of MMP2 to MT1-MMP but also inhibits MMP-2, creating a feedback system in the regulation of ECM proteolysis (Fridman R. et al., Biochem. J. 1993; 289(Pt 2): 411-416).

Inflammation and mediators of inflammation, also play a role in liver tissue remodeling (Giannelli G. et al., Histol. Histopathol. 2003; 18: 1267-1274). It has been reported that a number of different cytokines, including tumor necrosis factor (TNF)-α, interleukin (IL)-1β, transforming growth factor (TGF)-β1 and platelet-derived growth factor (PDGF) are up-regulated in liver parenchyma during chronic hepatitis (Castilla A. et al., N. Engl. J. Med. 1991; 324: 933-940). The altered network of cytokines is thought to play a role not only in mediating inflammation, but also in modulating the expression of MMPs and TIMPs, thereby influencing the local proteolysis of ECM proteins (Knittel T. et al., J. Hepatol. 1999; 30: 48-60).

5.1 Liver Fibrosis

The pathogenesis of hepatic fibrosis involves significant deposition of fibrillar collagen and other extracellular matrix proteins. It is a dynamic process of wound healing in response to a variety of persistent liver injuries caused by factors such as ethanol intake, viral infection, drugs, toxins, cholestasis and metabolic disorders. Liver fibrosis distorts the hepatic architecture, decreases the number of endothelial cell fenestrations and causes portal hypertension (Mormone E. et al., Chem. Biol. Interact. 2011 Sep. 30; 193(3): 225-231). Key events are the activation and transformation of quiescent hepatic stellate cells into myofibroblast-like cells with the subsequent up-regulation of proteins such as α-smooth muscle actin, interstitial collagens, matrix metalloproteinases, tissue inhibitor of metalloproteinases and proteoglycans (Mormone E. et al., Chem. Biol. Interact. 2011 Sep. 30; 193(3): 225-231). Oxidative stress is a major contributing factor to the onset of liver fibrosis, and it is typically associated with a decrease in the antioxidant defense (Mormone E. et al., Chem. Biol. Interact. 2011 Sep. 30; 193(3): 225-231). Currently, there is no effective therapy for advanced liver fibrosis. In its early stages, liver fibrosis is reversible upon cessation of the causative agent; recent developments in our understanding of the process of hepatic fibrinogenesis suggest that a capacity for recovery from advanced fibrosis is possible (Pellicoro A, et al., Fibrogenesis & Tissue Repair 2012, 5(Suppl 1): S26; Benyon R C and Iredale J P, Gut 2000; 46: 443-446 (April)).

5.1.1 Etiology

Most chronic liver diseases are associated with fibrosis and are characterized by parenchymal damage and inflammation. Alcohol abuse, chronic viral hepatitis (HBV and HCV), obesity, autoimmune hepatitis, parasitic diseases (e.g., schistosomiasis), metabolic disorders (e.g., hemochromatosis and Wilson's disease), biliary disease, persistent exposure to toxins and chemicals and drug-induced chronic liver diseases are the most common causes of hepatic fibrosis (Mormone E. et al., Chem. Biol. Interact. 2011 Sep. 30; 193(3): 225-231).

5.1.1.1 Alcohol Consumption

Alcohol consumption is a predominant etiological factor in the pathogenesis of chronic liver diseases worldwide, resulting in fatty liver, alcoholic hepatitis, fibrosis/cirrhosis, and hepatocellular carcinoma (Miller A M, et al., Alcoholism-Clinical and Experimental Research 2011; 35(5): 787-793). Acetaldehyde, the product of alcohol metabolism, increases the secretion of transforming growth factor β1 (TGFβ1) and induces TGFβ type II receptor expression in hepatic stellate cells (HSC), the key collagen-producing cell within the liver (Anania F A, et al., Arch. Biochem. Biophys. 1996; 331(2): 187-193). TGFβ1 is a critical factor in the progression of alcoholic liver disease (ALD) in patients with steatosis and steatohepatitis and plays a significant role as mediator of alcohol-induced liver fibrosis (Weng H L, et al., Hepatology 2009; 50(1): 230-243). Acetaldehyde also selectively induces phosphorylation of Smad3 but not of Smad2 (Greenwel P, et al., Hepatology 2000; 31(1): 109-116). Both ethanol and acetaldehyde induce the COL1A2 promoter and up-regulate collagen I protein expression (Chen A, Biochem. J. 2002; 368(Pt 3): 683-693).

Hepatic alcohol metabolism generates reactive oxygen species (ROS) causing significant cell death (Parola M and Robino G, J. Hepatol. 2001; 35(2): 297-306). Oxidative stress promotes hepatocyte necrosis and/or apoptosis. Generation of ROS within hepatocytes may be a consequence of an altered metabolic state, as it occurs in nonalcoholic fatty liver disease and non-alcoholic steatohepatitis (Mormone E. et al., Chem. Biol. Interact. 2011 Sep. 30; 193(3): 225-231). Alternatively, it could result from ethanol metabolism as in alcoholic steatohepatitis, with ROS being generated mainly by the mitochondrial electron transport chain, cytochrome P450 isoforms such as cytochrome P4502E1 (CYP2E1), damaged mitochondria, xanthine oxidase, NADPH oxidase and generation of lipid peroxidation-end products (Haorah J, et al., Free Radic. Biol. Med. 2008; 45(11): 1542-1550). In addition, it is known that chronic alcohol consumption lowers glutathione levels, thus contributing to liver injury (Cederbaum A I, World J. Gastroenterol. 2010; 16(11): 1366-1376). ROS-derived mediators released by damaged neighboring cells can directly affect hepatic stellate cell (HSC) behavior. ROS up-regulate the expression of critical genes related to fibrogenesis, including pro-collagen type I, monocyte chemoattractant protein 1 (MCP-1) and tissue inhibitor of metalloproteinase-1 (TIMP1), possibly via activation of a number of critical signal transduction pathways and transcription factors, including c-jun N-terminal kinases (JNKs), activator protein 1 (AP-1) and nuclear factor kappa B (NFκB) (Bataller R, et al., Journal of Clinical Investigation 2005; 115(2): 209-218).

5.1.1.2 Chronic Viral Hepatitis

Chronic hepatitis B virus (HBV) and C virus (HCV) are the most common causes of liver disease worldwide, with an estimated 350 and 170 million individuals, respectively, with chronic infection (Custer B, et al., J. Clin. Gastroenterol. 2004; 38(10): S158-S168). In both cases, there is significant chronic liver injury with subsequent progression to advanced liver fibrosis.

5.1.1.3 Other Causes of Liver Fibrosis

Other factors contributing to hepatic fibrosis are obesity and steatosis, which can lead to nonalcoholic fatty liver disease and to chronic steatohepatitis. Nonalcoholic fatty liver disease has also been reported in non-obese individuals in developing countries (Das K, et al., Hepatology, 2010; 51(5): 1593-1602).

Autoimmune hepatitis, which is the result of anomalous presentation of human leukocyte antigen (HLA) class II in hepatocytes, causes cell-mediated immune responses against the host liver, which can lead to liver fibrosis (Lim Y S, et al., J. Hepatology, 2008; 48(1): 133-139). Parasitic infections, like schistosomiasis, also have been shown to trigger advanced liver fibrosis and portal hypertension (Andersson K L and Chung R T, Curr Treat. Options Gastroenterol., 2007; 10(6): 504-512).

Metabolic disorders, such as hemochromatosis and Wilson's disease, are typically accompanied by chronic hepatitis and fibrosis (Lefkowitch J H, Curr. Opin. Gastroenterol., 2006; 22(3): 198-208). In hereditary hemochromatosis, the excessive absorption and accumulation of iron in tissues and organs, including liver, is related to mutations in the HFE (High-iron) gene (Feder J N, et al., J. Hepatol., 2003; 38(6): 704-709). Pathological accumulation of iron exacerbates oxidative stress resulting in increased lipid peroxidation. This leads to destruction of organelle membranes and in turn, cell death via hepatocyte necrosis and/or apoptosis (Sidorska K, et al., J. Biotech., Computational Bio. And Bionanotech., 2011; 92(1): 54-65). Wilson's disease or hepatolenticular degeneration is a genetic disorder leading to copper accumulation in the liver and is due to a mutation in the APTase (ATP7B) that transports copper (Zhang S, et al., Hum. Mol. Genet., 2011 Aug. 15; 20(16): 3176-3187). Wilson's disease patients are characterized by liver fibrosis caused by severe mitochondrial changes, associated with an increased number of peroxisomes, cytoplasmic lipid droplets and the presence of lipolysosomes, characteristic cytoplasmic bodies formed by lipid vacuoles surrounded by electron-dense lysosomes. Nuclei are frequently involved, with disorganization of the nucleoplasm and with glycogen inclusions (Fanni D, et al., Curr. Med. Chem., 2014; DOI: 10.2174/0929867321666140601163244).

Cholestasis due to bile duct obstruction leads to chronic portal fibrosis and eventually cirrhosis. Moreover, chronic exposure to toxins or chemicals such as N-nitrosodimethylamine, carbon tetrachloride ($CCl_4$) or thioacetamide leads to severe hepatic fibrosis in experimental animal models (George J, et al., Gene Therapy, 2007; 14(10): 790-803; Domoenicali M, et al., J. Hepatol., 2009; 51(6): 991-999; Salguero P R, et al., Lab. Invest. 2008; 88(11): 1192-1203).

Exposure to these chemicals in humans is rare and generally occurs in industries where these chemicals are routinely used (Mormone E. et al., Chem. Biol. Interact. 2011 Sep. 30; 193(3): 225-231).

5.2. Cell Types Involved in the Pathogenesis of Liver Fibrosis

5.2.1 Hepatic Stellate Cells

Hepatic stellate cells (HSCs) reside in the space of Disse between hepatocytes and sinusoidal endothelial cells (Friedman S L, Gastroenterology, 2008; 134(6): 1655-1669). Quiescent HSCs are characterized by significant expression of desmin and vitamin A storage. Following liver injury, HSCs lose their vitamin A content, increase expression of α-smooth muscle actin (α-SMA), acquire a myofibroblast-like phenotype, become proliferative, motile, pro-fibrogenic, and contractile, and show abundant rough endoplasmic reticulum (Gressner A M, Kidney International, 1996; 49: S39-S45).

Many factors are known to contribute to activation of HSCs. Damage to hepatocytes and Kupffer cell activation are still considered the primary effectors driving HSC activation (Nieto N, et al., J. Biol. Chem. 2002; 277(12): 9853-9864; Nieto N, Hepatology, 2006; 44(6): 1487-1501). Mediators released from damaged hepatocytes, such as lipid peroxidation products, intermediate metabolites of drugs or hepatotoxins, acetaldehyde and 1-hydroxyethyl radical from alcohol metabolism, as well as ROS (e.g., hydrogen peroxide and superoxide radicals) are strong inducers of HSC activation (Mormone E. et al., Chem. Biol. Interact. 2011 Sep. 30; 193(3): 225-231).

Activated Kupffer cells release ROS and cytokines that are crucial for HSC activation as well (Nieto N, Hepatology, 2006; 44(6): 1487-1501). They are a major source of TGFβ and platelet-derived growth factor (PDGF), two potent pro-fibrogenic cytokines that traditionally have been considered key fibrogenic and proliferative stimuli to HSC (Tsukamoto H, Alcoholism-Clinical and Experimental Research, 1992; 23(5): 911-916). Kupffer cell phagocytic activity generates large amounts of ROS that could further activate HSC and induce their fibrogenic potential. Furthermore, it has been shown that the addition of ethanol and arachidonic acid synergized to activate Kupffer cells modulated the fibrogenic response by a mechanism involving TNFα, reduced glutathione, and TGFβ (Cubero F J and Nieto N, Hepatology, 2008; 48(6): 2027-2039).

Likewise, cytochrome P450 2E1-dependent generation of ROS has been shown to be critical for increased collagen I protein synthesis in co-cultures of hepatocytes and HSCs (Nieto N, et al., J. Biol. Chem., 2002; 277(12): 9853-9864).

5.2.2 Portal Fibroblasts

The portal connective tissue in healthy liver is surrounded by quiescent portal fibroblasts, which constitute a second population of liver cells implicated in portal fibrosis (Tuchweber B, et al., Laboratory Investigation, 1996; 74(1): 265-278). Derived from small portal vessels, they express markers distinct from HSC (e.g. elastin) (Li Z, et al., Hepatology, 2007; 46(4): 1246-1256). Proliferation of biliary cells is often accompanied by proliferation of portal fibroblasts, which form onion-like configurations around biliary structures and acquire a myofibroblast phenotype. These cells are thought to be involved in the early deposition of extracellular matrix (ECM) in portal zones (Desmouliere A, et al., Lab Invest, 1997; 76(6): 765-778).

5.2.3 Bone Marrow-derived Mesenchymal Stem Cells

Evidence suggests that bone marrow-derived stem cells are recruited during both progression and regression of liver fibrosis. During regression from $CCl_4$-induced hepatic fibrosis, bone marrow-derived mesenchymal stem cells migrate into the fibrotic liver, where they can express matrix metalloprotease-13 (MMP13) and MMP9 (Cheng Y J, et al., Life Sci., 2009; 85(13-14): 517-525). In addition, granulocyte colony-stimulating factor (G-CSF) and hepatocyte growth factor (HGF) treatment significantly enhances migration of bone marrow-derived cells into the fibrotic liver and accelerates the regression of liver fibrosis (Higashiyama R, et al., Hepatology, 2007; 45(1): 213-222). Overexpression of hepatocyte growth factor (HGF) together with granulocyte colony-stimulating factor (G-CSF), synergistically stimulate MMP9 expression, which is followed by accelerated resolution of fibrotic scars (Bird T G, et al., Cell Tissue Res., 2008; 331(1): 283-300). Although a significant contribution of bone marrow-derived cells has been shown in human liver fibrosis, it is unclear what type of mesenchymal stem cells are involved (Forbes S J, et al., Gastroenterology, 2004; 126(4): 955-963).

5.2.4 Hepatocytes and Biliary Epithelial Cells

Epithelial-to-mesenchymal transition (EMT) is emerging as a possible source of injury-associated mesenchymal cells derived either from resident hepatocytes or from biliary epithelial cells (Dooley S, et al., Gastroenterology, 2008; 135(2): 642-659; Nitta T, et al., Hepatology, 2008; 48(3): 909-919). The main molecules inducing EMT are TGFβ, epidermal growth factor (EGF), insulin-like growth factor-II (IGF-II) and fibroblast growth factor-2 (FGF-2) (Zeisberg M, et al., J. Biol. Chem., 2007; 282(32): 23337-23347). Hepatocytes that express albumin also express fibroblast-specific protein-1 (FSP 1) in response to $CCl_4$ in vivo or to TGFβ1 in vitro (Zeisberg M, et al., J. Biol. Chem., 2007; 282(32): 23337-23347). It has been reported that hepatocytes express COL1A1 in response to TGFβ1 in vitro, and that Smad signaling mediates EMT (Kaimori A, et al., J. Biol. Chem., 2007; 282(30): 22089-22101).

Biliary epithelial cells have been described to be involved in EMT in liver fibrogenesis. In primary biliary cirrhosis, it has been shown that cells of the bile duct express fibroblast-specific protein-1 (FSP 1) and vimentin, early markers of fibroblasts (Robertson H, et al., Hepatology, 2007; 45(4): 977-981). A consequence of EMT in biliary epithelial cells is the amplification of the pool of portal fibroblasts, contributing significantly to portal fibrosis. In vitro studies with human biliary epithelial cells have confirmed these clinical observations (Rygiel K A, Lab. Invest., 2008; 88(2): 112-123). Thus, EMT could be considered a mechanism participating in the pathogenesis of chronic cholestatic liver disease.

5.2.5 Fibrocytes

Fibrocytes are a circulating, bone marrow-derived, $CD34^+$ cell subpopulation with fibroblast-like properties initially associated with tissue repair in subcutaneous wounds (Bucala R. et al., Mol. Med. 1994; 1(1): 71-81). They comprise a fraction of about 1% of the circulating pool of leukocytes expressing markers of mesenchymal cells (Moore B B, et al., Am. J. Pathol., 2005; 166(3): 675-684). It has been hypothesized that bone marrow-derived circulating $CD34^+$ fibrocytes represent key mediators of liver fibrogenesis in the $Abcb4^{-/-}$ mice, which represents a reproducible, well-characterized non-surgical mouse model for cholangiopathy in humans (Roderfeld M, et al., Hepatology, 2010; 51(1): 267-276).

5.3 Molecular Pathogenesis of Liver Fibrosis

5.3.1 Cell-Cell and Cell-Matrix Interactions

Alterations in normal cell-cell and cell-matrix interactions play a significant role in pathogenesis of liver fibrosis. When normal cell-cell and cell-matrix interactions are altered due to hepatocyte necrosis or invasion of inflammatory cells, new interactions are established that trigger a fibrogenic response (Mormone E. et al., Chem. Biol. Interact. 2011 Sep. 30; 193(3): 225-231). In the fibrotic liver, significant quantitative and qualitative changes occur in the composition of ECM in the periportal and perisinusoidal areas (Zeisberg M, et al., Mol. Cell Biochem., 2006; 283(1-2): 181-189). Fibrotic scars are typically composed of fibrillar collagen type I and III, proteoglycans, fibronectin and hyaluronic acid (George J, et al., International J. Biochem. & Cell Biol., 2004; 36(2): 307-319). As a result, alteration in the physiological architecture of the liver occurs, particularly in the space of Disse, where the low electron-dense ECM is replaced by one rich in fibrillar collagens and fibronectin. This leads to loss of endothelial cell fenestrations, impaired exchange of solutes among neighboring cells, altered hepatocyte function and subsequent non-parenchymal cell damage (Hernandez-Gea V. and Friedman S L, Annu. Rev. Pathol. 2011; 6: 425-456).

5.3.2 Oxidative Stress

The term "oxidative stress" as used herein refers to a disturbance in the balance between the production of reactive oxygen species (free radicals) and antioxidant defenses.

Chronic HBV infection and long-term consumption of alcohol induce cell damage through increased generation of reactive oxygen species (ROS) (Muriel P, Hepatol. Int. 2009; 3(4): 526-536).

Oxidative stress, which favors mitochondrial permeability transition, is able to promote hepatocyte necrosis and/or apoptosis (Mormone E. et al., Chem. Biol. Interact. 2011 Sep. 30; 193(3): 225-231). It has been hypothesized that in some clinically relevant conditions, generation of ROS within hepatocytes may represent an altered metabolic state as in non-alcoholic fatty liver disease and non-alcoholic steatohepatitis, or significant ethanol metabolism as it occurs in alcoholic steatohepatitis (Mormone E. et al., Chem. Biol. Interact. 2011 Sep. 30; 193(3): 225-231).

ROS are generated mainly via the mitochondrial electron transport chain or via activation of cytochrome P450 (mostly cytochrome P450 2E1), NADPH oxidase, xanthine oxidase or via mitochondrial damage. The ROS generated can directly affect HSC and myofibroblast behavior (Tilg H and Hotamisligil G S, Gastroenterology, 2006; 131(3): 934-945; Nieto N, Hepatology, 2006; 44(6): 1487-1501). ROS up-regulate the expression of critical fibrosis-associated genes such as COL1A1, COL1A2, MCP1 and TIMP1 via activation of signal transduction pathways and transcription factors, including JNK, activator protein-1 (AP-1) and NFκB (Bataller R and Brenner D A, Journal of Clinical Investigation, 2005; 115(2): 209-218). ROS generation in HSCs and myofibroblasts occurs in response to several known pro-fibrogenic mediators, including angiotensin II, platelet-derived growth factor (PDGF), TGFβ and leptin (De Minicis S, et al., Gastroenterology, 2006; 131(1): 272-275). Overall, a decrease in the antioxidant defense system, such as GSH, catalase or SOD, in conjunction with enhanced lipid peroxidation, leads to a pro-fibrogenic response by enhancing collagen I protein expression (George J, Clin. Chim. Acta, 2003; 335(1-2): 39-47).

p38 mitogen-activated protein kinases (MAPK) may be essential in the up-regulation of proinflammatory cytokines and can be activated by transforming growth factor β (TGFβ), tumor necrosis factor-α (TNFα), interleukin-1β (IL-1β), and oxidative stress (Tormos A M, et al., Hepatology, 2013; 57(5): 1950-1961). Substrates of p38 include protein kinases, such as MAPKAP kinase 2 (MK2) and MK5, and transcription factors, such as ATF2, p53, and Mitf (Hui L, et al., Cell Cycle, 2007; 6(20): 2429-2433). These diverse targets mediate the activated p38 signal to various types of cellular functions such as differentiation, apoptosis, cytokine production, and cell cycle control (Nakagawa H and Maeda S, Pathology Research International, 2012; doi: 10.1155/2012/172894). Recent in vivo studies have shown that stress-activated mitogen-activated protein kinase (MAPK) signaling converging on c-Jun NH2-terminal kinase (JNK) and p38 plays a central role in inflammation-mediated liver injury and compensatory hepatocyte proliferation (Sakurai T, et al., PNAS, 2006; 103(28): 10544-10551; Hui L, et al., Nature Genetics, 2007; 39(6): 741-749; Hui L, et al., JCI, 2008; 118(12): 3943-3953; Sakurai T, et al., Cancer Cell, 2008; 14(2): 156-165; Maeda S, Gastroenterology Research and Practice, 2010; doi: 10.1155/2010/367694; Wagner E F and Nebreda A R, Nature Reviews Cancer, 2009; 9(8): 537-549; Min L, et al., Seminars in Cancer Biology, 2011; 21(1): 10-20).

5.3.3 MMPs and TIMPs

The ECM is a highly dynamic milieu subject to constant remodeling. Life-threatening pathological conditions arise when ECM remodeling becomes excessive or uncontrolled. Among the cells involved in hepatic ECM degradation are HSCs, neutrophils and macrophages. MMPs are the main enzymes responsible for ECM degradation (Goto T, et al., Pathophysiology, 2004; 11(3): 153-158). Tissue inhibitors of matrix metalloproteinase-1 (TIMPs) have the ability to inhibit MMPs (Goto T, et al., Pathophysiology, 2004; 11(3): 153-158). Therefore, regulation of the MMP-TIMP balance is crucial for efficient ECM remodeling. The MMP-TIMP balance becomes tipped in response to multiple pro-fibrogenic insults. Activated HSCs not only synthesize and secrete ECM proteins such as collagens type I and type III, but also produce MMP1 and MMP13 (Iredale J P, et al., Clin. Sci. (Lond), 1995; 89(1): 75-81; Knittel T, et al., Hisotchem. Cell Biol., 2000; 113(6): 443-453). However, MMP1 and MMP13 expression decreases as HSC activation progresses, while the activity of other MMPs remains relatively constant, except for MMP2 and MMP9 (Benyon R C and Arthur M J, Semin. Liver Dis. 2001; 21(3): 373-384). The increase in MMP2 activity is associated with distortion of the normal lobular architecture, which further activates HSC (Benyon R C and Arthur M J, Semin. Liver Dis. 2001; 21(3): 373-384). Activated HSCs up-regulate the expression and synthesis of TIMP1 and TIMP2 (Iredale J P, et al., Hepatology, 1996; 24(1): 176-184). TIMP1 not only prevents the degradation of the rapidly increasing ECM by blocking MMPs, but also inhibits the apoptosis of activated HSCs (Murphy F R, et al., J. Biol. Chem., 2002; 277(13): 11069-11076). The net result is the deposition of mature collagen fibers within the space of Disse which results in scarring.

6. Renal Fibrosis

Renal fibrosis is the result of excessive accumulation of extracellular matrix that occurs in nearly every type of chronic kidney disease (Liu Y, Kidney International 2006; 69: 213-217). The progression from chronic kidney disease to renal fibrosis often results in widespread tissue scarring, complete destruction of kidney parenchyma, and end-stage renal failure, a condition that requires dialysis or kidney replacement (Schieppati A et al., Kidney International 2005; 68(Suppl 1): S7-S10). Renal fibrosis represents a failed wound-healing process of kidney tissue after chronic, sustained injury. Several cellular pathways, including mesangial and fibroblast activation, as well as tubular epithelial-mesenchymal transition, have been identified as generating the matrix-producing cells in renal disease conditions (Liu Y, Kidney International 2006; 69: 213-217).

6.1 Cellular Events in Renal Fibrosis

Renal fibrosis is often pathologically described as glomerulosclerosis, tubule-interstitial fibrosis, inflammatory infiltration and loss of renal parenchyma characterized by tubular atrophy, capillary loss and podocyte depletion (Liu Y, Kidney International 2006; 69: 213-217). The underlying cellular events leading to these histologic presentations include mesangial and fibroblast activation, tubular epithelial to mesenchymal transition (EMT), monocyte/macrophage, and T-cell infiltration, and cell apoptosis (Eddy A A, Pediatr. Nephrol. 2000; 15: 290-301; Iwano M and Neilson E G, Curr Opin. Nephrol. Hypertens. 2004; 13: 279-284; Hirschberg R, J. Am. Soc. Nephrol. 2005; 16: 9-11; Liu Y, J. Am. Soc. Nephrol. 2004; 15: 1-12).

6.2 Molecular Pathogenesis of Renal Fibrosis

Although more than a dozen different fibrogenic factors have been implicated in the pathogenesis of renal fibrosis, including various cytokines and hormonal, metabolic, and hemodynamic factors, it is widely accepted that transforming growth factor-β (TGF-β) and its downstream Smad signaling mediators play an essential role (Bottinger E P and Bitzer M, J. Am. Soc. Nephrol. 2002; 13: 2600-2610; Schnaper H W et al., Am. J. Physiol. Renal. Physiol. 2003; 284: F243-F252). In vitro, TGF-β as a sole factor can stimulate mesangial cells, interstitial fibroblasts, and tubular epithelial cells to undergo myofibroblastic activation or transition, to become matrix-producing fibrogenic cells (Liu Y, Kidney International 2006; 69: 213-217; Bottinger E P and Bitzer M, J. Am. Soc. Nephrol. 2002; 13: 2600-2610; Schnaper H W et al., Am. J. Physiol. Renal. Physiol. 2003; 284: F243-F252). Expression of exogenous TGF-β, either via gene delivery in vivo or in transgenic mice, causes renal fibrosis (Liu Y, Kidney International 2006). Conversely, inhibition of TGF-β by multiple strategies suppresses renal fibrotic lesions and prevents progressive loss of kidney function (Liu Y, Kidney International 2006; 69: 213-217; Bottinger E P and Bitzer M, J. Am. Soc. Nephrol. 2002; 13: 2600-2610; Schnaper H W et al., Am. J. Physiol. Renal. Physiol. 2003; 284: F243-F252). TGF-β induction also appears to be a convergent pathway that integrates, directly or indirectly, the effects of many other fibrogenic factors. Some of these, such as angiotensin II and high glucose, act as an upstream TGF-β inducer, whereas others, such as connective tissue growth factor, work as its downstream effector (Liu Y, Kidney International 2006; 69: 213-217; Bottinger E P and Bitzer M, J. Am. Soc. Nephrol. 2002; 13: 2600-2610; Schnaper H W et al., Am. J. Physiol. Renal. Physiol. 2003; 284: F243-F252).

The TGF-β signal is transduced through its cell membrane type I and type II serine/threonine kinase receptors (Bottinger E P and Bitzer M, J. Am. Soc. Nephrol. 2002; 13: 2600-2610). Receptor activation triggers the phosphorylation and activation of its downstream signaling mediators, Smad2 and Smad3 (Liu Y, Kidney International 2006). Phosphorylated Smad2/3 bind to common partner Smad4, and subsequently translocate into nuclei, where they control the transcription of TGF-β-responsive genes (Liu Y, Kidney International 2006; 69: 213-217; Bottinger E P and Bitzer M, J. Am. Soc. Nephrol. 2002; 13: 2600-2610; Schnaper H W et al., Am. J. Physiol. Renal. Physiol. 2003; 284: F243-F252). TGF-β/Smad signaling is regulated at both prereceptor and postreceptor stages through multiple levels of modulation, which include TGF-β gene expression, latent TGF-β activation, its receptor expression, and postreceptor Smad signaling (Liu Y, Kidney International 2006). In the fibrotic kidney, a multitude of mechanisms lead to a hyperactive TGF-β/Smad signaling, including induction of TGF-β expression, enhanced post-translational activation of TGF-β protein and its release from latent complexes. The receptors for TGF-β are also induced in diseased kidney (Liu Y, Kidney International 2006; 69: 213-217).

Smad signaling in normal kidney is tightly constrained by a family of proteins known as Smad transcriptional corepressors, which include SnoN, Ski, and TGIF (Liu Y, Kidney International 2006; 69: 213-217). Through various mechanisms, these Smad antagonists effectively confine Smad-mediated gene transcription, thereby safeguarding the tissue from unwanted TGF-β response (Liu Y, Kidney International 2006; 69: 213-217). Recently, it has been demonstrated that SnoN and Ski are progressively diminished in the fibrotic kidney, suggesting that the loss of Smad antagonists is an important mechanism that amplifies the TGF-β signal (Yang J et al., J. Am. Soc. Nephrol. 2003; 14: 3167-3177).

6.3 Matrix-Degrading Enzymes in Renal Fibrosis

It is generally believed that the excessive matrix accumulation seen in the fibrotic kidney results from both overproduction of matrix components and defects in its degradation. This notion is supported by many observations that plasminogen activator inhibitor-1 and tissue inhibitor of matrix metalloproteinase-1 are often upregulated in the diseased kidney. Renal tissue produces a number of proteases, in which the plasminogen/plasmin and matrix metalloproteinase (MMP) systems constitute a proteolytic network that is capable of degrading all components of matrix proteins (Liu Y, Kidney International 2006).

Given their proteolytic ability, matrix-degrading enzymes are historically considered to reduce matrix accumulation, thereby attenuating renal fibrosis after injury. However, recent genetic studies using knockout mice have painted a different and complex picture of the function of these proteins in relation to fibrotic lesions in vivo (Liu Y, Kidney International 2006). It has been reported that ablation of tissue-type plasminogen activator (tPA) protects the kidney from developing interstitial fibrosis in obstructive nephropathy, which seems to have little to do with its proteolytic activity (Yang J et al., J. Clin. Invest. 2002; 110: 1525-1538). The pathogenic effect of tPA in obstructive nephropathy primarily depends on its ability to induce MMP-9 gene expression (Liu Y, Kidney International 2006). Increased MMP-9 disrupts the integrity of tubular basement membrane, which leads to the promotion of tubular EMT. Further investigations reveal that tPA is able to bind to the cell membrane receptor low-density lipoprotein receptor-related protein-1, induces its phosphorylation on tyrosine residues, triggers intracellular signal transduction, and trans-activates MMP-9 gene expression in renal interstitial fibroblasts (Liu Y, Kidney International 2006).

Plasmin, a serine protease that can directly degrade matrix proteins and activate MMPs, is also thought to be beneficial in reducing renal fibrosis (Liu Y, Kidney International 2006). However, knockout of the plasminogen gene does not aggravate the fibrotic lesions after ureteral obstruction. Instead, mice lacking plasmin display a reduced collagen accumulation, suggesting a significant pathogenic effect of this enzyme (Edgtton K L et al., Kidney International 2004; 66: 68-76).

MMP-2 also is found to be necessary and sufficient to induce tubular EMT in vitro (Cheng S and Lovett D H, Am. J. Pathol. 2003; 162: 1937-1949). Transgenic mice with overexpression of MMP-2 display fibrotic lesions (Liu Y, Kidney International 2006). A recent study also demonstrates that MMP-3 induces Rac1 expression, which causes an increase in cellular reactive oxygen species and promotes EMT (Radisky D C et al., Nature 2005; 436: 123-127).

7. Drug-Induced Kidney Injury

Various in vitro and in vivo studies have shown that the administration of certain drugs acts as a stimulus to trigger various MAPK cascades, which in turn, mediate cellular responses to kidney injury (Naughton C. A., American Family Physician, vol. 78, no. 6, pp. 743-750, 2008). Activation and dysregulation of normal MAPK signaling pathways has been implicated in both acute and chronic kidney injury (Cassidy H et al., Journal of Signal Transduction, vol. 2012, Article ID 463617, 15 pages). Renal biopsies in humans have shown upregulation of MAPKs in a variety of renal conditions, suggesting involvement in human renal disease (Cassidy H et al., Journal of Signal Transduction, vol. 2012, Article ID 463617, 15 pages).

7.1 Antibiotic-induced Kidney Injury

Acute kidney injury (AKI) is a common side effect of antibiotic therapy. Several studies have implicated the MAPK signaling cascade in antibiotic-induced renal injury initiated by several distinct classes of antibiotics.

For example, Volpini et al. showed that MAPKs may be involved in the pathogenesis of acute renal failure following treatment with gentamicin (Volpini R. A. et al., Brazilian Journal of Medical and Biological Research, vol. 39, no. 6, pp. 817-823, 2006). Briefly, the expression of p-p38 MAPK and NF-κB in the kidney during the evolution of tubulointerstitial nephritis and its relationship with histological features and renal function was investigated in gentamicin-treated rats in the presence or absence of an NF-κB inhibitor. Data obtained in this study showed that p38 MAPK expression is increased during the development of gentamicin-induced interstitial nephritis and that such alteration is associated with enhancement of NF-κB expression and the inflammatory process in the renal cortex, suggesting the involvement of the p38 MAPK pathway in gentamicin-induced renal lesions (Volpini R. A. et al., Brazilian Journal of Medical and Biological Research, vol. 39, no. 6, pp. 817-823, 2006). Likewise, Ozbek et al. found that p38-MAPK is upregulated in rat kidneys following gentamicin treatment, and it has been shown that combination treatment with the lipid-lowering drug, atorvastatin, ameliorated gentamicin-induced nephrotoxicity, through inhibition of p38-MAPK and NF-κB expression (Ozbek E. et al., Renal Failure, vol. 31, no. 5, pp. 382-392, 2009).

A study investigating the effects of vancomycin exposure in renal $LLCPK_1$ cells on cell proliferation showed a dose- and time-dependent increase in cell number and total cellular protein (Cassidy H et al., Journal of Signal Transduction, vol. 2012, Article ID 463617, 15 pages; King D. W. and Smith M. A., Toxicology in Vitro, vol. 18, no. 6, pp. 797-803, 2004). These effects were inhibited by pretreatment with the MAPK inhibitor, PD098059, thus preventing vancomycin-induced entry into the cell cycle. This data suggests an association between the cell proliferative effects of vancomycin and the induction of MAPK signaling cascades (Cassidy H et al., Journal of Signal Transduction, vol. 2012, Article ID 463617, 15 pages; King D. W. and Smith M. A., Toxicology in Vitro, vol. 18, no. 6, pp. 797-803, 2004).

7.2 Calcineurin-Inhibitor-Induced Kidney Injury

The calcineurin inhibitors (CNIs) CsA and FK506 are widely used in transplant organ recipients. However, it has been shown that in kidney allografts, CsA and FK506 cause tubulointerstitial, as well as mesangial, fibrosis (Sutherland B. W. et al., Oncogene, vol. 24, no. 26, pp. 4281-4292, 2005). The fibrogenic effect of CNIs in the renal allograft is predominantly mediated by elevated intrarenal expression of TGF-β and subsequent excessive extracellular matrix (ECM) generation (Shihab F. S. et al., American Journal of Kidney Diseases, vol. 30, no. 1, pp. 71-81, 1997; Ignotz R. A. and Massague J., Journal of Biological Chemistry, vol. 261, no. 9, pp. 4337-4345, 1986; Schnaper H. W. et al., American Journal of Physiology, vol. 284, no. 2, pp. F243-F252, 2003). Studies using rat kidney mesangial cells have shown that CsA and FK-506 induce an extremely rapid and dose-dependent increase of Y-Box-binding protein-1 (YB-1) content in a cell type-specific manner. YB-1, a member of the family of cold-shock proteins with mitogenic properties which controls, among other things, TGF-β1 translation in proximal tubular cells, is a downstream target of MAPK ERK1/2 (Lu Z. H. et al., Molecular and Cellular Biology, vol. 25, no. 11, pp. 4625-4637, 2005; Fraser D. J. et al., Kidney International, vol. 73, no. 6, pp. 724-732, 2008; Hanssen L. et al., Journal of Immunology, vol. 187, no. 1, pp. 298-308, 2011).

7.3 Chemotherapeutic Agent-induced Kidney Injury

Cancer chemotherapeutics include, without limitation, alkylating agents (e.g., cyclophosphamide); antimetabolites (e.g., methotrexate); plant alkaloids (e.g., etoposide); anthracyclines (e.g., doxirubicin); antitumor antibiotics (e.g., mitomycin C); platinum compounds (e.g., cisplatin); and taxanes (e.g., taxol) (Chu E. and Devita Jr. V. T., Eds., Physicians' Cancer Chemotherapy Drug Manual 2001, Jones and Bartlett Publishers, London, U K, 2001). Chemotherapeutic agents can cause nephrotoxicity in various ways, with some drugs exerting immediate effects on renal function while others are known to have cumulative effects, causing renal injury after long periods of use (Vogelzang N. J., Oncology, vol. 5, no. 10, pp. 97-105, 1991). For example, cisplatin, one of the most successful antineoplastic agents to date, causes acute kidney injury with clinically measureable nephrotoxicity usually detected 10 days after administration (Cassidy H et al., Journal of Signal Transduction, vol. 2012, Article ID 463617, 15 pages).

It is believed that MAPK plays a pivotal role in cisplatin-induced nephrotoxicity. Arany et al. showed that ERK, and not p38 or JNK/SAPK inhibition, prevented cisplatin induced toxicity (Arany I. et al. American Journal of Physiology, vol. 287, no. 3, pp. F543-F549, 2004). Other studies have shown that pharmacological inhibition of p38 both in vitro and in vivo prevented toxicity (Ramesh G. and Reeves W. B., American Journal of Physiology, vol. 289, no. 1, pp. F166-F174, 2005; Francescato H. D. C. et al., Life Sciences, vol. 84, no. 17-18, pp. 590-597, 2009). It also has been shown that JNK/SAPK inhibition results in a significant reduction in cisplatin-induced nephrotoxicity in vivo (Francescato H. D. C. et al., Nephrology Dialysis Transplantation, vol. 22, no. 8, pp. 2138-2148, 2007). Pabla et al. identified PKCδ as a critical regulator of cisplatin nephrotoxicity. The data showed that during cisplatin nephrotoxicity, Src interacted with, phosphorylated, and activated PKCδ in mouse kidney lysates. After activation, PKCδ regulated MAPKs, but not p53, to induce renal cell apoptosis. Thus, inhibition of PKCδ, pharmacologically or genetically, attenuated kidney cell apoptosis and tissue damage, preserving renal function during cisplatin treatment. Conversely, inhibition of PKCδ enhanced cisplatin-induced cell death in multiple cancer cell lines and, remarkably, enhanced the chemotherapeutic effects of cisplatin in several xenograft and syngeneic mouse tumour models while protecting kidneys from nephrotoxicity (Pabla N. et al., Journal of Clinical Investigation, 7.4 Nonsteroidal Anti-Inflammatory Drug (NSAID)-Induced Kidney Injury Nonsteroidal anti-inflammatory drugs (NSAIDs) include carboxylic acids (e.g., aspirin); acetic acids (e.g., diclofenac); propionic acids (e.g., ibuprofen and ketoprofen); and Cox-2 inhibitors (e.g., celecoxib). NSAIDs are known to be nephrotoxic with the spectrum of nephrotoxicity including acute tubular necrosis, acute tubulointerstitial nephritis, glomerulonephritis, renal papillary necrosis, chronic renal failure, salt and water retention, hypertension, and hyperkalaemia (Perazella M. A. and Tray K., American Journal of Medicine, vol. 111, no. 1, pp. 64-67, 2001; Ejaz P. et al., Journal of Association of Physicians of India, vol. 52, pp. 632-640, 2004; Schier R. W. and Henrich W. L., Journal of the American Medical Association, vol. 251, no. 10, pp. 1301-1302, 1984).

Hou et al. investigated the molecular basis of the renal injury induced by NSAIDs by evaluating the expression of the stress marker, heme oxygenase-1 (HO-1), in celecoxib-stimulated glomerular mesangial cells (Ho C. C. et al., Annals of the New York Academy of Sciences, vol. 1042, pp. 235-245, 2005). Treatment with celecoxib resulted in a concentration- and time-dependent increase of HO-1 expression (Ho C. C. et al., Annals of the New York Academy of Sciences, vol. 1042, pp. 235-245, 2005). Conversely treatment with N-acetylcysteine, a free radical scavenger, strongly decreased HO-1 expression, suggesting the involvement of reactive oxygen species (ROS) (Ho C. C. et al., Annals of the New York Academy of Sciences, vol. 1042, pp. 235-245, 2005). Treatment with various MAPK inhibitors showed that only a specific JNK inhibitor attenuated celecoxib-induced HO-1 expression (Ho C. C. et al., Annals of the New York Academy of Sciences, vol. 1042, pp. 235-245, 2005). Kinase assays demonstrated increased phosphorylation and activation of c-JNK following NSAID treatment (Ho C. C. et al., Annals of the New York Academy of Sciences, vol. 1042, pp. 235-245, 2005). Treatment with a PI-3K specific inhibitor prevented the enhancement of HO-1 expression, which correlated with inhibition of the phosphorylation of the PDK-1 downstream substrate Akt/protein kinase B (PKB) (Ho C. C. et al., Annals of the New York Academy of Sciences, vol. 1042, pp. 235-245, 2005). The results of this study suggested that celecoxib-induced HO-1 expression in glomerular mesangial cells may be mediated by ROS via the JNK-PI-3K cascade (Ho C. C. et al., Annals of the New York Academy of Sciences, vol. 1042, pp. 235-245, 2005).

8. Vascular Fibrosis

Vascular fibrosis is characterized by reduced lumen diameter and arterial wall thickening, which is attributed to excessive deposition of extracellular matrix (ECM). It involves proliferation of vascular smooth muscle cell (VSMC), accumulation of ECM and inhibition of matrix degradation. It is associated with the renin-angiotensin-aldosterone system (RAAS), oxidative stress, inflammatory factors, growth factors and imbalance of endothelium-derived cytokine secretion. Specifically, Angiotensin II (Ang II) and aldosterone (the circulating effector hormones of RAAS) have been implicated in the pathophysiology of vascular fibrosis. Transforming growth factor-beta (TGF-beta) has been shown to play a critical role in ECM accumulation and vascular remodeling via up-regulation of connective tissue growth factor (CTGF) and fibroblast growth factor among others. An imbalance between matrix metalloproteinases (MMPs) and tissue inhibitors of metalloproteinases (TIMPs) results in collagen accumulation and adverse matrix remodeling. Aberrant expression or function of peroxisome proliferator-activated receptor gamma (PPAR gamma) has also been reported to contribute to the progression of pathological fibrosis and vascular remodeling (Lan T-H et al., Cardiovascular Pathology 22 (2013) 401-407).

It has been suggested that risk factors associated with cardiovascular disease, including hypertension, hyperglycemia, dyslipidemia and hyperhomocysteinemia (HHcy), also act as initiation and progression factors of vascular fibrosis (Lan T-H et al., Cardiovascular Pathology 22 (2013) 401-407).

8.1. Pathogenesis of Vascular Fibrosis 8.1.1. Renin-angiotensin-aldosterone system (RAAS)

RAAS has emerged as one of the essential links in the development of vascular remodeling (Sun Y, Congest. Heart Fail. 2002; 8:11-6). Angiotensin II (Ang II) and aldosterone, the circulating effector hormones of RAAS, are recognized as responsible for the pathophysiology of vascular fibrosis.

Ang II, the principal effector hormone of the RAAS, not only mediates immediate physiological effects of vasoconstriction and blood pressure regulation, but also regulates many processes implicated in vascular pathophysiology, including cell growth/apoptosis of vascular cells, migration of VSMCs, inflammatory responses and ECM remodeling (Ruiz-Ortega M et al., Hypertension 2001; 38:1382-7). Ang II acts through two main specific receptors, AT1 and AT2. Binding of Ang II to AT1 receptor activates a series of signaling cascades, including epidermal growth factor receptor (EGFR), platelet-derived growth factor receptor (PDGFR), insulin receptor, c-Src family kinases, Ca2+-dependent proline-rich tyrosine kinase 2 (Pyk2), focal adhesion kinase (FAK) and Janus kinases (JAK), which in turn regulate the Ang II pathologic effects in the vasculature (Hunyady L, Catt K J, Mol Endocrinol 2006; 20: 953-70). AT1 also has been implicated in cell growth and hypertrophy by activating PKC and MAPKs, including ERK1/2, p38 MAPK, and c-Jun NH2-terminal kinase (JNK) (Suzuki H et al., Curr Med Chem Cardiovasc Hematol Agents 2005; 3:305-22). Ang II-mediated EGFR activation occurs in a Src-dependent, redox-sensitive manner, and also by calcium-dependent and -independent pathways (Eguchi S et al., J Biol Chem 1998; 273:8890-6; Ushio-Fukai M et al., Arterioscler Thromb Vasc Biol 2001; 21:489-95). Evidence suggests that Ang II stimulates the phosphorylation of PDGF-β receptor (PDGFβ-R) through the binding of tyrosine-phosphorylated Shc to PDGFβ-R (Heeneman S et al., J Biol Chem 2000; 275: 15926-32). Ang II also has been shown to increase serine phosphorylation of the insulin receptor β-subunit, causing insulin receptor substrate (IRS-1) inactivation both by uncoupling it from downstream effectors (PI3K, PDK1, Akt) and by targeting it for degradation in the proteasomal pathway (Folli F et al., J Clin Invest 1997; 100: 2158-69; Natarajan R et al., Hypertension 1999; 33:378-84). Ang II promotes cellular proliferation and ECM synthesis and induction of several mediators, such as TGF-beta, connective tissue growth factor (CTGF), cytokines (e.g., IL-6, TNF-alpha), and monocyte chemoattractant protein type 1 (MCP-1). It is generally accepted that Ang II-induced ECM production is mainly mediated by up-regulation of TGF-β and its downstream mediator CTGF (Border W A, Noble N A, Hypertension 1998; 31:181-8; Wolf G, Kidney Int 2006; 70:1914-9). Ang II activates the binding of nuclear proteins to the binding site of the activator protein-1 (AP-1) of the TGF-β1 promoter through PKC and p38 MAPK-dependent pathways. Recent studies have shown that Ang II also induces CTGF expression via TGF-beta-independent Smad signaling pathways and increases the production of MMPs involved in matrix degradation, which leads to weakening of vessel walls (Rodriguez-Vita J et al., Circulation 2005; 111:2509-17; Yang F et al., Hypertension 2009; 54:877-84). Ang II is known to stimulate aldosterone production, thus promoting fibrosis and collagen formation (Brilla C G et al., J Mol Cell Cardiol 1994; 26:809-20).

Aldosterone promotes fibrosis and collagen formation through several mechanisms, including upregulation of Ang II receptors, stimulation of TGF-β and CTGF synthesis, stimulation of MMPs activity, and participation in VSMC hypertrophy and endothelial dysfunction (Epstein M, Nephrol Dial Transplant 2003; 18:1984-92). It has been reported that aldosterone stimulates the expression of plasminogen activator inhibitor-1 (PAI-1), the major physiological inhibitor of plasminogen activators, which is implicated in ECM accumulation by inhibiting matrix degradation and inducing CTGF expression via both p38 MAPK cascade and mineralocorticoid receptor (Brown N J, et al., Kidney Int 2000; 58:1219-27; Lee Y S et al., J Korean Med Sci 2004; 19: 805-11). Aldosterone has been shown to induce MMP activity in adult rat ventricular myocytes via activation of the mineralocorticoid receptor, PKC, and reactive oxygen species (ROS)-dependent activation of the MEK/ERK pathway (Rude M K et al., Hypertension 2005; 46:555-61).

8.1.2. Transforming Growth Factor-β (TGF-β)

Transforming growth factor (TGF)-β is a ubiquitously expressed cytokine that belongs to a large superfamily, of which TGF-β1 is most frequently up-regulated in ECM remodeling (Massague J et al., Cell 2000; 103:295-309). TGF-β signals through a heteromeric cell-surface complex of two types of transmembrane serine/threonine kinases, type I receptors and type II receptors (Derynck R et al., Nat Genet 2001; 29:117-2). Type I receptor phosphorylation, which is activated by type II receptors, is essential for the activation of downstream target proteins (Derynck R, Feng X H, Biochim Biophys Acta 1997; 1333:F105-50).

TGF-β predominantly transmits signals through transcription factors called Smads (Massague J et al., Genes Dev 2005; 19: 2783-810.). Smad2 and Smad3 are specific mediators of TGF-beta/activin pathways, whereas Smad1, Smad5 and Smad8 are involved in bone morphogenetic protein (BMP) signaling (especially BMP-7) which inhibits VSMC proliferation via I-Smad (Smad6 and Smad7) activation (Singh N N, Ramji D P, Cytokine Growth Factor Rev 2006; 17:487-99). Studies have shown that overexpression of Smad6 may selectively inhibit BMP receptor signaling whereas Smad7 inhibits both BMP and TGF-beta/activin receptor signaling (Nakao A et al., Trends Mol Med 2002; 8: 361-3). Smad7 expression, resulting in the inhibition of TGF-beta-induced fibronectin, collagen and CTGF expression, can also be induced by activation of the EGF receptor, IL-gamma signaling through signal transducer and activator of transcription (STAT), and TNF-alpha induced activation of NF-Kb (Wang M et al., Arterioscler Thromb Vasc Biol 2006; 26:1503-9; Ikedo H et al., Int J Mol Med 2003; 11: 645-50.).

In addition to the Smad pathway, non-Smad pathways also participate in TGF-beta signaling and serve as nodes for crosstalk with other major signaling pathways (Ruiz-Ortega M et al., Cardiovasc Res 2007; 74: 196-206; Bobik A, Arterioscler Thromb Vasc Biol 2006; 26: 1712-20). The JNK/p38, Erk/MAPK, Rho-like GTPase, and PI3/Akt pathways are believed to reinforce, attenuate or modulate downstream cellular responses possibly accounting for the varying effects of TGF-β (Zhang F et al., J Biol Chem 2009; 284:17564-74). TGF-β participates in the pathogenesis of many cardiovascular diseases, including hypertension, restenosis, atherosclerosis, cardiac hypertrophy, and heart failure. TGF-β plays a critical role in ECM accumulation and vascular remodeling via up-regulating the production of several agents, including growth factors (e.g., CTGF, FGF), related genes (e.g., c-myc, cjun, junBJI, p53) and PAI-1 (Perbal B, Lancet 2004; 363: 62-4; Hayashida T et al., FASEB J 2003; 17:1576-8; Samarakoon R et al., J Cell Physiol 2005; 204:236-46; Seay U et al., J Pharmacol Exp Ther 2005; 315:1005-12). Angiotensin II, mechanical stress, endothelin-I, high glucose, extremes of temperature and pH, steroids, and reactive oxygen species have been found to stimulate TGF-β activation as a mediator of vascular fibrosis (Ruiz-Ortega M et al., Curr Hypertens Rep 2003; 5: 73-9; Li J H et al., Kidney Int 2003; 63: 2010-9.). In addition, MMPs (such as MMP-2 and -9) enhance the release of TGF-β, which stimulates TIMP, ultimately resulting in the inhibition of ECM (i.e., ECM accumulation) and vascular remodeling (Derynck R, Zhang Y E, Nature 2003; 425:577-84).

8.1.3. Connective Tissue Growth Factor (CTGF)

CTGF, a potent pro-fibrotic growth factor, has been implicated in fibroblast proliferation, cellular adhesion, angiogenesis and ECM synthesis (Ruperez M et al., Circulation 2003; 108:1499-505). CTGF promotes VSMC proliferation, migration, and production of ECM, which may play a role in the development and progression of atherosclerosis (Leask A et al., Curr Rheumatol Rep 2002; 4: 136-42). CTGF expression is regulated by several agents, including TGF-β, TNF-α, cAMP, high glucose, dexamethasone, factor VIIa, and mechanical stress (Lau L F, Lam S C, Exp Cell Res 1999; 248: 44-57). TGF-β-induced CTGF production is involved with several signal pathways, including Smads, Ras/MEK/Erk, Ap-1/JNK, PKC, and Tyr, and its expression can be decreased by TNF-α, cAMP, PGE2, IL-4 and PPAR through TGF-β down-regulation (Leask A et al., J Biol Chem 2003; 278: 13008-15; Leask A, Abraham D J, Biochem Cell Biol 2003; 81: 355-63). CTGF also appears to increase the expression of MMP-2 (Fan W H, Karnovsky M J, J Biol Chem 2002; 277: 9800-5). It has been reported that the addition of CTGF to primary mesangial cells induced fibronectin production, cell migration, and cytoskeletal rearrangement, which were associated with recruitment of Src and phosphorylation of p42/44 MAPK and protein kinase B (Crean J K et al, J Biol Chem 2002; 277:44187-94).

8.1.4. Matrix metalloproteinases (MMPs)

MMPs, together with cysteine proteinases, aspartic proteinases, and serine proteinases are proteolytic enzymes involved in ECM and basement membranes (BMs) degradation (Lan T-H et al., Cardiovascular Pathology 22 (2013) 401-407). MMPs play important roles in the physiology of fibrosis, as in liver cirrhosis, fibrotic lung disease, otosclerosis, atherosclerosis, and multiple sclerosis. MMPs are thought to mediate the progression of stable atherosclerotic lesions to an unstable phenotype that is prone to rupture through the destruction of ECM proteins (Lan T-H et al., Cardiovascular Pathology 22 (2013) 401-407). MMP-1, MMP-2, MMP-3 and MMP-9 participate in weakening the connective tissue matrix in the intima, which leads to plaque rupture, acute thrombosis, and SMC proliferation and migration (Amalinei C et al., Rom J Morphol Embryol 2010; 51: 215-28). MMP degradation of the EC basement membrane during diapedesis of inflammatory cells could contribute to a decreased endothelial barrier function with increased influx of plasma proteins. All of these interactions have been shown to increase production of MMPs in macrophages, which may also provide stimuli for MMP production in neighboring cells and mechanisms for activation of secreted MMP zymogens resulting in developing atherosclerotic lesions that may facilitate further structural changes and enable their growth (Galis Z S, Khatri J J, Circ Res 2002; 90: 251-62).

The expression of most MMPs is up-regulated during certain physiological and pathological remodeling processes, and mediated by a variety of inflammatory cytokines, hormones, and growth factors, such as IL-1, IL-6, TNF-α, EGF, PDGF, basic fibroblast growth factor (bFGF), and CD40 [111-113]. TGF-β up-regulates the expression of MMP-2 and MMP-9, while it decreases the expression of MMP-1 and MMP-3 (Mauviel A, J Cell Biochem 1993; 53: 288-95).

Fully activated MMPs can be inhibited by tissue inhibitors of metalloproteinases (TIMPs). An imbalance between myocardial MMPs and TIMPs results in collagen accumulation, adverse matrix remodeling and reactive interstitial fibrosis (Nagase H et al., Cardiovasc Res 2006; 69: 562-73).

8.1.5. Peroxisome Proliferator-Activated Receptor Gamma (PPARγ)

It has been reported that aberrant expression or function of PPARγ contributes to the progression of pathological fibrosis and vascular remodeling (Wei J et al., Curr Opin Rheumatol 2010; 22: 671-6). The antagonistic effects of PPARγ on abrogating TGF-β induced stimulation of collagen and fibronectin synthesis and the secretion of fibrotic growth factors including TGF-β and CTGF revealed the anti-fibrotic role of PPARγ in fibrogenesis (Ghosh A K et al., Arthritis Rheum 2004; 50: 1305-18; Burgess H A et al., Am J Physiol Lung Cell Mol Physiol 2005; 288: L1146-53). It was observed that PPARγ abrogates Smad-dependent collagen stimulation by targeting the p300 transcriptional co-activator (Ghosh A K et al., FASEB J 2009; 23: 2968-77). It has been hypothesized that PPARγ-independent pathways might also be involved in the anti-fibrotic effects triggered by PPARγ ligands, including inhibition of fibroblast migration, adipocyte differentiation and myofibroblast transition (Lan T-H et al., Cardiovascular Pathology 22 (2013) 401-407).

9. Current and Emerging Therapeutic Approaches for Treating Fibrotic Diseases or Conditions Therapeutic agents currently being used to treat fibrotic diseases are disclosed in Datta et al., British Journal of Pharmacology, 163: 141-172, 2011; incorporated by reference herein). Non-limiting examples of such therapeutic agents include, but are not limited to, purified bovine Type V collagens (e.g., IW-001; ImmuneWorks; United Therapeutics), IL-13 receptor antagonists (e.g., QAX576; Novartis), protein tyrosine kinase inhibitors (e.g., imatinib (Gleevec®); Craig Daniels/Novartis), endothelial receptor antagonists (e.g., ACT-064992 (macitentan); Actelion), dual endothelin receptor antagonists (e.g., bosentan (Tracleer®); Actelion), prostacyclin analogs (inhaled iloprost (e.g., Ventavis®); Actelion), anti-CTGF monoclonal antibodies (e.g., FG-3019), endothelin receptor antagonists (A-selective) (e.g., ambrisentan (Letairis®), Gilead), AB0024 (Arresto), lysyl oxidase-like 2 (LOXL2) monoclonal antibodies (e.g., GS-6624 (formerly AB0024); Gilead), c-Jun N-terminal kinase (JNK) inhibitors (e.g., CC-930; Celgene), Pirfenidone (e.g., Esbriet® (InterMune), Pirespa® (Shionogi)), IFN-γ1b (e.g., Actimmune®; InterMune), pan-neutralizing IgG4 human antibodies against all three TGF-β isoforms (e.g., GC1008; Genzyme), TGF-β activation inhibitors (e.g., Stromedix (STX-100)) recombinant human Pentraxin-2 protein (rhPTX-2) (e.g., PRM151; Promedior), bispecific IL4/ IL13 antibodies (e.g., SAR156597; Sanofi), humanized monoclonal antibodies targeting integrin αvβ6 (BIBF 1120; Boehringer Ingelheim), N-acetylcysteine (Zambon SpA), Sildenafil (Viagra®), TNF antagonists (e.g., etanercept (Enbrel®); Pfizer), glucocorticoids (e.g., prednisone, budesonide, mometasone furoate, fluticasone propionate, and fluticasone furoate), bronchodilators (e.g., leukotriene modifers (e.g., Montelukast (SINGUAIR®)), anticholingertic bronchodilators (e.g., Ipratropium bromide and Tiotropium), short-acting β2-agonists (e.g., isoetharine mesylate (Bronkometer®), adrenalin, salbutanol/albuterol, and terbutaline), long-acting β2-agonists (e.g., salmeterol, formoterol, indecaterol (Onbrez®), and combination bronchodilators including, but not limited to, SYMBICORT® (containing both budesonide and formoterol), corticosteroids (e.g., prednisone, budesonide, mometasone furoate), methylated xanthine and its derivatives (e.g., caffeine, aminophylline, IBMX, paraxanthine, pentoxifylline, theobromine, and theophylline), neutrophil elastase inhibitors (e.g., ONO-5046, MR-889, L-694,458, CE-1037, GW-311616, and TEI-8362, and transition-state inhibitors, such as ONO-6818, AE-3763, FK-706, ICI-200,880, ZD-0892 and ZD-8321), phosphodiesterase inhibitors (e.g., roflumilast (DAXAS®; Daliresp®), cilomilast (Ariflo®, SB-207499) and sofosbuvir (Sovaldil®).

9.1. Current Therapies for Liver Fibrosis

Despite significant advances in understanding hepatic fibrosis and in defining targets for therapy, a limited number of anti-fibrotic drugs are approved for clinical use in patients with advanced liver disease (Mormone E. et al., Chem. Biol. Interact. 2011 Sep. 30; 193(3): 225-231). Regression of established fibrosis can be accomplished in selected individuals with chronic liver diseases subjected to effective interferon therapies (Shiratori Y, et al., Ann. Intern. Med. 2000; 132(7): 517-524). However, a large cohort of patients does not respond to conventional treatment and thus remain at risk for progression of fibrosis to cirrhosis (Mormone E. et al., Chem. Biol. Interact. 2011 Sep. 30; 193(3): 225-231).

Several compounds with potential antifibrotic activity, including colchicine and malotilate, have been studied in human trials, but were found not effective (Brenner D A and Alcorn J M, Semin. Liver Dis. 1990; 10(1): 75-83; Takase S, et al., Gastroenterol. Jpn., 1988; 23(6): 639-645). Many agents such as malotilate, genistein, curcumin and silymarin have been shown to be effective in vitro and in experimental animal models (Takase S, et al., Gastroenterol Jpn. 1988; 23(6): 639-645; Fu Y M, et al., Mol. Pharm., 2008; 3(2): 399-409; George J, et al., Biomedicine, 2006; 26(3-4): 18-26). Combination therapy that works at different mechanistic levels may be more appropriate to block HSC activation and the pathogenesis of liver fibrosis (Mormone E. et al., Chem. Biol. Interact. 2011 Sep. 30; 193(3): 225-231).

10. Kinases and Phosphorylation

Kinases are a ubiquitous group of enzymes that catalyze the phosphoryl transfer reaction from a phosphate donor (usually adenosine-5'-triphosphate (ATP)) to a receptor substrate. Although all kinases catalyze essentially the same phosphoryl transfer reaction, they display remarkable diversity in their substrate specificity, structure, and the pathways in which they participate. A recent classification of all available kinase sequences (approximately 60,000 sequences) indicates kinases can be grouped into 25 families of homologous (meaning derived from a common ancestor) proteins. These kinase families are assembled into 12 fold groups based on similarity of structural fold. Further, 22 of the 25 families (approximately 98.8% of all sequences) belong to 10 fold groups for which the structural fold is known. Of the other 3 families, polyphosphate kinase forms a distinct fold group, and the 2 remaining families are both integral membrane kinases and comprise the final fold group. These fold groups not only include some of the most widely spread protein folds, such as Rossmann-like fold (three or more parallel β strands linked by two α helices in the topological order β-α-β-α-β), ferredoxin-like fold (a common α+β protein fold with a signature βαβα secondary structure along its backbone), TIM-barrel fold (meaning a conserved protein fold consisting of eight α-helices and eight parallel β-strands that alternate along the peptide backbone), and antiparallel β-barrel fold (a beta barrel is a large beta-sheet that twists and coils to form a closed structure in which the first strand is hydrogen bonded to the last), but also all major classes (all α, all β, α+β, α/β) of protein structures. Within a fold group, the core of the nucleotide-binding domain of each family has the same architecture, and the topology of the protein core is either identical or related by circular permutation. Homology between the families within a fold group is not implied.

Group I (23,124 sequences) kinases incorporate protein S/T-Y kinase, atypical protein kinase, lipid kinase, and ATP grasp enzymes and further comprise the protein S/T-Y kinase, and atypical protein kinase family (22,074 sequences). These kinases include: choline kinase (EC 2.7.1.32); protein kinase (EC 2.7.137); phosphorylase kinase (EC 2.7.1.38); homoserine kinase (EC 2.7.1.39); I-phosphatidylinositol 4-kinase (EC 2.7.1.67); streptomycin 6-kinase (EC 2.7.1.72); ethanolamine kinase (EC 2.7.1.82); streptomycin 3'-kinase (EC 2.7.1.87); kanamycin kinase (EC 2.7.1.95); 5-methylthioribose kinase (EC 2.7.1.100); viomycin kinase (EC 2.7.1.103); [hydroxymethylglutaryl-CoA reductase (NADPH2)] kinase (EC 2.7.1.109); protein-tyrosine kinase (EC 2.7.1.112); [isocitrate dehydrogenase (NADP+)] kinase (EC 2.7.1.116); [myosin light-chain] kinase (EC 2.7.1.117); hygromycin-B kinase (EC 2.7.1.119); calcium/calmodulin-dependent protein kinase (EC 2.7.1.123); rhodopsin kinase (EC 2.7.1.125); [beta-adrenergic-receptor] kinase (EC 2.7.1.126); [myosin heavy-chain] kinase (EC 2.7.1.129); [Tau protein] kinase (EC 2.7.1.135); macrolide 2'-kinase (EC 2.7.1.136); I-phosphatidylinositol 3-kinase (EC 2.7.1.137); [RNA-polymerase]-subunit kinase (EC 2.7.1.141); phosphatidylinositol-4,5-bisphosphate 3-kinase (EC 2.7.1.153); and phosphatidylinositol-4-phosphate 3-kinase (EC 2.7.1.154). Group I further comprises the lipid kinase family (321 sequences). These kinases include: I-phosphatidylinositol-4-phosphate 5-kinase (EC 2.7.1.68); I D-myo-inositol-triphosphate 3-kinase (EC 2.7.1.127); inositol-tetrakisphosphate 5-kinase (EC 2.7.1.140); I-phosphatidylinositol-5-phosphate 4-kinase (EC 2.7.1.149); I-phosphatidylinositol-3-phosphate 5-kinase (EC 2.7.1.150); inositol-polyphosphate multikinase (EC 2.7.1.151); and inositol-hexakiphosphate kinase (EC 2.7.4.21). Group I further comprises the ATP-grasp kinases (729 sequences) which include inositol-tetrakisphosphate I-kinase (EC 2.7.1.134); pyruvate, phosphate dikinase (EC 2.7.9.1); and pyruvate, water dikinase (EC 2.7.9.2).

Group II (17,071 sequences) kinases incorporate the Rossman-like kinases. Group II comprises the P-loop kinase family (7,732 sequences). These include gluconokinase (EC 2.7.1.12); phosphoribulokinase (EC 2.7.1.19); thymidine kinase (EC 2.7.1.21); ribosylnicotinamide kinase (EC 2.7.1.22); dephospho-CoA kinase (EC 2.7.1.24); adenylylsulfate kinase (EC 2.7.1.25); pantothenate kinase (EC 2.7.1.33); protein kinase (bacterial) (EC 2.7.1.37); uridine kinase (EC 2.7.1.48); shikimate kinase (EC 2.7.1.71); deoxycytidine kinase (EC 2.7.1.74); deoxyadenosine kinase (EC 2.7.1.76); polynucleotide 5'-hydroxyl-kinase (EC 2.7.1.78); 6-phosphofructo-2-kinase (EC 2.7.1.105); deoxyguanosine kinase (EC 2.7.1.113); tetraacyldisaccharide 4'-kinase (EC 2.7.1.130); deoxynucleoside kinase (EC 2.7.1.145); adenosylcobinamide kinase (EC 2.7.1.156); polyphosphate kinase (EC 2.7.4.1); phosphomevalonate kinase (EC 2.7.4.2); adenylate kinase (EC 2.7.4.3); nucleoside-phosphate kinase (EC 2.7.4.4); guanylate kinase (EC 2.7.4.8); thymidylate kinase (EC 2.7.4.9); nucleoside-triphosphate-adenylate kinase (EC 2.7.4.10); (deoxy)nucleoside-phosphate kinase (EC 2.7.4.13); cytidylate kinase (EC 2.7.4.14); and uridylate kinase (EC 2.7.4.22). Group II further comprises the phosphoenolpyruvate carboxykinase family (815 sequences). These enzymes include protein kinase (HPr kinase/phosphatase) (EC 2.7.1.37); phosphoenolpyruvate carboxykinase (GTP) (EC 4.1.1.32); and phosphoenolpyruvate carboxykinase (ATP) (EC 4.1.1.49). Group II further comprises the phosphoglycerate kinase (1,351 sequences) family. These enzymes include phosphoglycerate kinase (EC 2.7.2.3) and phosphoglycerate kinase (GTP) (EC 2.7.2.10). Group II further comprises the aspartokinase family (2,171 sequences). These enzymes include carbamate kinase (EC 2.7.2.2); aspartate kinase (EC 2.7.2.4); acetylglutamate kinase (EC 2.7.2.8 1); glutamate 5-kinase (EC 2.7.2.1) and uridylate kinase (EC 2.7.4.). Group II further comprises the phosphofructokinase-like kinase family (1,998 sequences). These enzymes include 6-phosphofrutokinase (EC 2.7.1.11); NAD (+) kinase (EC 2.7.1.23); I-phosphofructokinase (EC 2.7.1.56); diphosphate-fructose-6-phosphate I-phosphotransferase (EC 2.7.1.90); sphinganine kinase (EC 2.7.1.91); diacylglycerol kinase (EC 2.7.1.107); and ceramide kinase (EC 2.7.1.138). Group II further comprises the ribokinase-like family (2,722 sequences). These enzymes include: glucokinase (EC 2.7.1.2); ketohexokinase (EC 2.7.1.3); fructokinase (EC 2.7.1.4); 6-phosphofructokinase (EC 2.7.1.11); ribokinase (EC 2.7.1.15); adenosine kinase (EC 2.7.1.20); pyridoxal kinase (EC 2.7.1.35); 2-dehydro-3-deoxygluconokinase (EC 2.7.1.45); hydroxymethylpyrimidine kinase (EC 2.7.1.49); hydroxyethylthiazole kinase (EC 2.7.1.50); I-phosphofructokinase (EC 2.7.1.56); inosine kinase (EC 2.7.1.73); 5-dehydro-2-deoxygluconokinase (EC 2.7.1.92); tagatose-6-phosphate kinase (EC 2.7.1.144); ADP-dependent phosphofructokinase (EC 2.7.1.146); ADP-dependent glucokinase (EC 2.7.1.147); and phosphomethylpyrimidine kinase (EC 2.7.4.7). Group II further comprises the thiamin pyrophosphokinase family (175 sequences) which includes thiamin pyrophosphokinase (EC 2.7.6.2). Group II further comprises the glycerate kinase family (107 sequences) which includes glycerate kinase (EC 2.7.1.31).

Group III kinases (10,973 sequences) comprise the ferredoxin-like fold kinases. Group III further comprises the nucleoside-diphosphate kinase family (923 sequences). These enzymes include nucleoside-diphosphate kinase (EC 2.7.4.6). Group III further comprises the HPPK kinase family (609 sequences). These enzymes include 2-amino-4-hydroxy-6-hydroxymethyldihydropteridine pyrophosphokinase (EC 2.7.6.3). Group III further comprises the guanido kinase family (324 sequences). These enzymes include guanidoacetate kinase (EC 2.7.3.1); creatine kinase (EC 2.7.3.2); arginine kinase (EC 2.7.3.3); and lombricine kinase (EC 2.7.3.5). Group III further comprises the histidine kinase family (9,117 sequences). These enzymes include protein kinase (histidine kinase) (EC 2.7.1.37); [pyruvate dehydrogenase (lipoamide)] kinase (EC 2.7.1.99); and [3-methyl-2-oxybutanoate dehydrogenase (lipoamide)] kinase (EC 2.7.1.115).

Group IV kinases (2,768 sequences) incorporate ribonuclease H-like kinases. These enzymes include hexokinase (EC 2.7.1.1); glucokinase (EC 2.7.1.2); fructokinase (EC 2.7.1.4); rhamnulokinase (EC 2.7.1.5); mannokinase (EC 2.7.1.7); gluconokinase (EC 2.7.1.12); L-ribulokinase (EC 2.7.1.16); xylulokinase (EC 2.7.1.17); erythritol kinase (EC 2.7.1.27); glycerol kinase (EC 2.7.1.30); pantothenate kinase (EC 2.7.1.33); D-ribulokinase (EC 2.7.1.47); L-fucolokinase (EC 2.7.1.51); L-xylulokinase (EC 2.7.1.53); allose kinase (EC 2.7.1.55); 2-dehydro-3-deoxygalactonokinase (EC 2.7.1.58); N-acetylglucosamine kinase (EC 2.7.1.59); N-acylmannosamine kinase (EC 2.7.1.60); polyphosphate-glucose phosphotransferase (EC 2.7.1.63); beta-glucoside kinase (EC 2.7.1.85); acetate kinase (EC 2.7.2.1); butyrate kinase (EC 2.7.2.7); branched-chain-fatty-acid kinase (EC 2.7.2.14); and propionate kinase (EC 2.7.2.15).

Group V kinases (1,119 sequences) incorporate TIM β-barrel kinases. These enzymes include pyruvate kinase (EC 2.7.1.40).

Group VI kinases (885 sequences) incorporate GHMP kinases. These enzymes include galactokinase (EC 2.7.1.6); mevalonate kinase (EC 2.7.1.36); homoserine kinase (EC 2.7.1.39); L-arabinokinase (EC 2.7.1.46); fucokinase (EC 2.7.1.52); shikimate kinase (EC 2.7.1.71); 4-(cytidine 5'-diphospho)-2-C-methyl-D-erythriol kinase (EC 2.7.1.148); and phosphomevalonate kinase (EC 2.7.4.2).

Group VII kinases (1,843 sequences) incorporate AIR synthetase-like kinases. These enzymes include thiamine-phosphate kinase (EC 2.7.4.16) and selenide, water dikinase (EC 2.7.9.3).

Group VIII kinases (565 sequences) incorporate riboflavin kinases (565 sequences). These enzymes include riboflavin kinase (EC 2.7.1.26).

Group IX kinases (197 sequences) incorporate dihydroxyacetone kinases. These enzymes include glycerone kinase (EC 2.7.1.29).

Group X kinases (148 sequences) incorporate putative glycerate kinases. These enzymes include glycerate kinase (EC 2.7.1.31).

Group XI kinases (446 sequences) incorporate polyphosphate kinases. These enzymes include polyphosphate kinases (EC 2.7.4.1).

Group XII kinases (263 sequences) incorporate integral membrane kinases. Group XII comprises the dolichol kinase family. These enzymes include dolichol kinases (EC 2.7.1.108). Group XII further comprises the undecaprenol kinase family. These enzymes include undecaprenol kinases (EC 2.7.1.66).

Kinases play indispensable roles in numerous cellular metabolic and signaling pathways, and they are among the best-studied enzymes at the structural level, biochemical level, and cellular level. Despite the fact that all kinases use the same phosphate donor (in most cases, ATP) and catalyze apparently the same phosphoryl transfer reaction, they display remarkable diversity in their structural folds and substrate recognition mechanisms. This probably is due largely to the extraordinary diverse nature of the structures and properties of their substrates.

10.1. Mitogen-Activated Protein Kinase-Activated Protein Kinases (MK2 and MK3)

Different groups of MAPK-activated protein kinases (MAP-KAPKs) have been defined downstream of mitogen-activated protein kinases (MAPKs). These enzymes transduce signals to target proteins that are not direct substrates of the MAPKs and, therefore, serve to relay phosphorylation-dependent signaling with MAPK cascades to diverse cellular functions. One of these groups is formed by the three MAPKAPKs: MK2, MK3 (also known as 3pK), and MK5 (also designated PRAK). Mitogen-activated protein kinase-activated protein kinase 2 (also referred to as "MAP-KAPK2", "MAPKAP-K2", or "MK2") is a kinase of the serine/threonine (Ser/Thr) protein kinase family. MK2 is highly homologous to MK3 (approximately 75% amino acid identity). The kinase domains of MK2 and MK3 are most similar (approximately 35% to 40% identity) to calcium/calmodulin-dependent protein kinase (CaMK), phosphorylase b kinase, and the C-terminal kinase domain (CTKD) of the ribosomal S6 kinase (RSK) isoforms. The mk2 gene encodes two alternatively spliced transcripts of 370 amino acids (MK2A) and 400 amino acids (MK2B). The mk3 gene encodes one transcript of 382 amino acids. The MK2- and MK3 proteins are highly homologous, yet MK2A possesses a shorter C-terminal region. The C-terminus of MK2B contains a functional bipartite nuclear localization sequence (NLS) (Lys-Lys-Xaa$_{10}$-Lys-Arg-Arg-Lys-Lys; SEQ ID NO: 23) that is not present in the shorter MK2A isoform, indicating that alternative splicing determines the cellular localization of the MK2 isoforms. MK3 possesses a similar nuclear localization sequence. The nuclear localization sequence found in both MK2B and MK3 encompasses a D domain (Leu-Leu-Lys-Arg-Arg-Lys-Lys; SEQ ID NO: 24) that studies have shown to mediate the specific interaction of MK2B and MK3 with p38α and p38β. MK2B and MK3 also possess a functional nuclear export signal (NES) located N-terminal to the NLS and D domain. The NES in MK2B is sufficient to trigger nuclear export following stimulation, a process which may be inhibited by leptomycin B. The sequence N-terminal to the catalytic domain in MK2 and MK3 is proline rich and contains one (MK3) or two (MK2) putative Src homology 3 (SH3) domain-binding sites, which studies have shown, for MK2, to mediate binding to the SH3 domain of c-Abl in vitro. Recent studies suggest that this domain is involved in MK2-mediated cell migration.

MK2B and MK3 are located predominantly in the nucleus of quiescent cells while MK2A is present in the cytoplasm. Both MK2B and MK3 are rapidly exported to the cytoplasm via a chromosome region maintenance protein (CRM1)-dependent mechanism upon stress stimulation. Nuclear export of MK2B appears to be mediated by kinase activation, as phosphomimetic mutation of Thr334 within the activation loop of the kinase enhances the cytoplasmic localization of MK2B. Without being limited by theory, it is thought that MK2B and MK3 may contain a constitutively active NLS and a phosphorylation-regulated NES.

MK2 and MK3 appear to be expressed ubiquitously, with predominant expression in the heart, in skeletal muscle, and in kidney tissues.

10.1.1. Activation

Various activators of p38α and p38β potently stimulate MK2 and MK3 activity. p38 mediates the in vitro and in vivo phosphorylation of MK2 on four proline-directed sites: Thr25, Thr222, Ser272, and Thr334. Of these sites, only Thr25 is not conserved in MK3. Without being limited by theory, while the function of phosphorylated Thr25 in unknown, its location between the two SH3 domain-binding sites suggests that it may regulate protein-protein interactions. Thr222 in MK2 (Thr201 in MK3) is located in the activation loop of the kinase domain and has been shown to be essential for MK2 and MK3 kinase activity. Thr334 in MK2 (Thr313 in MK3) is located C-terminal to the catalytic domain and is essential for kinase activity. The crystal structure of MK2 has been resolved and, without being limited by theory, suggests that Thr334 phosphorylation may serve as a switch for MK2 nuclear import and export. Phosphorylation of Thr334 also may weaken or interrupt binding of the C terminus of MK2 to the catalytic domain, exposing the NES and promoting nuclear export.

Studies have shown that, while p38 is capable of activating MK2 and MK3 in the nucleus, experimental evidence suggests that activation and nuclear export of MK2 and MK3 are coupled by a phosphorylation-dependent conformational switch that also dictates p38 stabilization and localization, and the cellular location of p38 itself is controlled by MK2 and possibly MK3. Additional studies have shown that nuclear p38 is exported to the cytoplasm in a complex with MK2 following phosphorylation and activation of MK2. The interaction between p38 and MK2 may be important for p38 stabilization since studies indicate that p38 levels are low in MK2-deficient cells and expression of a catalytically inactive MK2 protein restores p38 levels.

10.1.2. Substrates and Functions

Further studies have shown that the small heat shock protein HSPB1 (also known as heat shock protein 27 or Hsp27), lymphocyte-specific protein LSP-1, and vimentin are phosphorylated by MK2. HSPB1 is of particular interest because it forms large oligomers, which may act as molecular chaperones and protect cells from heat shock and oxidative stress. Upon phosphorylation, HSPB1 loses its ability to form large oligomers and is unable to block actin polymerization, suggesting that MK2-mediated phosphorylation of HSPB1 serves a homeostatic function aimed at regulating actin dynamics that otherwise would be destabilized during stress.

MK3 also was shown to phosphorylate HSPB1 in vitro and in vivo, but its role during stressful conditions has not yet been elucidated. MK2 shares many substrates with MK3. Both enzymes have comparable substrate preferences and phosphorylate peptide substrates with similar kinetic constants. The minimum sequence required for efficient phosphorylation by MK2 was found to be Hyd-Xaa-Arg-Xaa-Xaa-pSer/Thr (SEQ ID NO: 25), where Hyd is a bulky hydrophobic residue.

Experimental evidence supports a role for p38 in the regulation of cytokine biosynthesis and cell migration. The targeted deletion of the mk2 gene in mice suggested that although p38 mediates the activation of many similar kinases, MK2 seems to be the key kinase responsible for these p38-dependent biological processes. Loss of MK2 leads (i) to a defect in lipopolysaccharide (LPS)-induced synthesis of cytokines such as tumor necrosis factor alpha (TNF-α), interleukin-6 (IL-6), and gamma interferon (IFN-γ) and (ii) to changes in the migration of mouse embryonic fibroblasts, smooth muscle cells, and neutrophils.

Consistent with a role for MK2 in inflammatory responses, MK2-deficient mice showed increased susceptibility to *Listeria monocytogenes* infection and reduced inflammation-mediated neuronal death following focal ischemia. Since the levels of p38 protein also are reduced significantly in MK2-deficient cells, it was necessary to distinguish whether these phenotypes were due solely to the loss of MK2. To achieve this, MK2 mutants were expressed in MK2-deficient cells, and the results indicated that the catalytic activity of MK2 was not necessary to restore p38 levels but was required to regulate cytokine biosynthesis.

The knockout or knockdown studies of MK2 provided strong support that activated MK2 enhances stability of IL-6 mRNA through phosphorylation of proteins interacting with the AU-rich 3' untranslated region of IL-6 mRNA. In particular, it has been shown that MK2 is principally responsible for phosphorylation of hnRNPA0, an mRNA-binding protein that stabilizes IL-6 RNA. In addition, several additional studies investigating diverse inflammatory diseases have found that levels of pro-inflammatory cytokines, such as IL-6, IL-1β, TNF-α and IL-8, are increased in induced sputum from patients with stable chronic obstructive pulmonary disease (COPD) or from the alveolar macrophages of cigarette smokers (Keatings V. et al, *Am J Resp Crit Care Med*, 1996, 153:530-534; Lim, S. et al., *J Respir Crit Care Med*, 2000, 162:1355-1360). Elevated levels of pro-inflammatory cytokines, such as interleukin-8 (IL-8) and interleukin-6 (IL-6), as well as related downstream cell adhesion molecules (CAMs) such as intercellular adhesion molecule-1 (ICAM-1) and vascular cell adhesion molecule-1 (VCAM-1), matrix metalloproteinases such as matrix metalloproteinase-7 (MMP-7), and signaling molecules such as S100 calcium-binding protein A12 (S100A12, also known as calgranulin C), in the peripheral blood have been found to be associated with mortality, lung transplant-free survival, and disease progression in patients with idiopathic pulmonary fibrosis (Richards et al., *Am J Respir Crit Care Med*, 2012, 185: 67-76; Richards, T. et al., Am J Respir Crit Care Med, 181: A1120, 2010; Moodley, Y. et al., Am J Respir Cell Mol Biol., 29(4): 490-498, 2003). Taken together, these studies implicate that elevated levels of inflammatory cytokines induced by MK2 activation may be involved in the pathogenesis of airway or lung tissue diseases; and suggest a potential for anti-cytokine therapy for treating airway or lung tissue diseases, such as idiopathic pulmonary fibrosis and chronic obstructive pulmonary disease (COPD) (Chung, K., *Eur Respir J,* 2001, 18: Suppl. 34: 50-59).

10.1.3. Regulation of mRNA Translation

Previous studies using MK2 knockout mice or MK2-deficient cells have shown that MK2 increases the production of inflammatory cytokines, including TNF-α, IL-1, and IL-6, by increasing the rate of translation of its mRNA. No significant reductions in the transcription, processing, and shedding of TNF-α could be detected in MK2-deficient mice. The p38 pathway is known to play an important role in regulating mRNA stability, and MK2 represents a likely target by which p38 mediates this function. Studies utilizing MK2-deficient mice indicated that the catalytic activity of MK2 is necessary for its effects on cytokine production and migration, suggesting that, without being limited by theory, MK2 phosphorylates targets involved in mRNA stability. Consistent with this, MK2 has been shown to bind and/or phosphorylate the heterogeneous nuclear ribonucleoprotein (hnRNP) A0, tristetraprolin, the poly (A)-binding protein PABP1, and HuR, a ubiquitously expressed member of the elav (embryonic-lethal abnormal visual in Drosophila melanogaster) family of RNA-binding protein. These substrates are known to bind or copurify with mRNAs that contain AU-rich elements in the 3' untranslated region, suggesting that MK2 may regulate the stability of AU-rich mRNAs such as TNF-α. It currently is unknown whether MK3 plays similar functions, but LPS treatment of MK2-deficient fibroblasts completely abolished hnRNP A0 phosphorylation, suggesting that MK3 is not able to compensate for the loss of MK2.

MK3 participates with MK2 in phosphorylation of the eukaryotic elongation factor 2 (eEF2) kinase. eEF2 kinase phosphorylates and inactivates eEF2. eEF2 activity is critical for the elongation of mRNA during translation, and phosphorylation of eEF2 on Thr56 results in the termination of mRNA translation. MK2 and MK3 phosphorylation of eEF2 kinase on Ser377 suggests that these enzymes may modulate eEF2 kinase activity and thereby regulate mRNA translation elongation.

10.1.4. Transcriptional Regulation by MK2 and MK3

Nuclear MK2, similar to many MKs, contributes to the phosphorylation of cAMP response element binding (CREB), serum response factor (SRF), and transcription factor ER81. Comparison of wild-type and MK2-deficient cells revealed that MK2 is the major SRF kinase induced by stress, suggesting a role for MK2 in the stress-mediated immediate-early response. Both MK2 and MK3 interact with basic helix-loop-helix transcription factor E47 in vivo and phosphorylate E47 in vitro. MK2-mediated phosphorylation of E47 was found to repress the transcriptional activity of E47 and thereby inhibit E47-dependent gene expression, suggesting that MK2 and MK3 may regulate tissue-specific gene expression and cell differentiation.

10.1.5. Other Targets of MK2 and MK3.

Several other MK2 and MK3 substrates also have been identified, reflective of the diverse functions of MK2 and MK3 in several biological processes. The scaffolding protein 14-3-3ζ is a physiological MK2 substrate. Studies indicate 14-3-3ζ interacts with a number of components of cell signaling pathways, including protein kinases, phosphatases, and transcription factors. Additional studies have shown that MK2-mediated phosphorylation of 14-3-3ζ on Ser58 compromises its binding activity, suggesting that MK2 may affect the regulation of several signaling molecules normally regulated by 14-3-3ζ.

Additional studies have shown that MK2 also interacts with and phosphorylates the p16 subunit of the seven-member Arp2 and Arp3 complex (p16-Arc) on Ser77. p16-Arc has roles in regulating the actin cytoskeleton, suggesting that MK2 may be involved in this process.

MK2 and MK3 also may phosphorylate 5-lipoxygenase. 5-lipoxygenase catalyzes the initial steps in the formation of the inflammatory mediator leukotrienes. Tyrosine hydroxylase, glycogen synthase, and Akt also were shown to be phosphorylated by MK2. Finally, MK2 phosphorylates the tumor suppressor protein tuberin on Ser1210, creating a docking site for 14-3-3ζ. Tuberin and hamartin normally form a functional complex that negatively regulates cell growth by antagonizing mTOR-dependent signaling, suggesting that p38-mediated activation of MK2 may regulate cell growth by increasing 14-3-3ζ binding to tuberin.

10.2. Kinase Inhibition

The eukaryotic protein kinases constitute one of the largest superfamilies of homologous proteins that are related by virtue of their catalytic domains. Most related protein kinases are specific for either serine/threonine or tyrosine phosphorylation. Protein kinases play an integral role in the cellular response to extracellular stimuli. Thus, stimulation of protein kinases is considered to be one of the most common activation mechanisms in signal transduction systems. Many substrates are known to undergo phosphorylation by multiple protein kinases, and a considerable amount of information on primary sequence of the catalytic domains of various protein kinases has been published. These sequences share a large number of residues involved in ATP binding, catalysis, and maintenance of structural integrity. Most protein kinases possess a well conserved 30-32 kDa catalytic domain.

Studies have attempted to identify and utilize regulatory elements of protein kinases. These regulatory elements include inhibitors, antibodies, and blocking peptides.

10.2.1. Inhibitors

Enzyme inhibitors are molecules that bind to enzymes thereby decreasing enzyme activity. The binding of an inhibitor may stop a substrate from entering the active site of the enzyme and/or hinder the enzyme from catalyzing its reaction. Inhibitor binding is either reversible or irreversible. Irreversible inhibitors usually react with the enzyme and change it chemically (e.g., by modifying key amino acid residues needed for enzymatic activity) so that it no longer is capable of catalyzing its reaction. In contrast, reversible inhibitors bind non-covalently and different types of inhibition are produced depending on whether these inhibitors bind the enzyme, the enzyme-substrate complex, or both.

Enzyme inhibitors often are evaluated by their specificity and potency. The term "specificity" as used in this context refers to the selective attachment of an inhibitor or its lack of binding to other proteins. The term "potency" as used herein refers to an inhibitor's dissociation constant, which indicates the concentration of inhibitor needed to inhibit an enzyme.

Inhibitors of protein kinases have been studied for use as a tool in protein kinase activity regulation. Inhibitors have been studied for use with, for example, cyclin-dependent (Cdk) kinase, MAP kinase, serine/threonine kinase, Src Family protein tyrosine kinase, tyrosine kinase, calmodulin (CaM) kinase, casein kinase, checkpoint kinase (Chk1), glycogen synthase kinase 3 (GSK-3), c-Jun N-terminal kinase (JNK), mitogen-activated protein kinase 1 (MEK), myosin light chain kinase (MLCK), protein kinase A, Akt (protein kinase B), protein kinase C, protein kinase G, protein tyrosine kinase, Raf kinase, and Rho kinase.

10.2.2. Blocking Peptides

A peptide is a chemical compound that is composed of a chain of two or more amino acids whereby the carboxyl group of one amino acid in the chain is linked to the amino group of the other via a peptide bond. Peptides have been used inter alia in the study of protein structure and function. Synthetic peptides may be used inter alia as probes to see where protein-peptide interactions occur. Inhibitory peptides may be used inter alia in clinical research to examine the effects of peptides on the inhibition of protein kinases, cancer proteins and other disorders.

The use of several blocking peptides has been studied. For example, extracellular signal-regulated kinase (ERK), a MAPK protein kinase, is essential for cellular proliferation and differentiation. The activation of MAPKs requires a cascade mechanism whereby MAPK is phosphorylated by an upstream MAPKK (MEK) which then, in turn, is phosphorylated by a third kinase MAPKKK (MEKK). The ERK inhibitory peptide functions as a MEK decoy by binding to ERK.

Other blocking peptides include autocamtide-2 related inhibitory peptide (AIP). This synthetic peptide is a highly specific and potent inhibitor of $Ca^{2+}$/calmodulin-dependent protein kinase II (CaMKII). AIP is a non-phosphorylatable analog of autocamtide-2, a highly selective peptide substrate for CaMKII. AIP inhibits CaMKII with an $IC_{50}$ of 100 nM ($IC_{50}$ is the concentration of an inhibitor required to obtain 50% inhibition). The AIP inhibition is non-competitive with respect to syntide-2 (CaMKII peptide substrate) and ATP but competitive with respect to autocamtide-2. The inhibition is unaffected by the presence or absence of $Ca^{2+}$/calmodulin. CaMKII activity is inhibited completely by AIP (1 µM) while PKA, PKC and CaMKIV are not affected.

Other blocking peptides include cell division protein kinase 5 (Cdk5) inhibitory peptide (CIP). Cdk5 phosphorylates the microtubule protein tau at Alzheimer's Disease-specific phospho-epitopes when it associates with p25. p25 is a truncated activator, which is produced from the physiological Cdk5 activator p35 upon exposure to amyloid β peptides. Upon neuronal infections with CIP, CIPs selectively inhibit p25/Cdk5 activity and suppress the aberrant tau phosphorylation in cortical neurons. The reasons for the specificity demonstrated by CIP are not fully understood.

Additional blocking peptides have been studied for extracellular-regulated kinase 2 (ERK2), ERK3, p38/HOG1, protein kinase C, casein kinase II, $Ca^{2+}$/calmodulin kinase IV, casein kinase II, Cdk4, Cdk5, DNA-dependent protein kinase (DNA-PK), serine/threonine-protein kinase PAK3, phosphoinositide (PI)-3 kinase, PI-5 kinase, PSTAIRE (the cdk highly conserved sequence), ribosomal S6 kinase, GSK-4, germinal center kinase (GCK), SAPK (stress-activated protein kinase), SEK1 (stress signaling kinase), and focal adhesion kinase (FAK).

11. Cell Penetrating Peptides (CPPs)

Cell penetrating peptides (CPPs) are a class of peptides capable of penetrating the plasma membrane of mammalian cells and of transporting compounds of many types and molecular weights across the membrane. These compounds include effector molecules, such as proteins, DNA, conjugated peptides, oligonucleotides, and small particles such as liposomes. When CPPs are chemically linked or fused to other proteins, the resulting fusion proteins still are able to enter cells. Although the exact mechanism of transduction is unknown, internalization of these proteins is not believed to be receptor-mediated or transporter-mediated. CPPs are generally 10-16 amino acids in length and may be grouped according to their composition, such as, for example, peptides rich in arginine and/or lysine.

The use of CPPs capable of transporting effector molecules into cells has become increasingly attractive in the design of drugs as they promote the cellular uptake of cargo molecules. These cell-penetrating peptides, generally categorized as amphipathic (meaning having both a polar and a nonpolar end) or cationic (meaning of or relating to containing net positively charged atoms) depending on their sequence, provide a non-invasive delivery technology for macromolecules. CPPs often are referred to as "Trojan peptides," "membrane translocating sequences," "protein transduction domains (PTDs)," or "cell permeable proteins (CPPs)." CPPs also may be used to assist novel HSPB1 kinase inhibitors to penetrate cell membranes. (see U.S. application Ser. No. 11/972,459, entitled "Polypeptide Inhibitors of HSPB1 Kinase and Uses Therefor," filed Jan. 10, 2008, and Ser. No. 12/188,109, entitled "Kinase Inhibitors and Uses Thereof," filed Aug. 7, 2008, the contents of each application are incorporated by reference in their entirety herein).

11.1. Viral CPP Containing Proteins

The first proteins to be described as having transduction properties were of viral origin. These proteins still are the most commonly accepted models for CPP action. Among the cell-penetrating peptides, the arginine-rich cell-penetrating peptides, including but not limited to TAT peptide, have been the most widely studied (El-Sayed, A. et al., AAPS J. 11, 13-22, 2009; Wender, P. et al., Adv. Drug Deliv. Rev. 60, 452-472, 2008).

TAT (HIV-1 trans-activator gene product) is an 86-amino acid polypeptide, which acts as a powerful transcription factor of the integrated HIV-1 genome. TAT acts on the viral genome stimulating viral replication in latently infected cells. The translocation properties of the TAT protein enable it to activate quiescent infected cells, and it may be involved in priming of uninfected cells for subsequent infection by regulating many cellular genes, including cytokines. The minimal CPP of TAT is the 9 amino acid protein sequence RKKRRQRRR (TAT49-57; SEQ ID NO: 20). Studies utilizing a longer fragment of TAT demonstrated successful transduction of fusion proteins up to 120 kDa. The addition of multiple TAT-CPP as well as synthetic TAT derivatives has been demonstrated to mediate membrane translocation. TAT CPP containing fusion proteins have been used as therapeutic moieties in experiments involving cancer, transporting a death-protein into cells, and disease models of neurodegenerative disorders.

VP22 is the HSV-1 tegument protein, a structural part of the HSV virion. VP22 is capable of receptor independent translocation and accumulates in the nucleus. This property of VP22 classifies the protein as a CPPs containing peptide. Fusion proteins comprising full length VP22 have been translocated efficiently across the plasma membrane.

11.2. Homeoproteins with Intercellular Translocation Properties

Homeoproteins are highly conserved, transactivating transcription factors involved in morphological processes. They bind to DNA through a specific sequence of 60 amino acids. The DNA-binding homeodomain is the most highly conserved sequence of the homeoprotein. Several homeoproteins have been described to exhibit CPP-like activity; they are capable of efficient translocation across cell membranes in an energy-independent and endocytosis-independent manner without cell type specificity.

The Antennapedia protein (Antp) is a trans-activating factor capable of translocation across cell membranes; the minimal sequence capable of translocation is a 16 amino acid peptide corresponding to the third helix of the protein's homeodomain (HD). The internalization of this helix occurs at 4° C., suggesting that this process is not endocytosis dependent. Peptides up to 100 amino acids produced as fusion proteins with AntpHD penetrate cell membranes.

Other homeodomains capable of translocation include Fushi tarazu (Ftz) and Engrailed (En) homeodomain. Many homeodomains share a highly conserved third helix.

11.3. Human CPPs

Human CPPs may circumvent potential immunogenicity issues upon introduction into a human patient. Peptides with CPPs sequences include: Hoxa-5, Hox-A4, Hox-B5, Hox-B6, Hox-B7, HOX-D3, GAX, MOX-2, and FtzCPP. These proteins all share the sequence found in AntpCPPs. Other CPPs include Islet-1, interleukin-1, tumor necrosis factor, and the hydrophobic sequence from Kaposi-fibroblast growth factor or FGF-4) signal peptide, which is capable of energy-, receptor-, and endocytosis-independent translocation. Unconfirmed CPPs include members of the Fibroblast Growth Factor (FGF) family.

12. MK2 Inhibitors and Treatment of Fibrotic Diseases or Conditions

Mitogen-activated protein kinase activated protein kinase 2 (MAPKAPK2 or MK2), a serine/threonine kinase substrate downstream of p38MAPK, has been implicated in many inflammatory diseases that are complicated by scarring and fibrosis (Lopes, L. et al., Biochem Biophys Res Commun., 382(3):535-9, 2009). These include, but are not limited to, cancer, intimal hyperplasia, organ fibrosis, abdominal adhesions, inflammatory bowel disease, and rheumatoid arthritis. In addition to idiopathic pulmonary fibrosis (IPF), other disorders that involve inflammation and fibrosis and impact the lung include acute lung injury (ALI), organ transplant rejection (with lung transplant also a later-stage treatment for IPF), organ failure secondary to sepsis, acute lung failure, auto-immune diseases such as scleroderma, and chronic pulmonary obstructive disease (COPD).

The development of fibrosis is known to require inflammation, proliferation and recruitment of fibroblast that results in cells of myofibroblastic phenotype (Horowitz J. et al., *Semin Respir Crit Care Med.*, 27(6):600-612, 2006). MK2 has been shown to control gene expression at transcriptional and post-transcriptional levels (Neininger A. et al., *J Biol Chem.* 2002; 277(5):3065-8, Thomas T. et al., *J Neurochem.*, 105(5): 2039-52, 2008; Johansen C. et al., *J Immunol.*, 176(3):1431-8, 2006; Rousseau S. et al., *EMBO J.* 21(23):6505-14, 2002) as well as cytoskeletal architecture (Lopes, L. et al., *Biochem Biophys Res Commun.*, 382(3): 535-9, 2009). In addition, it was shown that activated MK2 increases translation and stability of inflammatory cytokine mRNAs and causes actin reorganization; and that inhibition of MK2 is associated with reduced inflammation (Ward, B. et al., *J Surg Res.*, 169(1):e27-36, 2011) and myofibroblast differentiation (Lopes, L. et al., *Biochem Biophys Res Commun.*, 382(3):535-9, 2009).

Together, these data suggest that inhibition of MK2 may provide therapeutic benefits to patients with fibrotic disorders or conditions, for example, idiopathic pulmonary fibrosis (IPF), acute lung injury (ALI), hepatic fibrosis, renal fibrosis, vascular fibrosis, and transplant rejection. In this respect, the described invention offers an approach to intervene in the process of inflammation and fibrosis using cell-penetrating, peptide base inhibitors of MK2.

SUMMARY OF THE INVENTION

According to one aspect, the described invention provides a method for reducing progression of a fibrosis in a tissue selected from a liver tissue, a kidney tissue or a vascular tissue, comprising: administering to a subject in need thereof a pharmaceutical composition comprising a therapeutic amount of a polypeptide of the amino acid sequence YARAAARQARAKALARQLGVAA (SEQ ID NO: 1) or a functional equivalent thereof made from a fusion between a first polypeptide that is a cell penetrating peptide (CPP) selected from the group consisting of a polypeptide of amino acid sequence WLRRIKAWLRRIKA (SEQ ID NO: 12), WLRRIKA (SEQ ID NO: 13), YGRKKRRQRRR (SEQ ID NO: 14), WLRRIKAWLRRI (SEQ ID NO: 15), FAKLAARLYR (SEQ ID NO: 16), KAFAKLAARLYR (SEQ ID NO: 17) and HRRIKAWLKKI (SEQ ID NO: 18), and a second polypeptide that is a therapeutic domain (TD) selected from the group consisting of a polypeptide of amino acid sequence KALARQLAVA (SEQ ID NO: 8), KALARQLGVA (SEQ ID NO: 9) and KALARQLGVAA (SEQ ID NO: 10), and a pharmaceutically acceptable carrier thereof, progression of the fibrosis being characterized by one or more of aberrant fibroblast proliferation and extracellular matrix deposition producing remodeling in liver tissue, kidney tissue or vascular tissue, wherein the therapeutic amount of the polypeptide is effective to reduce progression of the fibrosis, to treat remodeling of the tissue, or a combination thereof.

According to one embodiment, the fibrosis is further characterized by an inflammation in the tissue. According to another embodiment, the inflammation is an acute or a chronic inflammation. According to another embodiment, the inflammation is mediated by at least one cytokine selected from the group consisting of Tumor Necrosis Factor-alpha (TNF-α), Interleukin-6 (IL-6), and Interleukin-1β (IL-1β).

According to one embodiment, the aberrant fibroblast proliferation and extracellular matrix deposition in the tissue or the tissue is characterized by an aberrant activity of Mitogen-Activated Protein Kinase-Activated Protein Kinase 2 (MK2) in the tissue compared to the activity of Mitogen-Activated Protein Kinase-Activated Protein Kinase 2 (MK2) in the tissue of a normal healthy control subject, i.e., a subject having no symptoms or other evidence of a liver, kidney or vascular fibrotic condition, disorder or disease.

According to one embodiment, the step of administering occurs orally, intratracheally, parenterally, intravenously, or intraperitoneally.

According to one embodiment, the pharmaceutical composition further comprises one or more additional therapeutic agent(s). According to another embodiment, the additional therapeutic agent is an anti-infective agent. According to another embodiment, the anti-infective agent is an antiviral agent. According to another embodiment, the antiviral agent is one or more of sofosbuvir (Sovaldi®), an HCV boosted protease inhibitor (ABT-450, AbbVie), a nonnucleoside NS5B inhibitor (dasabuvir, ABT-333, AbbVie), an NS5a inhibitor (ombitasvir, ABT-267, AbbVie), ABT-450/r (ABT-450 with ritonavir), ABT-450 co-formulated with ABT-267, or ABT-450 formulated with sofosbuvir, ribavirin, or combinations thereof.

According to one embodiment, the additional therapeutic agent is a glucocorticoid selected from the group consisting of prednisone, budesonide, mometasone furoate, fluticasone propionate, fluticasone furoate, and a combination thereof.

According to one embodiment, the additional therapeutic agent is an analgesic agent.

According to one embodiment, the additional therapeutic agent is selected from the group consisting of a purified bovine Type V collagen, an IL-13 receptor antagonist, a protein tyrosine kinase inhibitor, an endothelial receptor antagonist, a dual endothelin receptor antagonist, a prostacyclin analog, an anti-CTGF antibody, an endothelin receptor antagonist (A-selective), AB0024, a lysyl oxidase-like 2 (LOXL2) antibody, a c-Jun N-terminal kinase (JNK) inhibitor, pirfenidone, IFN-γ1b, anantibody against all three TGF-β isoforms, a pan-neutralizing IgG4 human antibody against all three TGF-β isoforms, a TGF-β activation inhibitor, a recombinant human Pentraxin-2 protein (rhPTX-2), a bispecific IL-4/IL-13 antibody, an antibody targeting integrin αvβ6, N-acetylcysteine, sildenafil, a Tumor Necrosis Factor (TNF) antagonist (etanercept), and a combination thereof.

According to one embodiment, the functional equivalent of the polypeptide YARAAARQARAKALARQLGVAA (SEQ ID NO: 1) is of amino acid sequence FAKLAARLYRKALARQLGVAA (SEQ ID NO: 3). According to another embodiment, the functional equivalent of the polypeptide YARAAARQARAKALARQLGVAA (SEQ ID NO: 1) is of amino acid sequence KAFAKLAARLYRKALARQLGVAA (SEQ ID NO: 4). According to another embodiment, the functional equivalent of the polypeptide YARAAARQARAKALARQLGVAA (SEQ ID NO: 1) is of amino acid sequence YARAAARQARAKALARQLAVA (SEQ ID NO: 5). According to another embodiment, the functional equivalent of the polypeptide YARAAARQARAKALARQLGVAA (SEQ ID NO: 1) is of amino acid sequence YARAAARQARAKALARQLGVA (SEQ ID NO: 6). According to another embodiment, the functional equivalent of the polypeptide YARAAARQARAKALARQLGVAA (SEQ ID NO: 1) is of amino acid sequence HRRIKAWLKKIKALARQLGVAA (SEQ ID NO: 7). According to another embodiment, the functional equivalent of the polypeptide YARAAARQARAKALARQLGVAA (SEQ ID NO: 1) is of amino acid sequence YARAAARQARAKALNRQLAVAA (SEQ ID NO: 26). According to another embodiment, the functional equivalent of the polypeptide YARAAARQARAKALARQLGVAA (SEQ ID NO: 1) is of amino acid sequence YARAARQARAKALNRQLAVA (SEQ ID NO: 27).

According to one embodiment, the second polypeptide of the functional equivalent of the polypeptide YARAAARQARAKALARQLGVAA (SEQ ID NO: 1) made from the fusion of the first polypeptide that is the cell penetrating peptide (CPP) operatively linked to the second polypeptide that is the therapeutic domain (TD) is a polypeptide whose sequence has a substantial identity to amino acid sequence KALARQLGVAA (SEQ ID NO: 2).

According to one embodiment, the second polypeptide is a polypeptide of amino acid sequence KALARQLAVA (SEQ ID NO: 8). According to another embodiment, the second polypeptide is a polypeptide of amino acid sequence KALARQLGVA (SEQ ID NO: 9). According to another embodiment, the second polypeptide is a polypeptide of amino acid sequence KALARQLGVAA (SEQ ID NO: 10). According to another embodiment, the second polypeptide is a polypeptide of amino acid sequence KALNRQLAVAA (SEQ ID NO: 28). According to another embodiment, the second polypeptide is a polypeptide of amino acid sequence KALNRQLAVA (SEQ ID NO: 29).

According to one embodiment, the functional equivalent of the polypeptide YARAAARQARAKALARQLGVAA (SEQ ID NO: 1) is a fusion protein comprising a first polypeptide operatively linked to a second polypeptide, wherein the first polypeptide is a cell penetrating peptide functionally equivalent to YARAAARQARA (SEQ ID NO: 11) selected from the group consisting of a polypeptide of amino acid sequence WLRRIKAWLRRIKA (SEQ ID NO: 12), WLRRIKA (SEQ ID NO: 13), YGRKKRRQRRR (SEQ ID NO: 14), WLRRIKAWLRRI (SEQ ID NO: 15), FAKLAARLYR (SEQ ID NO: 16), KAFAKLAARLYR (SEQ ID NO: 17) and HRRIKAWLKKI (SEQ ID NO: 18), and the second polypeptide is of amino acid sequence KALARQLGVAA (SEQ ID NO: 2).

According to one embodiment, the first polypeptide is a polypeptide of amino acid sequence WLRRIKAWLRRIKA (SEQ ID NO: 12). According to another embodiment, the first polypeptide is a polypeptide of amino acid sequence WLRRIKA (SEQ ID NO: 13).

According to another embodiment, the first polypeptide is a polypeptide of amino acid sequence YGRKKRRQRRR (SEQ ID NO: 14). According to another embodiment, the first polypeptide is a polypeptide of amino acid sequence WLRRIKAWLRRI (SEQ ID NO: 15). According to another embodiment, the first polypeptide is a polypeptide of amino acid sequence FAKLAARLYR (SEQ ID NO: 16). According to another embodiment, the first polypeptide is a polypeptide of amino acid sequence KAFAKLAARLYR (SEQ ID NO: 17). According to another embodiment, the first polypeptide is a polypeptide of amino acid sequence HRRIKAWLKKI (SEQ ID NO: 18).

According to one embodiment, the carrier is selected from the group consisting of a controlled release carrier, a delayed release carrier, a sustained release carrier, and a long-term release carrier.

BRIEF DESCRIPTION OF THE DRAWINGS

FIG. 4 shows flow-rate independence of spray-dried neat peptide.

Figure 5:
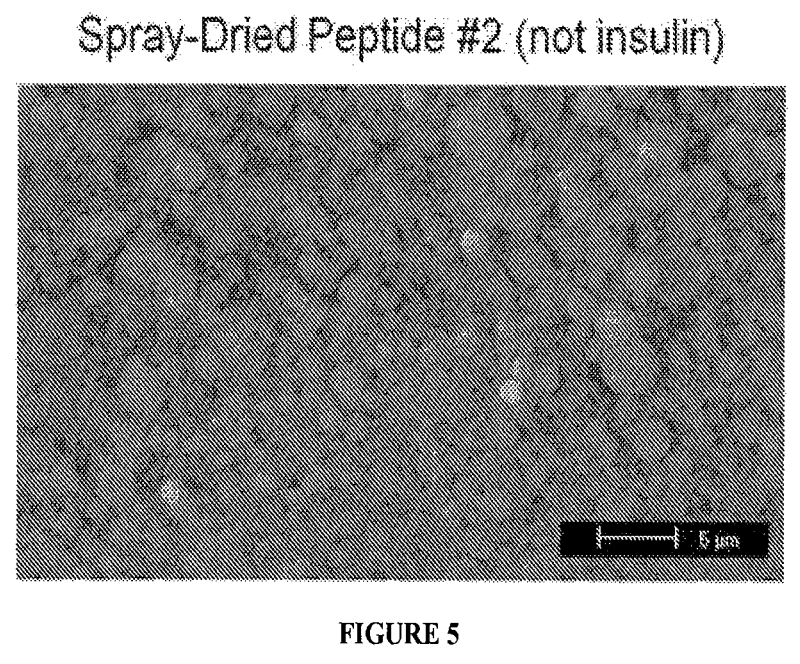

FIG. 5 shows a representative micrograph of a spray-dried peptide (not insulin).

(NEB)); and (iv) the bleomycin mice treated with intraperitoneal MMI-0100 (YARAAARQARAKALARQLGVAA (SEQ ID NO: 1)) (BLEO+MMI-0100 (IP)).

Figure 15:
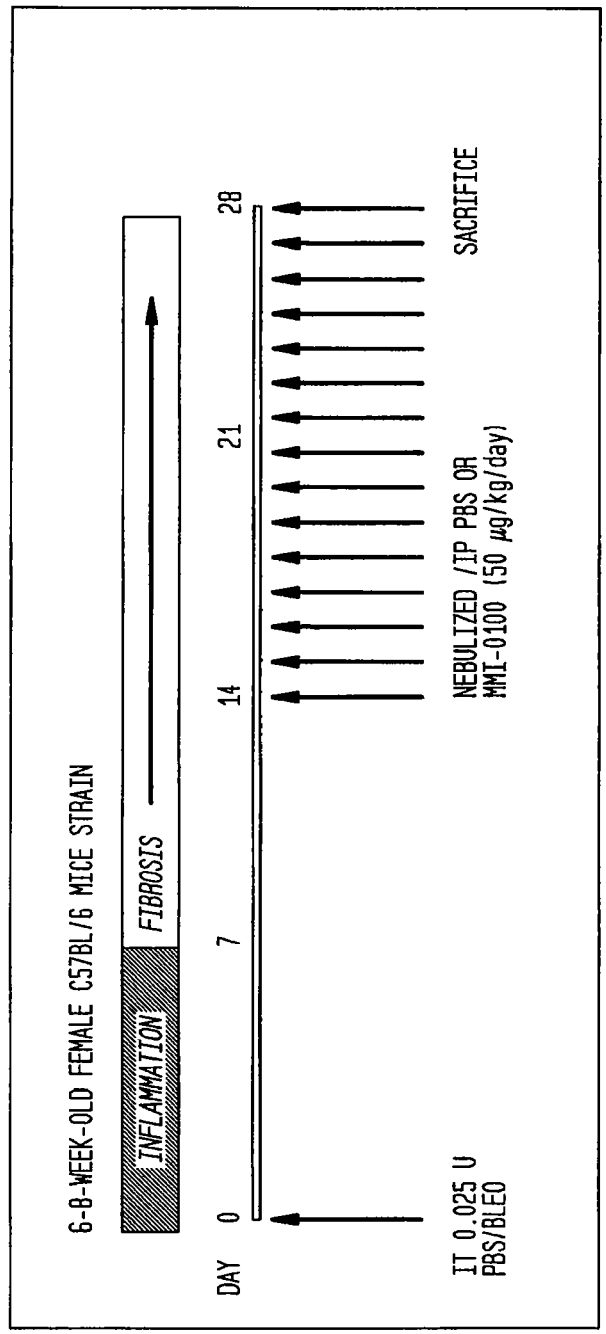

FIG. 15 shows a schematic diagram for testing ability of MMI-0100 (YARAAARQARAKALARQLGVAA; SEQ ID NO: 1) to abrogate fibrosis progression in the bleomycin model of idiopathic pulmonary fibrosis (IPF treatment model). PBS or MMI-0100 (YARAAARQARAKALARQLGVAA (SEQ ID NO: 1)) is administered via nebulization or intraperitoneally at the doses of 50 µg/kg daily starting at day 14 post bleomycin delivery until day 28 post bleomycin delivery.

Figure 16:
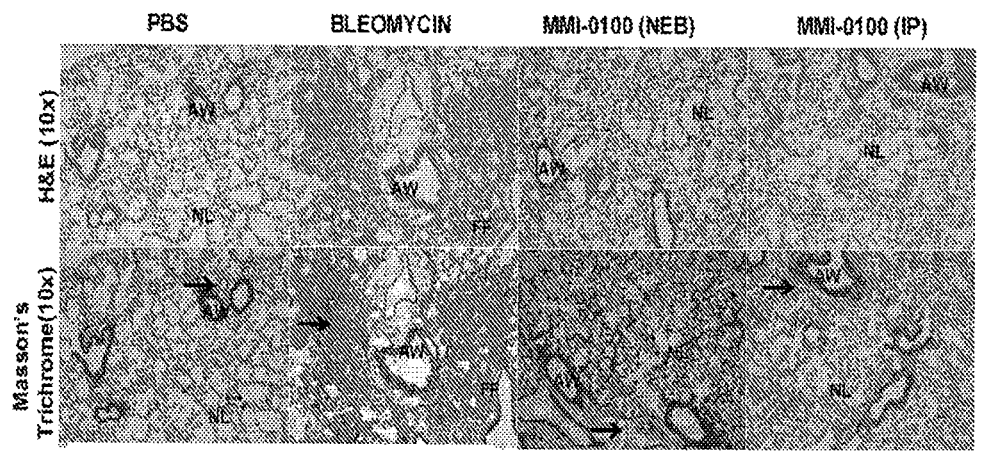

FIG. 16 shows that systemic (IP) or nebulized (NEB) administration of MMI-0100 (YARAAARQARAKALARQLGVAA; SEQ ID NO: 1) ameliorates bleomycin-induced lung fibrosis in mice. Upper panel: Hematoxylin and Eosin (H&E) staining; Lower panel: Masson's blue trichrome staining of the same fields. The abbreviations shown in FIG. 16 are as follows: PBS (wild type mice treated with PBS); BLEO (bleomycin mice treated with PBS); MMI-0100 (NEB) (bleomycin mice treated with nebulized MMI-0100 (YARAAARQARAKALARQLGVAA (SEQ ID NO: 1)); MMI-0100 (IP) (bleomycin mice treated with intraperitoneal MMI-0100 (YARAAARQARAKALARQLGVAA (SEQ ID NO: 1)); NL (normal lung architecture with alveolar sacs); AW (air way); FF (fibroblastic foci from a lung tissue explants with IPF)

Figure 17:
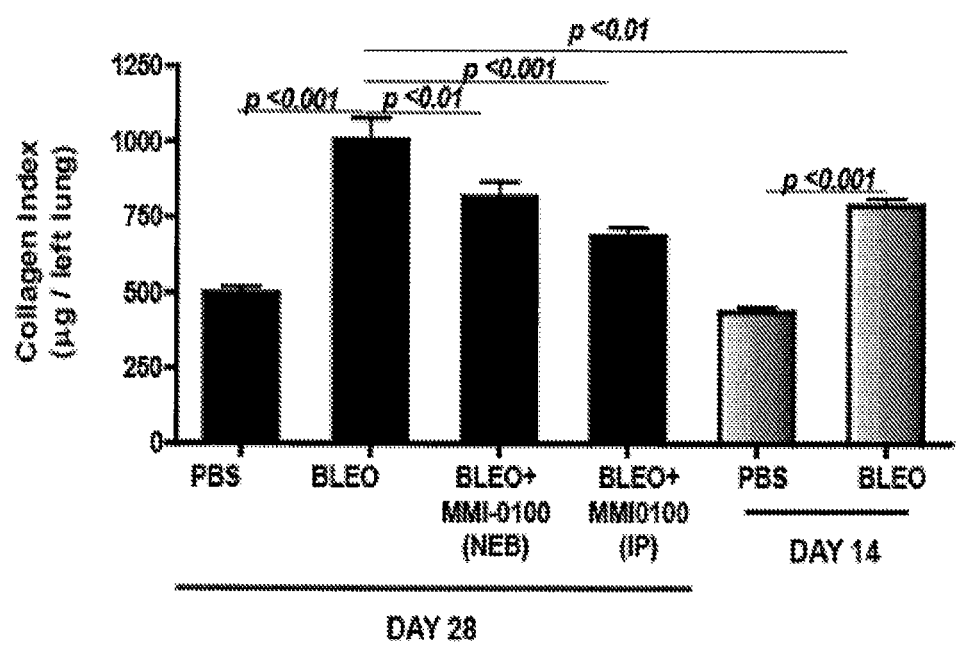

FIG. 17 shows that MMI-0100 (YARAAARQARAKALARQLGVAA (SEQ ID NO: 1)) arrests significant collagen deposition due to bleomycin injury. The abbreviations shown in FIG. 17 are as follows: PBS (wild type mice treated with PBS); BLEO (bleomycin mice treated with PBS); BLEO+MMI-0100 (NEB) (bleomycin mice treated with nebulized MMI-0100 (YARAAARQARAKALARQLGVAA (SEQ ID NO: 1)); BLEO+MMI-0100 (IP) (bleomycin mice treated with intraperitoneal MMI-0100 (YARAAARQARAKALARQLGVAA (SEQ ID NO: 1)). Values represent Means±SEM. n=5 animals per group. Collagen Index=constant factor for collagen 7.5× hydroxyproline concentrations.

Figure 18:
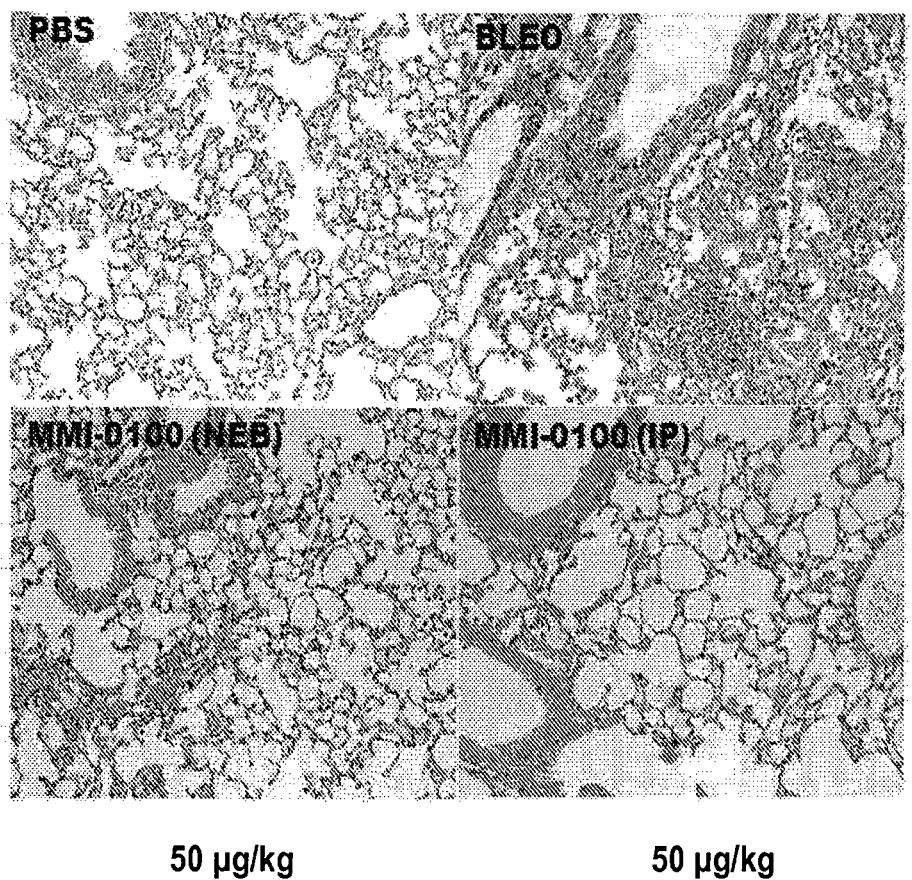

FIG. 18 shows a representative micrographs of anti-phospho-Thr$^{334}$-MAPKAPK2 (an activated form of MK2) staining of lung sections (at day 28 post bleomycin injury) from (i) wild type mice treated with PBS (PBS); (ii) bleomycin mice treated with PBS (BLEO); (iii) bleomycin mice treated with nebulized MMI-0100 (YARAAARQARAKALARQLGVAA (SEQ ID NO: 1)) (BLEO+MMI-0100 (NEB)); and (iv) bleomycin mice treated with intraperitoneal MMI-0100 (YARAAARQARAKALARQLGVAA (SEQ ID NO: 1)) (BLEO+MMI-0100 (IP)). C57-BL/6 mice were subjected to bleomycin injury at day 0. At day 14, the mice were administered 50 µg/kg of MMI-0100 (YARAAARQARAKALARQLGVAA; SEQ ID NO: 1) daily by intraperitoneal (IP) injection or nebulizer (NEB) until day 28 post bleomycin injury. Original magnifications: 20×.

Figure 19:
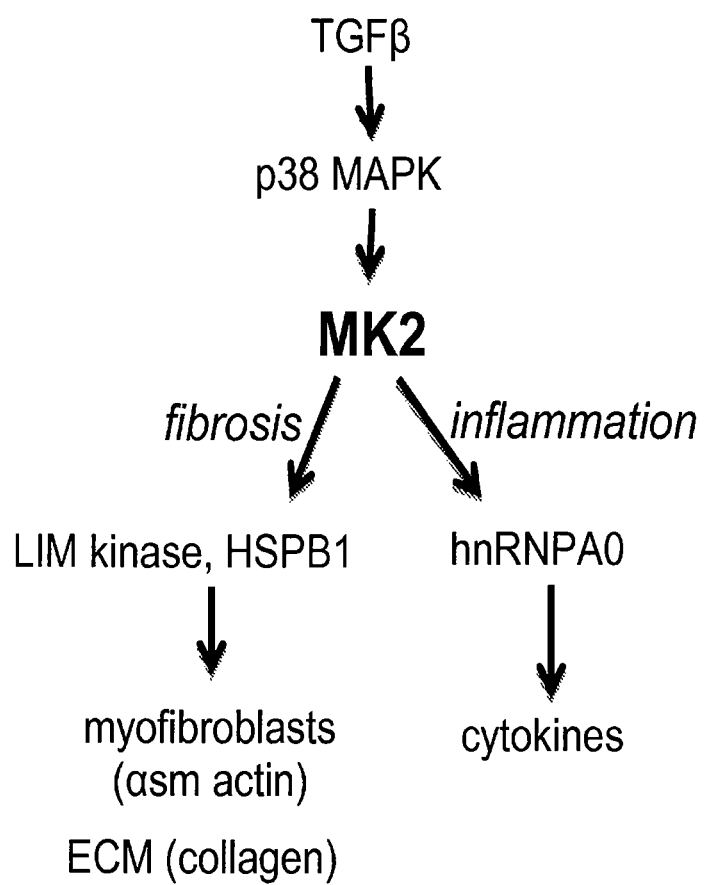

FIG. 19 shows key signaling molecules involved in TGF-β-mediated inflammatory and fibrotic pathways.

Figure 20:
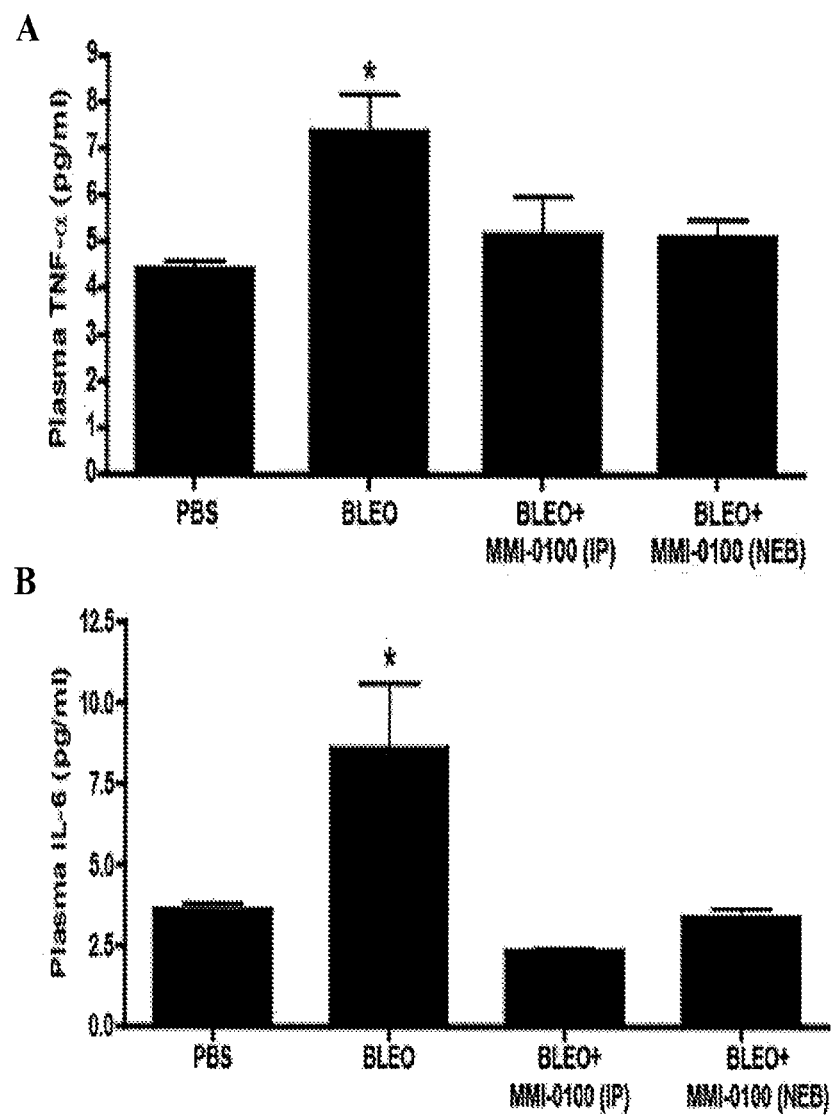

FIG. 20 shows that, 24 hours after final administration, MMI-0100 (YARAAARQARAKALARQLGVAA; SEQ ID NO: 1) downregulates the levels of circulating inflammatory cytokines in the bleomycin mouse model of idiopathic pulmonary fibrosis (treatment model).

Figure 21:
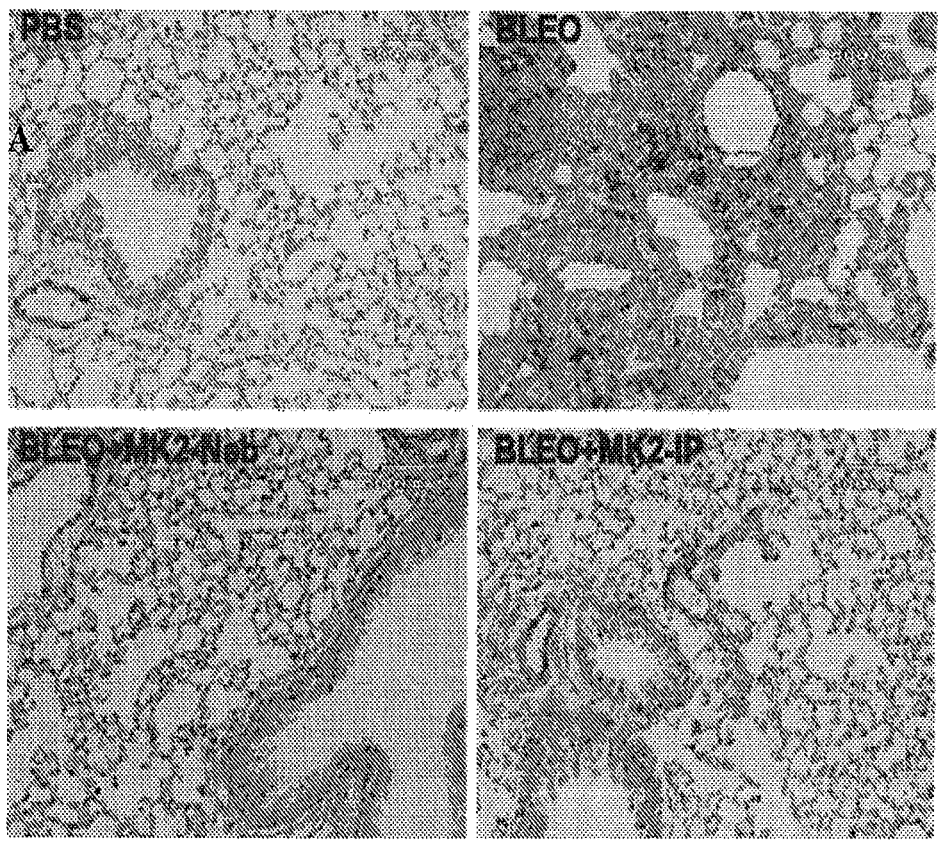

FIG. 21 shows that MMI-0100 (YARAAARQARAKALARQLGVAA; SEQ ID NO: 1) inhibits myofibroblast alpha-smooth muscle actin (α-SMA) activation in the idiopathic pulmonary fibrosis treatment model. C57-BL/6 mice were subjected to bleomycin injury at day 0. At day 14 through day 28, mice were administered 50 µg/kg/day MMI-0100 (YARAAARQARAKALARQLGVAA; SEQ ID NO: 1) by intraperitoneal (IP) injection or nebulizer (NEB). Formalin-fixed lung tissue sections were immunostained against α-SMA. Control staining was with biotinylated secondary IgG antibody. Streptavidin-conjugated horseradish peroxidase was used with 3,3'-diaminobenzidene as substrate and nuclei was counterstained with hematoxylin. Original magnifications: 20×

Figure 22:
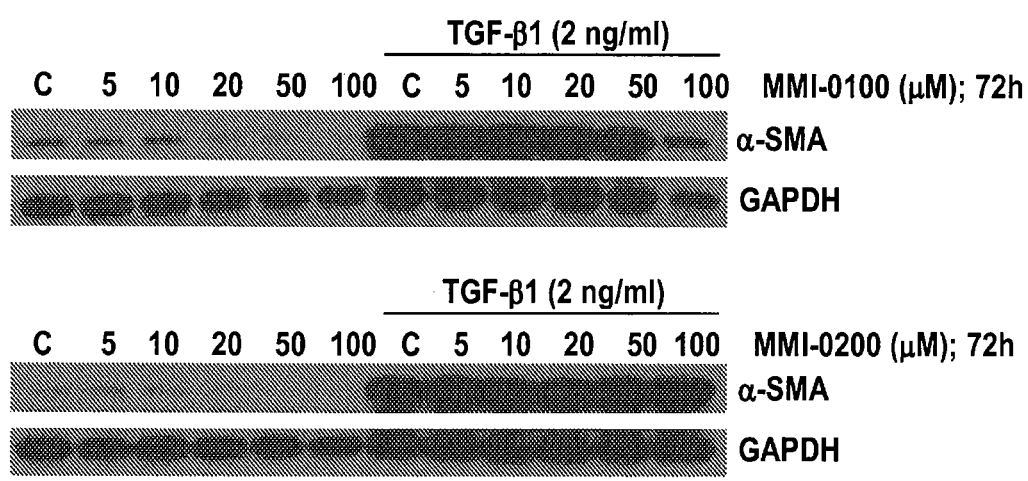

FIG. 22 shows modulation of TGF-β-induced myofibroblast activation by MK2 peptide inhibitors in normal human fetal lung fibroblasts (IMR-90). IMR-90 cells were pre-treated with MMI-0100 (YARAAARQARAKALARQLGVAA; SEQ ID NO: 1) or MMI-0200 (YARAAARQARAKALNRQLGVA; SEQ ID NO: 19) at the indicated doses for 1 h and then cultured in the presence or absence of TGF-β1 (2 ng/ml) for 48 h. Cell lysates were immunoblotted against antibodies for α-SMA (a marker for myofibroblast activation) and GAPDH (loading control).

Figure 23:
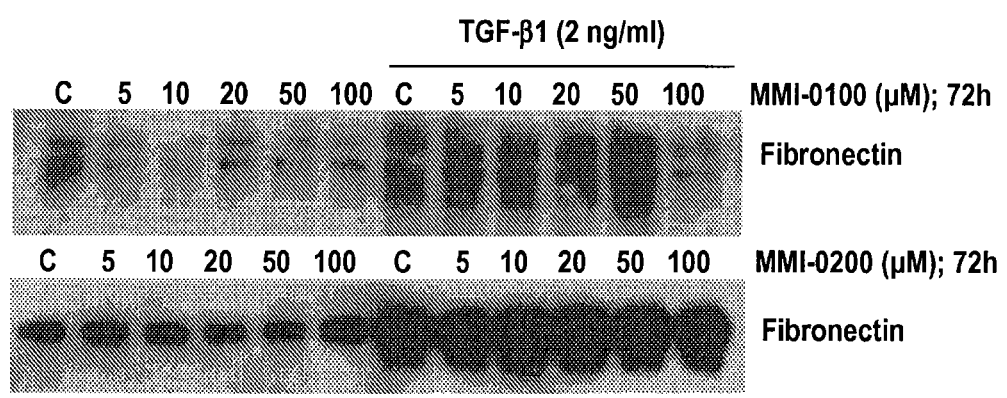

FIG. 23 shows modulation of TGF-β-mediated fibronectin expression in human fetal lung fibroblasts (IMR-90). IMR90 cells were pre-treated with MMI-0100 (YARAAARQARAKALARQLGVAA; SEQ ID NO: 1) or MMI-0200 (YARAAARQARAKALNRQLGVA; SEQ ID NO: 19) at the indicated doses for 1 h, and then cultured in the presence or absence of TGF-β1 (2 ng/ml) for 72 h. Fibronection was measured as secreted fragments in the conditioned media. Equal amounts (14 µg) of total proteins from the conditioned media were loaded in each lane.

Figure 24:
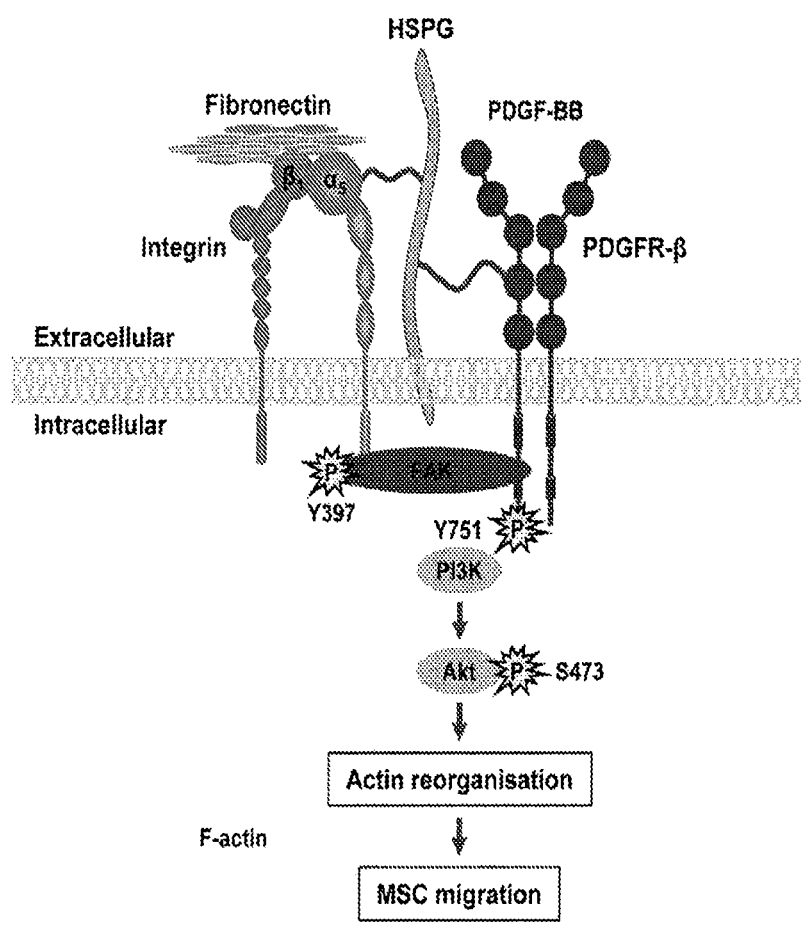

FIG. 24 shows key signaling molecules involved in the regulation of mesenchymal stem cell migration by fibronectin through α5β1-integrin-mediated activation of PDGFR-β (Veevers-Lowe J et al., J Cell Sci, 124: 1288-1300, 2011).

Figure 25:
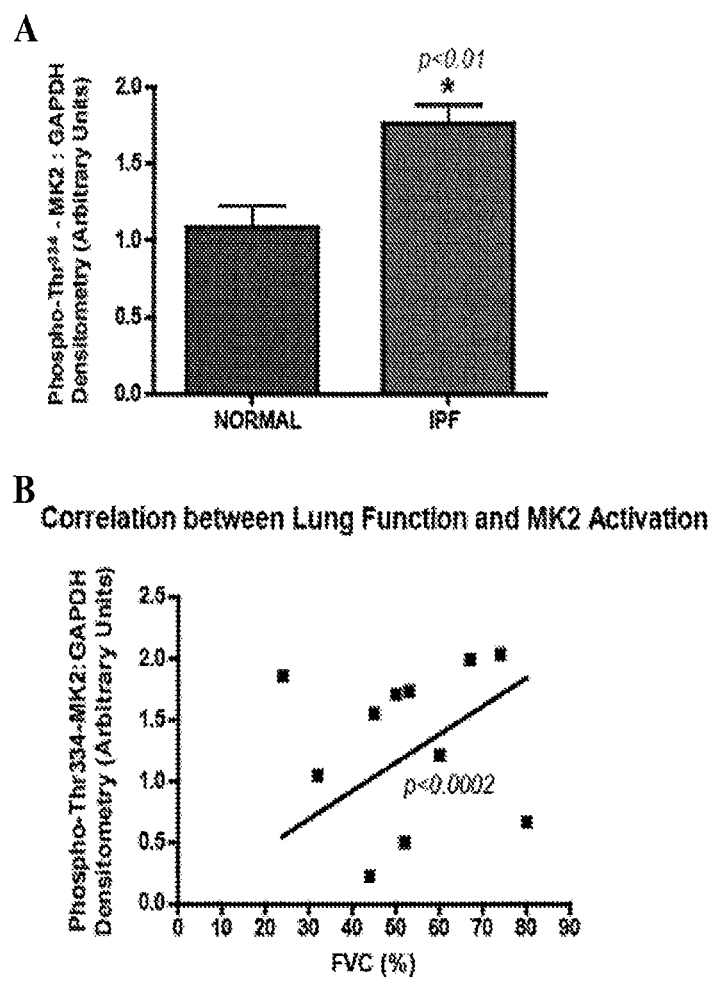

FIG. 25 shows increases in the level of an MK2 kinase activated form in IPF patients. (A) quantitative analysis of phospho-Thr$^{334}$ levels in normal and IPF tissues; (C) correlation between lung function and MK2 activation.

Figure 26:
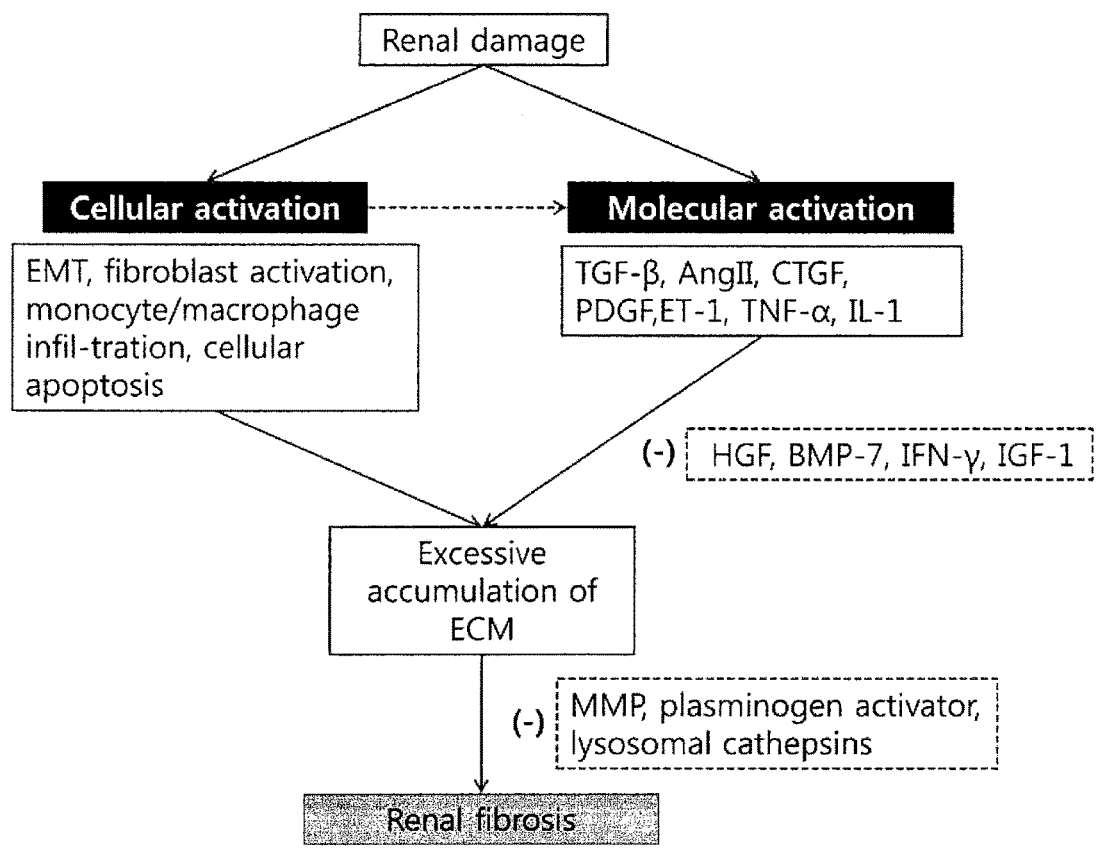

FIG. 26 shows a schematic diagram of the pathogenetic mechanism underlying renal fibrosis (Cho M H, Korean J. Pediatr. 2010; 53(7): 735-740).

DETAILED DESCRIPTION OF THE INVENTION

The described invention provides a composition and method for reducing progression of a fibrosis in a tissue selected from a liver tissue, a kidney tissue or a vascular tissue in a subject in need of thereof, the progression of which is characterized by one or more of aberrant fibroblast proliferation and extracellular matrix deposition producing tissue remodeling, the method comprising administering a therapeutic amount of a composition comprising a polypeptide having the amino acid sequence YARAAARQARAKALARQLGVAA (MMI-0100; SEQ ID NO: 1) or a functional equivalent thereof, wherein the therapeutic amount of the polypeptide is effective to reduce progression of the fibrosis, to treat remodeling of the tissue, or a combination thereof.

Glossary

The term "airway" as used herein refers to the passages through which air enters and leaves the body. The pulmonary airway comprises those parts of the respiratory tract through which air passes during breathing.

The term "airway obstruction" as used herein refers to any abnormal reduction in airflow. Resistance to airflow can occur anywhere in the airway from the upper airway to the terminal bronchi.

The term "airway disease" as used herein refers to a disease that affects the tubes (airways) that carry oxygen and other gases into and out of the lungs. Airway diseases include, but are not limited to, chronic obstructive pulmonary disease (COPD), including asthma, emphysema, and chronic bronchitis.

The term "lung tissue disease" as used herein refers to a disease that affects the structure of the lung tissue, e.g., pulmonary interstitium. Scarring or inflammation of lung tissue makes the lungs unable to expand fully ("restrictive lung disease"). It also makes the lungs less capable of taking up oxygen (oxygenation) and releasing carbon dioxide. Examples of lung tissue diseases include, but are not limited to, idiopathic pulmonary fibrosis (IPF), acute lung injury (ALI), a radiation-induced fibrosis in the lung, and a fibrotic condition associated with lung transplantation. Sarcoidosis is a disease in which swelling (inflammation) occurs in the lymph nodes, lungs, liver, eyes, skin, or other tissues.

The terms "lung interstitium" or "pulmonary interstitium" are used interchangeably herein to refer to an area located between the airspace epithelium and pleural mesothelium in the lung. Fibers of the matrix proteins, collagen and elastin, are the major components of the pulmonary interstitium. The primary function of these fibers is to form a mechanical scaffold that maintains structural integrity during ventilation.

The term "accessible surface area" or "ASA" as used herein refers to a surface area of a biomolecule that is exposed to solvent. The term "solvent accessible surface" or "SAS" as used herein refers to a percentage of the surface area of a given residue that is accessible to the solvent. It is calculated as a ratio between ASA of a residue in the three dimensional structure and the maximum ASA of its extended peptide confirmation The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids. The amino acids may be L- or D-amino acids. An amino acid may be replaced by a synthetic amino acid, which is altered so as to increase the half-life of the peptide, increase the potency of the peptide, or increase the bioavailability of the peptide.

The single letter designation for amino acids is used predominately herein. As is well known by one of skill in the art, such single letter designations are as follows:

A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine.

The following represents groups of amino acids that are conservative substitutions for one another: 1) Alanine (A), Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

As used herein, the singular forms "a", "an" and "the" include plural referents unless the context clearly dictates otherwise. For example, reference to a "polypeptide" means one or more polypeptides.

The term "addition" as used herein refers to the insertion of one or more bases, or of one or more amino acids, into a sequence.

The term "administer" as used herein refers to dispensing, supplying, applying, giving, apportioning or contributing. The terms "administering" or "administration" are used interchangeably and include in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing the conventional nontoxic pharmaceutically acceptable carriers, adjuvants, and vehicles as desired, or may be locally administered by means such as, but not limited to, injection, implantation, grafting, topical application, or parenterally. Additional administration may be performed, for example, intravenously, pericardially, orally, via implant, transmucosally, transdermally, topically, intramuscularly, subcutaneously, intraperitoneally, intrathecally, intralymphatically, intralesionally, or epidurally. Administering can be performed, for example, once, a plurality of times, and/or over one or more extended periods.

The term "allergic reaction" as used herein refers to a hypersensitive reaction of the immune system. Allergic reactions occur to normally harmless environmental substances known as allergens; these reactions are acquired, predictable, and rapid. Allergic reaction is characterized by excessive activation of certain white blood cells called mast cells and basophils by a type of antibody known as IgE, resulting in an extreme inflammatory response. Common allergic reactions include eczema, hives, hay fever, asthma attacks, food allergies, and reactions to the venom of stinging insects such as wasps and bees.

The term "α-smooth muscle actin" or "α-SMA" as used herein refers to an actin protein, alpha-actin-2 (ACTA2; also known as actin or aortic smooth muscle actin) first isolated in vascular smooth muscle cells. Actins are highly conserved proteins expressed in all eukaryotic cells. Actin filaments form part of the cytoskeleton and play essential roles in regulating cell shape and movement. Six distinct actin isotypes have been identified in mammalian cells. Each is encoded by a separated gene and is expressed in a developmentally regulated and tissue-specific manner. Alpha and beta cytoplasmic actins are expressed in a wide variety of cells, whereas expression of alpha skeletal, alpha cardiac, alpha vascular, and gamma enteric actins are more restricted to specialized muscle cell type. The gene for alpha-smooth muscle actin is one of a few genes whose expression is relatively restricted to vascular smooth muscle cells, but it is now most commonly used as a marker of myofibroblast formation. Expression of alpha smooth muscle actin is regulated by hormones and cell proliferation, and is altered by pathological conditions, including oncogenic transformation and atherosclerosis.

The term "alveolus" or "alveoli" as used herein refers to an anatomical structure that has the form of a hollow cavity. Found in the lung, the pulmonary alveoli are spherical outcroppings of the respiratory sites of gas exchange with the blood. The alveoli contain some collagen and elastic fibers. Elastic fibers allow the alveoli to stretch as they fill with air when breathing in. They then spring back during breathing out in order to expel the carbon dioxide-rich air.

The term "biomarker" (or "biosignature") as used herein refers to a peptide, a protein, a nucleic acid, an antibody, a gene, a metabolite, or any other substance used as an indicator of a biologic state. It is a characteristic that is measured objectively and evaluated as a cellular or molecular indicator of normal biologic processes, pathogenic processes, or pharmacologic responses to a therapeutic intervention.

The term "bleomycin" as used herein refers to a glycopeptide antibiotic produced by the bacterium *Streptomyces verticillus*. It works by inducing DNA strand breaks and inhibiting incorporation of thymidine into DNA strand. The most serious complication of bleomycin is pulmonary fibrosis and impaired lung function.

The term "bronchoalveolar lavage" or "BAL" as used herein refers to a medical procedure in which a bronchoscope is passed through the mouth or nose into the lungs and fluid is squirted into a small part of the lung and then recollected for examination. BAL typically is performed to diagnose lung disease. BAL commonly is used to diagnose infections in people with immune system problems, pneumonia in people on ventilators, some types of lung cancer, and scarring of the lung (interstitial lung disease). BAL is the most common manner to sample the components of the epithelial lining fluid (ELF) and to determine the protein composition of the pulmonary airways, and is often used in immunological research as a means of sampling cells or pathogen levels in the lung.

The terms "carrier" and "pharmaceutical carrier" as used herein refer to a pharmaceutically acceptable inert agent or vehicle for delivering one or more active agents to a subject, and often is referred to as "excipient." The (pharmaceutical) carrier must be of sufficiently high purity and of sufficiently low toxicity to render it suitable for administration to the subject being treated. The (pharmaceutical) carrier further should maintain the stability and bioavailability of an active agent, e.g., a polypeptide of the described invention. The (pharmaceutical) carrier can be liquid or solid and is selected, with the planned manner of administration in mind, to provide for the desired bulk, consistency, etc., when combined with an active agent and other components of a given composition. The (pharmaceutical) carrier may be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulphate, etc.). Other suitable (pharmaceutical) carriers for the compositions of the described invention include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like. Compositions that are for parenteral administration of a polypeptide of the described invention may include (pharmaceutical) carriers such as sterile aqueous solutions, non-aqueous solutions in common solvents such as alcohols, or solutions of the polypeptide in a liquid oil base.

The term "collagen" as used herein refers to a group of naturally occurring proteins found in the flesh and in connective tissues of mammals. It is the main component of connective tissue, and is the most abundant protein in mammals, making up about 25% to 35% of the whole-body protein content. Collagen, in the form of elongated fibrils, is mostly found in fibrous tissues, such as tendon, ligament, and skin, and is also abundant in cornea, cartilage, bone, blood vessels, the gut, and intervertebral disc. So far, 29 types of collagen have been identified and over 90% of the collagen in the body is of type I (skin, tendon, vascular, ligature, organs, bone), type II (cartilage), type III (reticulate (main component of reticular fibers), and type IV (which forms the bases of cell base membrane).

The term "condition" as used herein refers to a variety of health states and is meant to include disorders or diseases caused by any underlying mechanism, disorder, or injury.

The term "cytokine," which refers to small soluble protein substances secreted by cells that have a variety of effects on other cells, is generically used to refer to many signaling molecules including, without limitation, lymphokines, interleukins, and chemokines. Cytokines mediate many important physiological functions including growth, development, wound healing, and the immune response. They act by binding to their cell-specific receptors located in the cell membrane that allows a distinct signal transduction cascade to start in the cell, which eventually will lead to biochemical and phenotypic changes in target cells. Generally, cytokines act locally, although some have been found to have systemic immunomodulatory effects, with pleiotropic autocrine, paracrine, and endocrine effects similar to hormones. They include type I cytokines, which encompass many of the interleukins, as well as several hematopoietic growth factors; type II cytokines, including the interferons and interleukin-10; tumor necrosis factor ("TNF")-related molecules, including TNF-α and lymphotoxin; immunoglobulin superfamily members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The terms "disease" or "disorder" as used herein refer to an impairment of health or a condition of abnormal functioning, regardless of cause (whether heritable, environmental, dietary, infectious, due to trauma, or otherwise). Disorders may include, for example, but are not limited to, inflammatory and fibrotic diseases, fibrosis, acute lung injury, radiation-induced fibrosis, transplant rejection, chronic obstructive pulmonary disease (COPD), endotoxic shock, localized inflammatory disease, atherosclerotic cardiovascular disease, Alzheimer's disease, oncological diseases, neural ischemia, connective tissue and systemic autoimmune diseases, rheumatoid arthritis, Crohn's disease, inflammatory bowel disease, systemic lupus erythematosus (SLE), Sjögren's syndrome, scleroderma, vasculitis, intimal hyperplasia, stenosis, restenosis, atherosclerosis, smooth muscle cell tumors and metastasis, smooth muscle spasm, angina, Prinzmetal's angina, ischemia, stroke, bradycardia, hypertension, cardiac hypertrophy, renal failure, stroke, pulmonary hypertension, asthma, toxemia of pregnancy, preterm labor, pre-eclampsia, eclampsia, Raynaud's disease or phenomenon, hemolytic-uremia, anal fissure, achalasia, impotence, migraine, ischemic muscle injury associated with smooth muscle spasm, vasculopathy, bradyarrythmia, congestive heart failure, stunned myocardium, pulmonary hypertension, diastolic dysfunction, gliosis (proliferation of astrocytes, and may include deposition of extracellular matrix (ECM) deposition in damaged areas of the central nervous system), chronic obstructive pulmonary disease (i.e., respiratory tract diseases characterized by airflow obstruction or limitation; includes, but is not limited to, chronic bronchitis, emphysema, and chronic asthma), osteopenia, endothelial dysfunction, inflammation, degenerative arthritis, anklyosing spondylitis, Guillain-Barré disease, infectious disease, sepsis, endotoxemic shock, psoriasis, radiation enteritis, cirrhosis, interstitial fibrosis, pulmonary fibrosis (including idiopathic pulmonary fibrosis), colitis, appendicitis, gastritis, laryngitis, meningitis, pancreatitis, otitis, reperfusion injury, traumatic brain injury, spinal cord injury, peripheral neuropathy, multiple sclerosis, allergy, cardiometabolic diseases, obesity, type II diabetes mellitus, type I diabetes mellitus, and NASH/cirrhosis.

The term "domain" as used herein refers to a region of a protein with a characteristic tertiary structure and function and to any of the three-dimensional subunits of a protein that together makes up its tertiary structure formed by folding its linear peptide chain.

The term "therapeutic domain" (also referred to as "TD") as used herein refers to a peptide, peptide segment or variant, or derivative thereof, with substantial identity to peptide KALARQLGVAA (SEQ ID NO: 2), or segment thereof. Therapeutic domains by themselves generally are not capable of penetrating the plasma membrane of mammalian cells. Once inside the cell, therapeutic domains can inhibit the kinase activity of a specific group of kinases.

The term "cell penetrating peptide" (also referred to as "CPP," "protein transduction domain," "PTD", "Trojan peptide", "membrane translocating sequence", and "cell permeable protein") as used herein refers to a class of peptides generally capable of penetrating the plasma membrane of mammalian cells. It also refers to a peptide, peptide segment, or variant or derivative thereof, with substantial identity to peptide YARAAARQARA (SEQ ID NO: 11), or a functional segment thereof, and to a peptide, peptide segment, or variant or derivative thereof, which is functionally equivalent to SEQ ID NO: 11. CPPs generally are 10-16 amino acids in length and are capable of transporting compounds of many types and molecular weights across mammalian cells. Such compounds include, but are not limited to, effector molecules, such as proteins, DNA, conjugated peptides, oligonucleotides, and small particles such as liposomes. CPPs chemically linked or fused to other proteins ("fusion proteins") still are able to penetrate the plasma membrane and enter cells.

The term "extracellular matrix" as used herein refers to a scaffold in a cell's external environment with which the cell interacts via specific cell surface receptors. The extracellular matrix is composed of an interlocking mesh of fibrous proteins and glycosaminoglycans (GAGs). Examples of fibrous proteins found in the extracellular matrix include, without limitation, collagen, elastin, fibronectin, and laminin. Examples of GAGs found in the extracellular matrix include, without limitation, proteoglycans (e.g., heparin sulfate), chondroitin sulfate, keratin sulfate, and non-proteoglycan polysaccharide (e.g., hyaluronic acid). The term "proteoglycan" refers to a group of glycoproteins that contain a core protein to which is attached one or more glycosaminoglycans. The extracellular matrix serves many functions, including, but not limited to, providing support and anchorage for cells, segregating one tissue from another tissue, and regulating intracellular communication.

The terms "functional equivalent" or "functionally equivalent" are used interchangeably herein to refer to substances, molecules, polynucleotides, proteins, peptides, or polypeptides having similar or identical effects or use. A polypeptide functionally equivalent to polypeptide YARAAARQARAKALARQLGVAA (SEQ ID NO: 1), for example, may have a biologic activity, e.g., an inhibitory activity, kinetic parameters, salt inhibition, a cofactor-dependent activity, and/or a functional unit size that is substantially similar or identical to the expressed polypeptide of SEQ ID NO: 1.

Examples of polypeptides functionally equivalent to YARAAARQARAKALARQLGVAA (SEQ ID NO: 1) include, but are not limited to, a polypeptide of amino acid sequence FAKLAARLYRKALARQLGVAA (SEQ ID NO: 3), a polypeptide of amino acid sequence KAFAKLAARLYRKALARQLGVAA (SEQ ID NO: 4), a polypeptide of amino acid sequence YARAAARQARAKALARQLAVA (SEQ ID NO: 5), a polypeptide of amino acid sequence YARAAARQARAKALARQLGVA (SEQ ID NO: 6), a polypeptide of amino acid sequence YARAAARQARAKALNRQLAVAA (SEQ ID NO: 26), a polypeptide of amino acid sequence YARAARQARAKALNRQLAVA (SEQ ID NO: 27) and a polypeptide of amino acid sequence HRRIKAWLKKIKALARQLGVAA (SEQ ID NO: 7).

The MMI-0100 (YARAAARQARAKALARQLGVAA; SEQ ID NO: 1) peptide of amino acid sequence YARAAARQARAKALARQLGVAA (SEQ ID NO: 1) described in the present invention comprises a fusion protein in which a cell penetrating peptide (CPP; YARAAARQARA; SEQ ID NO: 11) is operatively linked to a therapeutic domain (KALARQLGVAA; SEQ ID NO: 2) in order to enhance therapeutic efficacy.

Examples of polypeptides functionally equivalent to the therapeutic domain (TD; KALARQLGVAA; SEQ ID NO: 2) of the polypeptide YARAAARQARAKALARQLGVAA (SEQ ID NO: 1) include, but are not limited to, a polypeptide of amino acid sequence KALARQLAVA (SEQ ID NO: 8), a polypeptide of amino acid sequence KALARQLGVA (SEQ ID NO: 9), a polypeptide of amino acid sequence KALARQLGVAA (SEQ ID NO: 10), a polypeptide of amino acid sequence KALNRQLAVAA (SEQ ID NO: 28), and a polypeptide of amino acid sequence KALNRQLAVA (SEQ ID NO: 29).

Examples of polypeptides functionally equivalent to the cell penetrating peptide (CPP; YARAAARQARA; SEQ ID NO: 11) of the polypeptide YARAAARQARAKALARQLGVAA (SEQ ID NO: 1) include, but are not limited to, a polypeptide of amino acid sequence WLRRIKAWLRRIKA (SEQ ID NO: 12), a polypeptide of amino acid sequence WLRRIKA (SEQ ID NO: 13), a polypeptide of amino acid sequence YGRKKRRQRRR (SEQ ID NO: 14), a polypeptide of amino acid sequence WLRRIKAWLRRI (SEQ ID NO: 15), a polypeptide of amino acid sequence FAKLAARLYR (SEQ ID NO: 16), a polypeptide of amino acid sequence KAFAKLAARLYR (SEQ ID NO: 17), and a polypeptide of amino acid sequence HRRIKAWLKKI (SEQ ID NO: 18).

The term "endogenous" as used herein refers to growing or originating from within, or derived internally.

The term "endothelium" as used herein refers to a thin layer of cells that lines the interior surface of blood vessels, forming an interface between circulating blood in the lumen and the rest of the vessel wall. Endothelial cells will line the entire circulatory system, from the heart to the smallest capillary. These cells reduce turbulence of the flow of blood allowing the fluid to be pumped farther.

The term "eosinophils" or "eosinophil granulocytes" as used herein refers to white blood cells responsible for combating multicellular parasites and certain infections in vertebrates. They are granulocytes that develop during hematopoiesis in the bone marrow before migrating into blood. Along with mast cells, they also control mechanisms associated with allergy and asthma. Following activation, eosinophils exert diverse functions, including (1) production of cationic granule proteins and their release by degranulation, (2) production of reactive oxygen species, such as, superoxide, peroxide, and hypobromite (hypobromous acid, which is preferentially produced by eosinophil peroxidase), (3) production of lipid mediators, such as, eicosanoids from leukotriene and prostaglandin families, (4) production of growth factors, such as transforming growth factor (TGF-β), vascular endothelial growth factor (VEGF), and platelet-derived growth factor (PDGF), and (5) production of cytokines such as IL-1, IL-2, IL-4, IL-5, IL-6, IL-8, IL-13, and TNF-α.

The term "epithelium" as used herein refers to a tissue composed of cells that line the cavities and surfaces of structures throughout the body. The basal surface of the epithelium faces underlying connective tissue, and the two layers are separated by a basement membrane.

The term "extravasation" as used herein refers to the movement of blood cell components from the capillaries to the tissues surrounding them (diapedesis). In the case of malignant cancer metastasis, it refers to cancer cells exiting the capillaries and entering organs.

The term "exudation" as used herein refers to a process by which a fluid from the circulatory system passes through the walls of the blood vessels into lesions or areas of inflammation. Blood exudates contain some or all plasma proteins, white blood cells, platelets and red blood cells.

The term "fibrin" as used herein refers to a fibrous protein involved in the clotting of blood. It is a fibrillar protein that is polymerized to form a "mesh" that forms a hemostatic plug or clot (in conjunction with platelets) over a wound site. Fibrin is involved in signal transduction, blood coagulation, platelet activation, and protein polymerization.

The term "fibroblast" as used herein refers to a connective tissue cell that makes and secretes the extracellular matrix proteins, including, but not limited to, collagen. Fibroblasts, the most common cell type found in connective tissues, play an important role in healing wounds. Like other cells of connective tissue, fibroblasts are derived from primitive mesenchyme (a type of loose connective tissue derived from all three germ layers and located in the embryos). In certain situations epithelial cells can give rise to fibroblasts, a process called epithelial-mesenchymal transition. Fibroblasts and fibrocytes are two states of the same cells, the former being the activated state, the latter the less active state, concerned with maintenance and tissue metabolism, with both terms occasionally used interchangeably.

The term "free radical" as used herein refers to a highly reactive and usually short-lived molecular fragment with one or more unpaired electrons. Free radicals are highly chemically reactive molecules. Because a free radical needs to extract a second electron from a neighboring molecule to pair its single electron, it often reacts with other molecules, which initiates the formation of many more free radical species in a self-propagating chain reaction. This ability to be self-propagating makes free radicals highly toxic to living organisms. Oxidative injury may lead to widespread biochemical damage within the cell. The molecular mechanisms responsible for this damage are complex. For example, free radicals may damage intracellular macromolecules, such as nucleic acids (e.g., DNA and RNA), proteins, and lipids. Free radical damage to cellular proteins may lead to loss of enzymatic function and cell death. Free radical damage to DNA may cause problems in replication or transcription, leading to cell death or uncontrolled cell growth. Free radical damage to cell membrane lipids may cause the damaged membranes to lose their ability to transport oxygen, nutrients or water to cells.

The term "myofibroblasts" as used herein refers to fibroblasts in wound areas that have some characteristics of smooth muscle, such as contractile properties and fibers, and are believed to produce, temporarily, type III collagen. Although there are many possible ways of myofibroblast development, myofibroblasts are cells that are in between fibroblasts and smooth muscle cells in their differentiation. In many organs like liver, lung, and kidney they are primarily involved in fibrosis. In wound tissue, they are implicated in wound strengthening (by extracellular collagen fiber deposition) and then wound contraction (by intracellular contraction and concomitant alignment of the collagen fibers by integrin mediated pulling o to the collagen bundles).

The term "fibronectin" as used herein refers to a high-molecular weight (~440 kDa) extracellular matrix glycoprotein that binds to membrane-spanning cell-surface matrix receptor proteins ("integrins") and to extracellular matrix components such as collagen, fibrin and heparan sulfate proteoglycans (e.g. syndecans). Fibronectin exists as a dimer, consisting of two nearly identical monomers linked by a pair of disulfide bonds. There are multiple isoforms of fibronectin. Plasma fibronectin is soluble and circulates in the blood and other body fluids, where it is thought to enhance blood clotting, wound healing and phagocytosis. The other isoforms assemble on the surface of cells and are deposited in the extracellular matrix as highly insoluble fibronectin fibrils. The fibronectin fibrils that form on or near the surface of fibroblasts usually are aligned with adjacent intracellular actin stress fibers, which promote the assembly of secreted fibronectin molecules into fibrils and influence fibril orientation. Fibronectin plays a major role in cell adhesion, cell growth, cell migration and cell differentiation, and it is important for processes such as wound healing and embryonic development.

The term "fibrosis" as used herein refers to the formation or development of excess fibrous connective tissue in an organ or tissue as a result of injury or inflammation of a part, or of interference with its blood supply. It may be a consequence of the normal healing response leading to a scar, an abnormal, reactive process, or without known or understood causation.

The term "inhalation" as used herein refers to the act of drawing in a medicated vapor with the breath.

The term "insufflation" as used herein refers to the act of delivering air, a gas, or a powder under pressure to a cavity or chamber of the body. For example, nasal insufflation relates to the act of delivering air, a gas, or a powder under pressure through the nose.

The term "inhalation delivery device" as used herein refers to a machine/apparatus or component that produces small droplets or an aerosol from a liquid or dry powder aerosol formulation and is used for administration through the mouth in order to achieve pulmonary administration of a drug, e.g., in solution, powder, and the like. Examples of inhalation delivery device include, but are not limited to, a nebulizer, a metered-dose inhaler, and a dry powder inhaler (DPI).

The term "nebulizer" as used herein refers to a device used to administer liquid medication in the form of a mist inhaled into the lungs.

The term "metered-dose inhaler", "MDI", or "puffer" as used herein refers to a pressurized, hand-held device that uses propellants to deliver a specific amount of medicine ("metered dose") to the lungs of a patient. The term "propellant" as used herein refers to a material that is used to expel a substance usually by gas pressure through a convergent, divergent nozzle. The pressure may be from a compressed gas, or a gas produced by a chemical reaction. The exhaust material may be a gas, liquid, plasma, or, before the chemical reaction, a solid, liquid or gel. Propellants used in pressurized metered dose inhalers are liquefied gases, traditionally chlorofluorocarbons (CFCs) and increasingly hydrofluoroalkanes (HFAs). Suitable propellants include, for example, a chlorofluorocarbon (CFC), such as trichlorofluoromethane (also referred to as propellant 11), dichlorodifluoromethane (also referred to as propellant 12), and 1,2-dichloro-1,1,2,2-tetrafluoroethane (also referred to as propellant 114), a hydrochlorofluorocarbon, a hydrofluorocarbon (HFC), such as 1,1,1,2-tetrafluoroethane (also referred to as propellant 134a, HFC-134a, or HFA-134a) and 1,1,1,2,3,3,3-heptafluoropropane (also referred to as propellant 227, HFC-227, or HFA-227), carbon dioxide, dimethyl ether, butane, propane, or mixtures thereof. In other embodiments, the propellant includes a chlorofluorocarbon, a hydrochlorofluorocarbon, a hydrofluorocarbon, or mixtures thereof. In other embodiments, a hydrofluorocarbon is used as the propellant. In other embodiments, HFC-227 and/or HFC-134a are used as the propellant.

The term "dry powder inhaler" or "DPI" as used herein refers to a device similar to a metered-dose inhaler, but where the drug is in powder form. The patient exhales out a full breath, places the lips around the mouthpiece, and then quickly breathes in the powder. Dry powder inhalers do not require the timing and coordination that are necessary with MDIs.

The term "particles" as used herein refers to refers to an extremely small constituent (e.g., nanoparticles, microparticles, or in some instances larger) in or on which is contained the composition as described herein.

The terms "pulmonary fibrosis", "idiopathic pulmonary fibrosis", and "cryptogenic fibrosing alveolitis" as used herein refer to a major component of interstitial lung disease characterized by abnormal fibroblast proliferation and deposition of extracellular matrix proteins that remodel the normal pulmonary tissue structure and compromise its function. The hallmark lesions of idiopathic pulmonary fibrosis are the fibroblast foci. These sites feature vigorous replication of mesenchymal cells and exuberant deposition of fresh extracellular matrix.

The terms "fibrotic loci" or "fibrotic foci" as used herein interchangeably refer to a specific location in a tissue formed or developed by excessive fibrous tissue.

The term "fusion protein" as used herein refers to a protein or polypeptide constructed by combining multiple protein domains or polypeptides for the purpose of creating a single polypeptide or protein with functional properties derived from each of the original proteins or polypeptides. Creation of a fusion protein may be accomplished by operatively ligating or linking two different nucleotides sequences that encode each protein domain or polypeptide via recombinant DNA technology, thereby creating a new polynucleotide sequences that codes for the desired fusion protein. Alternatively, a fusion protein maybe created by chemically joining the desired protein domains.

The term "idiopathic" as used herein means arising spontaneously or from an obscure or unknown cause.

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses.

The term "acute inflammation" as used herein refers to the rapid, short-lived (minutes to days), relatively uniform response to acute injury characterized by accumulations of fluid, plasma proteins, and neutrophilic leukocytes. Examples of injurious agents that cause acute inflammation include, but are not limited to, pathogens (e.g., bacteria, viruses, parasites), foreign bodies from exogenous (e.g. asbestos) or endogenous (e.g., urate crystals, immune complexes), sources, and physical (e.g., burns) or chemical (e.g., caustics) agents.

The term "chronic inflammation" as used herein refers to inflammation that is of longer duration and which has a vague and indefinite termination. Chronic inflammation takes over when acute inflammation persists, either through incomplete clearance of the initial inflammatory agent (e.g., cigarette smoking) or as a result of multiple acute events occurring in the same location. Chronic inflammation, which includes the influx of lymphocytes and macrophages and fibroblast growth, may result in tissue scarring at sites of prolonged or repeated inflammatory activity.

The term "inflammatory mediators" as used herein refers to the molecular mediators of the inflammatory and immune processes. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators; still others exhibit anti-inflammatory properties. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides, hormones (including steroid hormones such as glucocorticoids), and amines, including, but not limited to, histamine, serotonin, and neuropeptides, and proinflammatory cytokines, including, but not limited to, interleukin-1-beta (IL-1β), interleukin-4 (IL-4), interleukin-6 (IL-6), interleukin-8 (IL-8), tumor necrosis factor-alpha (TNF-α), interferon-gamma (IF-γ), interleukin-12 (IL-12), and interleukin-17 (IL-17).

Among the pro-inflammatory mediators, IL-1, IL-6, and TNF-α are known to activate hepatocytes in an acute phase response to synthesize acute-phase proteins that activate complement. Complement is a system of plasma proteins that interact with pathogens to mark them for destruction by phagocytes. Complement proteins can be activated directly by pathogens or indirectly by pathogen-bound antibody, leading to a cascade of reactions that occurs on the surface of pathogens and generates active components with various effector functions. IL-1, IL-6, and TNF-α also activate bone marrow endothelium to mobilize neutrophils, and function as endogenous pyrogens, raising body temperature, which helps eliminating infections from the body. A major effect of the cytokines is to act on the hypothalamus, altering the body's temperature regulation, and on muscle and fat cells, stimulating the catabolism of the muscle and fat cells to elevate body temperature. At elevated temperatures, bacterial and viral replications are decreased, while the adaptive immune system operates more efficiently.

The term "tumor necrosis factor" as used herein refers to a cytokine made by white blood cells in response to an antigen or infection, which induce necrosis (death) of tumor cells and possesses a wide range of pro-inflammatory actions. Tumor necrosis factor also is a multifunctional cytokine with effects on lipid metabolism, coagulation, insulin resistance, and the function of endothelial cells lining blood vessels.

The term "interleukin (IL)" as used herein refers to a cytokine from a class of homologously related proteins that were first observed to be secreted by, and acting on, leukocytes. It has since been found that interleukins are produced by a wide variety of body cells. Interleukins regulate cell growth, differentiation, and motility, and stimulates immune responses, such as inflammation. Examples of interleukins include, interleukin-1 (IL-1), interleukin-1β (IL-1β), interleukin-6 (IL-6), interleukin-8 (IL-8), interleukin-12 (IL-12), and interleukin-17 (IL-17).

The terms "inhibiting", "inhibit" or "inhibition" are used herein to refer to reducing the amount or rate of a process, to stopping the process entirely, or to decreasing, limiting, or blocking the action or function thereof. Inhibition may include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "inhibitor" as used herein refers to a second molecule that binds to a first molecule thereby decreasing the first molecule's activity. Enzyme inhibitors are molecules that bind to enzymes thereby decreasing enzyme activity. The binding of an inhibitor may stop a substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both. Enzyme inhibitors often are evaluated by their specificity and potency.

The term "injury" as used herein refers to damage or harm to a structure or function of the body caused by an outside agent or force, which may be physical or chemical.

The term "isolated" is used herein to refer to material, such as, but not limited to, a nucleic acid, peptide, polypeptide, or protein, which is: (1) substantially or essentially free from components that normally accompany or interact with it as found in its naturally occurring environment. The terms "substantially free" or "essentially free" are used herein to refer to considerably or significantly free of, or more than about 95% free of, or more than about 99% free of such components. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state. For example, a naturally occurring nucleic acid becomes an isolated nucleic acid if it is altered, or if it is transcribed from DNA that has been altered, by means of human intervention performed within the cell from which it originates. See, for example, Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868, each incorporated herein by reference in its entirety. Likewise, a naturally occurring nucleic acid (for example, a promoter) becomes isolated if it is introduced by non-naturally occurring means to a locus of the genome not native to that nucleic acid. Nucleic acids that are "isolated" as defined herein also are referred to as "heterologous" nucleic acids.

The term "kinase" as used herein refers to a type of enzyme that transfers phosphate groups from high-energy donor molecules to specific target molecules or substrates. High-energy donor groups may include, but are not limited, to ATP.

The term "leukocyte" or "white blood cell (WBC)" as used herein refers to a type of immune cell. Most leukocytes are made in the bone marrow and are found in the blood and lymph tissue. Leukocytes help the body fight infections and other diseases. Granulocytes, monocytes, and lymphocytes are leukocytes.

The term "lymphocytes" as used herein refers to a small white blood cell (leukocyte) that plays a large role in defending the body against disease. There are two main types of lymphocytes: B cells and T cells. The B cells make antibodies that attack bacteria and toxins while the T cells themselves attack body cells when they have been taken over by viruses or have become cancerous. Lymphocytes secrete products (lymphokines) that modulate the functional activities of many other types of cells and are often present at sites of chronic inflammation.

The term "macrophage" as used herein refers to a type of white blood cell that surrounds and kills microorganisms, removes dead cells, and stimulates the action of other immune system cells. After digesting a pathogen, a macrophage presents an antigen (a molecule, most often a protein found on the surface of the pathogen, used by the immune system for identification) of the pathogen to the corresponding helper T cell. The presentation is done by integrating it into the cell membrane and displaying it attached to an MHC class II molecule, indicating to other white blood cells that the macrophage is not a pathogen, despite having antigens on its surface. Eventually, the antigen presentation results in the production of antibodies that attach to the antigens of pathogens, making them easier for macrophages to adhere to with their cell membrane and phagocytose.

The term "mesenchymal cell" or "mesenchyme" as used herein refers to a cell derived from all three germ layers, which can develop into connective tissue, bone, cartilage, the lymphatic system, and the circulatory system.

The term "MK2 kinase" or "MK2" as used herein refers to mitogen-activated protein kinase-activated protein kinase 2 (also referred to as "MAPKAPK2", "MAPKAP-K2", "MK2"), which is a member of the serine/threonine (Ser/Thr) protein kinase family.

The term "mass median aerodynamic diameter" or "MMAD" as used herein refers to median of the distribution of airborne particle mass with respect to the aerodynamic diameter. MMADs are usually accompanied by the geometric standard deviation (g or sigma g), which characterizes the variability of the particle size distribution.

The term "modulate" as used herein means to regulate, alter, adapt, or adjust to a certain measure or proportion.

The term "monocyte" as used herein refers to a type of immune cell that is made in the bone marrow and travels through the blood to tissues in the body where it becomes a macrophage. A monocyte is a type of white blood cell and a type of phagocyte.

The term "neutrophils" or "polymorphonuclear neutrophils (PMNs)" as used herein refers to the most abundant type of white blood cells in mammals, which form an essential part of the innate immune system. They form part of the polymorphonuclear cell family (PMNs) together with basophils and eosinophils. Neutrophils are normally found in the blood stream. During the beginning (acute) phase of inflammation, particularly as a result of bacterial infection and some cancers, neutrophils are one of the first-responders of inflammatory cells to migrate toward the site of inflammation. They migrate through the blood vessels, then through interstitial tissue, following chemical signals such as interleukin-8 (IL-8) and C5a in a process called chemotaxis, the directed motion of a motile cell or part along a chemical concentration gradient toward environmental conditions it deems attractive and/or away from surroundings it finds repellent.

The term "normal healthy control subject" as used herein refers to a subject having no symptoms or other clinical evidence of airway or lung tissue disease.

The term "nucleic acid" is used herein to refer to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" is used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity."

(a) The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

(b) The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., *Nucleic Acids Research* 16:10881-90 (1988); Huang, et al., *Computer Applications in the Biosciences,* 8:155-65 (1992), and Pearson, et al., *Methods in Molecular Biology,* 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=-4, and a comparison of both strands. For amino acid sequences, the BLASTP program uses as defaults a word length (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, *Comput. Chem.*, 17:149-163 (1993)) and XNU (Claverie and States, *Comput. Chem.*, 17:191-201 (1993)) low-complexity filters may be employed alone or in combination.

(c) The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11-17 (1988) e.g., as implemented in the program PC/GENE (Intelligenetics, Mountain View, Calif., USA).

(d) The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The phrase "operatively linked" as used herein refers to a linkage in which two or more protein domains or polypeptides are ligated or combined via recombinant DNA technology or chemical reaction such that each protein domain or polypeptide of the resulting fusion protein retains its original function. For example, SEQ ID NO: 1 is constructed by operatively linking a cell penetrating peptide (SEQ ID NO: 11) with a therapeutic domain (SEQ ID NO: 2), thereby creating a fusion peptide that possesses both the cell penetrating function of SEQ ID NO: 11 and the kinase inhibitor function of SEQ ID NO: 2.

The term "oxidative stress" as used herein refers to a disturbance in the balance between the production of reactive oxygen species (free radicals) and antioxidant defenses.

The term "parenchyma" as used herein refers to an animal tissue that constitutes the essential part of an organ as contrasted with connective tissue or blood vessels. The term "parenchymal" means pertaining to the parenchyma of an organ.

The term "parenteral" as used herein refers to introduction into the body by way of an injection (i.e., administration by injection), including, for example, subcutaneously (i.e., an injection beneath the skin), intramuscularly (i.e., an injection into a muscle), intravenously (i.e., an injection into a vein), intrathecally (i.e., an injection into the space around the spinal cord or under the arachnoid membrane of the brain), intrasternal injection or infusion techniques, and including intraperitoneal injection or infusion into the body cavity (e.g. peritoneum). A parenterally administered composition is delivered using a needle, e.g., a surgical needle, or other corporal access device. The term "surgical needle" as used herein, refers to any access device adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

The term "particulate" as used herein refers to fine particles of solid or liquid matter suspended in a gas or liquid.

As used herein the term "pharmaceutically acceptable carrier" refers to any substantially non-toxic carrier conventionally useable for administration of pharmaceuticals in which the isolated polypeptide of the present invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids.

The terms "polypeptide" and "protein" also are used herein in their broadest sense to refer to a sequence of subunit amino acids, amino acid analogs, or peptidomimetics. The subunits are linked by peptide bonds, except where noted. The polypeptides described herein may be chemically synthesized or recombinantly expressed. Polypeptides of the described invention also can be synthesized chemically. Synthetic polypeptides, prepared using the well known techniques of solid phase, liquid phase, or peptide condensation techniques, or any combination thereof, can include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, *J. Am. Chem. Soc.* 85:2149-2154), or the base-labile N-α-amino protected 9-fluorenylmethoxycarbonyl (Fmoc) amino acids first described by Carpino and Han (1972, *J. Org. Chem.* 37:3403-3409). Both Fmoc and Boc N-α-amino protected amino acids can be obtained from Sigma, Cambridge Research Biochemical, or other chemical companies familiar to those skilled in the art. In addition, the polypeptides can be synthesized with other N-α-protecting groups that are familiar to those skilled in this art. Solid phase peptide synthesis may be accomplished by techniques familiar to those in the art and provided, for example, in Stewart and Young, 1984, *Solid Phase Synthesis*, Second Edition, Pierce Chemical Co., Rockford, Ill.; Fields and Noble, 1990, *Int. J. Pept. Protein Res.* 35:161-214, or using automated synthesizers. The polypeptides of the invention may comprise D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Synthetic amino acids include ornithine for lysine, and norleucine for leucine or isoleucine. In addition, the polypeptides can have peptidomimetic bonds, such as ester bonds, to prepare peptides with novel properties. For example, a peptide may be generated that incorporates a reduced peptide bond, i.e., R1-CH$_2$—NH—R2, where R1 and R2 are amino acid residues or sequences. A reduced peptide bond may be introduced as a dipeptide subunit. Such a polypeptide would be resistant to protease activity, and would possess an extended half-live in vivo. Accordingly, these terms also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, the protein is specifically reactive to antibodies elicited to the same protein but consisting entirely of naturally occurring amino acids.

The terms "polypeptide", "peptide" and "protein" also are inclusive of modifications including, but not limited to, glycosylation, lipid attachment, sulfation, gamma-carboxylation of glutamic acid residues, hydroxylation, and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well. In some embodiments, the peptide is of any length or size.

The term "proenzyme" or "zymogen" as used herein refers to an inactive enzyme precursor. A zymogen requires a biochemical change (such as a hydrolysis reaction revealing the active site, or changing the configuration to reveal the active site) for it to become an active enzyme. The biochemical change usually occurs in a lysosome where a specific part of the precursor enzyme is cleaved in order to activate it. The amino acid chain that is released upon activation is called the activation peptide.

The term "proliferation" as used herein refers to expansion of a population of cells by the continuous division of single cells into identical daughter cells.

The term "pulmonary interstitium" as used herein refers to the tissue and space around the air sacs of the lungs.

The term "pulmonary alveolus" as used herein refers to an anatomical structure that has the form of a hollow cavity. The alveoli are located in the respiratory zone of the lungs, at the distal termination of the alveolar ducts and atria, forming the termination point of the respiratory tract. The pulmonary alveoli are spherical outcroppings of the respiratory sites of gas exchange with the blood and only found in the mammalian lungs. The alveolar membrane is the gas-exchange surface. The blood brings carbon dioxide from the rest of the body for release into the alveoli, and the oxygen in the alveoli is taken up by the blood in the alveolar blood vessels, to be transported to all the cells in the body. The alveoli contain some collagen and elastic fibers. The elastic fibers allow the alveoli to stretch as they fill with air when breathing in. They then spring back during breathing out in order to expel the carbon dioxide-rich air. There are three major alveolar cell types in the alveolar wall, (1) sequamous alveolar cells that form the structure of an alveolar wall, (2) great alveolar cells that secrete pulmonary surfactant to lower the surface tension of water and allows the membrane to separate, thereby increasing the capability to exchange gasses, (3) macrophages that destroy foreign pathogens, such as bacteria.

The term "reactive oxygen species" ("ROS"), such as free radicals and peroxides, as used herein refers to a class of molecules that are derived from the metabolism of oxygen and exist inherently in all aerobic organisms. The term "oxygen radicals" as used herein refers to any oxygen species that carries an unpaired electron (except free oxygen). The transfer of electrons to oxygen also may lead to the production of toxic free radical species. The best documented of these is the superoxide radical. Oxygen radicals, such as the hydroxyl radical (OH—) and the superoxide ion (O2-) are very powerful oxidizing agents that cause structural damage to proteins, lipids and nucleic acids. The free radical superoxide anion, a product of normal cellular metabolism, is produced mainly in mitochondria because of incomplete reduction of oxygen. The superoxide radical, although unreactive compared with many other radicals, may be converted by biological systems into other more reactive species, such as peroxyl (ROO—), alkoxyl (RO—) and hydroxyl (OH—) radicals.

The phrase "remodeling in a tissue", "tissue remodeling" and the like as used herein refers to the dynamic process that occurs during fetal or adult life and involves a modification of the original organization and function of the tissue.

The term "similar" is used interchangeably with the terms analogous, comparable, or resembling, meaning having traits or characteristics in common.

The term "solution" as used herein refers to a homogeneous mixture of two or more substances. It is frequently, though not necessarily, a liquid. In a solution, the molecules of the solute (or dissolved substance) are uniformly distributed among those of the solvent.

The terms "soluble" and "solubility" refer to the property of being susceptible to being dissolved in a specified fluid (solvent). The term "insoluble" refers to the property of a material that has minimal or limited solubility in a specified solvent. In a solution, the molecules of the solute (or dissolved substance) are uniformly distributed among those of the solvent.

The term "stress fiber" as used herein refers to high order structures in cells consisting of actin filaments, crosslinking proteins (proteins that bind two or more filaments together), and myosin II motors. Actin is a globular protein (~43 kDa), which polymerizes and forms into an ordered filament structure which has two protofilaments wrapping around each other, to form a single "actin filament" also known as a "microfilament." The myosin motors in the stress fibers move, sliding actin filaments past one another, so the fiber can contract. In order for contraction to generate forces, the fibers must be anchored to something. Stress fibers can anchor to the cell membrane, and frequently the sites where this anchoring occurs are also connected to structures outside the cell (the matrix or some other substrate). These connection sites are called focal adhesions. Many proteins are required for proper focal adhesion production and maintenance. Contraction against these fixed external substrates is what allows the force generated by myosin motors and filament growth and rearrangement to move and reshape the cell.

The term "suspension" as used herein refers to a dispersion (mixture) in which a finely-divided species is combined with another species, with the former being so finely divided and mixed that it doesn't rapidly settle out. In everyday life, the most common suspensions are those of solids in liquid.

The terms "subject" or "individual" or "patient" are used interchangeably to refer to a member of an animal species of mammalian origin, including but not limited to, a mouse, a rat, a cat, a goat, sheep, horse, hamster, ferret, platypus, pig, a dog, a guinea pig, a rabbit and a primate, such as, for example, a monkey, ape, or human.

The phrase "subject in need of such treatment" as used herein refers to a patient who suffers from a disease, disorder, condition, or pathological process. In some embodiments, the term "subject in need of such treatment" also is used to refer to a patient who (i) will be administered at least one polypeptide of the invention; (ii) is receiving at least one polypeptide of the invention; or (iii) has received at least one polypeptide of the invention, unless the context and usage of the phrase indicates otherwise.

The term "substitution" is used herein to refer to a situation in which a base or bases are exchanged for another base or bases in a DNA sequence. Substitutions may be synonymous substitutions or nonsynonymous substitutions. As used herein, "synonymous substitutions" refer to substitutions of one base for another in an exon of a gene coding for a protein, such that the amino acid sequence produced is not modified. The term "nonsynonymous substitutions" as used herein refer to substitutions of one base for another in an exon of a gene coding for a protein, such that the amino acid sequence produced is modified.

The terms "therapeutic amount," an "amount effective," or "pharmaceutically effective amount" of an active agent are used interchangeably to refer to an amount that is sufficient to provide the intended benefit of treatment. For example, the "therapeutic amount" of a kinase inhibiting composition of the described invention includes, but is not limited to, an amount sufficient: (1) to remove, or decrease the size of, at least one fibrotic locus or (2) to reduce the rate of extracellular matrix, including collagen and fibronectin, deposition in the interstitia in the lungs of a pulmonary fibrosis patient. The term also encompasses an amount sufficient to suppress or alleviate at least one symptom of a pulmonary fibrosis patient, wherein the symptom includes, but is not limited to, oxygen saturation, dyspnea (difficulty breathing), nonproductive cough (meaning a sudden, noisy expulsion of air from the lungs that may be caused by irritation or inflammation and does not remove sputum from the respiratory tract), clubbing (a disfigurement of the fingers into a bulbous appearance), and crackles (crackling sound in lungs during inhalation, occasionally refered to as rales or crepitations).

An effective amount of an active agent that can be employed according to the described invention generally ranges from generally about 0.001 mg/kg body weight to about 10 g/kg body weight. However, dosage levels are based on a variety of factors, including the type of injury, the age, weight, sex, medical condition of the patient, the severity of the condition, the route and frequency of administration, and the particular active agent employed. Thus the dosage regimen may vary widely, but can be determined routinely by a physician using standard methods.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The terms "variants", "mutants", and "derivatives" are used herein to refer to nucleotide or polypeptide sequences with substantial identity to a reference nucleotide or polypeptide sequence. The differences in the sequences may be the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence.

A skilled artisan likewise can produce polypeptide variants of polypeptide YARAAARQARAKALARQLGVAA (SEQ ID NO: 1) having single or multiple amino acid substitutions, deletions, additions or replacements, but functionally equivalent to SEQ ID NO: 1. These variants may include inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (d) variants in which a target protein is fused with another peptide or polypeptide such as a fusion partner, a protein tag or other chemical moiety, that may confer useful properties to the target protein, for example, an epitope for an antibody. The techniques for obtaining such variants, including, but not limited to, genetic (suppressions, deletions, mutations, etc.), chemical, and enzymatic techniques, are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "vehicle" as used herein refers to a substance that facilitates the use of a drug or other material that is mixed with it.

The term "wound healing" or "wound repair" as used herein refers generally to the body's natural process of repairing tissue after trauma. When an individual is wounded, a set of complex biochemical events takes place to repair the damage including, hemostasis, inflammation, proliferation, and remodeling.

I. Compositions: Therapeutic Peptides for Preventing or Treating Diseases Characterized by Aberrant Fibroblast Proliferation and Collagen Deposition According to one aspect, the described invention provides a pharmaceutical composition for use in the treatment of a disease, condition, or process characterized by aberrant fibroblast proliferation and extracellular matrix deposition in a tissue of a subject, wherein the pharmaceutical composition comprises a therapeutic amount of a polypeptide of the amino acid sequence YARAAARQARAKALARQLGVAA (SEQ ID NO: 1) or a functional equivalent thereof, and a pharmaceutically acceptable carrier thereof, and wherein the therapeutic amount is effective to reduce the fibroblast proliferation and extracellular matrix deposition in the tissue of the subject.

According to one embodiment, the disease or the condition is Acute Lung Injury (ALI) or acute respiratory distress syndrome (ARDS).

According to another embodiment, the disease or the condition is radiation-induced fibrosis.

According to another embodiment, the disease or the condition is transplant rejection.

According to another embodiment, the tissue is a lung tissue.

According to another embodiment, the disease or the condition is an interstitial lung disease.

According to another embodiment, wherein the disease or the condition is pulmonary fibrosis.

According to another embodiment, wherein the pulmonary fibrosis is idiopathic pulmonary fibrosis.

According to another embodiment, the pulmonary fibrosis results from administration of bleomycin.

According to another embodiment, the pulmonary fibrosis results from an allergic reaction, inhalation of environmental particulates, smoking, a bacterial infection, a viral infection, mechanical damage to a lung of the subject, lung transplantation rejection, an autoimmune disorder, a genetic disorder, or a combination thereof.

According to another embodiment, the tissue is a liver tissue.

According to another embodiment, the disease or condition is liver fibrosis.

According to another embodiment, the tissue is a kidney tissue.

According to another embodiment, the disease or condition is renal fibrosis.

According to another embodiment, the tissue is a vascular tissue.

According to another embodiment, the disease or condition is vascular fibrosis.

According to another embodiment, the disease or the condition is further characterized by an inflammation in the tissue.

According to another embodiment, the inflammation is an acute or a chronic inflammation.

According to another embodiment, the inflammation is mediated by at least one cytokine selected from the group consisting of Tumor Necrosis Factor-alpha (TNF-α), Interleukin-6 (IL-6), and Interleukin-1β (IL-1β).

According to another embodiment, the pulmonary fibrosis is characterized by at least one pathology selected from the group consisting of an aberrant deposition of an extracellular matrix protein in a pulmonary interstitium, an aberrant promotion of fibroblast proliferation in the lung, an aberrant induction of myofibroblast differentiation in the lung, and an aberrant promotion of attachment of myofibroblasts to an extracellular matrix compared to a normal healthy control subject.

According to another embodiment, the aberrant fibroblast proliferation and extracellular matrix deposition in the tissue is characterized by an aberrant activity of Mitogen-Activated Protein Kinase-Activated Protein Kinase 2 (MK2) in the tissue compared to the activity of Mitogen-Activated Protein Kinase-Activated Protein Kinase 2 (MK2) in the tissue of a normal healthy control subject.

According to another embodiment, the aberrant fibroblast proliferation and extracellular matrix deposition in the tissue is evidenced by an aberrant amount or distribution of activated (phosphorylated) Mitogen-Activated Protein Kinase-Activated Protein Kinase 2 (MK2) in the tissue compared to the amount or distribution of activated Mitogen-Activated Protein Kinase-Activated Protein Kinase 2 (MK2) in the tissue of a normal healthy control subject.

According to another embodiment, the pharmaceutical composition inhibits a kinase activity of a kinase selected from the group listed in Table 1 herein.

According to another embodiment, this inhibition may, for example, be effective to reduce fibroblast proliferation, extracellular matrix deposition, or a combination thereof in the tissue of the subject.

According to another embodiment, this inhibition may, for example, be effective to reduce at least one pathology selected from the group consisting of an aberrant deposition of an extracellular matrix protein in a pulmonary interstitium, an aberrant promotion of fibroblast proliferation in the lung, an aberrant induction of myofibroblast differentiation, and an aberrant promotion of attachment of myofibroblasts to an extracellular matrix, compared to a normal healthy control subject.

According to some embodiments, inhibitory profiles of MMI inhibitors in vivo depend on dosages, routes of administration, and cell types responding to the inhibitors.

According to another embodiment, the pharmaceutical composition inhibits at least 50% of the kinase activity of the kinase. According to another embodiment, the pharmaceutical composition inhibits at least 65% of the kinase activity of the kinase. According to another embodiment, the pharmaceutical composition inhibits at least 75% of the kinase activity of that kinase. According to another embodiment, the pharmaceutical composition inhibits at least 80% of the kinase activity of that kinase. According to another embodiment, the pharmaceutical composition inhibits at least 85% of the kinase activity of that kinase. According to another embodiment, the pharmaceutical composition inhibits at least 90% of the kinase activity of that kinase. According to another embodiment, the pharmaceutical composition inhibits at least 95% of the kinase activity of that kinase.

According to some embodiments, the pharmaceutical composition inhibits a kinase activity of Mitogen-Activated Protein Kinase-Activated Protein Kinase 2 (MK2 kinase). According to some other embodiments, the pharmaceutical composition inhibits at least 50% of the kinase activity of MK2 kinase. According to some other embodiments, the pharmaceutical composition inhibits at least 65% of the kinase activity of MK2 kinase. According to another embodiment, the pharmaceutical composition inhibits at least 75% of the kinase activity of MK2 kinase. According to another embodiment, the pharmaceutical composition inhibits at least 80% of the kinase activity of MK2 kinase. According to another embodiment, the pharmaceutical composition inhibits at least 85% of the kinase activity of MK2 kinase. According to another embodiment, the pharmaceutical composition inhibits at least 90% of the kinase activity of MK2 kinase. According to another embodiment, the pharmaceutical composition inhibits at least 95% of the kinase activity of MK2 kinase.

According to another embodiment, the pharmaceutical composition inhibits a kinase activity of Mitogen-Activated Protein Kinase-Activated Protein Kinase 3 (MK3 kinase). According to another embodiment, the pharmaceutical composition inhibits at least 50% of the kinase activity of MK3 kinase. According to another embodiment, the pharmaceutical composition inhibits at least 65% of the kinase activity of MK3 kinase. According to another embodiment, the pharmaceutical composition inhibits at least 70% of the kinase activity of MK3 kinase. According to another embodiment, the pharmaceutical composition inhibits at least 75% of the kinase activity of MK3 kinase. According to another embodiment, the pharmaceutical composition inhibits at least 80% of the kinase activity of MK3 kinase. According to another embodiment, the pharmaceutical composition inhibits at least 85% of the kinase activity of MK3 kinase. According to another embodiment, the pharmaceutical composition inhibits at least 90% of the kinase activity of MK3 kinase. According to another embodiment, the pharmaceutical composition inhibits at least 95% of the kinase activity of MK3 kinase.

According to another embodiment, the pharmaceutical composition inhibits a kinase activity of calcium/calmodulin-dependent protein kinase I (CaMKI). According to another embodiment, the pharmaceutical composition further inhibits at least 50% of the kinase activity of $Ca^{2+}$/calmodulin-dependent protein kinase I (CaMKI). According to another embodiment, the pharmaceutical composition further inhibits at least 65% of the kinase activity of $Ca^{2+}$/calmodulin-dependent protein kinase I (CaMKI). According to another embodiment, the pharmaceutical composition further inhibits at least 70% of the kinase activity of $Ca^{2+}$/calmodulin-dependent protein kinase I (CaMKI). According to another embodiment, the pharmaceutical composition further inhibits at least 75% of the kinase activity of $Ca^{2+}$/calmodulin-dependent protein kinase I (CaMKI). According to another embodiment, the pharmaceutical composition further inhibits at least 80% of the kinase activity of $Ca^{2+}$/calmodulin-dependent protein kinase I (CaMKI). According to another embodiment, the pharmaceutical composition further inhibits at least 85% of the kinase activity of $Ca^{2+}$/calmodulin-dependent protein kinase I (CaMKI). According to another embodiment, the pharmaceutical composition further inhibits at least 90% of the kinase activity of $Ca^{2+}$/calmodulin-dependent protein kinase I (CaMKI). According to another embodiment, the pharmaceutical composition further inhibits at least 95% of the kinase activity of $Ca^{2+}$/calmodulin-dependent protein kinase I (CaMKI).

According to another embodiment, the pharmaceutical composition inhibits a kinase activity of BDNF/NT-3 growth factors receptor (TrkB). According to another embodiment, the pharmaceutical further inhibits at least 50% of the kinase activity of BDNF/NT-3 growth factors receptor (TrkB). According to another embodiment, the pharmaceutical further inhibits at least 65% of the kinase activity of BDNF/NT-3 growth factors receptor (TrkB). According to another embodiment, the pharmaceutical further inhibits at least 70% of the kinase activity of BDNF/NT-3 growth factors receptor (TrkB). According to another embodiment, the pharmaceutical further inhibits at least 75% of the kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2) and a kinase activity of Mitogen-Activated Protein Kinase-Activated Protein Kinase 3 (MK3).

According to another embodiment, the pharmaceutical composition inhibits a kinase activity of Mitogen-Activated Protein Kinase-Activated Protein Kinase 2 (MK2) and a kinase activity of calcium/calmodulin-dependent protein kinase I (CaMKI).

According to another embodiment, the pharmaceutical composition inhibits a kinase activity of Mitogen-Activated Protein Kinase-Activated Protein Kinase 2 (MK2) and a kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2), a kinase activity of Mitogen-Activated Protein Kinase-Activated Protein Kinase 3 (MK3), a kinase activity of calcium/calmodulin-dependent protein kinase I (CaMKI), and a kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2), a kinase activity of calcium/calmodulin-dependent protein kinase I (CaMKI), and a kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2).

According to another embodiment, the pharmaceutical composition inhibits at least 65% of the kinase activity of Mitogen-Activated Protein Kinase-Activated Protein Kinase 3 (MK3).

According to another embodiment, the pharmaceutical composition inhibits at least 65% of the kinase activity of calcium/calmodulin-dependent protein kinase I (CaMKI).

According to another embodiment, the pharmaceutical composition inhibits at least 65% of the kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2) and at least 65% of the kinase activity of Mitogen-Activated Protein Kinase-Activated Protein Kinase 3 (MK3).

According to another embodiment, the pharmaceutical composition inhibits at least 65% of the kinase activity of Mitogen-Activated Protein Kinase-Activated Protein Kinase 2 (MK2) and at least 65% of the kinase activity of calcium/calmodulin-dependent protein kinase I (CaMKI).

According to another embodiment, the pharmaceutical composition inhibits at least 65% of the kinase activity of Mitogen-Activated Protein Kinase-Activated Protein Kinase 2 (MK2) and at least 65% of the kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2), at least 65% of the kinase activity of Mitogen-Activated Protein Kinase-Activated Protein Kinase 3 (MK3), at least 65% of the kinase activity of calcium/calmodulin-dependent protein kinase I (CaMKI), and at least 65% of the kinase activity of BDNF/NT-3 growth factors receptor (TrkB).

According to another embodiment, the pharmaceutical composition inhibits the kinase activity of at least one kinase selected from the group of MK2, MK3, CaMKI, TrkB, without substantially inhibiting the activity of one or more other selected kinases from the remaining group listed in Table 1 herein.

According to some embodiments, inhibitory profiles of MMI inhibitors in vivo depend on dosages, routes of administration, and cell types responding to the inhibitors.

According to such embodiment, the pharmaceutical composition inhibits less than 50% of the kinase activity of the other selected kinase(s). According to such embodiment, the pharmaceutical composition inhibits less than 65% of the kinase activity of the other selected kinase(s). According to another embodiment, the pharmaceutical composition inhibits less than 50% of the kinase activity of the other selected kinase(s). According to another embodiment, the pharmaceutical composition inhibits less than 40% of the kinase activity of the other selected kinase(s). According to another embodiment, the pharmaceutical composition inhibits less than 20% of the kinase activity of the other selected kinase(s). According to another embodiment, the pharmaceutical composition inhibits less than 15% of the kinase activity of the other selected kinase(s). According to another embodiment, the pharmaceutical composition inhibits less than 10% of the kinase activity of the other selected kinase(s). According to another embodiment, the pharmaceutical composition inhibits less than 5% of the kinase activity of the other selected kinase(s). According to another embodiment, the pharmaceutical composition increases the kinase activity of the other selected kinases.

According to the embodiments of the immediately preceding paragraph, the one or more other selected kinase that is not substantially inhibited is selected from the group of $Ca^{2+}$/calmodulin-dependent protein kinase II (CaMKII, including its subunit CaMKIIδ), Proto-oncogene serine/threonine-protein kinase (PIM-1), cellular-Sarcoma (c-SRC), Spleen Tyrosine Kinase (SYK), C-src Tyrosine Kinase (CSK), and Insulin-like Growth Factor 1 Receptor (IGF-1R).

According to some embodiments, the pharmaceutical composition further comprises at least one additional therapeutic agent.

According to some such embodiments, examples of such additional therapeutic agents include, without limitation, purified bovine Type V collagens (e.g., IW-001; ImmuneWorks; United Therapeutics), IL-13 receptor antagonists (e.g., QAX576; Novartis), protein tyrosine kinase inhibitors (e.g., imatinib (Gleevec®); Craig Daniels/Novartis), endothelial receptor antagonists (e.g., ACT-064992 (macitentan); Actelion), dual endothelin receptor antagonists (e.g., bosentan (Tracleer®); Actelion), prostacyclin analogs (inhaled iloprost (e.g., Ventavis®); Actelion), anti-CTGF monoclonal antibodies (e.g., FG-3019), endothelin receptor antagonists (A-selective) (e.g., ambrisentan (Letairis®), Gilead), AB0024 (Arresto), lysyl oxidase-like 2 (LOXL2) monoclonal antibodies (e.g., GS-6624 (formerly AB0024); Gilead), c-Jun N-terminal kinase (JNK) inhibitors (e.g., CC-930; Celgene), Pirfenidone (e.g., Esbriet® (InterMune), Pirespa® (Shionogi)), IFN-γ1b (e.g., Actimmune®; InterMune), pan-neutralizing IgG4 human antibodies against all three TGF-β isoforms (e.g., GC1008; Genzyme), TGF-β activation inhibitors (e.g., Stromedix (STX-100)), recombinant human Pentraxin-2 protein (rhPTX-2) (e.g., PRM151; Promedior), bispecific IL4/IL13 antibodies (e.g., SAR156597; Sanofi), humanized monoclonal antibodies targeting integrin αvβ6 (BIBF 1120; Boehringer Ingelheim), N-acetylcysteine (Zambon SpA), Sildenafil (Viagra®), TNF antagonists (e.g., etanercept (Enbrel®); Pfizer), glucocorticoids (e.g., prednisone, budesonide, mometasone furoate, fluticasone propionate, and fluticasone furoate), bronchodilators (e.g., leukotriene modifers (e.g., Montelukast (SINGUAIR®)), anticholingertic bronchodilators (e.g., Ipratropium bromide and Tiotropium), short-acting β2-agonists (e.g., isoetharine mesylate (Bronkometer®), adrenalin, salbutanol/albuterol, and terbutaline), long-acting β2-agonists (e.g., salmeterol, formoterol, indecaterol (Onbrez®), sofosbuvir (Sovaldi®), an HCV boosted protease inhibitor (ABT-450, AbbVie), a nonnucleoside NS5B inhibitor (dasabuvir, ABT-333, AbbVie), an NS5a inhibitor (ombitasvir, ABT-267, AbbVie), ABT-450/r (ABT-450 with ritonavir), ABT-450 co-formulated with ABT-267, ABT-450 formulated with sofosbuvir, ribavirin, and combinations thereof.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to some other embodiments, the additional therapeutic agent is an anti-inflammatory agent.

According to some such embodiments, the anti-inflammatory agent is a nonsteroidal anti-inflammatory agent. The term "non-steroidal anti-inflammatory agent" as used herein refers to a large group of agents that are aspirin-like in their action, including, but not limited to, ibuprofen (Advil®), naproxen sodium (Aleve®), and acetaminophen (Tylenol®). Additional examples of non-steroidal anti-inflammatory agents that are usable in the context of the described invention include, without limitation, oxicams, such as piroxicam, isoxicam, tenoxicam, sudoxicam, and CP-14, 304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents also may be employed, as well as the dermatologically acceptable salts and esters of these agents. For example, etofenamate, a flufenamic acid derivative, is particularly useful for topical application.

According to another embodiment, the nonsteroidal anti-inflammatory agent comprises Transforming Growth Factor-β3 (TGF-β3), an anti-Tumor Necrosis Factor-alpha (TNF-α) agent, or a combination thereof.

According to another embodiment, the anti-inflammatory agent is a steroidal anti-inflammatory agent. The term "steroidal anti-inflammatory agent", as used herein, refer to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflucortolone valerate, fluadrenolone, fluclorolone acetonide, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

According to another embodiment, the steroidal anti-inflammatory agent comprises at least one corticosteroid selected from the group consisting of prednisone, budesonide, mometasone, beclemethasone, and a combination thereof.

According to another embodiment, the additional therapeutic agent comprises a xanthine or xanthine derivative, such as methylxanthine.

According to another embodiment, the additional therapeutic agent comprises a neutrophil elastase inhibitor.

According to another embodiment, the additional therapeutic agent is at least one neutrophil elastase inhibitor, including, but not limited to, ICI 200355, ONO-5046, MR-889, L-694,458, CE-1037, GW-311616, TEI-8362, ONO-6818, AE-3763, FK-706, ICI-200,880, ZD-0892, ZD-8321, and a combination thereof.

According to another embodiment, the additional therapeutic agent comprises at least one phosphodiesterase inhibitor, including, but not limited to, phosphodiesterase 4 inhibitor. Examples of phosphodiesterase 4 inhibitors include, but are not limited to, roflumilast, cilomilast or a combination thereof.

According to another embodiment, the additional therapeutic agent is an analgesic agent. According to some embodiments, the analgesic agent relieves pain by elevating the pain threshold without disturbing consciousness or altering other sensory modalities. According to some such embodiments, the analgesic agent is a non-opioid analgesic. "Non-opioid analgesics" are natural or synthetic substances that reduce pain but are not opioid analgesics. Examples of non-opioid analgesics include, but are not limited to, etodolac, indomethacin, sulindac, tolmetin, nabumetone, piroxicam, acetaminophen, fenoprofen, flurbiprofen, ibuprofen, ketoprofen, naproxen, naproxen sodium, oxaprozin, aspirin, choline magnesium trisalicylate, diflunisal, meclofenamic acid, mefenamic acid, and phenylbutazone. According to some other embodiments, the analgesic is an opioid analgesic. "Opioid analgesics", "opioid", or "narcotic analgesics" are natural or synthetic substances that bind to opioid receptors in the central nervous system, producing an agonist action. Examples of opioid analgesics include, but are not limited to, codeine, fentanyl, hydromorphone, levorphanol, meperidine, methadone, morphine, oxycodone, oxymorphone, propoxyphene, buprenorphine, butorphanol, dezocine, nalbuphine, and pentazocine.

According to another embodiment, the additional therapeutic agent is an anti-infective agent. According to another embodiment, the anti-infective agent is an antibiotic agent. The term "antibiotic agent" as used herein means any of a group of chemical substances having the capacity to inhibit the growth of, or to destroy bacteria and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

According to another embodiment, the pharmaceutical composition inhibits inflammation occurring in a lung of the subject. According to another embodiment, the inflammation is an acute inflammation. According to another embodiment, the inflammation is a chronic inflammation. According to another embodiment, the inflammation is mediated by Tumor Necrosis Factor-alpha (TNF-α). According to another embodiment, the inflammation is mediated by Interleukin-6 (IL-6). According to another embodiment, the inflammation is mediated by Interleukin-1β (IL-1β).

According to another embodiment, the pharmaceutical composition modulates an amount of Tumor Necrosis Factor-alpha (TNF-α) in the lung, compared to a control. According to another embodiment, the pharmaceutical composition modulates the amount of Interleukin-6 (IL-6) in the lung, compared to a control. According to another embodiment, the pharmaceutical composition modulates the amount of Interleukin-1β (IL-1β) in the lung, compared to a control.

According to another embodiment, the pharmaceutical composition inhibits an activity of Heat Shock 27 kDa protein 1 (HSPB1). According to another embodiment, the activity of HSPB1 inhibited by the pharmaceutical composition is an aberrant induction of fibroblast proliferation. According to another embodiment, the activity of HSPB1 inhibited by the pharmaceutical composition is an aberrant induction of myofibroblast differentiation. According to another embodiment, the activity of HSPB1 inhibited by the pharmaceutical composition is a deposition of an extracellular matrix protein into a pulmonary interstitium. According to another embodiment, the extracelluar matrix protein is collagen. According to another embodiment, the activity of HSPB1 inhibited by the pharmaceutical composition is a promotion of fibrotic loci formation. According to another embodiment, the activity of HSPB1 inhibited by the pharmaceutical composition is an increase of a myofibroblast contractile activity. According to another embodiment, the activity of HSPB1 inhibited by the pharmaceutical composition is a promotion of myofibroblast attachment to extracellular matrix.

According to some embodiments, the functional equivalent of the polypeptide YARAAARQARAKALARQLGVAA (SEQ ID NO: 1) has a substantial sequence identity to amino acid sequence YARAAARQARAKALARQLGVAA (SEQ ID NO: 1).

According to another embodiment, the functional equivalent of the polypeptide YARAAARQARAKALARQLGVAA (SEQ ID NO: 1) has at least 70 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 80 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 90 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 95 percent sequence identity to amino acid sequence YARAAARQARAKALARQLGVAA (SEQ ID NO: 1).

According to another embodiment, the functional equivalent of the polypeptide YARAAARQARAKALARQLGVAA (SEQ ID NO: 1) is of amino acid sequence FAKLAARLYRKALARQLGVAA (SEQ ID NO: 3).

According to another embodiment, the functional equivalent of the polypeptide YARAAARQARAKALARQLGVAA (SEQ ID NO: 1) is of amino acid sequence KAFAKLAARLYRKALARQLGVAA (SEQ ID NO: 4).

According to another embodiment, the functional equivalent of the polypeptide YARAAARQARAKALARQLGVAA (SEQ ID NO: 1) is of amino acid sequence YARAAARQARAKALARQLAVA (SEQ ID NO: 5).

According to another embodiment, the functional equivalent of the polypeptide YARAAARQARAKALARQLGVAA (SEQ ID NO: 1) is of amino acid sequence YARAAARQARAKALARQLGVA (SEQ ID NO: 6).

According to another embodiment, the functional equivalent of the polypeptide YARAAARQARAKALARQLGVAA (SEQ ID NO: 1) is of amino acid sequence HRRIKAWLKKIKALARQLGVAA (SEQ ID NO: 7).

According to another embodiment, the functional equivalent of the polypeptide YARAAARQARAKALARQLGVAA (SEQ ID NO: 1) is of amino acid sequence YARAAARQARAKALNRQLAVAA (SEQ ID NO: 26).

According to another embodiment, the functional equivalent of the polypeptide YARAAARQARAKALARQLGVAA (SEQ ID NO: 1) is of amino acid sequence YARAAARQARAKALNRQLAVA (SEQ ID NO: 27).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide is of amino acid sequence YARAAARQARA (SEQ ID NO: 11), and the second polypeptide comprises a therapeutic domain whose sequence has substantial identity to amino acid sequence KALARQLGVAA (SEQ ID NO: 2).

According to some such embodiments, the second polypeptide has at least 70 percent sequence identity to amino acid sequence KALARQLGVAA (SEQ ID NO: 2).

According some other embodiments, the second polypeptide has at least 80 percent sequence identity to amino acid sequence KALARQLGVAA (SEQ ID NO: 2). According to some other embodiments, the second polypeptide has at least 90 percent sequence identity to amino acid sequence KALARQLGVAA (SEQ ID NO: 2). According to some other embodiments, the second polypeptide has at least 95 percent sequence identity to amino acid sequence KALARQLGVAA (SEQ ID NO: 2).

According to some embodiments, the second polypeptide is a polypeptide of amino acid sequence KALARQLAVA (SEQ ID NO: 8).

According to another embodiment, the second polypeptide is a polypeptide of amino acid sequence KALARQLGVA (SEQ ID NO: 9).

According to another embodiment, the second polypeptide is a polypeptide of amino acid sequence KALARQLGVAA (SEQ ID NO: 10).

According to another embodiment, the second polypeptide is a polypeptide of amino acid sequence KALNRQLAVAA (SEQ ID NO: 28).

According to another embodiment, the second polypeptide is a polypeptide of amino acid sequence YKALNRQLAVA (SEQ ID NO: 29).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide comprises a cell penetrating peptide functionally equivalent to YARAAARQARA (SEQ ID NO: 11), and the second polypeptide is of amino acid sequence KALARQLGVAA (SEQ ID NO: 2).

According to another embodiment, the first polypeptide is a polypeptide of amino acid sequence WLRRIKAWLRRIKA (SEQ ID NO: 12). According to another embodiment, the first polypeptide is a polypeptide of amino acid sequence WLRRIKA (SEQ ID NO: 13). According to another embodiment, the first polypeptide is a polypeptide of amino acid sequence YGRKKRRQRRR (SEQ ID NO: 14). According to another embodiment, the first polypeptide is a polypeptide of amino acid sequence WLRRIKAWLRRI (SEQ ID NO: 15). According to another embodiment, the first polypeptide is a polypeptide of amino acid sequence FAKLAARLYR (SEQ ID NO: 16). According to another embodiment, the first polypeptide is a polypeptide of amino acid sequence KAFAKLAARLYR (SEQ ID NO: 17). According to another embodiment, the first polypeptide is a polypeptide of amino acid sequence HRRIKAWLKKI (SEQ ID NO: 18).

According to another aspect, the described invention also provides an isolated nucleic acid that encodes a protein sequence with at least 70% amino acid sequence identity to amino acid sequence YARAAARQARAKALARQLGVAA (SEQ ID NO: 1). According to some embodiments, the isolated nucleic acid encodes a protein sequence with at least 80% amino acid sequence identity to amino acid sequence YARAAARQARAKALARQLGVAA (SEQ ID NO: 1). According to some other embodiments, the isolated nucleic acid encodes a protein sequence with at least 90% amino acid sequence identity to amino acid sequence YARAAARQARAKALARQLGVAA (SEQ ID NO: 1). According to some other embodiments, the isolated nucleic acid encodes a protein sequence with at least 95% amino acid sequence identity to amino acid sequence YARAAARQARAKALARQLGVAA (SEQ ID NO: 1).

According to some other embodiments, the therapeutic amount of the therapeutic inhibitor peptide of the pharmaceutical composition is of an amount from about 0.000001 mg/kg body weight to about 100 mg/kg body weight. According to another embodiment, the therapeutic amount of the therapeutic inhibitory peptide of the pharmaceutical composition is of an amount from about 0.00001 mg/kg body weight to about 100 mg/kg body weight. According to another embodiment, the therapeutic amount of the therapeutic inhibitory peptide of the pharmaceutical composition is of an amount from about 0.0001 mg/kg body weight to about 100 mg/kg body weight. According to another embodiment, the therapeutic amount of the therapeutic inhibitory peptide of the pharmaceutical composition is of an amount from about 0.001 mg/kg body weight to about 10 mg/kg body weight. According to another embodiment, the therapeutic amount of the therapeutic inhibitory peptide of the pharmaceutical composition is of an amount from about 0.01 mg/kg body weight to about 10 mg/kg body weight. According to another embodiment, the therapeutic amount of the therapeutic inhibitory peptide of the pharmaceutical composition is of an amount from about 0.1 mg/kg (or 100 µg/kg) body weight to about 10 mg/kg body weight. According to another embodiment, the therapeutic amount of the therapeutic inhibitory peptide of the pharmaceutical composition is of an amount from about 1 mg/kg body weight to about 10 mg/kg body weight. According to another embodiment, the therapeutic amount of the therapeutic inhibitory peptide of the pharmaceutical composition is of an amount from about 10 mg/kg body weight to about 100 mg/kg body weight. According to another embodiment, the therapeutic amount of the therapeutic inhibitory peptide of the pharmaceutical composition is of an amount from about 2 mg/kg body weight to about 10 mg/kg body weight. According to another embodiment, the therapeutic amount of the therapeutic inhibitory peptide of the pharmaceutical composition is of an amount from about 3 mg/kg body weight to about 10 mg/kg body weight. According to another embodiment, the therapeutic amount of the therapeutic inhibitory peptide of the pharmaceutical composition is of an amount from about 4 mg/kg body weight to about 10 mg/kg body weight. According to another embodiment, the therapeutic amount of the therapeutic inhibitory peptide of the pharmaceutical composition is of an amount from about 5 mg/kg body weight to about 10 mg/kg body weight. According to another embodiment, the therapeutic amount of the therapeutic inhibitory peptide of the pharmaceutical composition is of an amount from about 60 mg/kg body weight to about 100 mg/kg body weight. According to another embodiment, the therapeutic amount of the therapeutic inhibitory peptide of the pharmaceutical composition is of an amount from about 70 mg/kg body weight to about 100 mg/kg body weight. According to another embodiment, the therapeutic amount of the therapeutic inhibitory peptide of the pharmaceutical composition is of an amount from about 80 mg/kg body weight to about 100 mg/kg body weight. According to another embodiment, the therapeutic amount of the therapeutic inhibitory peptide of the pharmaceutical composition is of an amount from about 90 mg/kg body weight to about 100 mg/kg body weight. According to another embodiment, the therapeutic amount of the therapeutic inhibitor peptide of the pharmaceutical composition is of an amount from about 0.000001 mg/kg body weight to about 90 mg/kg body weight. According to another embodiment, the therapeutic amount of the therapeutic inhibitor peptide of the pharmaceutical composition is of an amount from about 0.000001 mg/kg body weight to about 80 mg/kg body weight. According to another embodiment, the therapeutic amount of the therapeutic inhibitor peptide of the pharmaceutical composition is of an amount from about 0.000001 mg/kg body weight to about 70 mg/kg body weight. According to another embodiment, the therapeutic amount of the therapeutic inhibitor peptide of the pharmaceutical composition is of an amount from about 0.000001 mg/kg body weight to about 60 mg/kg body weight. According to another embodiment, the therapeutic amount of the therapeutic inhibitor peptide of the pharmaceutical composition is of an amount from about 0.000001 mg/kg body weight to about 50 mg/kg body weight. According to another embodiment, the therapeutic amount of the therapeutic inhibitor peptide of the pharmaceutical composition is of an amount from about 0.000001 mg/kg body weight to about 40 mg/kg body weight. According to another embodiment, the therapeutic amount of the therapeutic inhibitor peptide is of an amount from about 0.000001 mg/kg body weight to about 30 mg/kg body weight. According to another embodiment, the therapeutic amount of the therapeutic inhibitor peptide of the pharmaceutical composition is of an amount from about 0.000001 mg/kg body weight to about 20 mg/kg body weight. According to another embodiment, the therapeutic amount of the therapeutic inhibitor peptide of the pharmaceutical composition is of an amount from about 0.000001 mg/kg body weight to about 10 mg/kg body weight. According to another embodiment, the therapeutic amount of the therapeutic inhibitor peptide of the pharmaceutical composition is of an amount from about 0.000001 mg/kg body weight to about 1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.01 mg/kg body weight. According to another embodiment, the therapeutic amount of the therapeutic inhibitor peptide of the pharmaceutical composition is of an amount from about 0.000001 mg/kg body weight to about 0.001 mg/kg body weight. According to another embodiment, the therapeutic amount of the therapeutic inhibitor peptide of the pharmaceutical composition is of an amount from about 0.000001 mg/kg body weight to about 0.0001 mg/kg body weight. According to another embodiment, the therapeutic amount of the therapeutic inhibitor peptide of the pharmaceutical composition is of an amount from about 0.000001 mg/kg body weight to about 0.00001 mg/kg body weight.

According to some other embodiments, the therapeutic dose of the therapeutic inhibitor peptide of the pharmaceutical composition ranges from 1 µg/kg/day to 25 µg/kg/day. According to some other embodiments, the therapeutic dose of the therapeutic inhibitor peptide of the pharmaceutical composition ranges from 1 µg/kg/day to 2 µg/kg/day. According to some other embodiments, the therapeutic dose of the therapeutic inhibitor peptide of the pharmaceutical composition ranges from 2 µg/kg/day to 3 µg/kg/day. According to some other embodiments, the therapeutic dose of the therapeutic inhibitor peptide of the pharmaceutical composition ranges from 3 µg/kg/day to 4 µg/kg/day. According to some other embodiments, the therapeutic dose of the therapeutic inhibitor peptide of the pharmaceutical ranges from 4 µg/kg/day to 5 µg/kg/day. According to some other embodiments, the therapeutic dose of the therapeutic inhibitor peptide of the pharmaceutical composition ranges from 5 µg/kg/day to 6 µg/kg/day. According to some other embodiments, the therapeutic dose of the therapeutic inhibitor peptide of the pharmaceutical composition ranges from 6 µg/kg/day to 7 µg/kg/day. According to some other embodiments, the therapeutic dose of the therapeutic inhibitor peptide of the pharmaceutical composition ranges from 7 µg/kg/day to 8 µg/kg/day. According to some other embodiments, the therapeutic dose of the therapeutic inhibitor peptide of the pharmaceutical composition ranges from 8 µg/kg/day to 9 µg/kg/day. According to some other embodiments, the therapeutic dose of the therapeutic inhibitor peptide of the pharmaceutical composition ranges from 9 µg/kg/day to 10 µg/kg/day. According to some other embodiments, the therapeutic dose of the therapeutic inhibitor peptide of the pharmaceutical composition ranges from 1 µg/kg/day to 5 µg/kg/day. According to some other embodiments, the therapeutic dose of the therapeutic inhibitor peptide of the pharmaceutical composition ranges from 5 µg/kg/day to 10 µg/kg/day. According to some other embodiments, the therapeutic dose of the therapeutic inhibitor peptide of the pharmaceutical composition ranges from 10 µg/kg/day to 15 µg/kg/day. According to some other embodiments, the therapeutic dose of the therapeutic inhibitor peptide of the pharmaceutical composition ranges from 15 µg/kg/day to 20 µg/kg/day. According to some other embodiments, the therapeutic dose of the therapeutic inhibitor peptide of the pharmaceutical composition ranges from 25 µg/kg/day to 30 µg/kg/day. According to some other embodiments, the therapeutic dose of the therapeutic inhibitor peptide of the pharmaceutical composition ranges from 30 µg/kg/day to 35 µg/kg/day. According to some other embodiments, the therapeutic dose of the therapeutic inhibitor peptide of the pharmaceutical composition ranges from 35 µg/kg/day to 40 µg/kg/day. According to some other embodiments, the therapeutic dose of the therapeutic inhibitor peptide of the pharmaceutical composition ranges from 40 µg/kg/day to 45 µg/kg/day. According to some other embodiments, the therapeutic dose of the therapeutic inhibitor peptide of the pharmaceutical composition ranges from 45 µg/kg/day to 50 µg/kg/day. According to some other embodiments, the therapeutic dose of the therapeutic inhibitor peptide of the pharmaceutical composition ranges from 50 µg/kg/day to 55 µg/kg/day. According to some other embodiments, the therapeutic dose of the therapeutic inhibitor peptide of the pharmaceutical composition ranges from 55 µg/kg/day to 60 µg/kg/day. According to some other embodiments, the therapeutic dose of the therapeutic inhibitor peptide of the pharmaceutical composition ranges from 60 µg/kg/day to 65 µg/kg/day. According to some other embodiments, the therapeutic dose of the therapeutic inhibitor peptide of the pharmaceutical composition ranges from 65 µg/kg/day to 70 µg/kg/day. According to some other embodiments, the therapeutic dose of the therapeutic inhibitor peptide of the pharmaceutical composition ranges from 70 µg/kg/day to 75 µg/kg/day. According to some other embodiments, the therapeutic dose of the therapeutic inhibitor peptide of the pharmaceutical composition ranges from 80 µg/kg/day to 85 µg/kg/day. According to some other embodiments, the therapeutic dose of the therapeutic inhibitor peptide of the pharmaceutical composition ranges from 85 µg/kg/day to 90 µg/kg/day. According to some other embodiments, the therapeutic dose of the therapeutic inhibitor peptide of the pharmaceutical composition ranges from 90 µg/kg/day to 95 µg/kg/day. According to some other embodiments, the therapeutic dose of the therapeutic inhibitor peptide of the pharmaceutical composition ranges from 95 µg/kg/day to 100 µg/kg/day.

According to another embodiment, the therapeutic dose of the therapeutic inhibitor peptide of the pharmaceutical composition is 1 µg/kg/day.

According to another embodiment, the therapeutic dose of the therapeutic inhibitor peptide of the pharmaceutical composition is 2 µg/kg/day.

According to another embodiment, the therapeutic dose of the therapeutic inhibitor peptide of the pharmaceutical composition is 5 µg/kg/day.

According to another embodiment, the therapeutic dose of the therapeutic inhibitor peptide of the pharmaceutical composition is 10 µg/kg/day.

According to some embodiments, the polypeptide of the invention comprises D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Examples of synthetic amino acid substitutions include ornithine for lysine, and norleucine for leucine or isoleucine.

According to some embodiments, the polypeptide may be linked to other compounds to promote an increased half-life in vivo, such as polyethylene glycol or dextran. Such linkage can be covalent or non-covalent as is understood by those of skill in the art. According to some other embodiments, the polypeptide may be encapsulated in a micelle such as a micelle made of poly(ethyleneglycol)-block-poly(polypropylenglycol) or poly(ethyleneglycol)-block-polylactide. According to some other embodiments, the polypeptide may be encapsulated in degradable nano- or micro-particles composed of degradable polyesters including, but not limited to, polylactic acid, polyglycolide, and polycaprolactone.

According to another embodiment, the polypeptide may be prepared in a solid form (including granules, powders or suppositories) or in a liquid form (e.g., solutions, suspensions, or emulsions).

According to another embodiment, the compositions of the described invention may be in the form of a dispersible dry powder for delivery by inhalation or insufflation (either through the mouth or through the nose, respectively). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the described invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. Nos. 4,227,522; 4,192,309; and 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powders is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference in their entireties.

According to another embodiment, the carrier of the composition of the described invention includes a release agent, such as a sustained release or delayed release carrier. In such embodiments, the carrier can be any material capable of sustained or delayed release of the polypeptide to provide a more efficient administration, e.g., resulting in less frequent and/or decreased dosage of the polypeptide, improving ease of handling, and extending or delaying effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes may be formed from a variety of phospholipids, including, but not limited to, cholesterol, stearylamines or phosphatidylcholines.

Methods for synthesis and preparation of small peptides are well known in the art and are disclosed, for example, in U.S. Pat. Nos. 5,352,461; 5,503,852; 6,071,497; 6,331,318; 6,428,771 and U.S. Publication No. 20060040953. U.S. Pat. Nos. 6,444,226 and 6,652,885 describe preparing and providing microparticles of diketopiperazines in aqueous suspension to which a solution of active agent is added in order to bind the active agent to the particle. These patents further describe a method of removing a liquid medium by lyophilization to yield microparticles comprising an active agent. Altering the solvent conditions of such suspension to promote binding of the active agent to the particle is disclosed in U.S. application Ser. Nos. 60/717,524; 11/532,063; and 11/532,065; U.S. Pat. No. 6,440,463; and U.S. application Ser. Nos. 11/210,709 and 11/208,087. Each of these patents and patent applications is incorporated by reference herein.

In some embodiments, MMI-0100 (YARAAARQARAKALARQLGVAA; SEQ ID NO: 1) and its functional equivalents of the present invention can be dried by a method of spraying drying as disclosed in, for example, U.S. application Ser. No. 11/678,046 (incorporated by reference herein).

In yet another embodiment, the polypeptide of the invention may be applied in a variety of solutions. A suitable formulation is sterile, dissolves sufficient amounts of the polypeptides, and is not harmful for the proposed application. For example, the compositions of the described invention may be formulated as aqueous suspensions wherein the active ingredient(s) is (are) in admixture with excipients suitable for the manufacture of aqueous suspensions.

Such excipients include, without limitation, suspending agents (e.g., sodium carboxymethylcellulose, methylcellulose, hydroxy-propylmethylcellulose, sodium alginate, polyvinylpyrrolidone, gum tragacanth, and gum acacia), dispersing or wetting agents including, a naturally-occurring phosphatide (e.g., lecithin), or condensation products of an alkylene oxide with fatty acids (e.g., polyoxyethylene stearate), or condensation products of ethylene oxide with long chain aliphatic alcohols (e.g., heptadecaethyl-eneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate).

Compositions of the described invention also may be formulated as oily suspensions by suspending the active ingredient in a vegetable oil (e.g., arachis oil, olive oil, sesame oil or coconut oil) or in a mineral oil (e.g., liquid paraffin). The oily suspensions may contain a thickening agent (e.g., beeswax, hard paraffin or cetyl alcohol).

Compositions of the described invention also may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients also may be present.

According to some embodiments, the dry powder is produced by a spray drying process.

According to some other embodiments, the dry powder is produced by micronization According to another embodiment, the dry powder comprises microparticles with Mass Median Aerodynamic Diameter (MMAD) of 1 to 5 microns.

According to another embodiment, the dry powder comprises microparticles with Mass Median Aerodynamic Diameter (MMAD) of about 2 micron.

According to another embodiment, the pharmaceutical composition is packaged in an inhalation device, including, for example, but not limited to a nebulizer, a metered-dose inhaler (MDI), and a dry powder inhaler (DPI).

According to some other embodiments, the pharmaceutical composition is a liquid for aerosolized delivery using a nebulizer. According to some such embodiments, the flowrate of the pharmaceutical composition is at least 0.3 ml/min, and the pharmaceutical composition is delivered as 2 mm particles, with distribution into deepest alveoli.

Compositions of the described invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate.

According to some embodiments, the polypeptide of the described invention is chemically synthesized. Such a synthetic polypeptide, prepared using the well known techniques of solid phase, liquid phase, or peptide condensation techniques, or any combination thereof, may include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, *J. Am. Chem. Soc.* 85:2149-2154), or the base-labile N-α-amino protected 9-fluorenylmethoxycarbonyl (Fmoc) amino acids first described by Carpino and Han (1972, *J. Org. Chem.* 37:3403-3409). Both Fmoc and Boc N-α-amino protected amino acids can be obtained from Sigma, Cambridge Research Biochemical, or other chemical companies familiar to those skilled in the art. In addition, the polypeptide may be synthesized with other N-α-protecting groups that are familiar to those skilled in this art. Solid phase peptide synthesis may be accomplished by techniques familiar to those in the art and provided, for example, in Stewart and Young, 1984, *Solid Phase Synthesis*, Second Edition, Pierce Chemical Co., Rockford, Ill.; Fields and Noble, 1990, *Int. J. Pept. Protein Res.* 35:161-214, or using automated synthesizers, each incorporated by reference herein in its entirety.

II. Methods for Preventing or Treating Diseases Characterized by Aberrant Fibroblast Proliferation and Collagen Deposition According to another aspect, the described invention provides a method for treating a disease, condition, or process characterized by aberrant fibroblast proliferation and extracellular matrix deposition in a tissue of a subject, the method comprising:

administering to the subject a pharmaceutical composition comprising a therapeutic amount of a polypeptide of the amino acid sequence YARAAARQARAKALARQLGVAA (SEQ ID NO: 1) or a functional equivalent thereof, and a pharmaceutically acceptable carrier thereof, wherein the therapeutic amount is effective to reduce the fibroblast proliferation and extracellular matrix deposition in the tissue of the subject.

According to one embodiment of the method, the disease or the condition is Acute Lung Injury (ALI) or acute respiratory distress syndrome (ARDS).

According to another embodiment, the disease or the condition is radiation-induced fibrosis.

According to another embodiment, the disease or the condition is transplant rejection.

According to another embodiment, the tissue is a lung tissue.

According to another embodiment, the disease or the condition is an interstitial lung disease.

According to another embodiment, the disease or the condition is pulmonary fibrosis.

According to another embodiment, the pulmonary fibrosis is idiopathic pulmonary fibrosis.

According to another embodiment, the pulmonary fibrosis is caused by administration of bleomycin.

According to another embodiment, the pulmonary fibrosis results from an allergic reaction, inhalation of environmental particulates, smoking, a bacterial infection, a viral infection, mechanical damage to a lung of the subject, lung transplantation rejection, an autoimmune disorder, a genetic disorder, or a combination thereof.

According to another embodiment, the tissue is a liver tissue.

According to another embodiment, the disease or the condition is liver fibrosis.

Methods for detecting, diagnosing and assessing treatment of hepatic fibrosis include, but are not limited to, biopsy, imaging analysis and blood tests. Non-limiting examples of imaging analysis include ultrasonography, computed tomography (CT) and elastography. Examples of elastography include, but are not limited to, ultrasound elastography, magnetic resonance elastogrphy, and the like. Blood tests include, but are not limited to, blood tests for the detection of biomarkers. Non-limiting examples of biomarkers include peptides, proteins, nucleic acids (e.g., DNA, RNA and mRNA), antibodies and genes.

Biomarkers for liver fibrosis include, but are not limited to, direct biomarkers (also know as class I fibrosis markers); cytokines and chemokines; and indirect biomarkers (also known as class II fibrosis markers).

Ultrasonography is an imaging technique in which deep structures of the body are visualized by recording the reflections (i.e., echoes) of ultrasonic waves directed into the tissues. Frequencies in the range of 1 million to 10 million hertz are used in diagnostic ultrasonography.

The lower frequencies provide a greater depth of penetration and are used to examine abdominal organs. Frequencies in the upper range provide less penetration and are used predominantly to examine more superficial structures, such as the eye. The basic principle of ultrasonography is the same as that of depth-sounding in oceanographic studies of the ocean floor. The ultrasonic waves are confined to a narrow beam that may be transmitted through, refracted, absorbed, or reflected by the medium toward which they are directed, depending on the nature of the surface they strike. In diagnostic ultrasonography, the ultrasonic waves are produced by electrically stimulating a piezoelectric crystal called a transducer. As the beam strikes an interface or boundary between tissues of varying acoustic impedance (e.g. muscle and blood) some of the sound waves are reflected back to the transducer as echoes. The echoes are then converted into electrical impulses that are displayed on an oscilloscope, presenting a 'picture' of the tissues under examination. Ultrasonography can be utilized in examination, for example, of the heart (echocardiography) and in identifying size and structural changes in organs in the abdominopelvic cavity (e.g., of the liver in liver fibrosis, liver cirrhosis, etc.). It is also useful in identifying and distinguishing cancers and benign cysts.

Computerized tomography (CT) or computerized axial tomography (CAT) is an imaging technique in which an x-ray source and x-ray detector housed in a doughnut-shaped assembly move circularly around a patient who lies on a motorized table that is moved through the machine. Usually, multidetector scanners with 4 to 64 or more rows of detectors are used in order to allow quicker scanning and higher-resolution images. Data from the detectors essentially represent a series of x-ray images taken from multiple angles around the patient. The images are not viewed directly but are sent to a computer, which quickly reconstructs them into 2-dimensional images (tomograms) representing a slice of the body in any plane desired. Data can also be used to construct detailed 3-dimensional images. For some CT scans, the table moves incrementally and stops when each scan (slice) is taken. For other CT scans, the table moves continuously during scanning; because the patient is moving in a straight line and the detectors are moving in a circle, the series of images appear to be taken in a spiral fashion around the patient. Compared with plain x-rays, the tomographic slices of CT provide more spatial detail and can better differentiate between various soft-tissue densities. Because it provides so much more information, CT is preferred to plain x-rays for imaging most intracranial, head and neck, spinal, intrathoracic, and intra-abdominal structures. Three-dimensional images of lesions can help surgeons plan surgery. CT is the most accurate study for detecting and localizing urinary calculi. CT may be done with or without IV contrast. Noncontrast CT is used to detect, for example, acute hemorrhage in the brain, urinary calculi, and lung nodules, as well as to characterize bone fractures and other skeletal abnormalities. IV contrast is used, for example, to improve imaging of tumors, infection, inflammation, and trauma in soft tissues and to assess the vascular system, as when pulmonary embolism, aortic aneurysm, or aortic dissection is suspected.

Hepatic elastography is a method for estimating liver stiffness. Elastography can be accomplished by ultrasound or magnetic resonance.

Ultrasound Elastography (Also Called Transient Elastography)

A FibroScan device (EchoSens, Paris, France) uses a mild-amplitude, low-frequency (50-Hz) vibration transmitted through the liver. It induces an elastic shear wave that is detected by pulse-echo ultrasonography as the wave propagates through the organ. The velocity of the wave correlates with tissue stiffness, i.e., the wave travels faster through denser, fibrotic tissue. Ultrasound elastography can sample a much larger area than liver biopsy, providing a better understanding of the entire hepatic parenchyma. Moreover, it can be repeated often without risk.

Magnetic Resonance Elastography

Magnetic resonance elastography is similar to ultrasound elastography in that it uses a vibration device to induce a shear wave in the liver. However, in this case, the wave is detected by a modified magnetic resonance imaging machine, and a color-coded image is generated that depicts the wave velocity, and hence stiffness, throughout the organ. In magnetic resonance elastography, a value greater than 4.46 kPa indicates cirrhosis (and a value less than 4.13 indicates no cirrhosis) with a high degree of likelihood, and a value less than 2.84 excludes the likelihood of significant fibrosis.

Direct (class I) biomarkers of liver fibrosis include, but are not limited to, direct markers linked to matrix deposition and direct markers linked to matrix degradation. Non-limiting examples of direct markers linked to matrix deposition include, procollagen type 1 (PC1CP), procollagen type 3 (PCIIINP), type IV collagen, hyaluronic acid (HA), laminin and YXL-40 chondrex. Examples of direct markers linked to matrix degradation include, but are not limited to, matrix metalloproteinase-1 (MMP-1), matrix metalloproteinase-2 (MMP-2), matrix metalloproteinase-9 (MMP-9) and tissue inhibitors of matrix metalloproteinases (TIMPs)

Cytokine and chemokine biomarkers of liver fibrosis include, but are not limited to, transforming growth factor-β (TGFβ), transforming growth factor-α (TFGα) and platelet-derived growth factor (PDGF).

Indirect (class II) biomarkers of liver fibrosis include, but are not limited to, aspartate aminotransferase/alanine aminotransferase (AST/ALT) ratio, PGA (prothrombin index, γ glutamyl transferase (GGT), and apolipoprotein A1), APRI (AST/platent count ratio), FibroSpect II (HA, TIMP-1, α2-macroglobulin), FibroTest/FibroSure (γ2 macroglobulin, γ2 globulin, γ globulin, apolipoprotein A1, GGT, total bilirubin), Fibrolndex (platelet count, AST, GGT), FibroMeter (platelet count, γ2 macroglobulin, AST, age, prothrombin index, HA, blood urea nitrogen), Forns (age, platelet count, GGT, cholesterol levels), Hepascore (age, gender, bilirubin, GGT, HA, γ2 macroglobulin), FIB-4 (platelet count, ALT, AST, age), SHASTA index (HA, AST, albumin), Simple test (age, hyperglycemia, platelet count, albumin, AST/ALT, body mass index (BMI)) and OELF/ELF (age, HA, N-terminal propeptide of type III collagen, TIMP-1).

According to another embodiment, the tissue is a kidney tissue.

According to another embodiment, the disease or condition is renal fibrosis.

Methods for detecting, diagnosing and assessing treatment of renal fibrosis include, but are not limited to, biopsy, imaging analysis and blood tests. Non-limiting examples of imaging analysis include histological quantitive image analysis of pricrosirius red staining. Blood tests include, but are not limited to, blood tests for the detection of biomarkers. Non-limiting examples of biomarkers include peptides, proteins, nucleic acids (e.g., DNA, RNA and mRNA), antibodies and genes. Renal fibrosis biomarkers include, but are not limited to, hydroxyproline, MCP-1, Collagen 1a1, Collagen 3a1, TGF-β, Fibronectin-1, α-SMA, connective tissue growth factor-1 (CTGF-1) and the like.

According to another embodiment, the tissue is a vascular tissue.

According to another embodiment, the disease or condition is vascular fibrosis.

Methods for detecting, diagnosing and assessing treatment of vascular fibrosis include, but are not limited to, biopsy, imaging analysis and blood tests. Non-limiting examples of imaging analysis include histological quantitive image analysis of pricrosirius red staining, 3',3'-diaminobenzidine (DAB) and hematoxylin. Blood tests include, but are not limited to, blood tests for the detection of biomarkers. Non-limiting examples of biomarkers include peptides, proteins, nucleic acids (e.g., DNA, RNA and mRNA), antibodies and genes. Vascular fibrosis biomarkers include, but are not limited to, hydroxyproline, MCP-1, Collagen 1a1, Collagen 3a1, TGF-β, Fibronectin-1, α-SMA, connective tissue growth factor-1 (CTGF-1), PARAγ and the like.

According to another embodiment, the described invention utilizes isolated nucleic acids. Nucleic acids include, for example, DNA, RNA and mRNA. Nucleic acids can be isolated, for example, from tissues, cells, blood, serum, plasma, urine, saliva, semen and the like. Protocols and reagents for isolating nucleic acids are known. Non-limiting examples of reagents used for nucleic acid isolation include guanidine thiocyanate, guanidine hydrochloride and guanidinium thiocyanate-phenol-chloroform; the proprietary formulation of this reagent is known as Trizol®.

According to another embodiment, the described invention utilizes methods employing amplification of nucleic acids. Amplification of nucleic acids is accomplished by Polymerase Chain Reaction (PCR). Non-limiting examples of PCR include conventional PCR, real-time PCR, quantitative PCR, quantitative real-time PCR, multiplex PCR, conventional reverse-transcriptase PCR (RT-PCR), real-time RT-PCR, quantitative RT-PCR, quantitative real-time RT-PCR, multiplex RT-PCR and the like.

Primers for PCR amplification of target sequences (e.g., mRNA sequences of TGFβ and α-SMA genes) can be designed based on the sequence of the target sequence, in accordance with standard procedures. Primers function to anneal and amplify a unique target sequence and as generators of a signal for detection and monitoring of an amplification reaction. According to some embodiments, the primers are unlabeled (such as in conventional PCR), while in other embodiments, the primers are labeled, such as with a fluorescent moiety. Labeled primers can be of any type, including those that are typically used in quantitative RT-PCR reactions, such as Scorpions, Molecular Beacons, and the like.

Probes may be provided in addition to primers. Probes that can be used for detection of amplification of the unique genomic sequences (e.g., TaqMan® probes) can be designed to hybridize to a sequence between the two amplification primers, preferably within 5-15 bases of one of the primer binding sites. Typically, probes are present in reaction mixtures in conjunction with primers or sets of primers for a particular amplification reaction, for example, an amplification of a unique target sequence. However, probes may be provided as separate components, which are separate from the primer(s) or other components of a reaction mixture.

The primers and probes are designed to have a typical size for primers and probes for use in PCR reactions. In general, the primers are relatively short (about 10-30 bases in length) oligonucleotides, while the probes (e.g., TaqMan® probes) may be from about 15-35 bases in length. The primers and probes are designed through a process that includes identification of unique sequences on a target nucleic acid, designing short oligonucleotides to amplify or detect those sequences, and synthesizing the oligonucleotides. Several characteristics may be taken into consideration when designing the primers and probe: e.g., the probe melting temperature should be higher than the primer melting temperatures, and the distance between the 3'-end of one primer and the 5'-end of the probe may be greater than 8 nucleotides. One of skill in the art may select among such considerations and characteristics to provide suitable primers and probes. Protocols for synthesis of oligonucleotides are known to those skilled in the art. Any suitable protocol may be used in synthesizing the primers and probes of the invention.

Quantitative real-time RT-PCR is an accurate, precise, high throughput assay. Real-time PCR automates the process of quantitating reaction products for each sample in every cycle. According to some embodiments, real-time PCR systems rely upon the detection and quantitation of a fluorescent reporter, the signal of which increases in direct proportion to the amount of PCR product in a reaction.

According to another embodiment, for example, the reporter is the double-stranded DNA-specific dye SYBR® Green (Molecular Probes), which binds double-stranded DNA, and upon excitation emits light. Thus, as a PCR product accumulates, fluorescence increases. The SYBR® Green (Molecular Probes, Eugene, Oreg.) system is one way to detect and quantitate PCR products in real time. The SYBR® Green dye binds, in a sequence non-specific manner, to double-stranded nucleic acids. It thus can be used for detection and quantitation of double-stranded products produced from single-stranded templates (e.g., mRNA). Other detectable probes and primers, such as Amplifluor® probes, and DNAzymes, may be optimized to be used for quantitative detection of amplification products.

Alternatives to SYBR® Green include, but are not limited to, TaqMan® (Applied Biosystems, Foster City, Calif.) and molecular beacons, both of which are hybridization probes relying on fluorescence resonance energy transfer (FRET) for quantitation. TaqMan® Probes are oligonucleotides that contain a fluorescent dye, typically on the 5' base, and a quenching dye, typically located on the 3' base. More specifically, for TaqMan® probes, when the probe is intact, the quencher quenches the signal produced by the fluorescent label. However, upon binding of the probe to the target sequence and subsequent digestion of the probe by the 5'-3' exonuclease activity of a polymerase, such as Taq polymerase, the fluorescent moiety is released from the quencher moiety, and a detectable signal, which is proportional to the amount of target nucleic acid being produced, is produced and can be monitored. According to one embodiment, Taq polymerase is used in qRT-PCR due to its 5'-3' exonuclease activity, and it changes the fluorescence of the probes and allows amplification of CDR1 mRNA. TaqMan® probes rely on degradation by a polymerase to generate a detectable signal, while Scorpions® and Molecular Beacons rely on opening of a hairpin structure to provide a detectable signal Like TaqMan® probes, Scorpion® probes contain both a fluorescent moiety and quenching moiety on a single probe. However, unlike TaqMan® probes, Scorpions® are not degraded during the amplification reaction. Rather, they are designed as primers for amplification reactions. Scorpion® primers are designed to form hairpin structures in solution, which causes the fluorescent moiety and the quenching moiety to be in close proximity. Binding of the primers to target nucleic acids unfolds the hairpin structure and moves the quenching moiety a sufficient distance away from the fluorescent moiety that detectable fluorescence is emitted.

Molecular beacons also contain fluorescent and quenching dyes, but FRET only occurs when the quenching dye is directly adjacent to the fluorescent dye. Molecular beacons are designed to adopt a hairpin structure while free in solution, bringing the fluorescent dye and quencher in close proximity. When a molecular beacon hybridizes to a target, the fluorescent dye and quencher are separated, FRET does not occur, and the fluorescent dye emits light upon irradiation.

Multiplexing of PCR reactions is common. Multiplexing allows an investigator to assay two or more different gene targets in a single reaction through the use of multiple probes or primers, each specific for its own target and each comprising a fluorescent moiety that emits at a unique wavelength (as compared to the other probes). Multiplexing is possible with TaqMan® probes, Molecular Beacons, and Scorpions. Due to its non-specific binding nature, SYBR® Green may not be amenable to multiplexing.

Generally, a quantitative RT-PCR reaction is performed by one of two methods: comparison to a standard curve or comparison of Ct values. In the first of these methods, a standard curve of amplification products of a particular mRNA is made based on amplification of a series of different, known amounts of a pre-selected nucleic acid. Amplification results of reactions performed on a target nucleic acid are then compared to the standard curve to obtain a quantity, and that quantity can be extrapolated to an amount of the target in the original sample. While it is preferred to use an mRNA as the source for the standard curve, the stability of mRNA is known to affect the validity of such standard curves, and overcoming or minimizing this problem has proved to be difficult. To avoid the problems associated with using mRNA as a source for the standard curve, researchers have used DNA for generation of standard curves. While use of DNA overcomes the problems associated with use of mRNA, the mere fact that it avoids the problems creates yet another problem, i.e., because DNA templates are relatively stable, and because amplification of DNA does not require a first-strand synthesis step (which can be inefficient and variable across samples or preparations), the standard curves produced from DNA sources often do not correlate accurately to the amount of mRNA in a test sample.

In the Ct comparison method for quantitating PCR products, expression of a housekeeping gene (such as β-actin) is used as a standard against which amplification of a target nucleic acid (e.g., TGFβ and α-SMA) is compared. Often, in this method, a comparison of expression of the target nucleic acid under two different conditions is performed to determine changes in expression patterns. This method avoids the problems associated with instability of RNA or use of DNA as a control that is seen when using the classical standard curve method.

Controls are amplified in the same PCR reaction mixture as the target sequence in an effort to quantitate PCR products and determine amounts of target nucleic acids in a sample. These controls are often transcripts of housekeeping genes. Such housekeeping genes include, but are not limited to, β-actin and GAPDH. The control is added to the reaction mix and co-amplified with the target nucleic acid. Fluorescent probes specific for both are included in the mixture, and two amplification curves are obtained. The relative expression of the target nucleic acid with respect to the control is then determined. Using this technique, multiple, different samples can be compared for expression of a target gene (e.g., TGFβ and α-SMA), with reference back to the same control. Although adding a control to amplification reactions can be a useful alternative to other methods of quantitating expression levels, and can be a useful method for normalizing PCR reactions across samples, it does not allow one to determine absolute amounts of materials present in the amplification reaction mixture or in the original sample. Rather, the results are qualitative or semi-quantitative, giving an idea only of the amount of one nucleic acid (e.g., the target) in comparison to another (e.g., the control).

According to another embodiment, the described invention provides methods that detect a protein in a sample obtained from a subject. Such methods of protein detection include, but are not limited to, Western blot, immunohistochemistry, enzyme-linked immunosorbant assay (ELISA), radioimmunoassay and the like.

Methods that detect proteins may employ antibodies. Antibodies are serum proteins the molecules of which possess small areas of their surface that are complementary to small chemical groupings on their targets. These complementary regions (referred to as the antibody combining sites or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

Human antibodies show two kinds of light chains, κ and λ; individual molecules of immunoglobulin generally are only one or the other. In normal serum, 60% of the molecules have been found to have κ determinants and 30 percent λ. Many other species have been found to show two kinds of light chains, but their proportions vary. For example, in the mouse and rat, λ chains comprise but a few percent of the total; in the dog and cat, κ chains are very low; the horse does not appear to have any κ chain; rabbits may have 5 to 40% λ, depending on strain and b-locus allotype; and chicken light chains are more homologous to λ than κ.

In mammals, there are five classes of antibodies, IgA, IgD, IgE, IgG, and IgM, each with its own class of heavy chain—α (for IgA), δ (for IgD), ε (for IgE), γ (for IgG) and μ (for IgM). In addition, there are four subclasses of IgG immunoglobulins (IgG1, IgG2, IgG3, IgG4) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

All five immunoglobulin classes differ from other serum proteins in that they show a broad range of electrophoretic mobility and are not homogeneous. This heterogeneity—that individual IgG molecules, for example, differ from one another in net charge—is an intrinsic property of the immunoglobulins.

An antigenic determinant or epitope is an antigenic site on a molecule. Sequential antigenic determinants/epitopes essentially are linear chains. In ordered structures, such as helical polymers or proteins, the antigenic determinants/epitopes essentially would be limited regions or patches in or on the surface of the structure involving amino acid side chains from different portions of the molecule which could come close to one another. These are conformational determinants.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels. Brought down to the molecular level, specificity means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions. Cross reactions are of major importance in understanding the complementarity or specificity of antigen-antibody reactions. Immunological specificity or complementarity makes possible the detection of small amounts of impurities/contaminations among antigens.

Monoclonal antibodies (mAbs) can be generated by fusing mouse spleen cells from an immunized donor with a mouse myeloma cell line to yield established mouse hybridoma clones that grow in selective media. A hybridoma cell is an immortalized hybrid cell resulting from the in vitro fusion of an antibody-secreting B cell with a myeloma cell. In vitro immunization, which refers to primary activation of antigen-specific B cells in culture, is another well-established means of producing mouse monoclonal antibodies. The term "humanized monoclonal antibodies" refers to monoclonal antibodies in which the complementarity determining regions, ("CDRs"), which fashion the antibody binding site of a mouse monoclonal antibody, are replaced with a CDR of a human protein, while maintaining the framework and constant regions of the mouse antibody.

Diverse libraries of immunoglobulin heavy (VH) and light (Vκ and Vλ) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage.

The technique of guided selection is based on human immunoglobulin V gene shuffling with rodent immunoglobulin V genes. The method entails (i) shuffling a repertoire of human λ light chains with the heavy chain variable region (VH) domain of a mouse monoclonal antibody reactive with an antigen of interest; (ii) selecting half-human Fabs on that antigen (iii) using the selected λ light chain genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgG1, λ antibody molecule in the mouse myeloma According to another embodiment, the described invention utilizes multiplex bead technology (e.g., Luminex®) to detect protein and nucleic acid biomarkers. For example, color-coded polystyrene or superparamagnetic beads coated with analyte-specific antibodies (i.e., for protein biomarker detection) or anti-TAG sequences (i.e., for nucleic acid biomarker detection) recognizing different targets are mixed together and incubated with biotin-labeled targets (i.e., protein or nucleic acid biomarkers). Captured targets are subsequently detected using a streptavidin-phycoerythrin conjugate.

According to another embodiment, the disease or the condition is further characterized by an inflammation in the tissue.

According to another embodiment, the inflammation is an acute or a chronic inflammation.

According to another embodiment, the inflammation is mediated by at least one cytokine selected from the group consisting of Tumor Necrosis Factor-alpha (TNF-α), Interleukin-6 (IL-6), and Interleukin-1β (IL-1β).

According to another embodiment, the pulmonary fibrosis is characterized by at least one pathology selected from the group consisting of an aberrant deposition of an extracellular matrix protein in a pulmonary interstitium, an aberrant promotion of fibroblast proliferation in the lung, an aberrant induction of myofibroblast differentiation in the lung, and an aberrant promotion of attachment of myofibroblasts to an extracellular matrix compared to a normal healthy control subject.

According to another embodiment, the aberrant fibroblast proliferation and extracellular matrix deposition in the tissue is characterized by an aberrant activity of Mitogen-Activated Protein Kinase-Activated Protein Kinase 2 (MK2) in the tissue compared to the activity of Mitogen-Activated Protein Kinase-Activated Protein Kinase 2 (MK2) in the tissue of a normal healthy control subject.

According to another embodiment, the aberrant fibroblast proliferation and extracellular matrix deposition in the tissue is evidenced by an aberrant amount or distribution of activated (phosphorylated) Mitogen-Activated Protein Kinase-Activated Protein Kinase 2 (MK2) in the tissue compared to the amount or distribution of activated Mitogen-Activated Protein Kinase-Activated Protein Kinase 2 (MK2) in the tissue of a normal healthy control subject.

According to another embodiment, the pulmonary fibrosis is characterized by at least one pathology selected from the group consisting of an aberrant deposition of an extracellular matrix protein in a pulmonary interstitium, an aberrant promotion of fibroblast proliferation in the lung, an aberrant induction of differentiation of a population of fibroblasts into a population of myofibroblasts in the lung, and an aberrant promotion of attachment of myofibroblasts to an extracellular matrix compared to a normal healthy control subject.

According to another embodiment, the disease or condition is a chronic obstructive pulmonary disease (COPD). According to another embodiment, the chronic obstructive pulmonary disease (COPD) is caused by smoking. According to another embodiment, the chronic obstructive pulmonary disease (COPD) is caused by environmental particulates. According to another embodiment, the chronic obstructive pulmonary disease (COPD) is caused by alpha-1 antitrypsin deficiency. According to another embodiment, the chronic obstructive pulmonary disease (COPD) is caused by a childhood respiratory infection.

According to another embodiment, the pulmonary fibrosis is characterized by an abnormal activity of Heat Shock 27 kDa protein 1 (HSPB1) in a lung of the subject compared to a normal healthy control subject. According to another embodiment, the abnormal activity of HSPB1 is an aberrant deposition of an extracellular matrix protein in a pulmonary interstitium of the subject compared to a normal healthy control subject. According to another embodiment, the extracellular matrix protein is collagen. According to another embodiment, the abnormal activity of HSPB1 is an aberrant promotion of fibroblast proliferation in the lung compared to a normal healthy control subject. According to another embodiment, the abnormal activity of HSPB1 is aberrant induction of myofibroblast differentiation in the lung compared to a normal healthy control subject. According to another embodiment, the abnormal activity of HSPB1 is a promotion of fibrotic loci formation in the lung compared to a normal healthy control subject. According to another embodiment, the abnormal activity of HSPB1 is an increase of myofibroblast contractile activity in the lung compared to a normal healthy control subject. According to another embodiment, the abnormal activity of HSPB1 is an aberrant promotion of myofibroblast attachment to an extracellular matrix in the lung compared to a normal healthy control subject.

According to another embodiment, the pharmaceutical composition inhibits inflammation occurring in a lung of the subject. According to another embodiment, the inflammation is an acute inflammation. According to another embodiment, the inflammation is a chronic inflammation. According to another embodiment, the inflammation is mediated by Tumor Necrosis Factor-alpha (TNF-α). According to another embodiment, the inflammation is mediated by interleukin-1β (IL-1β). According to another embodiment, the inflammation is mediated by interleukin-6 (IL-6).

According to another embodiment, the pharmaceutical composition modulates an amount of Tumor Necrosis Factor-alpha (TNF-α) in the lung of the subject, compared to an untreated control. According to another embodiment, the pharmaceutical composition modulates an amount of interleukin-1β (IL-1β) in the lung of the subject, compared to a control. According to another embodiment, the pharmaceutical composition modulates an amount of interleukin-6 (IL-6) in the lung of the subject, compared to a control.

According to another embodiment, the pharmaceutical composition inhibits an abnormal activity of HSPB1 compared to a normal healthy control subject in a lung of the subject. According to another embodiment, the abnormal activity of HSPB1 is an aberrant deposition of an extracellular matrix protein in a pulmonary interstitium compared to a normal healthy control subject. According to another embodiment, the extracellular matrix protein is collagen. According to another embodiment, the abnormal activity of HSPB1 is an aberrant promotion of fibroblast proliferation in the lung compared to a normal healthy control subject. According to another embodiment, the abnormal activity of HSPB1 is an aberrant induction of fibroblast differentiation into myofibroblasts in the lung compared to a normal healthy control subject. According to another embodiment, the abnormal activity of HSPB1 is an aberrant promotion of fibrotic loci formation compared to a normal healthy control subject. According to another embodiment, the abnormal activity of HSPB1 is an aberrant increase in contractile activity of myofibroblasts compared to a normal healthy control subject. According to another embodiment, the myofibroblast contractile activity is characterized by an elevated level of alpha smooth muscle actin (α-SMA) compared to a normal healthy control subject. According to another embodiment, the myofibroblasts contractile activity is characterized by increases in stress-fiber formation compared to a normal healthy control subject. According to another embodiment, the abnormal activity of HSPB1 is aberrant promotion of myofibroblasts attachment to an extracellular matrix compared to a normal healthy control subject.

According to one embodiment, the pharmaceutical composition inhibits a kinase activity of Mitogen-Activated Protein Kinase-Activated Protein Kinase 2 (MK2 kinase). According to another embodiment, the pharmaceutical composition inhibits at least 50% of the kinase activity of MK2 kinase. According to another embodiment, the pharmaceutical composition inhibits at least 65% of the kinase activity of MK2 kinase. According to another embodiment, the pharmaceutical composition inhibits at least 75% of the kinase activity of MK2 kinase. According to another embodiment, the pharmaceutical composition inhibits at least 80% of the kinase activity of MK2 kinase. According to another embodiment, the pharmaceutical composition inhibits at least 85% of the kinase activity of MK2 kinase. According to another embodiment, the pharmaceutical composition inhibits at least 90% of the kinase activity of MK2 kinase. According to another embodiment, the pharmaceutical composition inhibits at least 95% of the kinase activity of MK2 kinase.

According to another embodiment, the pharmaceutical composition inhibits a kinase activity of Mitogen-Activated Protein Kinase-Activated Protein Kinase 3 (MK3 kinase). According to another embodiment, the pharmaceutical composition further inhibits at least 50% of the kinase activity of MK3 kinase. According to another embodiment, the pharmaceutical composition further inhibits at least 65% of the kinase activity of MK3 kinase. According to another embodiment, the pharmaceutical composition further inhibits at least 70% of the kinase activity of MK3 kinase. According to another embodiment, the pharmaceutical composition further inhibits at least 75% of the kinase activity of MK3 kinase. According to another embodiment, the pharmaceutical composition further inhibits at least 80% of the kinase activity of MK3 kinase. According to another embodiment, the pharmaceutical composition further inhibits at least 85% of the kinase activity of MK3 kinase. According to another embodiment, the pharmaceutical composition further inhibits at least 90% of the kinase activity of MK3 kinase. According to another embodiment, the pharmaceutical composition further inhibits at least 95% of the kinase activity of MK3 kinase.

According to another embodiment, the pharmaceutical composition inhibits a kinase activity of calcium/calmodulin-dependent protein kinase I (CaMKI). According to another embodiment, the pharmaceutical composition further inhibits at least 50% of the kinase activity of $Ca^{2+}$/calmodulin-dependent protein kinase I (CaMKI). According to another embodiment, the pharmaceutical composition further inhibits at least 65% of the kinase activity of $Ca^{2+}$/calmodulin-dependent protein kinase I (CaMKI). According to another embodiment, the pharmaceutical composition further inhibits at least 70% of the kinase activity of $Ca^{2+}$/ calmodulin-dependent protein kinase I (CaMKI). According to another embodiment, the pharmaceutical composition further inhibits at least 75% of the kinase activity of $Ca^{2+}$/calmodulin-dependent protein kinase I (CaMKI). According to another embodiment, the pharmaceutical composition further inhibits at least 80% of the kinase activity of $Ca^{2+}$/calmodulin-dependent protein kinase I (CaMKI). According to another embodiment, the pharmaceutical composition further inhibits at least 85% of the kinase activity of $Ca^{2+}$/calmodulin-dependent protein kinase I (CaMKI). According to another embodiment, the pharmaceutical composition further inhibits at least 90% of the kinase activity of $Ca^{2+}$/calmodulin-dependent protein kinase I (CaMKI). According to another embodiment, the pharmaceutical composition further inhibits at least 95% of the kinase activity of $Ca^{2+}$/calmodulin-dependent protein kinase I (CaMKI).

According to another embodiment, the pharmaceutical composition inhibits a kinase activity of BDNF/NT-3 growth factors receptor (TrkB). According to another embodiment, the pharmaceutical further inhibits at least 50% of the kinase activity of BDNF/NT-3 growth factors receptor (TrkB). According to another embodiment, the pharmaceutical further inhibits at least 65% of the kinase activity of BDNF/NT-3 growth factors receptor (TrkB). According to another embodiment, the pharmaceutical further inhibits at least 70% of the kinase activity of BDNF/NT-3 growth factors receptor (TrkB). According to another embodiment, the pharmaceutical further inhibits at least 75% of the kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2) and a kinase activity of Mitogen-Activated Protein Kinase-Activated Protein Kinase 3 (MK3).

According to another embodiment, the pharmaceutical composition inhibits a kinase activity of Mitogen-Activated Protein Kinase-Activated Protein Kinase 2 (MK2) and a kinase activity of calcium/calmodulin-dependent protein kinase I (CaMKI).

According to another embodiment, the pharmaceutical composition inhibits a kinase activity of Mitogen-Activated Protein Kinase-Activated Protein Kinase 2 (MK2) and a kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2), a kinase activity of Mitogen-Activated Protein Kinase-Activated Protein Kinase 3 (MK3), a kinase activity of calcium/calmodulin-dependent protein kinase I (CaMKI), and a kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2), a kinase activity of calcium/calmodulin-dependent protein kinase I (CaMKI), and a kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2).

According to another embodiment, the pharmaceutical composition inhibits at least 65% of the kinase activity of Mitogen-Activated Protein Kinase-Activated Protein Kinase 3 (MK3).

According to another embodiment, the pharmaceutical composition inhibits at least 65% of the kinase activity of calcium/calmodulin-dependent protein kinase I (CaMKI).

According to another embodiment, the pharmaceutical composition inhibits at least 65% of the kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2) and at least 65% of the kinase activity of Mitogen-Activated Protein Kinase-Activated Protein Kinase 3 (MK3).

According to another embodiment, the pharmaceutical composition inhibits at least 65% of the kinase activity of Mitogen-Activated Protein Kinase-Activated Protein Kinase 2 (MK2) and at least 65% of the kinase activity of calcium/calmodulin-dependent protein kinase I (CaMKI).

According to another embodiment, the pharmaceutical composition inhibits at least 65% of the kinase activity of Mitogen-Activated Protein Kinase-Activated Protein Kinase 2 (MK2) and at least 65% of the kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2), at least 65% of the kinase activity of Mitogen-Activated Protein Kinase-Activated Protein Kinase 3 (MK3), at least 65% of the kinase activity of calcium/calmodulin-dependent protein kinase I (CaMKI), and at least 65% of the kinase activity of BDNF/NT-3 growth factors receptor (TrkB).

According to another embodiment, the pharmaceutical composition inhibits the kinase activity of at least one kinase selected from the group of MK2, MK3, CaMKI, TrkB, without substantially inhibiting the activity of one or more other selected kinases from the remaining group listed in Table 1 herein.

According to another embodiment, the pharmaceutical composition inhibits a kinase activity of a kinase selected from the group listed in Table 1 herein.

According to another embodiment, this inhibition may, for example, be effective to reduce fibroblast proliferation, extracellular matrix deposition, or a combination thereof in the tissue of the subject.

According to another embodiment, this inhibition may, for example, be effective to reduce at least one pathology selected from the group consisting of an aberrant deposition of an extracellular matrix protein in a pulmonary interstitium, an aberrant promotion of fibroblast proliferation in the lung, an aberrant induction of myofibroblast differentiation, and an aberrant promotion of attachment of myofibroblasts to an extracellular matrix, compared to a normal healthy control subject.

According to some embodiments, inhibitory profiles of MMI inhibitors in vivo depend on dosages, routes of administration, and cell types responding to the inhibitors.

According to such embodiment, the pharmaceutical composition inhibits less than 50% of the kinase activity of the other selected kinase(s). According to such embodiment, the pharmaceutical composition inhibits less than 65% of the kinase activity of the other selected kinase(s). According to another embodiment, the pharmaceutical composition inhibits less than 50% of the kinase activity of the other selected kinase(s). According to another embodiment, the pharmaceutical composition inhibits less than 40% of the kinase activity of the other selected kinase(s). According to another embodiment, the pharmaceutical composition inhibits inhibits less than 20% of the kinase activity of the other selected kinase(s). According to another embodiment, the pharmaceutical composition inhibits less than 15% of the kinase activity of the other selected kinase(s). According to another embodiment, the pharmaceutical composition inhibits less than 10% of the kinase activity of the other selected kinase (s). According to another embodiment, the pharmaceutical composition inhibits less than 5% of the kinase activity of the other selected kinase(s). According to another embodiment, the pharmaceutical composition increases the kinase activity of the other selected kinases.

According to the embodiments of the immediately preceding paragraph, the one or more other selected kinase that is not substantially inhibited is selected from the group of $Ca^{2+}$/calmodulin-dependent protein kinase II (CaMKII, including its subunit CaMKIIδ), Proto-oncogene serine/threonine-protein kinase (PIM-1), cellular-Sarcoma (c-SRC), Spleen Tyrosine Kinase (SYK), C-src Tyrosine Kinase (CSK), and Insulin-like Growth Factor 1 Receptor (IGF-1R).

According to some embodiments, the pharmaceutical composition further comprises an additional therapeutic agent.

According to some such embodiments, the additional therapeutic agent is one or more selected from the group consisting of purified bovine Type V collagens (e.g., IW-001; ImmuneWorks; United Therapeutics), IL-13 receptor antagonists (e.g., QAX576; Novartis), protein tyrosine kinase inhibitors (e.g., imatinib (Gleevec®); Craig Daniels/Novartis), endothelial receptor antagonists (e.g., ACT-064992 (macitentan); Actelion), dual endothelin receptor antagonists (e.g., bosentan (Tracleer®); Actelion), prostacyclin analogs (inhaled iloprost (e.g., Ventavis®); Actelion), anti-CTGF monoclonal antibodies (e.g., FG-3019), endothelin receptor antagonists (A-selective) (e.g., ambrisentan (Letairis®), Gilead), AB0024 (Arresto), lysyl oxidase-like 2 (LOXL2) monoclonal antibodies (e.g., GS-6624 (formerly AB0024); Gilead), c-Jun N-terminal kinase (JNK) inhibitors (e.g., CC-930; Celgene), Pirfenidone (e.g., Esbriet® (InterMune), Pirespa® (Shionogi)), IFN-γ1b (e.g., Actimmune®; InterMune), pan-neutralizing IgG4 human antibodies against all three TGF-β isoforms (e.g., GC1008; Genzyme), TGF-β activation inhibitors (e.g., Stromedix (STX-100)), recombinant human Pentraxin-2 protein (rhPTX-2) (e.g., PRM151; Promedior), bispecific IL4/IL13 antibodies (e.g., SAR156597; Sanofi), humanized monoclonal antibodies targeting integrin αvβ6 (BIBF 1120; Boehringer Ingelheim), N-acetylcysteine (Zambon SpA), Sildenafil (Viagra®), TNF antagonists (e.g., etanercept (Enbrel®); Pfizer), glucocorticoids (e.g., prednisone, budesonide, mometasone furoate, fluticasone propionate, and fluticasone furoate), bronchodilators (e.g., leukotriene modifers (e.g., Montelukast (SINGUAIR®)), anticholingertic bronchodilators (e.g., Ipratropium bromide and Tiotropium), short-acting β2-agonists (e.g., isoetharine mesylate (Bronkometer®), adrenalin, salbutanol/albuterol, and terbutaline), long-acting β2-agonists (e.g., salmeterol, formoterol, indecaterol (Onbrez®), sofosbuvir, an HCV boosted protease inhibitor (ABT-450, AbbVie), a nonnucleoside NS5B inhibitor (dasabuvir, ABT-333, AbbVie), an NS5a inhibitor (ombitasvir, ABT-267, AbbVie), ABT-450/r (ABT-450 with ritonavir), ABT-450 co-formulated with ABT-267, or ABT-450 formulated with sofosbuvir. According to another embodiment, an additional therapeutic agent for HCV treatment is ribavirin, and a combination thereof.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, sofosbuvir (Sovaldi®) or a combination thereof.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to another embodiment, the additional therapeutic agent is an anti-inflammatory agent.

According to another embodiment, the anti-inflammatory agent is a nonsteroidal anti-inflammatory agent. Mixtures of non-steroidal anti-inflammatory agents also may be employed, as well as the dermatologically acceptable salts and esters of these agents. For example, etofenamate, a flufenamic acid derivative, is particularly useful for topical application.

According to another embodiment, wherein the nonsteroidal anti-inflammatory agent comprises Transforming Growth Factor-β3 (TGF-β3), an anti-Tumor Necrosis Factor-alpha (TNF-α) agent, or a combination thereof.

According to another embodiment, the anti-inflammatory agent is a steroidal anti-inflammatory agent. According to another embodiment, the steroidal anti-inflammatory agent comprises at least one corticosteroid selected from the group consisting of prednisone, budesonide, mometasone, beclemethasone, and a combination thereof.

According to another embodiment, the additional therapeutic agent comprises a methylxanthine.

According to another embodiment, the additional therapeutic agent comprises a neutrophil elastase inhibitor.

According to another embodiment, the additional therapeutic agent is at least one neutrophil elastase inhibitor, including, but not limited to, ICI 200355, ONO-5046, MR-889, L-694,458, CE-1037, GW-311616, TEI-8362, ONO-6818, AE-3763, FK-706, ICI-200,880, ZD-0892, ZD-8321, and a combination thereof.

According to another embodiment, the additional therapeutic agent comprises at least one phosphodiesterase inhibitor, including, but not limited to, phosphodiesterase 4 inhibitor. Examples of phosphodiesterase 4 inhibitors include, but are not limited to, roflumilast, cilomilast or a combination thereof.

According to another embodiment, the additional therapeutic agent is an analgesic agent. According to some such embodiments, the analgesic agent is a non-opioid analgesic. According to some other embodiments, the analgesic is an opioid analgesic.

According to another embodiment, the additional therapeutic agent is an anti-infective agent. According to another embodiment, the anti-infective agent is an antibiotic agent.

According to some embodiments, the functional equivalent of the polypeptide YARAAARQARAKALARQLGVAA (SEQ ID NO: 1) has a substantial sequence identity to amino acid sequence YARAAARQARAKALARQLGVAA (SEQ ID NO: 1).

According to some such embodiments, the functional equivalent of the polypeptide YARAAARQARAKALARQLGVAA (SEQ ID NO: 1) has at least 70 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 80 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 90 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 95 percent sequence identity to amino acid sequence YARAAARQARAKALARQLGVAA (SEQ ID NO: 1).

According to another embodiment, the functional equivalent of the polypeptide YARAAARQARAKALARQLGVAA (SEQ ID NO: 1) is of amino acid sequence FAKLAARLYRKALARQLGVAA (SEQ ID NO: 3).

According to another embodiment, the functional equivalent of the polypeptide YARAAARQARAKALARQLGVAA (SEQ ID NO: 1) is of amino acid sequence KAFAKLAARLYRKALARQLGVAA (SEQ ID NO: 4).

According to another embodiment, the functional equivalent of the polypeptide YARAAARQARAKALARQLGVAA (SEQ ID NO: 1) is of amino acid sequence YARAAARQARAKALARQLAVA (SEQ ID NO: 5).

According to another embodiment, the functional equivalent of the polypeptide YARAAARQARAKALARQLGVAA (SEQ ID NO: 1) is of amino acid sequence YARAAARQARAKALARQLGVA (SEQ ID NO: 6).

According to another embodiment, the functional equivalent of the polypeptide YARAAARQARAKALARQLGVAA (SEQ ID NO: 1) is of amino acid sequence YARAAARQARAKALNRQLAVAA (SEQ ID NO: 26).

According to another embodiment, the functional equivalent of the polypeptide YARAAARQARAKALARQLGVAA (SEQ ID NO: 1) is of amino acid sequence YARAAARQARAKALNRQLAVA (SEQ ID NO: 27).

According to another embodiment, the functional equivalent of the polypeptide YARAAARQARAKALARQLGVAA (SEQ ID NO: 1) is of amino acid sequence HRRIKAWLKKIKALARQLGVAA (SEQ ID NO: 7).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide is of amino acid sequence YARAAARQARA (SEQ ID NO: 11), and the second polypeptide comprises a therapeutic domain whose sequence has a substantial identity to amino acid sequence KALARQLGVA (SEQ ID NO: 2).

According to another embodiment, the second polypeptide has at least 70 percent sequence identity to amino acid sequence KALARQLGVAA (SEQ ID NO: 2). According to some other embodiments, the second polypeptide has at least 80 percent sequence identity to amino acid sequence KALARQLGVAA (SEQ ID NO: 2). According to some other embodiments, the second polypeptide has at least 90 percent sequence identity to amino acid sequence KALARQLGVAA (SEQ ID NO: 2). According to some other embodiments, the second polypeptide has at least 95 percent sequence identity to amino acid sequence KALARQLGVAA (SEQ ID NO: 2).

According to another embodiment, the second polypeptide is a polypeptide of amino acid sequence KALARQLAVA (SEQ ID NO: 8).

According to another embodiment, the second polypeptide is a polypeptide of amino acid sequence KALARQLGVA (SEQ ID NO: 9).

According to another embodiment, the second polypeptide is a polypeptide of amino acid sequence KALARQLGVAA (SEQ ID NO: 10).

According to another embodiment, the second polypeptide is a polypeptide of amino acid sequence KALNRQLAVAA (SEQ ID NO: 28).

According to another embodiment, the second polypeptide is a polypeptide of amino acid sequence KALNRQLAVA (SEQ ID NO: 29).

According to some embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide comprises a cell penetrating peptide functionally equivalent to YARAAARQARA (SEQ ID NO: 11), and the second polypeptide is of amino acid sequence KALARQLGVAA (SEQ ID NO: 2), and the pharmaceutical composition inhibits both the kinase activity of Mitogen-Activated Protein Kinase-Activated Protein Kinase 2 (MK2).

According to another embodiment, the first polypeptide is a polypeptide of amino acid sequence WLRRIKAWLRRIKA (SEQ ID NO: 12).

According to another embodiment, the first polypeptide is a polypeptide of amino acid sequence WLRRIKA (SEQ ID NO: 13).

According to another embodiment, the first polypeptide is a polypeptide of amino acid sequence YGRKKRRQRRR (SEQ ID NO: 14).

According to another embodiment, the first polypeptide is a polypeptide of amino acid sequence WLRRIKAWLRRI (SEQ ID NO: 15).

According to another embodiment, the first polypeptide is a polypeptide of amino acid sequence FAKLAARLYR (SEQ ID NO: 16). According to some such embodiments, the first polypeptide is a polypeptide of amino acid sequence KAFAKLAARLYR (SEQ ID NO: 17).

According to some such embodiments, the first polypeptide is a polypeptide of amino acid sequence HRRIKAWLKKI (SEQ ID NO: 18).

According to another aspect, the described invention also provides an isolated nucleic acid that encodes a protein sequence with at least 70% amino acid sequence identity to amino acid sequence YARAAARQARAKALARQLGVAA (SEQ ID NO: 1).

According to some such embodiments, the isolated nucleic acid encodes a protein sequence with at least 80% amino acid sequence identity to amino acid sequence YARAAARQARAKALARQLGVAA (SEQ ID NO: 1). According to some other embodiments, the isolated nucleic acid encodes a protein sequence with at least 90% amino acid sequence identity to amino acid sequence YARAAARQARAKALARQLGVAA (SEQ ID NO: 1). According to some other embodiments, the isolated nucleic acid encodes a protein sequence with at least 95% amino acid sequence identity to amino acid sequence YARAAARQARAKALARQLGVAA (SEQ ID NO: 1).

According to another embodiment, the step of administering may occur systemically either orally, buccally, parenterally, topically, by inhalation, by insufflation, or rectally, or may occur locally by means such as, but not limited to, injection, implantation, grafting, topical application, or parenterally. Additional administration may be performed, for example, intravenously, transmucosally, transdermally, intramuscularly, subcutaneously, intratracheally (including by pulmonary inhalation), intraperitoneally, intrathecally, intralymphatically, intralesionally, or epidurally. Administering can be performed, for example, once, a plurality of times, and/or over one or more extended periods either as individual unit doses or in the form of a treatment regimen comprising multiple unit doses of multiple drugs and/or substances.

According to some other embodiments, the step of administering occurs at one time as a single dose. According to some other embodiments, the step of administering is performed as a plurality of doses over a period of time. According to some such embodiments, the period of time is a day, a week, a month, a month, a year, or multiples thereof. According to some embodiments, the step of administering is performed daily for a period of at least one week. According to some embodiments, the step of administering is performed weekly for a period of at least one month. According to some embodiments, the step of administering is performed monthly for a period of at least two months. According to another embodiment, the step of administering is performed repeatedly over a period of at least one year. According to another embodiment, the step of administering is performed at least once monthly. According to another embodiment, the step of administering is performed at least once weekly. According to another embodiment, the step of administering is performed at least once daily.

According to some other embodiments, the therapeutic amount of the pharmaceutical composition is administered via an inhalation device. Examples of the inhalation device that can be used for administering the pharmaceutical composition include, but are not limited to, a nebulizer, a metered-dose inhaler (MDI), a dry powder inhaler (DPI), and a dry powder nebulizer.

According to another embodiment, the dry powder comprises microparticles with Mass Median Aerodynamic Diameter (MMAD) of 1 to 5 microns. According to another embodiment, the dry powder comprises microparticles with Mass Median Aerodynamic Diameter (MMAD) of about 2 micron.

According to some other embodiments, the therapeutic amount of the therapeutic inhibitor peptide of the pharmaceutical composition is of an amount from about 0.000001 mg/kg body weight to about 100 mg/kg body weight. According to another embodiment, the therapeutic amount of the therapeutic inhibitory peptide of the pharmaceutical composition is of an amount from about 0.00001 mg/kg body weight to about 100 mg/kg body weight. According to another embodiment, the therapeutic amount of the therapeutic inhibitory peptide of the pharmaceutical composition is of an amount from about 0.0001 mg/kg body weight to about 100 mg/kg body weight. According to another embodiment, the therapeutic amount of the therapeutic inhibitory peptide of the pharmaceutical composition is of an amount from about 0.001 mg/kg body weight to about 10 mg/kg body weight. According to another embodiment, the therapeutic amount of the therapeutic inhibitory peptide of the pharmaceutical composition is of an amount from about 0.01 mg/kg body weight to about 10 mg/kg body weight. According to another embodiment, the therapeutic amount of the therapeutic inhibitory peptide of the pharmaceutical composition is of an amount from about 0.1 mg/kg (or 100 μg/kg) body weight to about 10 mg/kg body weight. According to another embodiment, the therapeutic amount of the therapeutic inhibitory peptide of the pharmaceutical composition is of an amount from about 1 mg/kg body weight to about 10 mg/kg body weight. According to another embodiment, the therapeutic amount of the therapeutic inhibitory peptide of the pharmaceutical composition is of an amount from about 10 mg/kg body weight to about 100 mg/kg body weight. According to another embodiment, the therapeutic amount of the therapeutic inhibitory peptide of the pharmaceutical composition is of an amount from about 2 mg/kg body weight to about 10 mg/kg body weight. According to another embodiment, the therapeutic amount of the therapeutic inhibitory peptide of the pharmaceutical composition is of an amount from about 3 mg/kg body weight to about 10 mg/kg body weight. According to another embodiment, the therapeutic amount of the therapeutic inhibitory peptide of the pharmaceutical composition is of an amount from about 4 mg/kg body weight to about 10 mg/kg body weight. According to another embodiment, the therapeutic amount of the therapeutic inhibitory peptide of the pharmaceutical composition is of an amount from about 5 mg/kg body weight to about 10 mg/kg body weight. According to another embodiment, the therapeutic amount of the therapeutic inhibitory peptide of the pharmaceutical composition is of an amount from about 60 mg/kg body weight to about 100 mg/kg body weight. According to another embodiment, the therapeutic amount of the therapeutic inhibitory peptide of the pharmaceutical composition is of an amount from about 70 mg/kg body weight to about 100 mg/kg body weight. According to another embodiment, the therapeutic amount of the therapeutic inhibitory peptide of the pharmaceutical composition is of an amount from about 80 mg/kg body weight to about 100 mg/kg body weight. According to another embodiment, the therapeutic amount of the therapeutic inhibitory peptide of the pharmaceutical composition is of an amount from about 90 mg/kg body weight to about 100 mg/kg body weight. According to another embodiment, the therapeutic amount of the therapeutic inhibitor peptide of the pharmaceutical composition is of an amount from about 0.000001 mg/kg body weight to about 90 mg/kg body weight. According to another embodiment, the therapeutic amount of the therapeutic inhibitor peptide of the pharmaceutical composition is of an amount from about 0.000001 mg/kg body weight to about 80 mg/kg body weight. According to another embodiment, the therapeutic amount of the therapeutic inhibitor peptide of the pharmaceutical composition is of an amount from about 0.000001 mg/kg body weight to about 70 mg/kg body weight. According to another embodiment, the therapeutic amount of the therapeutic inhibitor peptide of the pharmaceutical composition is of an amount from about 0.000001 mg/kg body weight to about 60 mg/kg body weight. According to another embodiment, the therapeutic amount of the therapeutic inhibitor peptide of the pharmaceutical composition is of an amount from about 0.000001 mg/kg body weight to about 50 mg/kg body weight. According to another embodiment, the therapeutic amount of the therapeutic inhibitor peptide of the pharmaceutical composition is of an amount from about 0.000001 mg/kg body weight to about 40 mg/kg body weight. According to another embodiment, the therapeutic amount of the therapeutic inhibitor peptide is of an amount from about 0.000001 mg/kg body weight to about 30 mg/kg body weight. According to another embodiment, the therapeutic amount of the therapeutic inhibitor peptide of the pharmaceutical composition is of an amount from about 0.000001 mg/kg body weight to about 20 mg/kg body weight. According to another embodiment, the therapeutic amount of the therapeutic inhibitor peptide of the pharmaceutical composition is of an amount from about 0.000001 mg/kg body weight to about 10 mg/kg body weight. According to another embodiment, the therapeutic amount of the therapeutic inhibitor peptide of the pharmaceutical composition is of an amount from about 0.000001 mg/kg body weight to about 1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.01 mg/kg body weight. According to another embodiment, the therapeutic amount of the therapeutic inhibitor peptide of the pharmaceutical composition is of an amount from about 0.000001 mg/kg body weight to about 0.001 mg/kg body weight. According to another embodiment, the therapeutic amount of the therapeutic inhibitor peptide of the pharmaceutical composition is of an amount from about 0.000001 mg/kg body weight to about 0.0001 mg/kg body weight. According to another embodiment, the therapeutic amount of the therapeutic inhibitor peptide of the pharmaceutical composition is of an amount from about 0.000001 mg/kg body weight to about 0.00001 mg/kg body weight.

According to some other embodiments, the therapeutic dose of the therapeutic inhibitor peptide of the pharmaceutical composition ranges from 1 µg/kg/day to 25 µg/kg/day. According to some other embodiments, the therapeutic dose of the therapeutic inhibitor peptide of the pharmaceutical composition ranges from 1 µg/kg/day to 2 µg/kg/day. According to some other embodiments, the therapeutic dose of the therapeutic inhibitor peptide of the pharmaceutical composition ranges from 2 µg/kg/day to 3 µg/kg/day. According to some other embodiments, the therapeutic dose of the therapeutic inhibitor peptide of the pharmaceutical composition ranges from 3 µg/kg/day to 4 µg/kg/day. According to some other embodiments, the therapeutic dose of the therapeutic inhibitor peptide of the pharmaceutical ranges from 4 µg/kg/day to 5 µg/kg/day. According to some other embodiments, the therapeutic dose of the therapeutic inhibitor peptide of the pharmaceutical composition ranges from 5 µg/kg/day to 6 µg/kg/day. According to some other embodiments, the therapeutic dose of the therapeutic inhibitor peptide of the pharmaceutical composition ranges from 6 µg/kg/day to 7 µg/kg/day. According to some other embodiments, the therapeutic dose of the therapeutic inhibitor peptide of the pharmaceutical composition ranges from 7 µg/kg/day to 8 µg/kg/day. According to some other embodiments, the therapeutic dose of the therapeutic inhibitor peptide of the pharmaceutical composition ranges from 8 µg/kg/day to 9 µg/kg/day. According to some other embodiments, the therapeutic dose of the therapeutic inhibitor peptide of the pharmaceutical composition ranges from 9 µg/kg/day to 10 µg/kg/day. According to some other embodiments, the therapeutic dose of the therapeutic inhibitor peptide of the pharmaceutical composition ranges from 1 µg/kg/day to 5 µg/kg/day. According to some other embodiments, the therapeutic dose of the therapeutic inhibitor peptide of the pharmaceutical composition ranges from 5 µg/kg/day to 10 µg/kg/day. According to some other embodiments, the therapeutic dose of the therapeutic inhibitor peptide of the pharmaceutical composition ranges from 10 µg/kg/day to 15 µg/kg/day. According to some other embodiments, the therapeutic dose of the therapeutic inhibitor peptide of the pharmaceutical composition ranges from 15 µg/kg/day to 20 µg/kg/day. According to some other embodiments, the therapeutic dose of the therapeutic inhibitor peptide of the pharmaceutical composition ranges from 25 µg/kg/day to 30 µg/kg/day. According to some other embodiments, the therapeutic dose of the therapeutic inhibitor peptide of the pharmaceutical composition ranges from 30 µg/kg/day to 35 µg/kg/day. According to some other embodiments, the therapeutic dose of the therapeutic inhibitor peptide of the pharmaceutical composition ranges from 35 µg/kg/day to 40 µg/kg/day. According to some other embodiments, the therapeutic dose of the therapeutic inhibitor peptide of the pharmaceutical composition ranges from 40 µg/kg/day to 45 µg/kg/day. According to some other embodiments, the therapeutic dose of the therapeutic inhibitor peptide of the pharmaceutical composition ranges from 45 µg/kg/day to 50 µg/kg/day. According to some other embodiments, the therapeutic dose of the therapeutic inhibitor peptide of the pharmaceutical composition ranges from 50 µg/kg/day to 55 µg/kg/day. According to some other embodiments, the therapeutic dose of the therapeutic inhibitor peptide of the pharmaceutical composition ranges from 55 µg/kg/day to 60 µg/kg/day. According to some other embodiments, the therapeutic dose of the therapeutic inhibitor peptide of the pharmaceutical composition ranges from 60 µg/kg/day to 65 µg/kg/day. According to some other embodiments, the therapeutic dose of the therapeutic inhibitor peptide of the pharmaceutical composition ranges from 65 µg/kg/day to 70 µg/kg/day. According to some other embodiments, the therapeutic dose of the therapeutic inhibitor peptide of the pharmaceutical composition ranges from 70 µg/kg/day to 75 µg/kg/day. According to some other embodiments, the therapeutic dose of the therapeutic inhibitor peptide of the pharmaceutical composition ranges from 80 µg/kg/day to 85 µg/kg/day. According to some other embodiments, the therapeutic dose of the therapeutic inhibitor peptide of the pharmaceutical composition ranges from 85 µg/kg/day to 90 µg/kg/day. According to some other embodiments, the therapeutic dose of the therapeutic inhibitor peptide of the pharmaceutical composition ranges from 90 µg/kg/day to 95 µg/kg/day. According to some other embodiments, the therapeutic dose of the therapeutic inhibitor peptide of the pharmaceutical composition ranges from 95 µg/kg/day to 100 µg/kg/day.

According to another embodiment, the therapeutic dose of the therapeutic inhibitor peptide of the pharmaceutical composition is 1 µg/kg/day.

According to another embodiment, the therapeutic dose of the therapeutic inhibitor peptide of the pharmaceutical composition is 2 µg/kg/day.

According to another embodiment, the therapeutic dose of the therapeutic inhibitor peptide of the pharmaceutical composition is 5 µg/kg/day.

According to another embodiment, the therapeutic dose of the therapeutic inhibitor peptide of the pharmaceutical composition is 10 µg/kg/day.

III. Systems for Preventing or Treating Diseases Characterized by Aberrant Fibroblast Proliferation and Collagen Deposition According to another aspect, the described invention provides a system for the treatment of a disease, condition, or process characterized by aberrant fibroblast proliferation and extracellular matrix deposition in a tissue of a subject, wherein the pharmaceutical composition comprises a therapeutic amount of a polypeptide of the amino acid sequence YARAAARQARAKALARQLGVAA (SEQ ID NO: 1) or a functional equivalent thereof, and a pharmaceutically acceptable carrier thereof, and wherein the therapeutic amount is effective to reduce the fibroblast proliferation and extracellular matrix deposition in the tissue of the subject.

According to one embodiment of the method, the disease or the condition is Acute Lung Injury (ALI) or acute respiratory distress syndrome (ARDS).

According to another embodiment, the disease or the condition is radiation-induced fibrosis.

According to another embodiment, the disease or the condition is transplant rejection.

According to another embodiment, the tissue is a lung tissue.

According to another embodiment, the disease or the condition is an interstitial lung disease.

According to another embodiment, the disease or the condition is pulmonary fibrosis.

According to another embodiment, the pulmonary fibrosis is idiopathic pulmonary fibrosis.

According to another embodiment, the pulmonary fibrosis results from administration of bleomycin.

According to another embodiment, the pulmonary fibrosis results from an allergic reaction, inhalation of environmental particulates, a bacterial infection, a viral infection, mechanical damage to a lung of the subject, lung transplantation rejection, an autoimmune disorder, a genetic disorder, or a combination thereof.

According to another embodiment, the tissue is a liver tissue.

According to another embodiment, the disease or condition is liver fibrosis.

According to another embodiment, the tissue is a kidney tissue.

According to another embodiment, the disease or condition is renal fibrosis.

According to another embodiment, the tissue is vascular tissue.

According to another embodiment, the disease or condition is vascular fibrosis.

According to another embodiment, the disease or condition is further characterized by an inflammation in the tissue.

According to another embodiment, the inflammation is an acute or a chronic inflammation.

According to another embodiment, the inflammation is mediated by at least one cytokine selected from the group consisting of Tumor Necrosis Factor-alpha (TNF-α), Interleukin-6 (IL-6), and Interleukin-1β (IL-1β).

According to another embodiment, the aberrant fibroblast proliferation and extracellular matrix deposition in the tissue is characterized by an aberrant activity of Mitogen-Activated Protein Kinase-Activated Protein Kinase 2 (MK2) in the tissue compared to the activity of Mitogen-Activated Protein Kinase-Activated Protein Kinase 2 (MK2) in the tissue of a normal healthy control subject.

According to another embodiment, the aberrant fibroblast proliferation and extracellular matrix deposition in the tissue is evidenced by an aberrant amount or distribution of activated (phosphorylated) Mitogen-Activated Protein Kinase-Activated Protein Kinase 2 (MK2) in the tissue compared to the amount or distribution of activated Mitogen-Activated Protein Kinase-Activated Protein Kinase 2 (MK2) in the tissue of a normal healthy control subject.

According to another embodiment, the pulmonary fibrosis is characterized by at least one pathology selected from the group consisting of an aberrant deposition of an extracellular matrix protein in a pulmonary interstitium, an aberrant promotion of fibroblast proliferation in the lung, an aberrant induction of differentiation of a population of fibroblasts into a population of myofibroblasts in the lung, and an aberrant promotion of attachment of myofibroblasts to an extracellular matrix compared to a normal healthy control subject.

According to another embodiment, the pharmaceutically acceptable carrier includes, but is not limited to, a controlled release carrier, a delayed release carrier, a sustained release carrier, and a long-term release carrier.

According to another embodiment, the inhalation device is a nebulizer.

According to another embodiment, the inhalation device is a metered-dose inhaler (MDI).

According to another embodiment, the inhalation device is a dry powder inhaler (DPI).

According to another embodiment, the inhalation device is a dry powder nebulizer.

According to another embodiment, the pharmaceutical composition is in a form of a dry powder.

According to another embodiment, the dry powder comprises microparticles with Mass Median Aerodynamic Diameter (MMAD) of 1 to 5 microns.

According to another embodiment, the dry powder comprises microparticles with Mass Median Aerodynamic Diameter (MMAD) of about 2 micron.

According to some embodiments, the pharmaceutical composition further comprises an additional therapeutic agent.

According to some such embodiments, the additional therapeutic agent is selected from the group consisting of purified bovine Type V collagens (e.g., IW-001; ImmuneWorks; United Therapeutics), IL-13 receptor antagonists (e.g., QAX576; Novartis), protein tyrosine kinase inhibitors (e.g., imatinib (Gleevec®); Craig Daniels/Novartis), endothelial receptor antagonists (e.g., ACT-064992 (macitentan); Actelion), dual endothelin receptor antagonists (e.g., bosentan (Tracleer®); Actelion), prostacyclin analogs (inhaled iloprost (e.g., Ventavis®); Actelion), anti-CTGF monoclonal antibodies (e.g., FG-3019), endothelin receptor antagonists (A-selective) (e.g., ambrisentan (Letairis®), Gilead), AB0024 (Arresto), lysyl oxidase-like 2 (LOXL2) monoclonal antibodies (e.g., GS-6624 (formerly AB0024); Gilead), c-Jun N-terminal kinase (JNK) inhibitors (e.g., CC-930; Celgene), Pirfenidone (e.g., Esbriet® (InterMune), Pirespa® (Shionogi)), IFN-γ1b (e.g., Actimmune®; InterMune), pan-neutralizing IgG4 human antibodies against all three TGF-β isoforms (e.g., GC1008; Genzyme), TGF-β activation inhibitors (e.g., Stromedix (STX-100)), recombinant human Pentraxin-2 protein (rhPTX-2) (e.g., PRM151; Promedior), bispecific IL4/IL13 antibodies (e.g., SAR156597; Sanofi), humanized monoclonal antibodies targeting integrin αvβ6 (BIBF 1120; Boehringer Ingelheim), N-acetylcysteine (Zambon SpA), Sildenafil (Viagra®), TNF antagonists (e.g., etanercept (Enbrel®); Pfizer), glucocorticoids (e.g., prednisone, budesonide, mometasone furoate, fluticasone propionate, and fluticasone furoate), bronchodilators (e.g., leukotriene modifers (e.g., Montelukast (SINGUAIR®)), anticholingertic bronchodilators (e.g., Ipratropium bromide and Tiotropium), short-acting β2-agonists (e.g., isoetharine mesylate (Bronkometer®), adrenalin, salbutanol/albuterol, and terbutaline), long-acting β2-agonists (e.g., salmeterol, formoterol, indecaterol (Onbrez®), sofosbuvir (Sovaldi®), an HCV boosted protease inhibitor (ABT-450, AbbVie), a nonnucleoside NS5B inhibitor (dasabuvir, ABT-333, AbbVie), an NS5a inhibitor (ombitasvir, ABT-267, AbbVie), ABT-450/r (ABT-450 with ritonavir), ABT-450 co-formulated with ABT-267, ABT-450 formulated with sofosbuvir, ribavirin, and combinations thereof.

According to some other embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to some such embodiments, the additional therapeutic agent comprises a bronchodilator including, but not limited to, a leukotriene modifier, an anticholinergic bronchodilator, a β2-agonist, or a combination thereof.

According to another embodiment, the additional therapeutic agent comprises a corticosteroid including, but not limited to, prednisone, budesonide, mometasone, beclemethasone, or a combination thereof.

According to another embodiment, the additional therapeutic agent is an anti-inflammatory agent.

According to another embodiment, the anti-inflammatory agent is a nonsteroidal anti-inflammatory agent. Mixtures of non-steroidal anti-inflammatory agents also may be employed, as well as the dermatologically acceptable salts and esters of these agents. For example, etofenamate, a flufenamic acid derivative, is particularly useful for topical application.

According to another embodiment, wherein the nonsteroidal anti-inflammatory agent comprises Transforming Growth Factor-β3 (TGF-β3), an anti-Tumor Necrosis Factor-alpha (TNF-α) agent, or a combination thereof.

According to another embodiment, the anti-inflammatory agent is a steroidal anti-inflammatory agent. According to another embodiment, the steroidal anti-inflammatory agent comprises at least one corticosteroid selected from the group consisting of prednisone, budesonide, mometasone, beclemethasone, and a combination thereof.

According to another embodiment, the additional therapeutic agent comprises a methylxanthine.

According to another embodiment, the additional therapeutic agent comprises a neutrophil elastase inhibitor.

According to another embodiment, the additional therapeutic agent is at least one neutrophil elastase inhibitor, including, but not limited to, ICI 200355, ONO-5046, MR-889, L-694,458, CE-1037, GW-311616, TEI-8362, ONO-6818, AE-3763, FK-706, ICI-200,880, ZD-0892, ZD-8321, and a combination thereof.

According to another embodiment, the additional therapeutic agent comprises at least one phosphodiesterase inhibitor, including, but not limited to, phosphodiesterase 4 inhibitor. Examples of phosphodiesterase 4 inhibitors include, but are not limited to, roflumilast, cilomilast or a combination thereof.

According to another embodiment, the additional therapeutic agent is an analgesic agent. According to some such embodiments, the analgesic agent is a non-opioid analgesic. According to some other embodiments, the analgesic is an opioid analgesic.

According to another embodiment, the additional therapeutic agent is an anti-infective agent. According to another embodiment, the anti-infective agent is an antibiotic agent.

According to another embodiment, the additional therapeutic agent is an anti-viral agent. Examplary such antiviral agents include, without limitation, an HCV boosted protease inhibitor (ABT-450, AbbVie), a nonnucleoside NS5B inhibitor (dasabuvir, ABT-333, AbbVie), an NS5a inhibitor (ombitasvir, ABT-267, AbbVie), ABT-450/r (ABT-450 with ritonavir), ABT-450 co-formulated with ABT-267, ABT-450 formulated with sofosbuvir, ribavirin, or sofosbuvir. According to another embodiment, the pharmaceutical composition inhibits inflammation occurring in a lung of the subject. According to another embodiment, the inflammation is an acute inflammation. According to another embodiment, the inflammation is a chronic inflammation. According to another embodiment, the inflammation is mediated by an elevated level of Tumor Necrosis Factor-alpha (TNF-α). According to another embodiment, the inflammation is mediated by an elevated level of Interleukin-6 (IL-6). According to another embodiment, the inflammation is mediated by an elevated level of Interleukin-1β (IL-1β).

According to another embodiment, the pharmaceutical composition modulates an amount of Tumor Necrosis Factor-alpha (TNF-α) in the lung, compared to a control. According to another embodiment, the pharmaceutical composition modulates an amount of Interleukin-6 (IL-6) in the lung, compared to a control. According to another embodiment, the pharmaceutical composition modulates an amount of Interleukin-1β (IL-1β) in the lung, compared to a control.

According to another embodiment, the pharmaceutical composition inhibits an activity of HSPB1. According to another embodiment, the activity of HSPB1 inhibited by the pharmaceutical composition is an aberrant induction of fibroblast proliferation. According to another embodiment, the activity of HSPB1 inhibited by the pharmaceutical composition is an aberrant induction of differentiation of a population of fibroblasts into a population of myofibroblasts. According to another embodiment, the activity of HSPB1 inhibited by the pharmaceutical composition is a deposition of an extracellular matrix protein into a pulmonary interstitium. According to another embodiment, the extracellular matrix protein is collagen. According to another embodiment, the activity of HSPB1 inhibited by the pharmaceutical composition is a promotion of fibrotic loci formation. According to another embodiment, the activity of HSPB1 inhibited by the pharmaceutical composition is an increase of myofibroblast contractile activity. According to another embodiment, the activity of HSPB1 inhibited by the pharmaceutical composition is a promotion of myofibroblast attachment to extracellular matrix.

According to another embodiment, the aberrant fibroblast proliferation and extracellular matrix deposition in the tissue is evidenced by an aberrant amount or distribution of activated (phosphorylated) Mitogen-Activated Protein Kinase-Activated Protein Kinase 2 (MK2) in the tissue compared to the amount or distribution of activated Mitogen-Activated Protein Kinase-Activated Protein Kinase 2 (MK2) in the tissue of a normal healthy control subject.

According to another embodiment, the pharmaceutical composition inhibits a kinase activity of a kinase selected from the group listed in Table 1 herein.

According to another embodiment, the pharmaceutical composition inhibits at least 50% of the kinase activity of the kinase. According to another embodiment, the pharmaceutical composition inhibits at least 65% of the kinase activity of the kinase. According to another embodiment, the pharmaceutical composition inhibits at least 75% of the kinase activity of that kinase. According to another embodiment, the pharmaceutical composition inhibits at least 80% of the kinase activity of that kinase. According to another embodiment, the pharmaceutical composition inhibits at least 85% of the kinase activity of that kinase. According to another embodiment, the pharmaceutical composition inhibits at least 90% of the kinase activity of that kinase. According to another embodiment, the pharmaceutical composition inhibits at least 95% of the kinase activity of that kinase.

According to some embodiments, inhibitory profiles of MMI inhibitors in vivo depend on dosages, routes of administration, and cell types responding to the inhibitors.

According to another embodiment, the pharmaceutical composition inhibits at least 50% of the kinase activity of the kinase. According to another embodiment, the pharmaceutical composition inhibits at least 65% of the kinase activity of the kinase. According to another embodiment, the pharmaceutical composition inhibits at least 75% of the kinase activity of that kinase. According to another embodiment, the pharmaceutical composition inhibits at least 80% of the kinase activity of that kinase. According to another embodiment, the pharmaceutical composition inhibits at least 85% of the kinase activity of that kinase. According to another embodiment, the pharmaceutical composition inhibits at least 90% of the kinase activity of that kinase. According to another embodiment, the pharmaceutical composition inhibits at least 95% of the kinase activity of that kinase.

According to another embodiment, the pharmaceutical composition inhibits a kinase activity of Mitogen-Activated Protein Kinase-Activated Protein Kinase 2 (MK2 kinase). According to another embodiment, the pharmaceutical composition inhibits at least 50% of the kinase activity of MK2 kinase. According to another embodiment, the pharmaceutical composition inhibits at least 65% of the kinase activity of MK2 kinase. According to another embodiment, the pharmaceutical composition inhibits at least 75% of the kinase activity of MK2 kinase. According to another embodiment, the pharmaceutical composition inhibits at least 80% of the kinase activity of MK2 kinase. According to another embodiment, the pharmaceutical composition inhibits at least 85% of the kinase activity of MK2 kinase. According to another embodiment, the pharmaceutical composition inhibits at least 90% of the kinase activity of MK2 kinase. According to another embodiment, the pharmaceutical composition inhibits at least 95% of the kinase activity of MK2 kinase.

According to another embodiment, the pharmaceutical composition inhibits a kinase activity of Mitogen-Activated Protein Kinase-Activated Protein Kinase 3 (MK3 kinase). According to another embodiment, the pharmaceutical composition further inhibits at least 50% of the kinase activity of MK3 kinase. According to another embodiment, the pharmaceutical composition further inhibits at least 65% of the kinase activity of MK3 kinase. According to another embodiment, the pharmaceutical composition further inhibits at least 70% of the kinase activity of MK3 kinase. According to another embodiment, the pharmaceutical composition further inhibits at least 75% of the kinase activity of MK3 kinase. According to another embodiment, the pharmaceutical composition further inhibits at least 80% of the kinase activity of MK3 kinase. According to another embodiment, the pharmaceutical composition further inhibits at least 85% of the kinase activity of MK3 kinase. According to another embodiment, the pharmaceutical composition further inhibits at least 90% of the kinase activity of MK3 kinase. According to another embodiment, the pharmaceutical composition further inhibits at least 95% of the kinase activity of MK3 kinase.

According to another embodiment, the pharmaceutical composition inhibits a kinase activity of calcium/calmodulin-dependent protein kinase I (CaMKI). According to another embodiment, the pharmaceutical composition further inhibits at least 50% of the kinase activity of $Ca^{2+}$/calmodulin-dependent protein kinase I (CaMKI). According to another embodiment, the pharmaceutical composition further inhibits at least 65% of the kinase activity of $Ca^{2+}$/calmodulin-dependent protein kinase I (CaMKI). According to another embodiment, the pharmaceutical composition further inhibits at least 70% of the kinase activity of $Ca^{2+}$/calmodulin-dependent protein kinase I (CaMKI). According to another embodiment, the pharmaceutical composition further inhibits at least 75% of the kinase activity of $Ca^{2+}$/calmodulin-dependent protein kinase I (CaMKI). According to another embodiment, the pharmaceutical composition further inhibits at least 80% of the kinase activity of $Ca^{2+}$/calmodulin-dependent protein kinase I (CaMKI). According to another embodiment, the pharmaceutical composition further inhibits at least 85% of the kinase activity of $Ca^{2+}$/calmodulin-dependent protein kinase I (CaMKI). According to another embodiment, the pharmaceutical composition further inhibits at least 90% of the kinase activity of $Ca^{2+}$/calmodulin-dependent protein kinase I (CaMKI). According to another embodiment, the pharmaceutical composition further inhibits at least 95% of the kinase activity of $Ca^{2+}$/calmodulin-dependent protein kinase I (CaMKI).

According to another embodiment, the pharmaceutical composition inhibits a kinase activity of BDNF/NT-3 growth factors receptor (TrkB). According to another embodiment, the pharmaceutical further inhibits at least 50% of the kinase activity of BDNF/NT-3 growth factors receptor (TrkB). According to another embodiment, the pharmaceutical further inhibits at least 65% of the kinase activity of BDNF/NT-3 growth factors receptor (TrkB). According to another embodiment, the pharmaceutical further inhibits at least 70% of the kinase activity of BDNF/NT-3 growth factors receptor (TrkB). According to another embodiment, the pharmaceutical further inhibits at least 75% of the kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2) and a kinase activity of Mitogen-Activated Protein Kinase-Activated Protein Kinase 3 (MK3).

According to another embodiment, the pharmaceutical composition inhibits a kinase activity of Mitogen-Activated Protein Kinase-Activated Protein Kinase 2 (MK2) and a kinase activity of calcium/calmodulin-dependent protein kinase I (CaMKI).

According to another embodiment, the pharmaceutical composition inhibits a kinase activity of Mitogen-Activated Protein Kinase-Activated Protein Kinase 2 (MK2) and a kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2), a kinase activity of Mitogen-Activated Protein Kinase-Activated Protein Kinase 3 (MK3), a kinase activity of calcium/calmodulin-dependent protein kinase I (CaMKI), and a kinase activity of BDNF/NT-3 growth factors receptor (TrkB).

According to another embodiment, the pharmaceutical composition inhibits a kinase activity of Mitogen-Activated Protein Kinase-Activated Protein Kinase 2 (MK2), a kinase activity of calcium/calmodulin-dependent protein kinase I (CaMKI), and a kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2).

According to another embodiment, the pharmaceutical composition inhibits at least 65% of the kinase activity of Mitogen-Activated Protein Kinase-Activated Protein Kinase 3 (MK3).

According to another embodiment, the pharmaceutical composition inhibits at least 65% of the kinase activity of calcium/calmodulin-dependent protein kinase I (CaMKI).

According to another embodiment, the pharmaceutical composition inhibits at least 65% of the kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2) and at least 65% of the kinase activity of Mitogen-Activated Protein Kinase-Activated Protein Kinase 3 (MK3).

According to another embodiment, the pharmaceutical composition inhibits at least 65% of the kinase activity of Mitogen-Activated Protein Kinase-Activated Protein Kinase 2 (MK2) and at least 65% of the kinase activity of calcium/calmodulin-dependent protein kinase I (CaMKI).

According to another embodiment, the pharmaceutical composition inhibits at least 65% of the kinase activity of Mitogen-Activated Protein Kinase-Activated Protein Kinase 2 (MK2) and at least 65% of the kinase activity of BDNF/NT-3 growth factors receptor (TrkB).

According to another embodiment, the pharmaceutical composition inhibits at least 65% of the kinase activity of Mitogen-Activated Protein Kinase-Activated Protein Kinase 2 (MK2), at least 65% of the kinase activity of Mitogen-Activated Protein Kinase-Activated Protein Kinase 3 (MK3), at least 65% of the kinase activity of calcium/calmodulin-dependent protein kinase I (CaMKI), and at least 65% of the kinase activity of BDNF/NT-3 growth factors receptor (TrkB).

According to another embodiment, the pharmaceutical composition inhibits the kinase activity of at least one kinase selected from the group of MK2, MK3, CaMKI, TrkB, without substantially inhibiting the activity of one or more other selected kinases from the remaining group listed in Table 1 herein.

According to another embodiment, the pharmaceutical composition inhibits a kinase activity of a kinase selected from the group listed in Table 1 herein.

According to another embodiment, this inhibition may, for example, be effective to reduce fibroblast proliferation, extracellular matrix deposition, or a combination thereof in the tissue of the subject.

According to another embodiment, this inhibition may, for example, be effective to reduce at least one pathology selected from the group consisting of an aberrant deposition of an extracellular matrix protein in a pulmonary interstitium, an aberrant promotion of fibroblast proliferation in the lung, an aberrant induction of myofibroblast differentiation, and an aberrant promotion of attachment of myofibroblasts to an extracellular matrix, compared to a normal healthy control subject.

According to some embodiments, inhibitory profiles of MMI inhibitors in vivo depend on dosages, routes of administration, and cell types responding to the inhibitors.

According to such embodiment, the pharmaceutical composition inhibits less than 50% of the kinase activity of the other selected kinase(s). According to such embodiment, the pharmaceutical composition inhibits less than 65% of the kinase activity of the other selected kinase(s). According to such embodiment, the pharmaceutical composition inhibits less than 50% of the kinase activity of the other selected kinase(s). According to another embodiment, the pharmaceutical composition inhibits less than 40% of the kinase activity of the other selected kinase(s). According to another embodiment, the pharmaceutical composition inhibits less than 20% of the kinase activity of the other selected kinase(s). According to another embodiment, the pharmaceutical composition inhibits less than 15% of the kinase activity of the other selected kinase(s). According to another embodiment, the pharmaceutical composition inhibits less than 10% of the kinase activity of the other selected kinase(s). According to another embodiment, the pharmaceutical composition inhibits less than 5% of the kinase activity of the other selected kinase(s). According to another embodiment, the pharmaceutical composition increases the kinase activity of the other selected kinases.

According to the embodiments of the immediately preceding paragraph, the one or more other selected kinase that is not substantially inhibited is selected from the group of $Ca^{2+}$/calmodulin-dependent protein kinase II (CaMKII, including its subunit CaMKIIδ), Proto-oncogene serine/threonine-protein kinase (PIM-1), cellular-Sarcoma (c-SRC), Spleen Tyrosine Kinase (SYK), C-src Tyrosine Kinase (CSK), and Insulin-like Growth Factor 1 Receptor (IGF-1R).

According to some embodiments, the functional equivalent of the polypeptide YARAAARQARAKALARQLGVAA (SEQ ID NO: 1) has a substantial sequence identity to amino acid sequence YARAAARQARAKALARQLGVAA (SEQ ID NO: 1).

According to another embodiments, the functional equivalent of the polypeptide YARAAARQARAKALARQLGVAA (SEQ ID NO: 1) has at least 70 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 80 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 90 percent sequence identity to amino acid sequence YARAAARQARAKALARQLGVAA (SEQ ID NO: 1). According to another embodiment, the functional equivalent of the polypeptide YARAAARQARAKALARQLGVAA (SEQ ID NO: 1) has at least 95 percent sequence identity to amino acid sequence YARAAARQARAKALARQLGVAA (SEQ ID NO: 1).

According to another embodiment, the functional equivalent of the polypeptide YARAAARQARAKALARQLGVAA (SEQ ID NO: 1) is of amino acid sequence FAKLAARLYRKALARQLGVAA (SEQ ID NO: 3).

According to another embodiment, the functional equivalent of the polypeptide YARAAARQARAKALARQLGVAA (SEQ ID NO: 1) is of amino acid sequence KAFAKLAARLYRKALARQLGVAA (SEQ ID NO: 4).

According to another embodiment, the functional equivalent of the polypeptide YARAAARQARAKALARQLGVAA (SEQ ID NO: 1) is of amino acid sequence YARAAARQARAKALARQLAVA (SEQ ID NO: 5).

According to another embodiment, the functional equivalent of the polypeptide YARAAARQARAKALARQLGVAA (SEQ ID NO: 1) is of amino acid sequence YARAAARQARAKALARQLGVA (SEQ ID NO: 6).

According to another embodiment, the functional equivalent of the polypeptide YARAAARQARAKALARQLGVAA (SEQ ID NO: 1) is of amino acid sequence HRRIKAWLKKIKALARQLGVAA (SEQ ID NO: 7).

According to another embodiment, the functional equivalent of the polypeptide YARAAARQARAKALARQLGVAA (SEQ ID NO: 1) is of amino acid sequence YARAAARQARAKALNRQLAVAA (SEQ ID NO: 26).

According to another embodiment, the functional equivalent of the polypeptide YARAAARQARAKALARQLGVAA (SEQ ID NO: 1) is of amino acid sequence YARAAARQARAKALNRQLAVA (SEQ ID NO: 27).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide is of amino acid sequence YARAAARQARA (SEQ ID NO: 11), and the second polypeptide comprises a therapeutic domain whose sequence has a substantial identity to amino acid sequence KALARQLGVAA (SEQ ID NO: 2).

According to another embodiment, the second polypeptide has at least 70 percent sequence identity to amino acid sequence KALARQLGVAA (SEQ ID NO: 2). According to some other embodiments, the second polypeptide has at least 80 percent sequence identity to amino acid sequence KALARQLGVAA (SEQ ID NO: 2). According to some other embodiments, the second polypeptide has at least 90 percent sequence identity to amino acid sequence KALARQLGVAA (SEQ ID NO: 2). According to some other embodiments, the second polypeptide has at least 95 percent sequence identity to amino acid sequence KALARQLGVAA (SEQ ID NO: 2).

According to another embodiment, the second polypeptide is a polypeptide of amino acid sequence KALARQLAVA (SEQ ID NO: 8).

According to another embodiment, the second polypeptide is a polypeptide of amino acid sequence KALARQLGVA (SEQ ID NO: 9).

According to another embodiment, the second polypeptide is a polypeptide of amino acid sequence KALARQLGVAA (SEQ ID NO: 10).

According to another embodiment, the second polypeptide is a polypeptide of amino acid sequence KALNRQLAVAA SEQ ID NO: 28).

According to another embodiment, the second polypeptide is a polypeptide of amino acid sequence KALNRQLAVA SEQ ID NO: 29).

According to some other embodiments, the functional equivalent of the polypeptide YARAAARQARAKALARQLGVAA (SEQ ID NO: 1) is a fusion protein comprising a first polypeptide operatively linked to a second polypeptide, wherein the first polypeptide comprises a cell penetrating peptide functionally equivalent to YARAAARQARA (SEQ ID NO: 11), and the second polypeptide is of amino acid sequence KALARQLGVAA (SEQ ID NO: 2).

According to a further embodiment, the first polypeptide is a polypeptide of amino acid sequence WLRRIKAWLRRIKA (SEQ ID NO: 12).

According to another embodiment, the first polypeptide is a polypeptide of amino acid sequence WLRRIKA (SEQ ID NO: 13).

According to another embodiment, the first polypeptide is a polypeptide of amino acid sequence YGRKKRRQRRR (SEQ ID NO: 14).

According to another embodiment, the first polypeptide is a polypeptide of amino acid sequence WLRRIKAWLRRI (SEQ ID NO: 15).

According to another embodiment, the first polypeptide is a polypeptide of amino acid sequence FAKLAARLYR (SEQ ID NO: 16).

According to another embodiment, the first polypeptide is a polypeptide of amino acid sequence KAFAKLAARLYR (SEQ ID NO: 17).

According to another embodiment, the first polypeptide is a polypeptide of amino acid sequence HRRIKAWLKKI (SEQ ID NO: 18).

According to another aspect, the described invention also provides an isolated nucleic acid that encodes a protein sequence with at least 70% amino acid sequence identity to amino acid sequence YARAAARQARAKALARQLGVAA (SEQ ID NO: 1). According to some such embodiments, the isolated nucleic acid encodes a protein sequence with at least 80% amino acid sequence identity to amino acid sequence YARAAARQARAKALARQLGVAA (SEQ ID NO: 1). According to some such embodiments, the isolated nucleic acid encodes a protein sequence with at least 90% amino acid sequence identity to amino acid sequence YARAAARQARAKALARQLGVAA (SEQ ID NO: 1). According to some such embodiments, the isolated nucleic acid encodes a protein sequence with at least 95% amino acid sequence identity to amino acid sequence YARAAARQARAKALARQLGVAA (SEQ ID NO: 1).

According to some other embodiments, the therapeutic amount of the therapeutic inhibitor peptide of the pharmaceutical composition is of an amount from about 0.000001 mg/kg body weight to about 100 mg/kg body weight. According to another embodiment, the therapeutic amount of the therapeutic inhibitory peptide of the pharmaceutical composition is of an amount from about 0.00001 mg/kg body weight to about 100 mg/kg body weight. According to another embodiment, the therapeutic amount of the therapeutic inhibitory peptide of the pharmaceutical composition is of an amount from about 0.0001 mg/kg body weight to about 100 mg/kg body weight. According to another embodiment, the therapeutic amount of the therapeutic inhibitory peptide of the pharmaceutical composition is of an amount from about 0.001 mg/kg body weight to about 10 mg/kg body weight. According to another embodiment, the therapeutic amount of the therapeutic inhibitory peptide of the pharmaceutical composition is of an amount from about 0.01 mg/kg body weight to about 10 mg/kg body weight. According to another embodiment, the therapeutic amount of the therapeutic inhibitory peptide of the pharmaceutical composition is of an amount from about 0.1 mg/kg (100 µg/kg) body weight to about 10 mg/kg body weight. According to another embodiment, the therapeutic amount of the therapeutic inhibitory peptide of the pharmaceutical composition is of an amount from about 1 mg/kg body weight to about 10 mg/kg body weight. According to another embodiment, the therapeutic amount of the therapeutic inhibitory peptide of the pharmaceutical composition is of an amount from about 10 mg/kg body weight to about 100 mg/kg body weight. According to another embodiment, the therapeutic amount of the therapeutic inhibitory peptide of the pharmaceutical composition is of an amount from about 2 mg/kg body weight to about 10 mg/kg body weight. According to another embodiment, the therapeutic amount of the therapeutic inhibitory peptide of the pharmaceutical composition is of an amount from about 3 mg/kg body weight to about 10 mg/kg body weight. According to another embodiment, the therapeutic amount of the therapeutic inhibitory peptide of the pharmaceutical composition is of an amount from about 4 mg/kg body weight to about 10 mg/kg body weight. According to another embodiment, the therapeutic amount of the therapeutic inhibitory peptide of the pharmaceutical composition is of an amount from about 5 mg/kg body weight to about 10 mg/kg body weight. According to another embodiment, the therapeutic amount of the therapeutic inhibitory peptide of the pharmaceutical composition is of an amount from about 60 mg/kg body weight to about 100 mg/kg body weight. According to another embodiment, the therapeutic amount of the therapeutic inhibitory peptide of the pharmaceutical composition is of an amount from about 70 mg/kg body weight to about 100 mg/kg body weight. According to another embodiment, the therapeutic amount of the therapeutic inhibitory peptide of the pharmaceutical composition is of an amount from about 80 mg/kg body weight to about 100 mg/kg body weight. According to another embodiment, the therapeutic amount of the therapeutic inhibitory peptide of the pharmaceutical composition is of an amount from about 90 mg/kg body weight to about 100 mg/kg body weight. According to another embodiment, the therapeutic amount of the therapeutic inhibitor peptide of the pharmaceutical composition is of an amount from about 0.000001 mg/kg body weight to about 90 mg/kg body weight. According to another embodiment, the therapeutic amount of the therapeutic inhibitor peptide of the pharmaceutical composition is of an amount from about 0.000001 mg/kg body weight to about 80 mg/kg body weight. According to another embodiment, the therapeutic amount of the therapeutic inhibitor peptide of the pharmaceutical composition is of an amount from about 0.000001 mg/kg body weight to about 70 mg/kg body weight. According to another embodiment, the therapeutic amount of the therapeutic inhibitor peptide of the pharmaceutical composition is of an amount from about 0.000001 mg/kg body weight to about 60 mg/kg body weight. According to another embodiment, the therapeutic amount of the therapeutic inhibitor peptide of the pharmaceutical composition is of an amount from about 0.000001 mg/kg body weight to about 50 mg/kg body weight. According to another embodiment, the therapeutic amount of the therapeutic inhibitor peptide of the pharmaceutical composition is of an amount from about 0.000001 mg/kg body weight to about 40 mg/kg body weight. According to another embodiment, the therapeutic amount of the therapeutic inhibitor peptide is of an amount from about 0.000001 mg/kg body weight to about 30 mg/kg body weight. According to another embodiment, the therapeutic amount of the therapeutic inhibitor peptide of the pharmaceutical composition is of an amount from about 0.000001 mg/kg body weight to about 20 mg/kg body weight. According to another embodiment, the therapeutic amount of the therapeutic inhibitor peptide of the pharmaceutical composition is of an amount from about 0.000001 mg/kg body weight to about 10 mg/kg body weight. According to another embodiment, the therapeutic amount of the therapeutic inhibitor peptide of the pharmaceutical composition is of an amount from about 0.000001 mg/kg body weight to about 1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.01 mg/kg body weight. According to another embodiment, the therapeutic amount of the therapeutic inhibitor peptide of the pharmaceutical composition is of an amount from about 0.000001 mg/kg body weight to about 0.001 mg/kg body weight. According to another embodiment, the therapeutic amount of the therapeutic inhibitor peptide of the pharmaceutical composition is of an amount from about 0.000001 mg/kg body weight to about 0.0001 mg/kg body weight. According to another embodiment, the therapeutic amount of the therapeutic inhibitor peptide of the pharmaceutical composition is of an amount from about 0.000001 mg/kg body weight to about 0.00001 mg/kg body weight.

According to some other embodiments, the therapeutic dose of the therapeutic inhibitor peptide of the pharmaceutical composition ranges from 1 µg/kg/day to 25 µg/kg/day. According to some other embodiments, the therapeutic dose of the therapeutic inhibitor peptide of the pharmaceutical composition ranges from 1 µg/kg/day to 2 µg/kg/day. According to some other embodiments, the therapeutic dose of the therapeutic inhibitor peptide of the pharmaceutical composition ranges from 2 µg/kg/day to 3 µg/kg/day. According to some other embodiments, the therapeutic dose of the therapeutic inhibitor peptide of the pharmaceutical composition ranges from 3 µg/kg/day to 4 µg/kg/day. According to some other embodiments, the therapeutic dose of the therapeutic inhibitor peptide of the pharmaceutical ranges from 4 µg/kg/day to 5 µg/kg/day. According to some other embodiments, the therapeutic dose of the therapeutic inhibitor peptide of the pharmaceutical composition ranges from 5 µg/kg/day to 6 µg/kg/day. According to some other embodiments, the therapeutic dose of the therapeutic inhibitor peptide of the pharmaceutical composition ranges from 6 µg/kg/day to 7 µg/kg/day. According to some other embodiments, the therapeutic dose of the therapeutic inhibitor peptide of the pharmaceutical composition ranges from 7 µg/kg/day to 8 µg/kg/day. According to some other embodiments, the therapeutic dose of the therapeutic inhibitor peptide of the pharmaceutical composition ranges from 8 µg/kg/day to 9 µg/kg/day. According to some other embodiments, the therapeutic dose of the therapeutic inhibitor peptide of the pharmaceutical composition ranges from 9 µg/kg/day to 10 µg/kg/day. According to some other embodiments, the therapeutic dose of the therapeutic inhibitor peptide of the pharmaceutical composition ranges from 1 µg/kg/day to 5 µg/kg/day. According to some other embodiments, the therapeutic dose of the therapeutic inhibitor peptide of the pharmaceutical composition ranges from 5 µg/kg/day to 10 µg/kg/day. According to some other embodiments, the therapeutic dose of the therapeutic inhibitor peptide of the pharmaceutical composition ranges from 10 µg/kg/day to 15 µg/kg/day. According to some other embodiments, the therapeutic dose of the therapeutic inhibitor peptide of the pharmaceutical composition ranges from 15 µg/kg/day to 20 µg/kg/day. According to some other embodiments, the therapeutic dose of the therapeutic inhibitor peptide of the pharmaceutical composition ranges from 25 µg/kg/day to 30 µg/kg/day. According to some other embodiments, the therapeutic dose of the therapeutic inhibitor peptide of the pharmaceutical composition ranges from 30 µg/kg/day to 35 µg/kg/day. According to some other embodiments, the therapeutic dose of the therapeutic inhibitor peptide of the pharmaceutical composition ranges from 35 µg/kg/day to 40 µg/kg/day. According to some other embodiments, the therapeutic dose of the therapeutic inhibitor peptide of the pharmaceutical composition ranges from 40 µg/kg/day to 45 µg/kg/day. According to some other embodiments, the therapeutic dose of the therapeutic inhibitor peptide of the pharmaceutical composition ranges from 45 µg/kg/day to 50 µg/kg/day. According to some other embodiments, the therapeutic dose of the therapeutic inhibitor peptide of the pharmaceutical composition ranges from 50 µg/kg/day to 55 µg/kg/day. According to some other embodiments, the therapeutic dose of the therapeutic inhibitor peptide of the pharmaceutical composition ranges from 55 µg/kg/day to 60 µg/kg/day. According to some other embodiments, the therapeutic dose of the therapeutic inhibitor peptide of the pharmaceutical composition ranges from 60 µg/kg/day to 65 µg/kg/day. According to some other embodiments, the therapeutic dose of the therapeutic inhibitor peptide of the pharmaceutical composition ranges from 65 µg/kg/day to 70 µg/kg/day. According to some other embodiments, the therapeutic dose of the therapeutic inhibitor peptide of the pharmaceutical composition ranges from 70 µg/kg/day to 75 µg/kg/day. According to some other embodiments, the therapeutic dose of the therapeutic inhibitor peptide of the pharmaceutical composition ranges from 80 µg/kg/day to 85 µg/kg/day. According to some other embodiments, the therapeutic dose of the therapeutic inhibitor peptide of the pharmaceutical composition ranges from 85 µg/kg/day to 90 µg/kg/day. According to some other embodiments, the therapeutic dose of the therapeutic inhibitor peptide of the pharmaceutical composition ranges from 90 µg/kg/day to 95 µg/kg/day. According to some other embodiments, the therapeutic dose of the therapeutic inhibitor peptide of the pharmaceutical composition ranges from 95 µg/kg/day to 100 µg/kg/day.

According to another embodiment, the therapeutic dose of the therapeutic inhibitor peptide of the pharmaceutical composition is 1 µg/kg/day.

According to another embodiment, the therapeutic dose of the therapeutic inhibitor peptide of the pharmaceutical composition is 2 µg/kg/day.

According to another embodiment, the therapeutic dose of the therapeutic inhibitor peptide of the pharmaceutical composition is 5 µg/kg/day.

According to another embodiment, the therapeutic dose of the therapeutic inhibitor peptide of the pharmaceutical composition is 10 µg/kg/day.

Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.), all of which are incorporated herein by reference.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with the publications are cited.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges also is encompassed within the invention, subject to any specifically excluded limit in the stated range. Where the stated range includes one or both of the limits, ranges excluding either both of those included limits also are included in the invention.

It must also be noted that as used herein and in the appended claims, the singular forms "a," "and" and "the" include plural referents unless the context clearly dictates otherwise. All technical and scientific terms used herein have the same meaning.

The publications discussed herein are incorporated herein by reference in their entirety and are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

It should be understood by those skilled in the art that various changes may be made and equivalents may be substituted without departing from the true spirit and scope of the Invention. In addition, many modifications may be made to adapt a particular situation, material, composition of matter, process, process step or steps, to the objective, spirit and scope of the described invention. All such modifications are intended to be within the scope of the claims appended hereto.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

I. Materials and Methods

MMI-0100 Drug Development

For good manufacturing practice (GMP) production of MMI-0100 (YARAAARQARAKALARQLGVAA; SEQ ID NO: 1), approximately 1 kg of Fmoc-Ala-Wang Resin is transferred into a 50 L glass solid phase synthesis reaction vessel equipped with a mechanical stirrer. The resin is allowed to swell in dimethylformide (DMF) for no less than (NLT) 2 hours before draining the DMF. The resin beads then are washed with consecutive rinses of DMF. The N-terminal protecting group (i.e. Fmoc) is removed (deblocking step) by treatment with 20% piperidine in DMF and the resin is washed with DMF. The next amino acid in the sequence is coupled in the presence of 1-hydroxybenzotriazole (HOBt) and diisopropylcarbodiimide (DIC). Generally, 2.5-3.5 molar equivalents of Fmoc-amino acid (Fmoc-AA) to the synthesis scale are used for coupling. The Fmoc-AA is dissolved in DMF and activated by the addition of HOBt and DIC. The completion of each coupling is monitored by the Ninhydrin test. If a coupling is incomplete, a second coupling with the same amino acid is performed by using the symmetrical anhydride method. Generally, 3.0-6.0 molar equivalents of Fmoc-AA to the synthesis scale are used for coupling. The Fmoc-AA is dissolved in dichloromethane (DCM) and a minimal volume of DMF and activated through the addition of DIC in a molar ratio of Fmoc-AA/DIC=1.0/0.5. When the full peptide sequence is completed, the peptide resin is rinsed thoroughly with successive washes of DMF and MeOH. The resin then is dried under vacuum for NLT 3 hours. Typical recovery of the total dried peptide resin is approximately 2800 grams, representing a peptide resin yield of ~65%.

Approximately 370-500 grams of peptide resin then are transferred into a suitably sized glass bottle equipped with a magnetic stir bar. The flask containing the peptide resin is cooled in an ice/water bath or in a refrigerator for no later than 30 minutes. The trifluoroacetic acid (TFA) cocktail (a mixture of TFA, TIS, and water in the ratio of 95 mL:2.5 mL:2.5 mL) is pre-chilled in an ice/water bath for no later than 30 minutes. Approximately 8-12 mL of TFA cleavage cocktail per gram of resin is added to this vessel. As soon as the peptide resin and TFA cocktail are combined, the ice/water bath is removed and the reaction mixture is stirred at room temperature for 2-3 hours. The reaction mixture then is filtered through a coarse glass filter and the resin is washed two times with 0.5-1.0 mL of TFA per gram of resin per wash. The combined filtrate is collected and the resin is discarded. The filtrate is then added to ether that is pre-chilled in a refrigerator for less than 30 minutes, in a ratio of 1 mL of filtrate per 10 mL ether, to precipitate the cleaved peptide. The peptide-ether mixture is equilibrated to room temperature for no later than 30 minutes. The precipitated peptide is collected on a medium glass filter. The precipitate is washed thoroughly with cold ether three times, using enough ether to at least cover all the precipitate on the filter. The ether then is eluted through the same medium glass filter. The crude peptide is transferred into a plastic bottle and is placed in a desiccator connected to a mechanical vacuum pump to dry for no later than 12 hours. After drying, the crude peptide is stored at 5±3° C. The cleavage procedure is repeated multiple times until all the peptide resin is cleaved. A typical batch recovery of total dried crude peptide is approximately 1250 grams, representing a cleavage yield of approximately 110%.

The crude peptide from cleavage is prepared for high-performance liquid chromatography (HPLC) purification by dissolving the peptide in HPLC buffer at a final crude peptide concentration of 20 mg/mL. The peptide solution is filtered through a 1 μm glass filter membrane and loaded onto a C18 reverse phase column, which is operated by a preparative HPLC system. The column is washed and equilibrated. A linear gradient is used to elute the crude peptide from the column. Following each crude purification, the fractions are analyzed by an analytical HPLC system using a Kromasil C18, 5 μm, 100 Å 4.6×250 mm column. Fractions generated from the initial purification are pooled based on the HPLC purity and impurity profile of each fraction. Peptide pools are stored at 2-8° C. until further processing. This process is repeated until all of the crude peptide was purified through the HPLC column and meet the Main Pool purity criteria. A salt exchange to acetate salt is performed by HPLC. The final peptide solution is filtered through a 0.22 μm filter and loaded onto a tray lyophilizer. The peptide is pre-frozen at 40° C. for no later than 720 minutes before starting the lyophilization cycle. The lyophilization takes approximately 5 days. Approximately 50-55% final yield results from the purification and lyophilization steps.

Radiometric $IC_{50}$ Determination

The $IC_{50}$ value was estimated from a 10-point curve of one-half log dilutions. Peptide was supplied in dimethyl sulfoxide (DMSO). Specifically, human recombinant MK2 (h) (5-10 mU) was incubated with 50 mM sodium 3-glycerophosphate (pH=7.5), 0.1 mM EGTA, 30 μM of substrate peptide (KKLNRTLSVA; SEQ ID NO: 21), 10 mM magnesium acetate, and 90 uM $\gamma$-$^{33}$P-ATP (final volume of 25 μL) for 40 minutes at room temperature. Then, the reaction was stopped with 3% phosphoric acid. 10 μL of this mixture was spotted onto a P30 filtermat and washed three times for five minutes with 75 mM phosphoric acid and once with methanol. Finally, the membrane was dried and a scintillation counter was used. An ATP concentration within 15 μM of the apparent Km for ATP was chosen, because Hayess and Benndorf (*Biochem Pharmacol*, 1997, 53(9): 1239-47) showed that the mechanism of their original inhibitor peptide (i.e., the peptide KKKALNRQLGVAA; SEQ ID NO: 22) was not competitive with ATP binding.

In addition to determining the $IC_{50}$ value for MMI-0100 (YARAAARQARAKALARQLGVAA; SEQ ID NO: 1), inhibitory activity against 266 human kinases was tested using Millipore's $IC_{50}$ Profiler Express service (Millipore, Billerica, Mass.).

For specificity analysis, 100 μM of each MMI-0100 (YARAAARQARAKALARQLGVAA; SEQ ID NO: 1), MMI-0200 (YARAAARQARAKALNRQLGVA; SEQ ID NO: 19), MMI-0300 (FAKLAARLYRKALARQLGVAA; SEQ ID NO: 3), MMI-0400 (KAFAKLAARLYRKALARQLGVAA; SEQ ID NO: 4), and MMI-0500 (HRRIKAWLKKIKALARQLGVAA; SEQ ID NO: 7), dissolved in dimethyl sulfoxide (DMSO) was used. The 100 μM concentration was chosen because this concentration inhibited adhesion formation in an in vivo study (as disclosed in U.S. application Ser. No. 12/582,516 filed Oct. 20, 2009, the content of which is incorporated herein by reference in its entirety). Every kinase activity measurement was conducted in duplicate.

Histochemistry and Immunohistochemistry

A mouse model of pulmonary fibrosis was generated by administering 0.025 U of bleomycin/PBS intratracheally to C57BL/6 mice. MMI-0100 (YARAAARQARAKALARQLGVAA; SEQ ID NO: 1) or MMI-0200 (YARAAARQARAKALNRQLGVA; SEQ ID NO: 19) (at dosages of 50 μg/kg, 75 μg/kg, and 100 μg/kg per day) was administered daily starting at day 7 post bleomycin injury (for analysis of post-inflammatory/pre-fibrotic phase; a prevention model) or at day 14 post bleomycin injury (for analysis of post-fibrotic phase; treatment model), either intraperitoneally or via nebulization, through day 21 or 28 post bleomycin delivery. At 21 day post bleomycin delivery (for prevention model) or 28 post bleomycin delivery (for treatment model), groups of mice were sacrificed with a sodium pentobarbital injection (120 mg/kg) and the chest cavity was opened. The right mainstem bronchus was ligated and the right lung was removed. The trachea was cannulated and the left lung was perfused with 4% formaldehyde at 21 cm $H_2O$ pressure. The tissue blocks then were embedded in paraffin, and 4-mm sections were prepared for staining. Sections from each animal were stained with hematoxylin and eosin (H&E) to visualize cells or with Masson's Trichrome staining to highlight collagen deposition. After incubation, sections were washed with 0.2% acetic acid, dehydrated by immersing into 95% alcohol, and cleared with xylene (3-4 times) in a staining dish. Stained sections were mounted onto a labeled glass slide with organic mounting medium.

II. Results

Example 1

IC$_{50}$ and Specificity of MMI-0100 (YARAAARQARAKALARQLGVAA; SEQ ID NO: 1)

IC$_{50}$ (half maximal inhibitory concentrations) value for the MK2 inhibitor peptide (MMI-0100; YARAAAR-QARAKALARQLGVAA (SEQ ID NO: 1)) was determined using Millipore's IC$_{50}$ Profiler Express service. This quantitative assay measures how much of an inhibitor is needed to inhibit 50% of a given biological process or component of a process (i.e., an enzyme, cell, or cell receptor) [IC$_{50}$]. Specifically, in these assays, a positively charged substrate is phosphorylated with a radiolabeled phosphate group from an ATP if the kinase is not inhibited by an inhibitor peptide. The positively charged substrate then is attracted to a negatively charged filter membrane, quantified with a scintillation counter, and compared to a 100% activity control.

ATP concentrations within 15 µM of the apparent Km for ATP were chosen since an ATP concentration near the Km may allow for the kinases to have the same relative amount of phosphorylation activity. The IC$_{50}$ of the MMI-0100 (YARAAARQARAKALARQLGVAA; SEQ ID NO: 1) was determined to be 22 µM.

In addition to determining the IC$_{50}$ of the compound, the specificity of MK2 inhibitory peptides was assessed by examining activities of all 266 human kinases available for testing in the Millipore kinase profiling service (Table 1). For analysis, the kinases that were inhibited more than 65% by MMI-0100 (YARAAARQARAKALARQLGVAA; SEQ ID NO: 1); MMI-0200 (YARAAARQARAKALNRQL-GVA; SEQ ID NO: 19); MMI-0300 (FAKLAARLYRKA-LARQLGVAA; SEQ ID NO: 3); MMI-0400 (KAFAK-LAARLYRKALARQLGVAA; SEQ ID NO: 4); and MMI-0500 (HRRIKAWLKKIKALARQLGVAA; SEQ ID NO: 7) were determined.

As shown in Table 1, at 100 µM, MK2 inhibitory peptides MMI-0100 (SEQ ID NO: 1), MMI-0200 (SEQ ID NO: 19), MMI-0300 (SEQ ID NO: 3); MMI-0400 (SEQ ID NO: 4); and MMI-0500 (SEQ ID NO: 5) inhibited a specific group of kinases and showed very limited off-target kinase inhibition. More specifically, MK2 inhibitory peptides MMI-0100 (SEQ ID NO: 1), MMI-0200 (SEQ ID NO: 19), MMI-0300 (SEQ ID NO: 3); MMI-0400 (SEQ ID NO: 4); and MMI-0500 (SEQ ID NO: 5) inhibited in vitro more than 65% of the kinase activities of Mitogen-Activated Protein Kinase-Activated Protein Kinase 2 (MK2), Mitogen-Activated Protein Kinase-Activated Protein Kinase 3 (MK3), Calcium/Calmodulin-Dependent Protein Kinase I (CaMKI, serine/threonine-specific protein kinase), and BDNF/NT-3 growth factors receptor (TrkB, tyrosine kinase).

TABLE 1

Kinase Profiling Assay

|  | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
|---|---|---|---|---|---|
| Abl (h) | 136 | 107 | 69 | 84 | 16 |
| Abl (H396P) (h) | 130 | 121 | 101 | 105 | 51 |
| Abl (M351T) (h) | 128 | 119 | 90 | 121 | 61 |
| Abl (Q252H) (h) | 105 | 107 | 82 | 98 | 40 |
| Abl(T315I) (h) | 98 | 108 | 97 | 105 | 16 |
| Abl(Y253F) (h) | 104 | 102 | 86 | 78 | 29 |
| ACK1 (h) | 106 | 97 | 104 | 95 | 64 |
| ALK (h) | 118 | 95 | 19 | 16 | 12 |
| ALK4 (h) | 124 | 152 | 140 | 130 | 81 |
| Arg (h) | 89 | 82 | 72 | 84 | 22 |
| AMPKα1 (h) | 107 | 108 | 71 | 87 | 35 |
| AMPKα2 (h) | 121 | 88 | 54 | 58 | 9 |
| ARK5 (h) | 108 | 93 | 78 | 69 | 20 |
| ASK1 (h) | 100 | 101 | 80 | 69 | −4 |
| Aurora-A (h) | 120 | 107 | 92 | 119 | 110 |
| Aurora-B (h) | 94 | 166 | 128 | 150 | 5 |
| Axl (h) | 81 | 99 | 52 | 41 | 12 |
| Bmx (h) | 62 | 76 | N/D | 26 | 45 |
| BRK (h) | 70 | 127 | 35 | 18 | 41 |
| BrSK1 (h) | 100 | 93 | 67 | 76 | 72 |
| BrSK2 (h) | 129 | 102 | 83 | 86 | 84 |
| BTK (h) | 112 | 100 | 102 | 94 | 18 |
| BTK(R28H) (h) | 91 | 104 | 74 | 24 | 10 |
| CaMKI (h) | 13 | 21 | 1 | 0 | −1 |
| CaMKIIβ (h) | 58 | 53 | 2 | 11 | 3 |
| CaMKIIγ (h) | 106 | 94 | 5 | 3 | 3 |
| CaMKIδ (h) | 59 | 47 | 10 | 17 | 0 |
| CaMKIIδ (h) | 89 | 2 | 1 | 2 | 1 |
| CaMKIV (h) | 87 | 71 | 17 | 18 | −1 |
| CDK1/cyclinB (h) | 96 | 115 | 73 | 74 | 57 |
| CDK2/cyclinA (h) | 97 | 114 | 86 | 92 | 87 |
| CDK2/cyclinE (h) | 106 | 112 | 94 | 83 | 19 |
| CDK3/cyclinE (h) | 106 | 104 | 94 | 92 | 8 |
| CDK5/p25 (h) | 114 | 97 | 89 | 92 | 66 |
| CDK5/p35 (h) | 94 | 92 | 79 | 76 | 59 |
| CDK6/cyclinD3 (h) | 103 | 100 | 86 | 85 | 23 |
| CDK7/cyclinH/MAT1 (h) | 89 | 67 | 65 | 47 | 15 |

TABLE 1-continued

Kinase Profiling Assay

|  | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
|---|---|---|---|---|---|
| CDK9/cyclin T1 (h) | 228 | 103 | 91 | 235 | 6 |
| CHK1 (h) | 97 | 115 | 91 | 87 | 65 |
| CHK2 (h) | 104 | 105 | 66 | 54 | 13 |
| CHK2(I157T) (h) | 97 | 85 | 43 | 41 | 3 |
| CHK2(R145W) (h) | 97 | 81 | 33 | 31 | 3 |
| CK1γ1 (h) | 110 | 98 | 111 | 116 | 109 |
| CK1γ2 (h) | 119 | 104 | 123 | 114 | 119 |
| CK1γ3 (h) | 105 | 96 | 125 | 115 | 114 |
| CK1δ (h) | 115 | 92 | 92 | 93 | 78 |
| CK2 (h) | 90 | 83 | 90 | 101 | 93 |
| CK2α2 (h) | 104 | 88 | 105 | 96 | 103 |
| CLK2 (h) | 88 | 97 | 103 | 116 | 116 |
| CLK3 (h) | 108 | 76 | 61 | 84 | 76 |
| cKit (h) | 95 | 110 | 53 | 43 | 45 |
| cKit(D816V) (h) | 117 | 118 | 60 | 35 | 30 |
| cKit(D816H) (h) | 79 | 106 | 126 | 143 | 194 |
| cKit(V560G) (h) | 94 | 115 | 102 | 124 | 198 |
| cKit(V654A) (h) | 69 | 113 | 134 | 150 | 223 |
| CSK (h) | 70 | 33 | 49 | 16 | 2 |
| c-RAF (h) | 97 | 115 | 107 | 102 | 19 |
| cSRC (h) | 70 | 32 | 26 | 14 | 30 |
| DAPK1 (h) | 97 | 113 | 46 | 36 | 0 |
| DAPK2 (h) | 41 | 92 | 32 | 16 | 3 |
| DCAMKL2 (h) | 146 | 131 | 81 | 70 | 56 |
| DDR2 (h) | 105 | 104 | 94 | 95 | 79 |
| DMPK (h) | 60 | 66 | 59 | 54 | 12 |
| DRAK1 (h) | 47 | 34 | 14 | 14 | 8 |
| DYRK2 (h) | 99 | 142 | 155 | 195 | 127 |
| eEF-2K (h) | 113 | 136 | 91 | 43 | 43 |
| EGFR (h) | 95 | 83 | 21 | 16 | −1 |
| EGFR(L858R) (h) | 76 | 120 | N/D | 52 | 26 |
| EGFR(L861Q) (h) | 53 | 74 | 25 | 22 | 15 |
| EGFR(T790M) (h) | 106 | 113 | 100 | 106 | 70 |
| EGFR(T790M, L858R) (h) | 93 | 108 | 85 | 78 | 53 |
| EphA1 (h) | 114 | 136 | 73 | 61 | 40 |
| EphA2 (h) | 58 | 95 | 31 | 17 | N/D |
| EphA3 (h) | 107 | 117 | 6 | 12 | 33 |
| EphA4 (h) | 110 | 127 | 88 | 65 | 48 |
| EphA5 (h) | 110 | 123 | 18 | 24 | 42 |
| EphA7 (h) | 193 | 220 | 159 | 222 | 189 |
| EphA8 (h) | 181 | 133 | 93 | 146 | 337 |
| EphB2 (h) | 68 | 128 | 18 | 22 | 70 |
| EphB1 (h) | 99 | 95 | 44 | 58 | 37 |
| EphB3 (h) | 109 | 128 | 62 | 47 | 79 |
| EphB4 (h) | 62 | 131 | 44 | 28 | 38 |
| ErbB4 (h) | 73 | 82 | 40 | 0 | 2 |
| FAK (h) | 98 | 110 | 111 | 96 | 94 |
| Fer (h) | 117 | 101 | 130 | 108 | 196 |
| Fes (h) | 44 | 74 | 20 | 16 | 23 |
| FGFR1 (h) | 120 | 97 | 55 | 59 | 18 |
| FGFR1(V561M) (h) | 108 | 72 | 74 | 74 | 113 |
| FGFR2 (h) | 49 | 73 | 14 | 18 | 12 |
| FGFR2(N549H) (h) | 95 | 104 | 116 | 112 | 105 |
| FGFR3 (h) | 73 | 208 | 102 | 0 | 10 |
| FGFR4 (h) | 67 | 75 | 28 | 19 | 3 |
| Fgr (h) | 54 | 71 | 60 | 47 | 109 |
| Flt1 (h) | 109 | 96 | 69 | 48 | 27 |
| Flt3(D835Y) (h) | 120 | 115 | 80 | 71 | 65 |
| Flt3 (h) | 104 | 99 | 84 | 18 | 17 |
| Flt4 (h) | 135 | 105 | 83 | 89 | 73 |
| Fms (h) | 89 | 92 | 45 | 37 | 14 |
| Fms(Y969C) (h) | 126 | 88 | 72 | 91 | N/D |
| Fyn (h) | 71 | 75 | 74 | 54 | 83 |
| GCK (h) | 98 | 99 | 70 | 66 | 30 |
| GRK5 (h) | 117 | 135 | 136 | 131 | 116 |
| GRK6 (h) | 131 | 132 | 147 | 141 | 174 |
| GRK7 (h) | 111 | 124 | 122 | 100 | 93 |
| GSK3α (h) | 183 | 119 | 157 | 164 | 175 |
| GSK3β (h) | 113 | 132 | 205 | 202 | 238 |
| Haspin (h) | 127 | 71 | 48 | 36 | 25 |
| Hck (h) | 354 | 107 | 72 | 72 | 78 |
| Hck (h) activated | 58 | 100 | 82 | 81 | 67 |
| HIPK1 (h) | 94 | 115 | 74 | 91 | 47 |
| HIPK2 (h) | 98 | 102 | 73 | 90 | 38 |

TABLE 1-continued

| | Kinase Profiling Assay | | | | |
|---|---|---|---|---|---|
| | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
| HIPK3 (h) | 105 | 105 | 93 | 105 | 85 |
| IGF-1R (h) | 102 | 49 | 119 | 90 | 117 |
| IGF-1R (h), activated | 126 | 94 | 80 | 77 | 45 |
| IKKα (h) | 108 | 104 | 93 | 87 | 50 |
| IKKβ (h) | 105 | 109 | 84 | 84 | 71 |
| IR (h) | 112 | 90 | 96 | 85 | 95 |
| IR (h), activated | 127 | 105 | 79 | 59 | 90 |
| IRR (h) | 85 | 69 | 8 | 8 | 10 |
| IRAK1 (h) | 97 | 101 | 95 | 93 | 5 |
| IRAK4 (h) | 100 | 110 | 59 | 59 | 3 |
| Itk (h) | 99 | 98 | 77 | 63 | 7 |
| JAK2 (h) | 89 | 131 | 133 | 119 | 49 |
| JAK3 (h) | 150 | 117 | 121 | 122 | 95 |
| JNK1α1 (h) | 91 | 106 | 97 | 98 | 109 |
| JNK2α2 (h) | 114 | 109 | 98 | 96 | 81 |
| JNK3 (h) | 104 | 90 | 89 | 70 | 171 |
| KDR (h) | 100 | 110 | 101 | 94 | 15 |
| Lck (h) | 346 | 113 | −2 | 228 | 359 |
| Lck (h) activated | 106 | 90 | 243 | 216 | 76 |
| LIMK1 (h) | 103 | 109 | 88 | 92 | 87 |
| LKB1 (h) | 111 | 99 | 101 | 89 | 51 |
| LOK (h) | 37 | 67 | 37 | 18 | 7 |
| Lyn (h) | 113 | 98 | 69 | 3 | 31 |
| MAPK1 (h) | 108 | 97 | 107 | 100 | 102 |
| MAPK2 (h) | 98 | 105 | 98 | 93 | 60 |
| MAPKAP-K2 (h) | 19 | 35 | 5 | 5 | 9 |
| MAPKAP-K3 (h) | 27 | 39 | 3 | 7 | 9 |
| MEK1 (h) | 86 | 116 | 77 | 77 | 21 |
| MARK1 (h) | 109 | 102 | 132 | 120 | 110 |
| MELK (h) | 74 | 59 | 16 | 17 | 0 |
| Mer (h) | 47 | 90 | 52 | 50 | 17 |
| Met (h) | 104 | 71 | 65 | 62 | 27 |
| Met(D1246H) (h) | 99 | 139 | 125 | 68 | 150 |
| Met(D1246N) (h) | 114 | 149 | 82 | 31 | 90 |
| Met(M1268T) (h) | 114 | 143 | 255 | 265 | 239 |
| Met(Y1248C) (h) | 77 | 141 | 84 | 36 | 73 |
| Met(Y1248D) (h) | 87 | 118 | 102 | 31 | 218 |
| Met(Y1248H) (h) | 88 | 153 | 117 | 63 | 126 |
| MINK (h) | 96 | 103 | 48 | 52 | 5 |
| MKK6 (h) | 74 | 98 | 48 | 44 | 18 |
| MKK7β (h) | 137 | 117 | 100 | 94 | 102 |
| MLCK (h) | 85 | 103 | 2 | 1 | 0 |
| MLK1 (h) | 77 | 84 | 40 | 33 | 43 |
| Mnk2 (h) | 94 | 106 | 89 | 86 | 6 |
| MRCKα (h) | 98 | 103 | 104 | 97 | 5 |
| MRCKβ (h) | 103 | 102 | 83 | 71 | −10 |
| MSK1 (h) | 52 | 50 | 32 | 28 | 8 |
| MSK2 (h) | 105 | 88 | 56 | 52 | 14 |
| MSSK1 (h) | 82 | 100 | 77 | 75 | 22 |
| MST1 (h) | 85 | 72 | 14 | 6 | 3 |
| MST2 (h) | 98 | 104 | 19 | 11 | 2 |
| MST3 (h) | 104 | 95 | 45 | 36 | 4 |
| mTOR (h) | 102 | 110 | 91 | 93 | 135 |
| mTOR/FKBP12 (h) | 117 | 118 | 145 | 125 | 140 |
| MuSK (h) | 85 | 106 | 93 | 93 | 27 |
| NEK2 (h) | 102 | 97 | 78 | 61 | 0 |
| NEK3 (h) | 100 | 100 | 92 | 85 | 20 |
| NEK6 (h) | 109 | 98 | 82 | 85 | 49 |
| NEK7 (h) | 97 | 96 | 84 | 87 | 89 |
| NEK11 (h) | 102 | 95 | 53 | 33 | 2 |
| NLK (h) | 100 | 106 | 87 | 90 | 19 |
| p70S6K (h) | 89 | 84 | 35 | 33 | 3 |
| PAK2 (h) | 71 | 69 | 65 | 59 | 44 |
| PAK4 (h) | 92 | 98 | 94 | 89 | 86 |
| PAK3 (h) | N/D | 50 | 140 | 121 | 102 |
| PAK5 (h) | 97 | 100 | 110 | 117 | 125 |
| PAK6 (h) | 121 | 105 | 104 | 100 | 107 |
| PAR-1Bα (h) | 62 | 110 | 113 | 109 | 97 |
| PASK (h) | 81 | 60 | 29 | 28 | 9 |
| PDGFRα (h) | 104 | 108 | 65 | 40 | 40 |
| PDGFRα (D842V) (h) | 103 | 107 | 114 | 118 | 170 |
| PDGFRα (V561D) (h) | 58 | 106 | 82 | 100 | 146 |
| PDGFRβ (h) | 116 | 137 | 81 | 53 | 40 |
| PDK1 (h) | 144 | 143 | 135 | 159 | 178 |

TABLE 1-continued

| | Kinase Profiling Assay | | | | |
|---|---|---|---|---|---|
| | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
| PhKγ2 (h) | 62 | 86 | 46 | 38 | 16 |
| Pim-1 (h) | 44 | 18 | 8 | 7 | 0 |
| Pim-2 (h) | 117 | 74 | 76 | 92 | 46 |
| Pim-3 (h) | 98 | 94 | 80 | 80 | 37 |
| PKA (h) | 138 | 110 | 119 | 119 | 118 |
| PKBα (h) | 140 | 110 | 57 | 67 | 30 |
| PKBβ (h) | 284 | 250 | 84 | 98 | 21 |
| PKBγ (h) | 105 | 103 | 20 | 41 | 20 |
| PKCα (h) | 94 | 100 | 89 | 86 | 3 |
| PKCβI (h) | 88 | 98 | 78 | 78 | 1 |
| PKCβII (h) | 102 | 100 | 82 | 75 | 3 |
| PKCγ (h) | 94 | 101 | 89 | 79 | 6 |
| PKCδ (h) | 100 | 101 | 101 | 90 | 61 |
| PKCε (h) | 102 | 98 | 79 | 59 | 23 |
| PKCη (h) | 105 | 101 | 103 | 98 | 45 |
| PKCτ (h) | 110 | 97 | 68 | 46 | 7 |
| PKCμ (h) | 79 | 73 | 22 | 14 | 10 |
| PKCθ (h) | 102 | 101 | 88 | 76 | 62 |
| PKCζ (h) | 82 | 98 | 81 | 75 | 7 |
| PKD2 (h) | 84 | 78 | 33 | 25 | 10 |
| PKG1α (h) | 82 | 70 | 64 | 58 | 25 |
| PKG1β (h) | 71 | 57 | 50 | 53 | 24 |
| Plk1 (h) | 109 | 128 | 115 | 119 | 104 |
| Plk3 (h) | 107 | 107 | 127 | 129 | 122 |
| PRAK (h) | 159 | 115 | 128 | 118 | 95 |
| PRK2 (h) | 72 | 74 | 33 | 27 | 7 |
| PrKX (h) | 84 | 112 | 61 | 76 | 57 |
| PTK5 (h) | 135 | 108 | 132 | 129 | 96 |
| Pyk2 (h) | 113 | 127 | 47 | 34 | 46 |
| Ret (h) | 108 | 96 | 140 | 145 | 174 |
| Ret (V804L) (h) | 113 | 100 | 79 | 73 | 20 |
| Ret(V804M) (h) | 92 | 105 | 95 | 87 | 36 |
| RIPK2 (h) | 92 | 98 | 97 | 98 | 30 |
| ROCK-I (h) | 99 | 117 | 79 | 73 | 17 |
| ROCK-II (h) | 102 | 85 | 74 | 77 | 2 |
| Ron (h) | 117 | 120 | 93 | 79 | 46 |
| Ros (h) | 107 | 86 | 95 | 99 | 150 |
| Rse (h) | 109 | 88 | 88 | 89 | 63 |
| Rsk1 (h) | 86 | 102 | 46 | 54 | 34 |
| Rsk2 (h) | 65 | 101 | 51 | 38 | 14 |
| Rsk3 (h) | 76 | 109 | 76 | 71 | 23 |
| Rsk4 (h) | 99 | 125 | 90 | 91 | 29 |
| SAPK2a (h) | 110 | 107 | 90 | 85 | 52 |
| SAPK2a(T106M) (h) | 101 | 100 | 97 | 99 | 32 |
| SAPK2b (h) | 99 | 95 | 81 | 82 | 42 |
| SAPK3 (h) | 106 | 97 | 84 | 79 | 24 |
| SAPK4 (h) | 98 | 106 | 96 | 91 | 48 |
| SGK (h) | 128 | 115 | 48 | 54 | 2 |
| SGK2 (h) | 103 | 119 | 56 | 98 | −1 |
| SGK3 (h) | 95 | 58 | 10 | 8 | −3 |
| SIK (h) | 113 | 102 | 66 | 68 | 40 |
| Snk (h) | 94 | 109 | 114 | 131 | 122 |
| Src(1-530) (h) | 95 | 75 | 23 | 19 | 21 |
| Src(T341M) (h) | 98 | 56 | 70 | 76 | 59 |
| SRPK1 (h) | 69 | 93 | 90 | 96 | 80 |
| SRPK2 (h) | 92 | 100 | 106 | 97 | 80 |
| STK33 (h) | 99 | 98 | 45 | 52 | 16 |
| Syk (h) | 45 | 36 | 24 | 9 | 5 |
| TAK1 (h) | 116 | 124 | 122 | 177 | N/D |
| TAO1 (h) | 99 | 105 | 82 | 73 | 24 |
| TAO2 (h) | 95 | 93 | 70 | 74 | 15 |
| TAO3 (h) | 45 | 102 | 77 | 67 | 12 |
| TBK1 (h) | 106 | 98 | 37 | 39 | 16 |
| Tec (h) activated | 100 | 77 | 56 | 29 | 33 |
| Tie2 (h) | 28 | 53 | 26 | 21 | 22 |
| Tie2(R849W) (h) | 102 | 89 | 117 | 108 | 106 |
| Tie2(Y897S) (h) | 99 | 85 | 83 | 87 | 80 |
| TLK2 (h) | 113 | 129 | 114 | 151 | 133 |
| TrkA (h) | 74 | N/D | 25 | 17 | 24 |
| TrkB (h) | 4 | 7 | 5 | 8 | 12 |
| TSSK1 (h) | 99 | 98 | 79 | 79 | 46 |
| TSSK2 (h) | 107 | 91 | 98 | 94 | 92 |
| Txk (h) | 87 | 98 | 48 | 37 | 10 |
| ULK2 (h) | 123 | 132 | 122 | 131 | 124 |

TABLE 1-continued

| Kinase Profiling Assay | | | | | |
|---|---|---|---|---|---|
| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
| ULK3 (h) | 142 | 164 | 167 | 147 | 177 |
| WNK2 (h) | 95 | 94 | 64 | 54 | 8 |
| WNK3 (h) | 100 | 97 | 77 | 74 | 9 |
| VRK2 (h) | 112 | 109 | 161 | 185 | 169 |
| Yes (h) | 49 | 93 | 67 | 14 | N/D |
| ZAP-70 (h) | 79 | 58 | 75 | 33 | 1 |
| ZIPK (h) | 80 | 67 | 28 | 13 | 1 |

N/D: % activity could not be determined as the duplicates.

YARAAARQARAKALARQLGVAA (SEQ ID NO: 1)

YARAAARQARAKALNRQLGVA (SEQ ID NO: 19)

FAKLAARLYRKALARQLGVAA (SEQ ID NO: 3)

KAFAKLAARLYRKALARQLGVAA (SEQ ID NO: 4)

HRRIKAWLKKIKALARQLGVAA (SEQ ID NO: 7)

Example 2

Formulation of MMI-0100 (YARAAARQARAKALARQLGVAA; SEQ ID NO: 1) and its Functional Equivalents According to some embodiments, MMI-0100 (YARAAARQARAKALARQLGVAA; SEQ ID NO: 1) and its functional equivalents are formulated as a lyophilized powder via spray drying, micronization (e.g., jet-milling), or as liquid formulation for nebulization.

Spray Drying

In some embodiments, spray drying is utilized for preparing MMI-0100 (YARAAARQARAKALARQLGVAA; SEQ ID NO: 1) and its functional equivalents in consideration of the following factors:

(a) proteins and peptides are prone to denaturation—that is, disruption to tertiary and sometimes secondary structures;

(b) the denaturation can be reversible or irreversible and can be caused by a variety of conditions such as increase in temperature, decrease in temperature, extremes of pH, addition of solvents, pressure, and shear denaturation (this applies to micronization);

(c) denatured proteins are less active and not therapeutic, sometimes completely inactive;

(d) spray drying is able to turn these amorphous, large molecules into discrete spherical particles with a specified particle size distribution, controlled by processing parameters; the spray dried particles can be very spherical, donut-shaped and are typically hollow, meaning that particles >5 µm can still be respirable but be resistant to clearance mechanisms in the lungs; and (e) Spray drying, with or without excipients, generally improves the stability of proteins.

A lyophilized formulation of MMI-0100 (YARAAARQARAKALARQLGVAA; SEQ ID NO: 1) and its functional equivalents is assessed for potential synergy with the spray drying process (e.g., matching of optimal moisture levels buffer concentrations/pH, excipient selection and the like) to ensure protection of peptide stability.

Initial spray drying runs target mutually agreed acceptance criteria with the aim of defining process parameters for the spray drying operation. For an inhalation product, particle size is considered an important criterion. For alveolar deposition in the region of interest (Type IIs), Mass Median Aerodynamic Diameters (MMADs) of 1-5 microns generally are accepted as being suitable for peripheral deposition in the alveolar spaces (Heyder, J. Proc Am Thorac Soc, 1(4): 315-320, 2004, incorporated by reference herein). Other studies have suggested that MMADs of 1-3 microns are a desirable starting target particle sizes for the spray drying process. Since the likely biospace target for MMI-0100 (YARAAARQARAKALARQLGVAA; SEQ ID NO: 1) is the alveolar region, a MMAD in the about 2 micron range is targeted initially to ensure deposition into the alveolar space.

Acceptance criteria include, but are not limited to, (1) particle size (i.e., $D_{90}$ of about 2 µm); (2) moisture levels (i.e., moisture less than 3% w/w); (3) powder density; and (4) surface appearance (spherical, rough, toroidal).

A process design experiment then is conducted to optimize spray drying process parameters, including, for example, but not limited to, (1) inlet pressure and drying temperature; (2) feedstock concentration and federate; and (3) peptide/excipient ratio (excipients are, for example, buffer salts and a monosaccharide)

Example 3

Production of Batches of MMI-0100 (YARAAARQARAKALARQLGVAA; SEQ ID NO: 1) for Continued Aerosol Performance Assessment 2-3 spray drying runs at the defined process parameters described above are performed to generate material for aerosol performance assessment.

Figure 1:
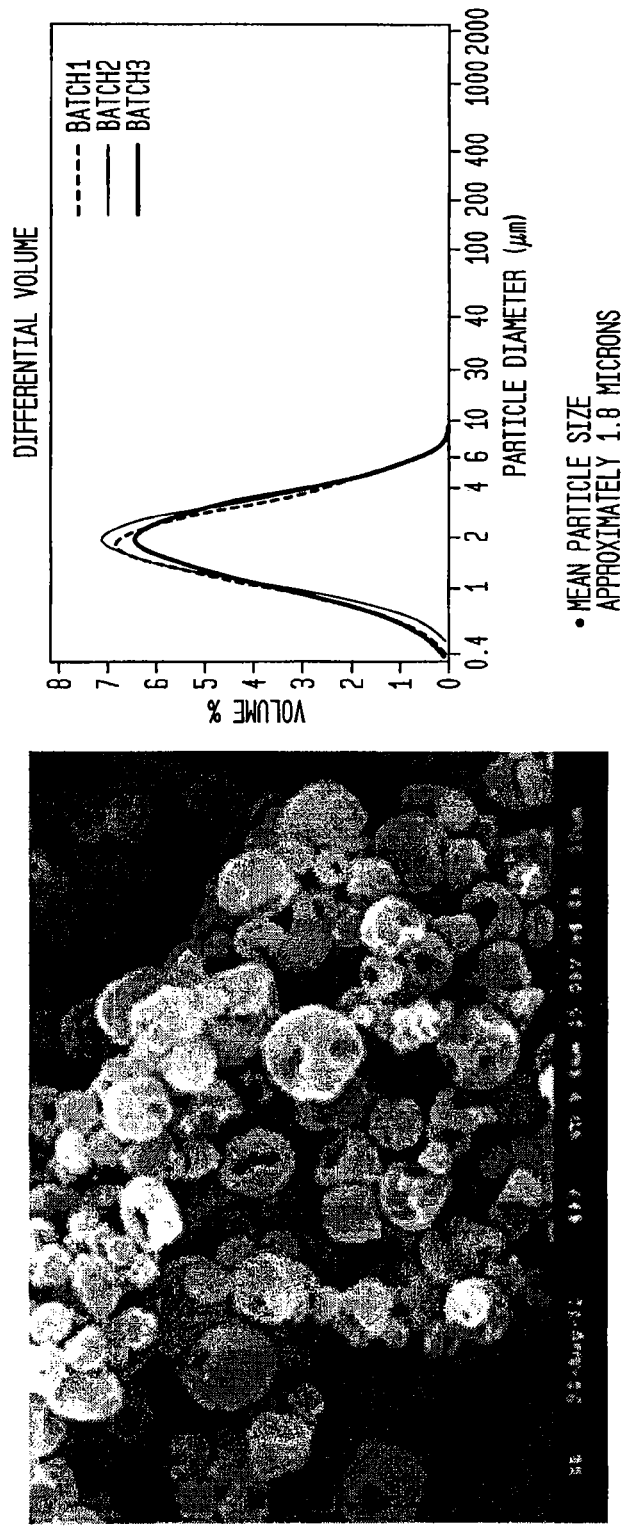
FIG. 1 shows delivery performance of neat spray-dried insulin.
Figure 2:
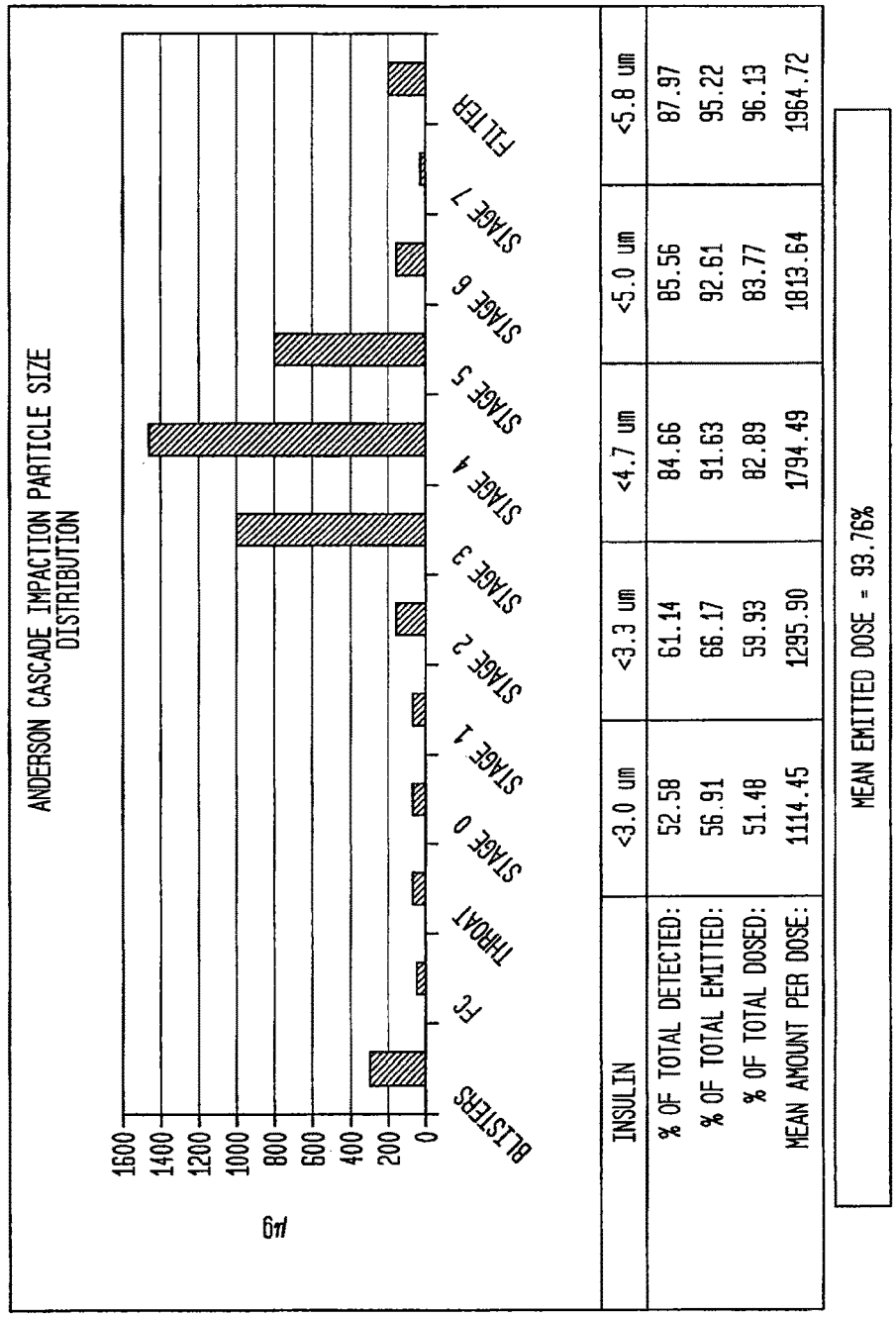
FIG. 2 shows particle size distribution of spray-dried insulin, which is determined by Anderson Cascade Impaction (ACI).

Spray-dried powders are well suited for delivery from an inhaler, for example, without limitation, a MicroDose inhaler. MicroDose routinely achieves both high emitted dose, and high fine particle fraction and dose with this formulation approach, both for neat as well as co-spray-dried blends. Exemplary aerosol performances for spray-dried insulin are shown in FIGS. 1 and 2.

Although dry micronization is a preferred powder production method for small molecules for pulmonary delivery, in contrast to spray-drying, it is a stressful method, which uses high shear forces. Because use of high shear forces may lead to fracturing of proteins and peptides, dry micronization is not routinely used for large molecules. In addition, if dose sizes are small, bulking agents are needed to improve the flowability and allow accurate measurement of the powders in filling operations. The primary excipient, and one of the only excipients approved for pulmonary delivery for this purpose is lactose, may need to be tested for chemical compatibility with MMI-0100 (YARAAARQARAKALARQLGVAA; SEQ ID NO: 1) or its functional equivalents as lactose is incompatible with certain peptides.

The micronization process is fairly straightforward and well known in the art. Briefly, lyophilized dry powder of MMI-0100 (YARAAARQARAKALARQLGVAA; SEQ ID NO: 1) and its functional equivalents are run through milling stages until the prescribed target particle size distribution (i.e., MMAD, D10, D50, D90) is achieved. This neat micronized powder is tested for potency to ensure its activity post micronization, optimized for delivery from the inhaler, and its chemical and physical stability tested in the primary (heat sealed blister) packaging. The neat powder then is blended with a prioritized selection of approved pulmonary lactose grades to a target, tested for blend homogeneity, and run through the same inhaler optimization and stability testing.

MicroDose Dry Powder Inhaler (DPI)

Figure 3:
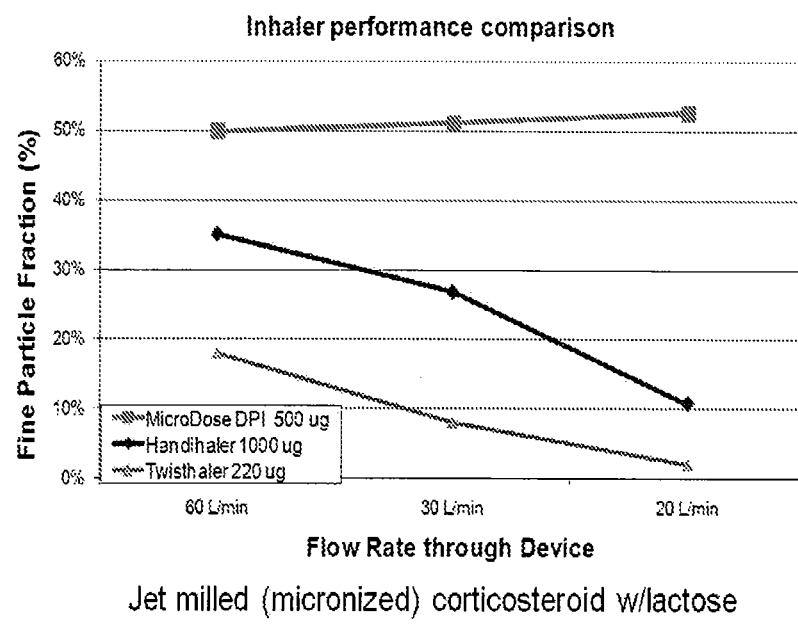
FIG. 3 shows efficiency and flow rate comparison of MicroDose Dry Powder Inhaler (DPI) vs. two marketed "passive" Dry Powder Inhalers (DPIs).
Figure 6:
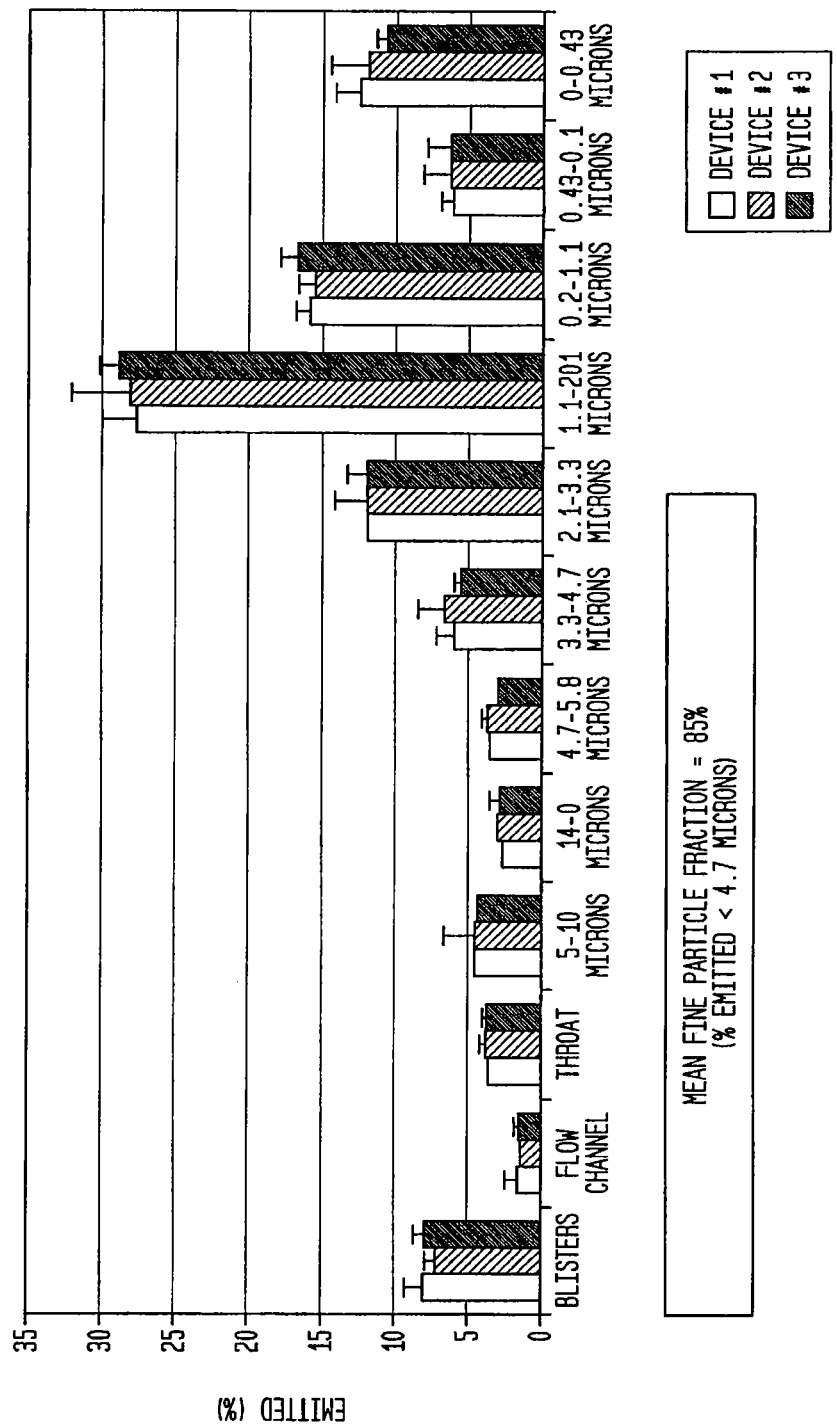
FIG. 6 shows particle size distribution of a spray-dried peptide (not insulin).
Figure 7:
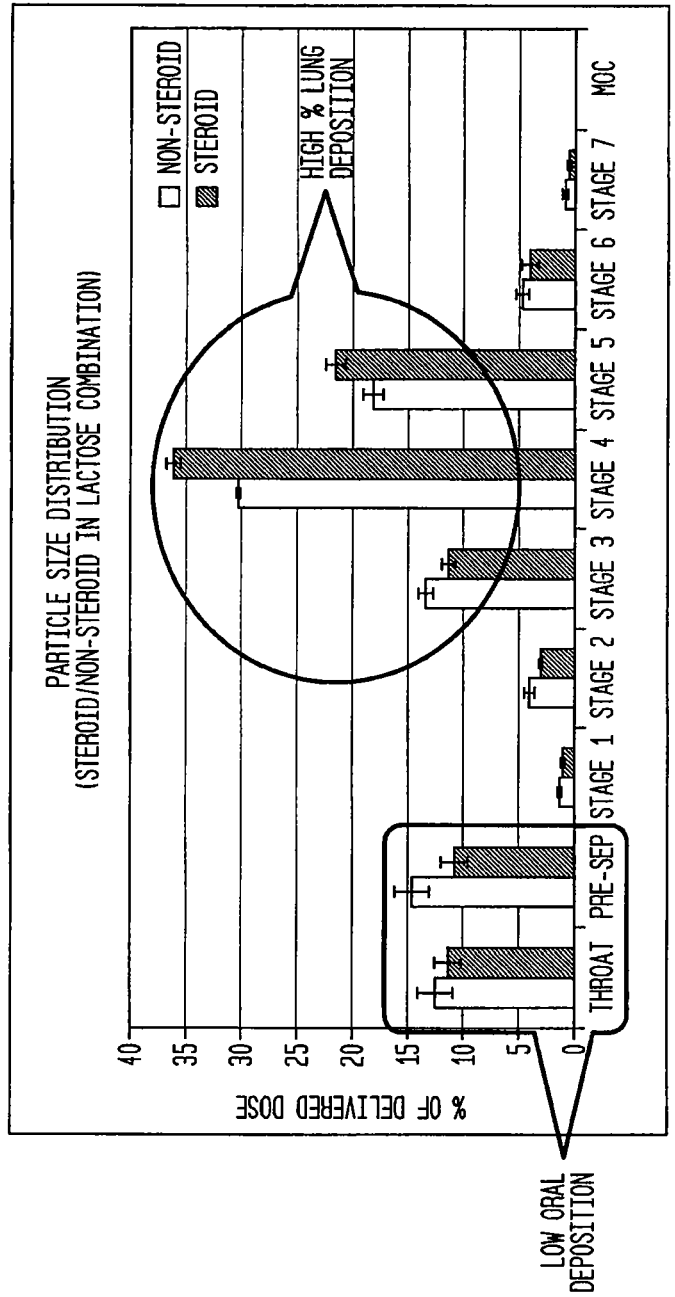
FIG. 7 shows particle size distribution of micronized/lactose blend combination, which is determined by Next Generation Impactor (NGI)
Figure 8:
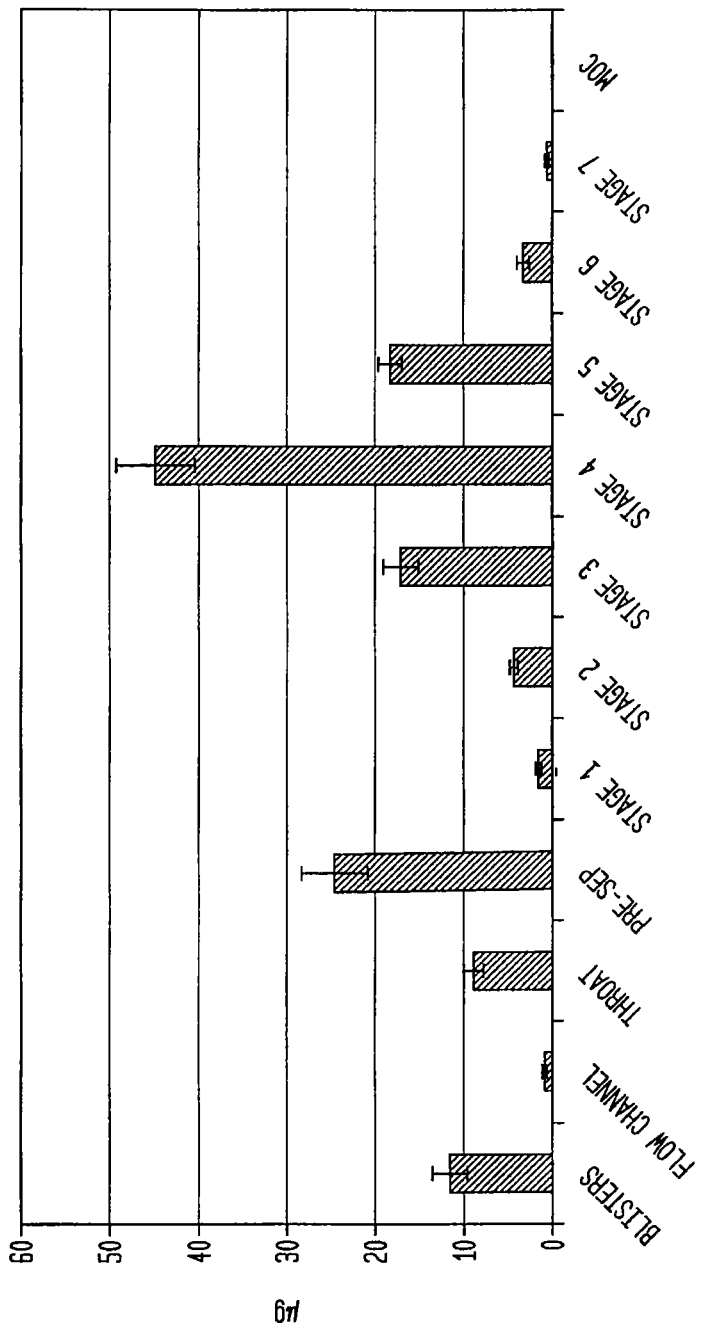
FIG. 8 shows delivery performance of micronized a small molecule (long-acting muscarinic agents (LAMA)/lactose blend).

According to some embodiment, MMI-0100 (YARAAARQARAKALARQLGVAA; SEQ ID NO: 1) and its functional equivalents can be administered using a dry powder inhaler (DPI). For example, the MicroDose dry powder inhaler (DPI) has an 'active' piezo driven aerosol generator that is breath actuated and achieves high efficiency of lung delivery independent of the patient's inhalation flow rate and volume. Unlike 'passive' DPIs that require a strong and forceful inhalation on the order of 40-60 liters per minute (LPM) flow for effective lung delivery, there is no breathing maneuver required for the MicroDose DPI, as it can deliver effectively over a very broad range of flow rates from as low as 10 LPM up to 90 LPM flow, with equivalent performance (see performance examples in FIGS. 3 and 4).

According to some other embodiments, MMI-0100 (YARAAARQARAKALARQLGVAA; SEQ ID NO: 1) and its functional equivalents can be administered using a tidal breathing application, such as a 'dry powder nebulizer' (DPN). The DPN delivers dry powder doses synchronized to inhalation tidal breathing with triggering as low as 2 liter per minute (LPM), expected peak flows of between 5 and 15 LPM and tidal volumes as low as 30 ml, which are much more challenging conditions than are expected with adult IPF patients. This new DPN has successfully completed its second clinical trial in adults, with completion of its first study in November, 2011. These results are accessible via internet on the world wide web (www) at the URL "clinicaltrials.gov/ct2/show/NCT01489306?spons=Microdose&rank=1."

The MicroDose electronic inhaler system is an extremely flexible formulation, can accurately and efficiently deliver both formulation modalities above with particularly high efficiency with spray dried drug products, and has shown this performance capability with over 30 small and large molecules. Spray-dried insulin in the primary packaging, for example, can last at least 18 months. Examples of delivery performance for both spray-dried peptides and micronized small molecules are shown in FIGS. 5-8.

As for the effect of the dry powder formulation on pulmonary membranes, e.g., sensitization, dry powder delivery, especially at low powder loads (<4-5 mg), is unlikely to affect pulmonary membranes or cause sensitization (cough, etc.) unless this is an intrinsic property of the active molecule (which we have not observed in animal studies). Excipients that have already been pulmonarily approved with excellent pulmonary biocompatibility are selected, and are present in very low quantities (i.e., low mg range). For instance, mannitol at low quantities is not likely to have an effect.

Liquid Nebulization

Alternatively, MMI-0100 (YARAAARQARAKALARQLGVAA; SEQ ID NO: 1) or its functional equivalents can be delivered via liquid nebulization. Previous preclinical studies have shown that MMI-0100 (YARAAARQARAKALARQLGVAA; SEQ ID NO: 1) can be delivered to rodents via an AeroGen® nebulizer system adapted for animal use.

In order to specifically address MMI-0100's (YARAAARQARAKALARQLGVAA; SEQ ID NO: 1) ability to be delivered to positively impact compromised lung, in the bleomycin animal model efficacy experiments, a solution of MMI-0100 (YARAAARQARAKALARQLGVAA; SEQ ID NO: 1) is effectively aerosolized. Local lung MMI-0100 (YARAAARQARAKALARQLGVAA; SEQ ID NO: 1) administration is achieved via a rodent nebulizer device designed and manufactured by Aerogen® (www.aerogen.com). The Aeroneb® Lab Micropump Nebulizer uses a high-efficiency aerosolization technology for use in preclinical aerosol research and inhalation studies, providing a valuable link between preclinical and clinical product development. The flow-rate is >0.3 ml/min, and is designed to deliver 2 mm-sized particles, with distribution into deepest alveoli. Efficacy of nebulized MMI-0100 (YARAAARQARAKALARQLGVAA; SEQ ID NO: 1) and cellular uptake throughout the lung has been demonstrated in the bleomycin mouse model of pulmonary fibrosis (see FIG. 16). Localized, clinically-relevant inhaled administration is as effective as conventional systemic injections in attenuating MK2 activation Example 4

The Level of Activated MK2 is Increased in Fibrotic Lesions of Patient Lungs with Idiopathic Pulmonary Fibrosis (IPF)

Mitogen-activated protein kinase (MAPK)-activated protein kinase 2 (MK2) is activated upon stress by p38MAPK-α and β. These two isoforms of p38MAPK bind to a basic docking motif in the carboxy terminus of MK2, which subsequently phosphorylate its regulatory sites. As a result of activation, MK2 is exported from the nucleus to the cytoplasm and co-transports active p38 MAPK to this compartment. MK2 stabilizes p38MAPK localization and is essential for differentiation, migration and cytokine production (Kotlyarov, A., Mol Cell Biol. 22(13): 4827-4835, 2002).

Figure 9:
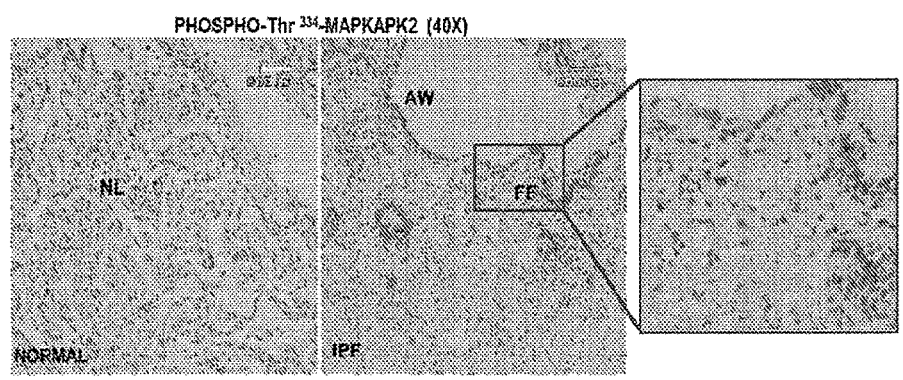
FIG. 9 shows immunohistochemical analysis of paraffin-embedded human idiopathic pulmonary fibrosis IPF lungs, showing nuclear localization of activated MK2 (i.e., Phospho-Thr$^{334}$-MAPKAPK2) at the fibroblastic focus. Normal lungs (left panel); IPF lung tissue biopsy section (right panel). Inset shows disruption of epithelial lining at the foci with cells staining positive (dark grey) for activated MK2. The abbreviations shown in FIG. 9 are as follows: NL (normal lung architecture with alveolar sacs); AW (air way); FF (fibroblastic foci from a lung tissue explants with IPF)

Therefore, in order to examine whether the p38MAPK-MK2 signaling pathway is activated in the lungs affected by IPF, lung sections obtained from normal and IPF patients were stained with a phospho-specific antibody against an activated form of MK2 (anti-phospho-Thr$^{334}$-MAPKAPK2). Normal lung and IPF lung tissues were immunostained using DAB and nucleus was counterstained with Hematoxylin. As shown in FIG. 9, increased expression of activated MK2 was observed cells in the fibrotic foci from lung tissue explants derived from patients with IPF as compared with normal lung biopsy tissue (left). These results suggest that fibrosis formation in the lungs of IPF patients is characterized by aberrant activation of the p38MAPK-MK2 signaling pathway.

Example 5

Nebulized and Systemic Administration of MMI-0100 (YARAAARQARAKALARQLGVAA; SEQ ID NO: 1) Protects Against Bleomycin-Induced Lung Fibrosis in Mice One of the hallmarks of idiopathic pulmonary fibrosis (IPF) is the activation of mesenchymal cells and exuberant deposition of matrix, specifically collagen. The resultant accumulation of collagen in the lung can be measured both by histological and biochemical techniques, most notably via accumulation of hydroxyproline, which is almost totally derived from collagen in the lung and thus serves as a surrogate for whole lung collagen content (Umezawa H. et al., Cancer, 20(5):891-895, 1967).

Therefore, the therapeutic efficacy of the MMI-0100 peptide (YARAAARQARAKALARQLGVAA; SEQ ID NO: 1) on treating pulmonary fibrosis was assessed using a mouse model of bleomycin-induced pulmonary fibrosis by delivering the MMI-0100 (YARAAARQARAKALARQLGVAA; SEQ ID NO: 1) peptide systemically (intraperitoneal) or locally (via nebulized dosing) during prophylaxis or pre-fibrotic stage (i.e., drug administration beginning at day 7 post bleomycin injury; See FIG. 10) and by measuring the levels of collagen as indices of fibrosis in the bleomycin mouse.

Figure 10:
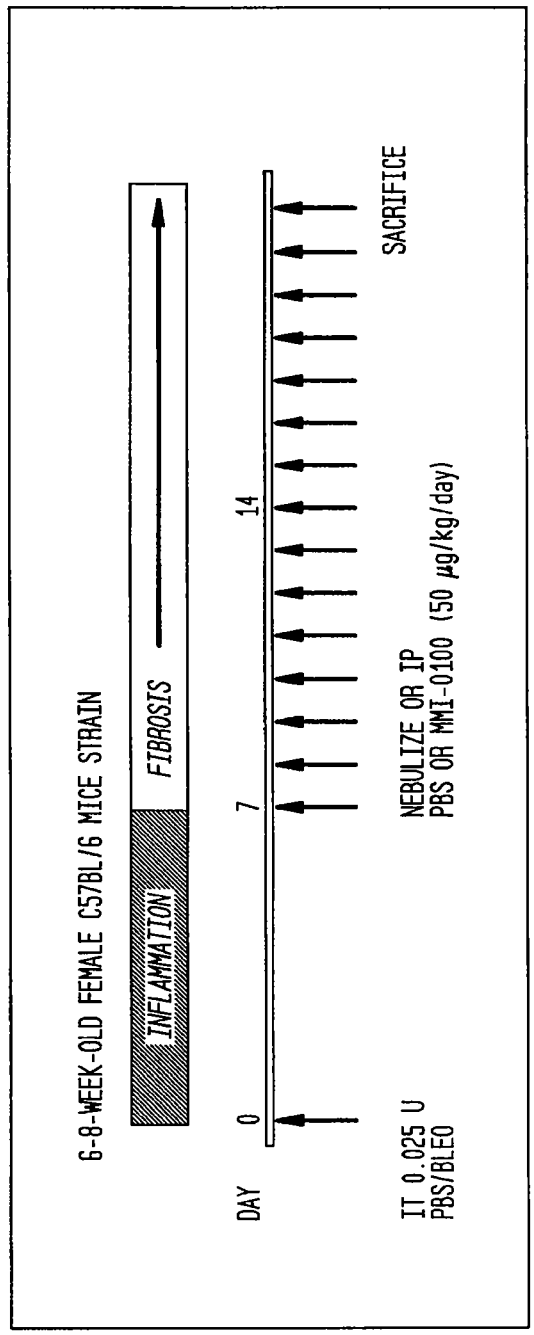
FIG. 10 shows a schematic diagram for testing ability of a compound to inhibit the development of fibrosis in the bleomycin mouse model of pulmonary fibrosis (Idiopathic Pulmonary Fibrosis (IPF) prevention model). Phosphate-buffered saline (PBS) or MMI-0100 (YARAAARQARAKALARQLGVAA (SEQ ID NO: 1)) is administered daily, either via nebulization or intraperitoneally, starting at day 7 post bleomycin delivery when inflammation subsides and fibrotic mechanisms are activated, until day 21 post bleomycin delivery when significant fibrosis is observed.

Briefly, fibrotic loci in the lungs of the mice were induced by delivering intratracheally about 0.025 U of bleomycin (dissolved in PBS) to C57BL/6 mice. In order to examine the efficacy of MMI-0100 (YARAAARQARAKALARQLGVAA; SEQ ID NO: 1) in the treatment of the bleomycin-injured lungs in the prophylaxis/pre-fibrotic phase, a control (PBS) or MMI-0100 (YARAAARQARAKALARQLGVAA; SEQ ID NO: 1) was administered daily, either intraperitoneally or via nebulization, starting at day 7 post bleomycin delivery (when inflammation subsides and fibrotic mechanisms are activated) until day 21 post bleomycin delivery (when significant fibrosis is observed) (FIG. 10). At 21 day post bleomycin delivery, lung tissues from the bleomycin mice treated with MMI-0100 (YARAAARQARAKALARQLGVAA; SEQ ID NO: 1) or a control (PBS), were isolated, fixed, embedded in paraffin, and sectioned for staining. Briefly, mice were sacrificed with a sodium pentobarbital injection (120 mg/kg) and the chest cavity was opened. The right mainstem bronchus was ligated and the right lung was removed. The trachea was cannulated and the left lung was perfused with 4% formaldehyde at 21 cm $H_2O$ pressure. The tissue blocks then were embedded in paraffin, and 4-mm sections were prepared, and stained with hematoxylin and eosin (H&E; for pathological examination) or Masson's Trichrome (for collagen staining)

Figure 11:
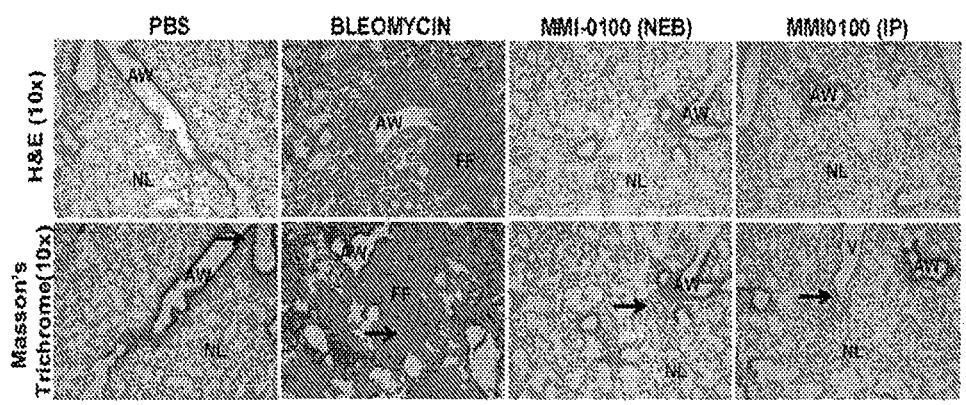
FIG. 11 shows that inhalation therapy and systemic administration of MMI-0100 (YARAAARQARAKALARQLGVAA; SEQ ID NO: 1) protects against bleomycin-induced lung fibrosis in mice. Upper panel: Hematoxylin and Eosin (H&E) staining of representative mouse lung tissues at day 21. Lower panel: Masson's blue trichrome staining of the same fields reveal extensive collagen deposition (arrows) with bleomycin injury. Abbreviations: AW: airway; NL: normal lung architecture; FF: fibrotic foci; V: vein.

As shown in FIG. 11, the lung sections from PBS-treated mice exhibited normal lung structures (NL) and airways (AW). In contrast, the lung sections from the bleomycin mice (at day 21) revealed narrowed airway (AW) structure with formation of fibrotic foci (FF) (upper panel; Hematoxylin & Eosin (H&E) staining) and increased accumulation of collagen (arrows in the lower panel; Masson's Trichrome staining) in lung tissues, which are reminiscence of those found in IPF patients. Administration of MMI-0100 (YARAAARQARAKALARQLGVAA; SEQ ID NO: 1), either via nebulization or intraperitoneally, however, significantly reduced development of fibrotic loci formation (upper panel, MMI-0100 (NEB) and MMI-0100 (IP)) and reduced collagen accumulation (lower panel, MMI-0100(NEB) and MMI-0100 (IP)) in the lungs of the bleomycin mice.

Figure 12:
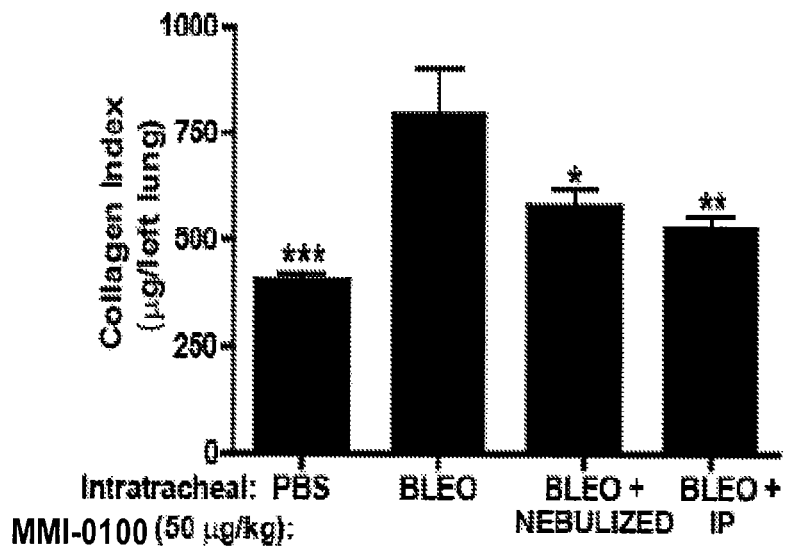
FIG. 12 shows that MMI-0100 (YARAAARQARAKALARQLGVAA; SEQ ID NO: 1) prevents significant collagen deposition due to bleomycin injury. Values represent means±SEM. n=5 animals per group. '*' $p<0.05$; '' $p<0.01$; '*' $p<0.001$. Collagen Index=constant factor for collagen 7.5× hydroxy proline concentrations.

Next, total collagen levels in the lungs of the bleomycin-injured mice (FIG. 12) were analyzed quantitatively by computing a constant conversion factor (7.5) for collagen from hydroxyproline concentrations (Neuman R. and Logan M, J Biol Chem., 186(2):549-56, 1950, incorporated by reference). As shown in FIG. 12, both nebulized (BLEO+NEBULIZED) and systemic (BLEO+IP) administration of MMI-0100 (YARAAARQARAKALARQLGVAA; SEQ ID NO: 1) during the post-inflammatory/pre-fibrotic stage significantly decreased collagen deposition compared to the bleomycin control.

Example 6

Figure 13:
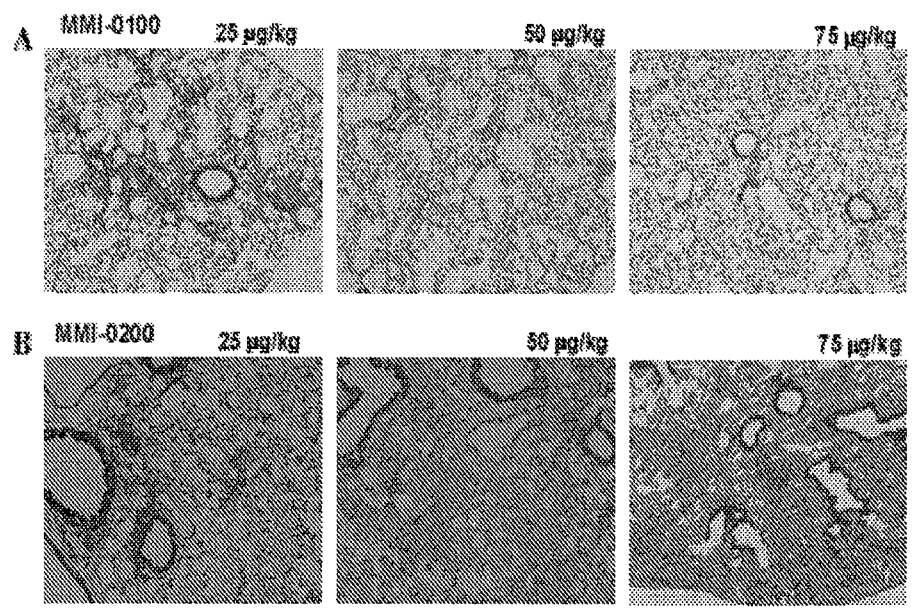
FIG. 13 shows that MMI-0100 (YARAAARQARAKALARQLGVAA; SEQ ID NO: 1) prevents fibrosis due to bleomycin injury in a dose-dependent manner. Masson's blue trichrome staining of lung sections of bleomycin mice. (A) MMI-0100 (YARAAARQARAKALARQLGVAA; SEQ ID NO: 1); (B) MMI-0200 (YARAAARQARAKALNRQLGVA; SEQ ID NO: 19).

Dose-Response Data of MK2 Peptide Inhibitors in the Idiopathic Pulmonary Fibrosis Prevention Model Next, the effect of increasing doses of MK2 peptide inhibitors on collagen deposition was examined in vivo using the bleomycin mouse model of idiopathic pulmonary fibrosis (prevention model). Briefly, C57-BL/6 mice were subjected to bleomycin injury at day 0. Beginning at day 7 and continuing through day 21, mice were administered 25, 50 or 75 µg/kg of MMI-0100 (YARAAARQARAKALARQLGVAA; SEQ ID NO: 1) or MMI-0200 (YARAAARQARAKALNRQLGVA; SEQ ID NO: 19) daily via intraperitoneal (IP) injection. As shown in FIG. 13, Masson's blue trichrome staining revealed a decrease in collagen levels in the lung of the bleomycin injured mouse treated with MMI-0100 (YARAAARQARAKALARQLGVAA; SEQ ID NO: 1), suggesting that MMI-0100 (YARAAARQARAKALARQLGVAA; SEQ ID NO: 1) can protect fibrosis in the lungs due to bleomycin injury in a dose-dependent manner. These data suggest that MMI-0100 (YARAAARQARAKALARQLGVAA; SEQ ID NO: 1) retains its potential as a fibroprotective compound even at higher doses.

In contrast, treatment of the bleomycin injured mice with MMI-0200 (YARAAARQARAKALNRQLGVA; SEQ ID NO: 19) did not reduce, but rather increased the collagen deposition in the lung at the doses tested. This result, however, is consistent with a previous study involving MK2 knockout mice and MK2–/– mouse embryonic fibroblast (MEFs), in which all MK2 activity was ablated, which exhibited an aggravated fibrosis phenotype (Liu et al., Am J Respir Cell Mol Biol, 37: 507-517, 2007).

Without being limited by theory, these results suggest (1) that MK2 inhibitory peptides of the described invention may exhibit a spectrum of inhibitory activities against a specific group of kinases; (2) MMI-0100 (YARAAARQARAKALARQLGVAA; SEQ ID NO: 1) and MMI-0200 (YARAAARQARAKALNRQLGVA; SEQ ID NO: 19) may inhibit MK2 and other kinases differentially, which, depending on the dose applied, contributes to this spectrum of inhibitory activities; (3) that myofibroblast formation and/or migration might also be a part of the repair phase of fibrosis rather than of active damage; and (4) that a certain level of MK2 activity is, therefore, necessary for that process to occur (Liu et al., *Am J Respir Cell Mol Biol,* 37: 507-517, 2007).

In addition, the MK2 inhibitory peptides of the described invention were derived from the substrate binding site of MK2 downstream target HSPB1. Therefore, they can competitively inhibit the kinase activity of MK2 toward HSPB1. Without being limited by theory, the differential effects of MMI-0200 (YARAAARQARAKALNRQLGVA; SEQ ID NO: 19) on fibrosis may be attributed to its sequence differences, its homology to the HSPB1 biding sites, its differential inhibition of MK2 kinase activity toward a distinct target protein binding site, or a combination thereof.

Example 7

Administration of MMI-0100 (YARAAARQARAKALARQLGVAA; SEQ ID NO: 1) Effectively Blocks Systemic T-Cell Activation in Idiopathic Pulmonary Fibrosis Prevention Model Recent studies highlighted a key role for T lymphocytes in bleomycin-induced fibrosis (Wilson, M. et al., *The Journal of Experimental Medicine*, 207(3): 535-552, 2010). Therefore, in order to investigate the functional role of splenic (pan) T cells in the bleomycin injured mice treated with MMI-0100 (YARAAARQARAKALARQLGVAA; SEQ ID NO: 1), the autologous mixed lymphocyte reaction (MLR) was performed as described previously (Wilkes, D. et al., *Journal of Leukocyte Biology*, 64(5):578-586, 1998, incorporated by reference herein). Specifically, the ability of C57BL/6 purified antigen-presenting cells to induce proliferation in C57BL/6 T lymphocytes was examined in the assay.

C57-BL/6 mice were subjected to bleomycin injury at day 0. At day 7, the mice were administered 50 µg/kg/day MMI-0100 (YARAAARQARAKALARQLGVAA; SEQ ID NO: 1) daily by intraperitoneal (IP) injection or nebulizer (NEB) until day 21. Splenic T cells were isolated and cultured alone or in the presence of autologous antigen presenting cells (APCs from C57-BL/6 mice) or stimulated with antibodies against CD3 (α-CD3) for 48 h. The cells then were radiolabeled with triturated thymidine for 16 h and assessed for proliferation rates.

Figure 14:
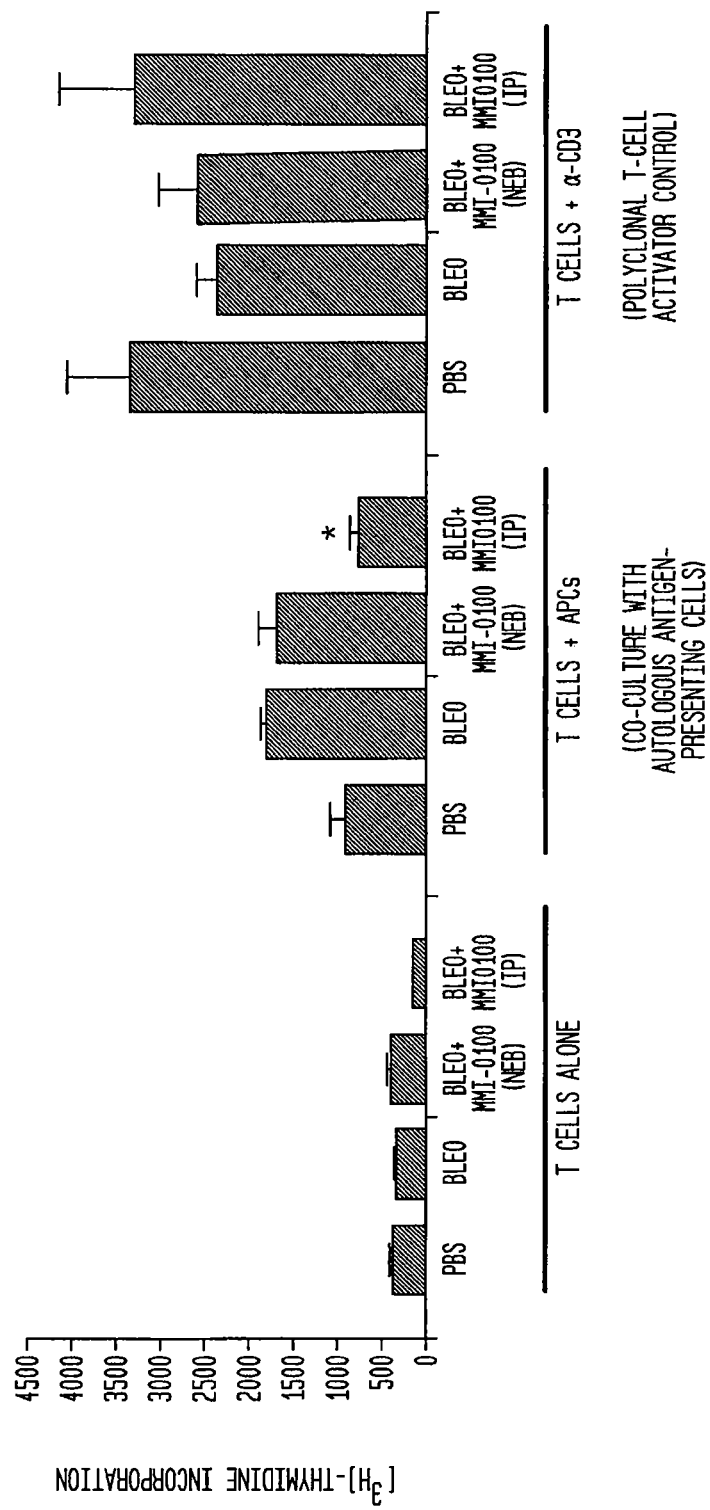
FIG. 14 shows that systemically-administered MMI-0100 (YARAAARQARAKALARQLGVAA; SEQ ID NO: 1) abrogates systemic T cell activation due to bleomycin injury. Values represent mean±SEM. 'p' value <0.01. n=4 animals/group. The abbreviations shown in FIG. 14 are as follows: (i) wild type mice treated with PBS (PBS); (ii) the bleomycin mice treated with PBS (BLEO); (iii) the bleomycin mice treated with nebulized MMI-0100 (YARAAARQARAKALARQLGVAA (SEQ ID NO: 1)) (BLEO+MMI-0100

As shown in FIG. 14, T cells alone, regardless of treatment, exhibited very low proliferative capacity. However, when the T cells were co-cultured with autologous antigen presenting cells (i.e., APCs isolated from C57-BL/6 mice), the proliferative capacity was significantly higher for bleomycin-injured mice than for control mice. Interestingly, the proliferation of T cells from bleomycin treated mice seen in the presence of antigen presenting cells was significantly reduced by the systemic administration of MMI-0100 (YARAAARQARAKALARQLGVAA; SEQ ID NO: 1), but as expected, not by the inhaled mode. These data suggest the suppression of splenic T cell activation by MMI-0100 (YARAAARQARAKALARQLGVAA; SEQ ID NO: 1), and indicate that the peptide MK2 inhibitor is fibro-protective.

The viability of the T cells also was confirmed by stimulating the cells with antibodies against α-CD3, a polyclonal T cell activator. α-CD3 induced robust proliferation of the cells irrespective of the treatment group. The proliferative response to the polyclonal activator suggests that the MMI-0100 (YARAAARQARAKALARQLGVAA; SEQ ID NO: 1) peptide inhibitor does not affect the functional property of the splenic T cells, and that there is no toxicity with the administration of MMI-0100 (YARAAARQARAKALARQLGVAA; SEQ ID NO: 1) at this particular dose. In addition, the lack of splenic T cell response to nebulized MMI-0100 (YARAAARQARAKALARQLGVAA; SEQ ID NO: 1) suggests that little systemic distribution occurs with this mode of peptide delivery.

Example 8

Systemic or Nebulized MMI-0100 (YARAAARQARAKALARQLGVAA; SEQ ID NO: 1) Treatment Protects Bleomycin Injured Lungs in the Post-Fibrotic Phase The classic bleomycin model, as depicted in FIG. 10, has been used widely in the literature in the pre-fibrotic stage to test efficacy of any intervention. Since both nebulized and systemic administration of the MMI-0100 (YARAAARQARAKALARQLGVAA; SEQ ID NO: 1) significantly protected the lung from bleomycin-induced fibrosis, the effect of systemic (intraperitoneal) or local (nebulized) administration of MMI-0100 (YARAAARQARAKALARQLGVAA; SEQ ID NO: 1) in the treatment of bleomycin injured lungs was examined further at the post-fibrotic stage, with drug intervention being begun at day 14, a time point when the lungs are significantly fibrosed (FIG. 15) (Pottier, N. et al., *American Journal of Respiratory and Critical Care Medicine*, 176(11): 1098-1107, 2007, incorporated by reference herein). The rescuing of scarred lungs that is shown in this model is clinically relevant, given that lungs of IPF patients already are scarred at the time of diagnosis.

More specifically, fibrotic loci in the lungs were induced by delivering intratracheally about 0.025 U of bleomycin (dissolved in PBS) to C57BL/6 mice. In order to examine the efficacy of MMI-0100 (YARAAARQARAKALARQLGVAA; SEQ ID NO: 1) in the treatment of bleomycin-injured lungs in the post-fibrotic phase, PBS (control) or MMI-0100 (YARAAARQARAKALARQLGVAA; SEQ ID NO: 1) was administered to the mice either intraperitoneally or via nebulization daily starting at day 14 post bleomycin delivery until day 28 post bleomycin delivery. At 28 day post bleomycin delivery, the lung tissues of the bleomycin mice treated with MMI-0100 (YARAAARQARAKALARQLGVAA; SEQ ID NO: 1) or a control (PBS), were isolated, fixed, embedded in paraffin, and sectioned for staining. Mice were sacrificed with a sodium pentobarbital injection (120 mg/kg) and the chest cavity was opened. The right mainstem bronchus was ligated and the right lung is removed. The trachea was cannulated and the left lung was perfused with 4% formaldehyde at 21 cm $H_2O$ pressure. The tissue blocks then were embedded in paraffin, and 4-mm sections were prepared, and stained with hematoxylin and eosin (H&E; for pathological examination) or Masson's Trichrome (for collagen staining)

As shown in FIG. 16, regardless of the mode of drug administration, i.e., whether intraperitoneally delivered or locally applied to the lung, MMI-0100 (YARAAARQARAKALARQLGVAA; SEQ ID NO: 1) treatment "rescued" severely scarred lungs. Histological assessment was employed to examine lung architecture (Hematoxylin & Eosin (H&E) staining, top panel) and collagen distribution (Masson's blue trichrome staining, bottom panel). The histochemistry results show that while bleomycin-injured lungs are severely scarred, MMI-0100 (YARAAARQARAKALARQLGVAA; SEQ ID NO: 1)-treated mice have a clearer lung parenchyma.

Next, collagen deposition was determined quantitatively by using the standard hydroxyproline assay with whole left lung. Total collagen (soluble and insoluble) deposition was assessed by analyzing hydroxyproline concentrations in murine lungs day 28 post bleomycin injury. MMI-0100 (YARAAARQARAKALARQLGVAA (SEQ ID NO: 1)) was administered at the dose of 50 µg/kg/day by intraperitoneal injection (IP) or nebulizer (NEB) beginning at day 14 post bleomycin injury.

As shown in FIG. 17, MMI-0100 (YARAAAR-QARAKALARQLGVAA; SEQ ID NO: 1) treatment significantly arrested further progression of collagen deposition, as compared to baseline, at 28 days post-bleomycin injury and the onset of MMI-0100 (YARAAARQARAKA-LARQLGVAA; SEQ ID NO: 1) treatment. This is significant because while current literature shows effective prophylaxis in drug development, when IPF patients are diagnosed, there is pre-existing fibrosis. These results also suggest that MMI-0100 (YARAAARQARAKALARQL-GVAA; SEQ ID NO: 1) has the potential to effectively halt or slow further progression of the disease and improve quality of life; and that the MMI-0100 (YARAAAR-QARAKALARQLGVAA; SEQ ID NO: 1) peptide, if used at a higher dose and/or for a longer treatment period, may result in even greater improvement in lung histology and physiology, and diminished fibrosis.

Example 9

Either Systemic or Local Administration of MMI-0100 (YARAAARQARAKALARQLGVAA; SEQ ID NO: 1) is Correlated with Reduced Activated MK2 in the Bleomycin Mouse Model of Idiopathic Pulmonary Fibrosis As discussed above, one of the principal targets of MMI-0100 (YARAAARQARAKALARQLGVAA; SEQ ID NO: 1) and its functional equivalents in the lung is MK2 kinase, which elicits inflammatory and fibrotic responses in the affected lungs. Therefore, in order to further validate the effects of MMI-0100 (YARAAARQARAKALARQL-GVAA; SEQ ID NO: 1) in vivo, levels of activated MK2 (phospho-Thr$^{334}$-MAPKAPK2) were examined in untreated bleomycin injured mice as well as in MMI-0100 (YARAAARQARAKALARQLGVAA; SEQ ID NO: 1)-treated mice.

Briefly, C57-BL/6 mice were subjected to bleomycin injury at day 0. At day 14, the mice were administered 50 µg/kg of MMI-0100 (YARAAARQARAKALARQLGVAA; SEQ ID NO: 1) daily by intraperitoneal (IP) injection or nebulizer (NEB) until day 28 post bleomycin injury. Formalin-fixed lung tissue sections were immunostained against phospho-Thr$^{334}$ MK2. Control staining was with biotinylated secondary IgG antibody. Streptavidin-conjugated horseradish peroxidase was used with 3,3'-diaminobenzidene as substrate and nuclei was counterstained with hematoxylin. Whereas the bleomycin mice showed a visible increase in activated MK2 presence (dark nodules) if left untreated, most particularly in areas of significant collagen deposition, mice treated with MMI-0100 exhibited activated MK2 presence similar to normal tissue, with such distribution concentrated in peri-airway and blood vessel regions.

As shown in FIG. 18, regardless of the mode of delivery, i.e., either systemic or local administration, in contrast to the control, administration of nebulized or intraperitoneal MMI-0100 (YARAAARQARAKALARQLGVAA; SEQ ID NO: 1) was associated with decreased phospho-Thr$^{334}$-MAP-KAPK2 staining (activated form of MK2) in the bleomycin mouse model.

Example 10

MMI-0100 (YARAAARQARAKALARQLGVAA; SEQ ID NO: 1) Downregulates Inflammatory Cytokines in Idiopathic Pulmonary Fibrosis Treatment Model One potential mechanism by which MMI-0100 (YARAAARQARAKALARQLGVAA; SEQ ID NO: 1) can inhibit fibrosis formation in the lung is by decreasing local concentrations of pro-inflammatory cytokines, and thereby deterring recruitment of monocytes and aberrant extracellular remodeling by macrophages in the lung (e.g., increase in collagen deposition, increase in cell adhesion and migration, decrease in matrix degradation). To explore this possibility, the ability of the MMI-0100 (YARAAARQARAKALAR-QLGVAA; SEQ ID NO: 1) peptide to inhibit production of pro-inflammatory cytokines was examined by measuring changes in interleukin-6 (IL-6) and Tumor Necrosis Factor-alpha (TNF-α) levels upon treatment with MMI-0100 (YARAAARQARAKALARQLGVAA; SEQ ID NO: 1) intraperitoneally or via nebulization.

Interleukin-6 (IL-6) is a multifunctional cytokine whose major actions include enhancement of immunoglobulin synthesis, activation of T cells, and modulation of acute-phase protein synthesis. Many different types of cells are known to produce IL-6, including monocytes, macrophages, endothelial cells, and fibroblasts, and expression of the IL-6 gene in these cells is regulated by a variety of inducers. Interleukin-1β (IL-1β) and tumor necrosis factor (TNF-α) are two key known inducers of IL-6 gene expression. Other inducers include activators of protein kinase C, calcium inophore A23187, and various agents causing elevation of intracellular cyclic AMP (cAMP) levels.

Tumor necrosis factor (TNF, also referred as TNF-α) is a cytokine involved in systemic inflammation and is a member of a group of cytokines that stimulate the acute phase reaction. Studies have shown that TNF-α induces expression of IL-6 via three distinct signaling pathways inside the cell, i.e., 1) NF-κB pathway 2) MAPK pathway, and 3) death signaling pathway.

As shown in FIG. 20, administration of either intraperitoneal (BLEO+MMI-0100 (IP)) or nebulized (BLEO+MMI-0100 (NEB)) MMI-0100 (YARAAARQARAKALARQL-GVAA; SEQ ID NO: 1) significantly reduced the plasma level of both TNF-α (A, upper panel) and IL-6 (B, lower panel) in the bleomycin mouse model of idiopathic pulmonary fibrosis.

Example 11

Either Systemic or Local Administration of MMI-0100 (YARAAARQARAKALARQLGVAA; SEQ ID NO: 1) Effectively Blocks Myofibroblast Activation Accumulation in Murine Lung that is Significantly Scarred Due to Bleomycin-Injury The hallmark of idiopathic pulmonary fibrosis (IPF) is the accumulation of myofibroblasts at fibrotic lesions and expression of abundant alpha-smooth muscle actin (α-SMA), a marker for myofibroblast activation. Furthermore, activated myofibroblasts are in part responsible for rigidity of the lung parenchyma and aggravation of lung function.

Therefore, the expression level of α-SMA in bleomycin-injured lungs was assessed in the lungs of bleomycin-injured mice treated with MMI-0100 (YARAAARQARAKALAR- QLGVAA; SEQ ID NO: 1), either systemically (via intraperitoneal administration) or locally (via nebulization). As shown in FIG. 21, the level of α-SMA was significantly attenuated in MMI-0100 (YARAAARQARAKALARQL-GVAA; SEQ ID NO: 1)-treated lungs compared to the level of α-SMA in untreated bleomycin-injured lungs.

Example 12

Dose Response Studies of MMI-0100 (YARAAARQARAKALARQLGVAA; SEQ ID NO: 1) in Modulating TGF-β1-Induced Myofibroblast Activation In Vitro The major hallmarks of idiopathic pulmonary fibrosis (IPF) are the presence of atypical and apoptotic epithelial cells, along with activated myofibroblasts that secrete exuberant amounts of matrix proteins including collagens, fibronectin and matrix metalloproteinases (Horowitz, J and Thannickal, V., Treatments in Respiratory Medicine, 5(5): 325-42, 2006). Under normal wound healing processes, a provisional matrix is formed by the myofibroblasts as a temporary scaffolding. Contraction of the provisional matrix results in subsequent re-epithelialization and eventual wound healing. However, when activated myofibroblasts are resistant to apoptosis, the resultant exuberant collagen deposition leads to stabilization of the matrix (Tomasek, J. et al., *Nature Reviews Molecular Cell Biology*, 3(5): 349-63, 2002). The end-result of unchecked myofibroblast proliferation, activation and resistance to apoptosis results in fibrotic lesions with stabilized matrix due to collagen deposition and thus eventual distortion of lung architecture (Yamashita, C. et al., *The American Journal of Pathology*, 179(4): 1733-45, 2011).

Therefore, since fibroblasts are the key cells involved in scar formation, the effect of MMI-0100 (YARAAAR-QARAKALARQLGVAA; SEQ ID NO: 1) on myofibroblast activation was assessed by examining the protein levels of α-smooth muscle actin (α-SMA) and fibronectin in cultured human fetal lung fibroblasts (IMR-90 cells) treated with TGF-β. As shown in FIGS. 22 and 23, MMI-0100 (YARAAARQARAKALARQLGVAA; SEQ ID NO: 1) effectively prevented myofibroblast activation induced by TGF-β in a dose-dependent manner, as shown by decreases in the levels of both α-smooth muscle actin (α-SMA) (FIG. 22) and fibronectin (FIG. 23).

In contrast, MMI-0200 (YARAAARQARAKALNRQL-GVA; SEQ ID NO: 19) at the doses tested did not affect the TGF-β-mediated myofibroblast activation, as indicated by no changes in the protein level of myofibroblast activation markers α-smooth muscle actin (FIG. 21) and fibronectin (FIG. 23). Without being limited by theory, these results suggest (1) that MK2 inhibitory peptides of the described invention may exhibit a spectrum of inhibitory activities against a specific group of kinases; (2) that MMI-0100 (SEQ ID NO: 1) and MMI-0200 (SEQ ID NO: 19) may inhibit MK2 and other kinases differentially, which, depending on the dose applied, contributes to this spectrum of inhibitory activities; (3) that there might be compensatory pathways that regulate α-smooth muscle actin; (4) that myofibroblast formation and/or migration might also be a part of the repair phase of fibrosis rather than of active damage; and (5) that a certain level of MK2 activity is, therefore, necessary for that process to occur (Liu et al., Am J Respir Cell Mol Biol, 37: 507-517, 2007).

In addition, the MK2 inhibitory peptides of the described invention were derived from the substrate binding site of MK2 downstream target HSPB1. Therefore, they can competitively inhibit the kinase activity of MK2 toward HSPB1. Without being limited by theory, the differential effects of MMI-0200 (SEQ ID NO: 19) on fibrosis may be attributed to its sequence differences, its homology to the HSPB1 biding sites, and its differential inhibition of MK2 kinase activity toward a distinct target protein binding site.

Example 12

Efficacy of MMI-0100 (YARAAARQARAKALARQLGVAA; SEQ ID NO: 1) and MMI-0100 in Combination with an Antiviral, Agent, e.g., Sofosbuvir (Sovaldi®), on Liver Fibrosis in a Murine Liver Fibrosis Model The most commonly used approach to induce experimental liver inflammation and fibrinogenesis is the periodic administration of carbon tetrachloride ($CCl_4$) in mice (Liedtke C, et al., Fibrogenesis & Tissue Repair, 2013; 6:19). The $CCl_4$ model resembles all the important properties of human liver fibrosis, including inflammation, regeneration, fiber formation and potentially fibrosis regression (Liedtke C, et al., Fibrogenesis & Tissue Repair, 2013; 6:19; Heindryckx F, et al., Int. J. Exp. Pathol., 2009; 90: 367-386; Iredale J P, et al., J. Clin. Invest., 1998; 102: 538-549; Kisseleva T, et al., PNAS, 2012; 109: 9448-9453). Most studies still rely on the $CCl_4$-model to induce toxic liver fibrosis in mice due to its good comparability with the abundance of previous publications, excellent reproducibility and moderate burden for the animals (Liedtke C, et al., Fibrogenesis & Tissue Repair, 2013; 6:19).

Pathogen free 8-10 week old female BALB/c mice can be obtained from Charles River Laboratories (Wilmington, Mass.). The mice can be divided into three groups: Group 1 to receive MMI-0100 (YARAAARQARAKALARQL-GVAA; SEQ ID NO: 1) or a functional equivalent; Group 2 to receive MMI-0100 (YARAAARQARAKALARQL-GVAA; SEQ ID NO: 1) or a functional equivalent+one of Sofosbuvir (Sovaldi®), an HCV boosted protease inhibitor (ABT-450, AbbVie), a nonnucleoside NS5B inhibitor (dasabuvir, ABT-333, AbbVie), an NS5a inhibitor (ombitasvir, ABT-267, AbbVie), ABT-450/r (ABT-450 with ritonavir), ABT-450 co-formulated with ABT-267, ABT-450 formulated with sofosbuvir, ribavirin, or a combination. Group 3 to receive phosphate buffer saline (PBS) (Control Group). Mice can be injected intraperitoneally two to three times per week with $CCl_4$ (Sigma-Aldrich, St. Louis, Mo.) (0.5 to 2 mL/kg body weight diluted in corn oil) for 4 to 6 weeks. At the time of $CCl_4$ injection, Group 1 mice can be administered MMI-0100 or a functional equivalent intraperitoneally (e.g., 3, 30, 100, 300 ng/kg) in 100 μL PBS; Group 2 mice can be administered MMI-0100 or a functional equivalent+ an antiviral agent intraperitoneally (e.g., 3, 30, 100, 300 ng/kg) in 100 μL PBS; and Group 3 mice can be administered 100 μL PBS intraperitoneally. Samples can be collected throughout the duration of the study (e.g., blood samples can be collected from tail veins immediately preceding each intraperitoneal injection). At the end of the study, mice can be anaesthetized and blood and liver tissue samples can be collected prior to sacrifice in order to determine the effect of MMI-0100 or a functional equivalent and MMI-0100 or a functional equivalent+an antiviral agent on liver fibrosis.

For example, liver function can be determined by measuring serum levels of alanine aminotransferase (ALT), aspartate aminotransferase (AST), gamma-glutamyl transferase (GGT) and albumin using commercially available kits according to manufacturer's instructions (e.g., Sigma-Aldrich, St. Louis, Mo.).

The level of liver fibrosis can be evaluated in liver tissue, for example, by hydroxyproline content, histology and immunohistochemistry, and mRNA expression of profibrotic and inflammatory biomarkers.

The hydroxyproline content of a liver tissue sample can be determined in the following manner. 100 mg of liver sample can be hydrolyzed in 6 M HCl at 110° C. for 24 hours. Next, the sample is centrifuged at 2,000 rpm at 48° C. for 5 minutes. 2 mL of supernatant is collected and mixed with 50 mL of 1% phenolphthalein and 8 N KOH to pH 7-8. A 5 mL sample can be subjected to a spectrophotometer at 560 nm to determine hydroxyproline content.

Histology and immunohistochemistry can be performed as follows. Liver tissues can be fixed in 10% neutral buffered formaldehyde and embedded in paraffin. Paraffin sections can be stained with Masson's Trichrome (Sigma-Aldrich, St. Louis, Mo.) and periodic acid-Schiff (PAS) stain (Millipore, Billerica, Mass.) to examine collagen deposition. Specific staining for α-smooth muscle actin (α-SMA) and collagen proteins can be performed using anti-α-SMA and anti-collagen I and III antibodies (R&D Systems, Minneapolis, Minn.; EMD Millipore, Billerica, Mass.; and abcam, Cambridge, Mass. respectively). Microscopic images of ×100-magnification can be acquired for liver sections stained with Masson's trichrome, collagen 1, collagen III and α-SMA. Images can be encoded on 24-bits per pixel on three channels (red, green and blue) and quantitative assessment of the percentage of fibrotic modification revealed by Masson's trichrome, collagen 1, collagen III and α-SMA can be performed on the images. Colored images can be processed using ImageJ (Wyne Rasband, National Institutes of Health, Bethesda, Md.) and Matlab (The MathWorks Inc., Natick, Mass.) to produce maps showing only the areas stained by Masson's trichrome, collagen 1, collagen III and α-SMA. A map can be defined as the stained area corresponding to the fibrotic component(s) deposited in the ECM of the liver. The Biomarker Index of Fibrosis (BIF) can be calculated as the percentage of a biomarker's (e.g., Masson's trichrome, collagen 1, collagen III and α-SMA) map to the whole image as described by Salazar-Montes, et al. (European Journal of Pharmacology, 2008; 595(1-3): 69-77) and Salgado, et al. (Molecular Therapy, 2000; 2: 545-551).

mRNA expression of profibrotic and inflammatory biomarkers, including MCP-1, Collagen 1a1, Collagen 3a1, TGFβ, Fibronecin-1, α-SMA and connective tissue growth factor-1 (CTGF-1) can be assessed by Luminex® (Life Technologies, Carlsbad, Calif.) assay according to manufacturer's instructions. Relative expression can be normalized to hypoxanthine phosphorbosyltransferase (HPRT).

Data can be expressed as mean±standard error of mean (SEM). Statistical analysis can be performed using computer software such as GraphPad Prism® (GraphPad Software, Inc., San Diego, Calif.). Treatment differences between groups can be analyzed by unpaired t-Test and ANOVA.

Example 13

Efficacy of MMI-0100 (YARAAARQARAKALARQLGVAA; SEQ ID NO: 1) on Renal Fibrosis in a Murine Renal Fibrosis Model An increasingly used and popular animal model of renal fibrosis is complete unilateral ureteral obstruction (UUO) (Cho M H, Korean J. Pediatr. 2010; 53(7): 735-740). The UUO procedure has the advantage that it mimics, in an accelerated manner, the different stages of human obstructive nephropathy leading to tubulointerstitial fibrosis: cellular infiltration, tubular proliferation and apoptosis, epithelial-mesenchmyal transition (EMT), (myo)fibroblast accumulation, increased extracellular matrix (ECM) deposition and tubular atrophy (Bascands J-L and Schanstra J P, Kidney Int. 2005; 68(3): 925-937). These pathological features appear rapidly (all within around 1 week after the UUO procedure) and are highly reproducible from one experiment to another (Bascands J-L and Schanstra J P, Kidney Int. 2005; 68(3): 925-937).

Pathogen free 7-8 week old male CD-1 mice can be obtained from Charles River Laboratories (Wilmington, Mass.). The mice can be divided into three groups: Group 1 to receive MMI-0100 (YARAAARQARAKALARQL-GVAA; SEQ ID NO: 1) or a functional equivalent; Group 2 to receive phosphate buffer saline (PBS) (Control Group); Group 3 to undergo sham surgery (i.e., without ligation) and to receive PBS. UUO can be performed as described by Yamashita et al. (Journal of the American Society of Nephrology 2004; 15(1): 91-101). Briefly, after induction of general anesthesia by intraperitoneal injection of pentobarbital (50 mg/kg body weight), the abdominal cavity can be exposed via midline incision and the right ureter can be ligated at three points with 4-0 silk. From days 0 to 5, Group 1 mice can be administered MMI-0100 or a functional equivalent intraperitoneally (e.g., 3, 30, 100, 300 ng/kg) in 100 µL PBS. Group 2 and Group 3 mice can be administered 100 µL PBS intraperitoneally. Samples can be collected throughout the duration of the study (e.g., blood samples can be collected from tail veins immediately preceding each intraperitoneal injection). On day 5, mice can be anaesthetized and blood and kidney tissue samples can be collected prior to sacrifice in order to determine the effect of MMI-0100 or a functional equivalent on renal fibrosis. UUO can be confirmed by observation of dilation of the pelvis and proximal ureter and collapse of the distal ureter. Sham-operated kidneys without ligation can be used as controls.

Study endpoints can include, for example, body and kidney weights; fibrosis in obstructed kidney evaluated via histological quantitative image analysis of picrosirius red staining (Polysciences, Inc., catalog no. 24901-250, Warrington, Pa.) (e.g., ten images/depth/kidney obtained and assessed in a blinded fashion using light microscopy at 200× to enable sampling of 60-70% of the renal cortical area) and quantified by a composite Collagen Volume Fraction (CVF (% total area imaged)) score expressed as the average positive stain across three anatomically distinct (e.g., 200-250 um apart) tissue sections, or depths, from the obstructed kidney; hydroxyproline content of frozen renal cortical tissue biopsies as assessed by biochemical analyses; and mRNA expression of profibrotic and inflammatory biomarkers such as MCP-1, Collagen 1a1, Collagen 3a1, TGF-β, Fibronectin-1, α-SMA and connective tissue growth factor-1 (CTGF-1) assessed by Luminex® (Life Technologies, Carlsbad, Calif.) assay according to manufacturer's instructions with relative expression normalized to hypoxanthine phosphorbosyltransferase (HPRT).

Data can be expressed as mean±standard error of mean (SEM). Statistical analysis can be performed using computer software such as GraphPad Prism® (GraphPad Software, Inc., San Diego, Calif.). Treatment differences between groups can be analyzed by unpaired t-Test and ANOVA.

Example 14

Efficacy of MMI-0100 (YARAAARQARAKALARQLGVAA; SEQ ID NO: 1) on Vascular Fibrosis in Spontaneously Hypertensive Rats (SHRs)

Spontaneously hypertensive rats (SHRs) are commonly used to study vascular fibrosis (Gao D et al., PPAR Res. 2012; 2012: 856426). For this study, 8-10 week old male SHR and age-matched male Wistar Kyoto (WKY) rats can be obtained from Charles River Laboratories (Wilmington, Mass.). SHRs can receive MMI-0100 (YARAAARQARAKALARQLGVAA; SEQ ID NO: 1) or a functional equivalent (experimental Group 1); WKY rats (control group 1) can receive MMI-0100 (YARAAARQARAKALARQLGVAA; SEQ ID NO: 1) or a functional equivalent; and SHR rats can receive vehicle (PBS) only (control group 2). Experimental Group 1 and control group 1 rats can be administered MMI-0100 or a functional equivalent intraperitoneally (e.g., 3, 30, 100, 300 ng/kg) in 100 µL PBS; control group 2 rats can receive vehicle only. Samples can be collected throughout the duration of the study (e.g., blood samples can be collected from tail veins immediately preceding each intraperitoneal injection). At the end of the study, rats can be anaesthetized and blood and vascular tissue samples can be collected prior to sacrifice in order to determine the effect of MMI-0100 or a functional equivalent on vascular fibrosis.

For example, mRNA expression of profibrotic and inflammatory biomarkers, including PPARγ MCP-1, Collagen 1a1, Collagen 3a1, TGFβ, Fibronecin-1, α-SMA and connective tissue growth factor-1 (CTGF-1) can be assessed by Luminex® (Life Technologies, Carlsbad, Calif.) assay according to manufacturer's instructions. Relative expression can be normalized to glyceraldehyde-3-phosphate dehydrogenase (GAPDH).

Protein expression of profibrotic biomarkers including CTGF and TGF-β can be assessed, for example, by Western blot. Briefly, protein samples (20 ug) can be resolved on 10% SDS-PAGE, transferred to polyvinylidene difluoride membranes in a semidry system (Bio-Rad, Hercules, Calif.) and incubated with antibodies against CTGF (1:500) (Santa Cruz Biotechnology, Santa Cruz, Calif.), TGF-β (1:500) (Santa Cruz Biotechnology, Santa Cruz, Calif.) and β-actin (1:2000) (Santa Cruz Biotechnology, Santa Cruz, Calif.). Protein can be visualized by chemiluminescence (Pierce Corp., Rockford, Ill.) and quantified using a Gel Doc 2000 system (Bio-Rad).

Protein expression of profibrotic biomarkers including PARAγ and collagen type III (Col III) can be assessed, for example, by immunohistochemistry. Briefly, paraffin-embedded rat thoracic aorta sections can be incubated with primary antibodies against PPARγ(1:300) (Upstate Inc., Chicago, Ill.) and Col III (1:250) (Upstate Inc., Chicago, Ill.) overnight at 4° C. and then biotinylated and affinity-purified IgG (Zymed USA) secondary antibody for 1 hr at 37° C. A streptavidin-enzyme conjugate can be sequentially added for 20 min. and samples can be incubated with substrate 3',3'-diaminobenzidine (DAB) (Sigma-Aldrich, St. Louis, Mo.) followed by hematoxylin counterstaining (Sigma-Aldrich, St. Louis, Mo.). Quantitative analysis can be performed using a Qwin 550 quantitative image analysis system (Leica, Germany) by measuring the gray scale. A negative control can include paraffin-embedded sections not incubated with primary antibody.

Data can be expressed as mean±standard error of mean (SEM). Statistical analysis can be performed using computer software such as GraphPad Prism® (GraphPad Software, Inc., San Diego, Calif.). Treatment differences between groups can be analyzed by unpaired t-Test and ANOVA.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A method for reducing progression of a fibrosis in liver tissue, kidney tissue or vascular tissue; treating fibrotic remodeling of the liver tissue, kidney tissue or vascular tissue; or both, in a subject in need thereof, comprising:
   administering to the subject a pharmaceutical composition comprising a therapeutic amount of a polypeptide of the amino acid sequence YARAAARQARAKALARQLGVAA (SEQ ID NO: 1) or a functional equivalent thereof selected from the group consisting of a polypeptide of the amino acid sequence FAKLAARLYRKALARQLGVAA (SEQ ID NO: 3) and a polypeptide of the amino acid sequence KAFAKLAARLYRKALARQLGVAA (SEQ ID NO: 4), and a pharmaceutically acceptable carrier thereof,
   progression of the fibrosis being characterized by one or more of aberrant fibroblast proliferation and extracellular matrix deposition producing remodeling in liver tissue, kidney tissue or vascular tissue, wherein the therapeutic amount of the pharmaceutical composition inhibits at least 65% of activity of MK2, MK3, CaMKI, and TrkB, with limited off-target kinase inhibition, and wherein the therapeutic amount of the polypeptide reduces progression of the fibrosis, treats remodeling of the liver tissue, kidney tissue or vascular tissue due to the fibrosis, or both reduces progression of the fibrosis in liver, kidney or vascular tissue and treats remodeling of the liver tissue, kidney tissue or vascular tissue due to the fibrosis.

2. The method according to claim 1, wherein the tissue fibrosis is further characterized by an inflammation in the tissue.

3. The method according to claim 2, wherein the inflammation is an acute or a chronic inflammation.

4. The method according to claim 2, wherein the inflammation is mediated by at least one cytokine selected from the group consisting of Tumor Necrosis Factor-alpha (TNF-α), Interleukin-6 (IL-6), and Interleukin-10 (IL-1β).

5. The method according to claim 1, wherein the aberrant fibroblast proliferation and extracellular matrix deposition in the tissue is characterized by an aberrant activity of Mitogen-Activated Protein Kinase-Activated Protein Kinase 2 (MK2) in the tissue compared to the activity of Mitogen-Activated Protein Kinase-Activated Protein Kinase 2 (MK2) in the tissue of a normal healthy control subject.

6. The method according to claim 1, wherein the step of administering occurs orally, intratracheally, parenterally, intravenously, or intraperitoneally.

7. The method according to claim 1, wherein the pharmaceutical composition further comprises at least one additional therapeutic agent.

8. The method according to claim 7, wherein the additional therapeutic agent is an anti-infective agent.

9. The method according to claim 8, wherein the anti-infective agent is an antiviral agent.

10. The method according to claim 9, wherein the antiviral agent is one or more of sofosbuvir, an HCV boosted protease inhibitor, a nonnucleoside NSSB inhibitor, an NS5a inhibitor, ABT-450 with ritonavir, ABT-450 co-formulated with ABT-267, ABT-450 formulated with sofosbuvir, and ribavirin.

11. The method according to claim 7, wherein the additional therapeutic agent is a glucocorticoid selected from the group consisting of prednisone, budesonide, mometasone furoate, fluticasone propionate, fluticasone furoate, and a combination thereof.

12. The method according to claim 7, wherein the additional therapeutic agent is an analgesic agent.

13. The method according to claim 7, wherein the additional therapeutic agent is selected from the group consisting of a purified bovine Type V collagen, an IL-13 receptor antagonist, a protein tyrosine kinase inhibitor, an endothelial receptor antagonist, a dual endothelin receptor antagonist, a prostacyclin analog, an anti-CTGF monoclonal antibody, an endothelin receptor antagonist, AB0024, a lysyl oxidase-like 2 (LOXL2) antibody, a c-Jun N-terminal kinase (JNK) inhibitor, pirfenidone, IFN-γ1b, a human antibody against all three TGF-β isoforms, a TGF-β activation inhibitor, a recombinant human Pentraxin-2 protein (rhPTX-2), a bispecific IL-4/IL-13 antibody, an antibody targeting integrin αvβ6, N-acetylcysteine, sildenafil, a Tumor Necrosis Factor (TNF) antagonist, and a combination thereof.

14. The method according to claim 1, wherein the carrier is selected from the group consisting of a controlled release carrier, a delayed release carrier, a sustained release carrier, and a long-term release carrier.

15. The method according to claim 13, wherein the endothelin receptor antagonist is A-selective.

16. The method according to claim 13, wherein the TNF antagonist is etanercept.

* * * * *